(12) United States Patent
Bakthavatchalam et al.

(10) Patent No.: US 6,723,730 B2
(45) Date of Patent: Apr. 20, 2004

(54) CAPSAICIN RECEPTOR LIGANDS

(75) Inventors: Rajagopal Bakthavatchalam, Wilmington, DE (US); Alan Hutchinson, Madison, CT (US); Robert W. DeSimone, Durham, CT (US); Kevin J. Hodgetts, Killingworth, CT (US); James E. Krause, Madison, CT (US); Geoffrey G. White, Guilford, CT (US)

(73) Assignee: Neurogen Corporation, Branford, CT (US)

( * ) Notice: Subject to any disclaimer, the term of this patent is extended or adjusted under 35 U.S.C. 154(b) by 0 days.

(21) Appl. No.: 09/910,442

(22) Filed: Jul. 20, 2001

(65) Prior Publication Data

US 2002/0132853 A1 Sep. 19, 2002

Related U.S. Application Data

(60) Provisional application No. 60/280,223, filed on Mar. 30, 2001, provisional application No. 60/230,726, filed on Sep. 7, 2000, and provisional application No. 60/219,529, filed on Jul. 20, 2000.

(51) Int. Cl.$^7$ ................ C07D 295/192; C07D 295/194; C07D 401/04; C07D 401/14; A61K 31/496

(52) U.S. Cl. .................. 514/284; 544/363; 544/364; 544/365; 544/360; 544/368; 544/369; 544/370; 544/371; 544/372; 544/376; 544/379; 544/389; 544/390; 544/391; 544/284; 544/353; 544/355; 544/356; 544/357; 544/235; 514/354; 514/356; 514/357; 514/405; 514/400; 206/570

(58) Field of Search ................ 544/363, 364, 544/365, 360, 368, 369, 370, 371, 372, 376, 379, 389, 390, 391, 284, 353, 355, 356, 357, 235; 206/570; 514/284, 354, 356, 357, 405, 400

(56) References Cited

U.S. PATENT DOCUMENTS

| | | | | |
|---|---|---|---|---|
| 4,439,606 A | | 3/1984 | Du .................. | 544/356 |
| 4,450,272 A | * | 5/1984 | Du et al. .............. | 544/357 |
| 5,354,747 A | | 10/1994 | Hansen ............... | 514/211.14 |
| 5,430,033 A | * | 7/1995 | Cliffe et al. ........... | 514/254 |
| 5,442,064 A | | 8/1995 | Pieper et al. ........... | 544/360 |
| 5,461,047 A | | 10/1995 | Hansen ............... | 514/211 |
| 5,756,504 A | * | 5/1998 | Bock et al. ........... | 514/252.11 |
| 5,789,412 A | | 8/1998 | Halazy ................ | 514/255 |
| 5,792,768 A | * | 8/1998 | Kulagowski et al. .. | 514/254.06 |
| 6,028,195 A | | 2/2000 | Cho .................. | 544/360 |
| 6,169,088 B1 | | 1/2001 | Matsuno .............. | 514/252.16 |
| 6,329,395 B1 | | 12/2001 | Dugar ................ | 514/329 |

FOREIGN PATENT DOCUMENTS

| | | |
|---|---|---|
| EP | 0 100 200 A1 | 2/1984 |
| EP | 0 100 200 B1 | 5/1987 |
| EP | 0 790 240 A1 | 8/1997 |
| EP | 1 122 242 A1 | 8/2001 |
| EP | 11 122 242 A1 | 8/2001 |
| WO | WO 94/29286 | 12/1994 |
| WO | WO 96/01820 | 1/1996 |
| WO | WO 96/02525 A1 | 2/1996 |
| WO | WO 96/21648 | 7/1996 |
| WO | WO 98/00402 | 1/1998 |
| WO | WO 98/14431 | 4/1998 |
| WO | WO 98/00402 | * 9/1998 |
| WO | WO 99/07672 | 2/1999 |
| WO | WO 99/51582 | 10/1999 |
| WO | WO 99/64394 | 12/1999 |
| WO | WO 00/17163 | 3/2000 |
| WO | WO 00/27822 | 5/2000 |
| WO | WO 00/52001 | 9/2000 |
| WO | WO 00/63171 | 10/2000 |
| WO | WO 02/05819 | 1/2002 |

OTHER PUBLICATIONS

Kwak et al., Neuroscience (1998) 86: pp. 619–626.
Liu and Simon, Neuroscience Letters (1997) 228: pp. 29–32.
Ohkubo and M. Shibata, J. Dental Res. (1997) 76: pp. 848–851.
Pan and Sun, Tetrahedron Letters (1998) 39: pp. 9505–9508.
Santos and Calizto, Neuroscience Letters (1997) 235: pp. 73–76.
Urban, et al., Pain 89 (2000) pp. 65–74.
Wu et al., Gen Pharmacol (1996) 27: pp. 151–158.
Mokrosz et al (1992) J. Med. Chem. 35:2369–74—note compound 31 on pate 2370.
Prasad et al. (1968) J. Med. Chem. 11:1144–50—note table 4.

(List continued on next page.)

Primary Examiner—Mark L. Berch
Assistant Examiner—Kahsay Habte
(74) Attorney, Agent, or Firm—McDonnell Boehnen Hulbert & Berghoff

(57) ABSTRACT

Disclosed are diaryl piperazines and related compounds of the following Formula:

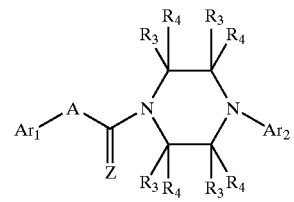

wherein the variables are as defined in the specification. These compounds are selective modulators of capsaicin receptors, including human capsaicin receptors, that are, therefore, useful in the treatment of a chronic and acute pain conditions, itch and urinary incontinence. Methods of treatment of such disorders and well as packaged pharmaceutical compositions are also provided. Compounds of the invention are also useful as probes for the localization of capsaicin receptors and as standards in assays for capsaicin receptor binding and capsaicin receptor mediated cation conductance. Methods of using the compounds in receptor localization studies are given.

185 Claims, No Drawings

OTHER PUBLICATIONS

Kwak et al., *Neuroscience* (1998) 86: pp. 619–626.
Liu and Simon, *Neuroscience Letters* (1997) 228: pp. 29–32.
Ohkubo and M. Shibata, *J. Dental Res.* (1997) 76: pp. 848–851.
Pan and Sun, *Tetrahedron Letters* (1998) 39: pp. 9505–9508.
Santos and Calizto, *Neuroscience Letters* (1997) 235: pp. 73–76.
Urban, et al. *Pain 89* (2000) pp. 65–74.
Wu et al., *Gen Pharmacol* (1996) 27: pp. 151–158.

* cited by examiner

CAPSAICIN RECEPTOR LIGANDS

RELATED APPLICATION INFORMATION

This application claims the benefit of priority under 35 U.S.C. section 119(e) to Provisional Patent Applications No. 60/280,223, filed Mar. 30, 2001; No. 60/230,726, filed Sep. 7, 2000; and No. 60/219,529, filed Jul. 20, 2000. These applications are hereby incorporated by reference in their entirety.

BACKGROUND OF THE INVENTION

1. Field of the Invention

This invention relates compounds that bind with high selectivity and high affinity to Vanilloid Receptors, especially Type I Vanilloid Receptors, also known as capsaicin receptors or VR1 Receptors. In an important aspect the invention provides capsaicin receptor, preferably human VR1 receptor, antagonists that are not capsaicin analogs (e.g., they do not contain a phenyl ring with two oxygen atoms bound to two adjacent ring carbons), are free of agonist activity, and exhibit an unprecedented level of affinity for the VR1 receptor. In another aspect, the invention provides aryl piperazines and related compounds that act as VR1 receptor ligands. In addition, this invention relates to such VR1 receptor ligands, high affinity antagonists and pharmaceutical compositions comprising such compounds and to the use of such compounds in treatment of diseases and other health-related conditions. Additionally this invention relates to the use of aryl piperazines and related compounds as tool for the analysis of VR1 receptors and as probes for the quantitative measurement and localization of VR1 receptors in cell and tissue samples.

2. Background

The sensation of pain can be triggered by any number of physical or chemical stimuli. In mammals, the peripheral terminals of a group of specialized small diameter sensory neurons, termed "nociceptors" mediate this response to a potentially harmful stimulus.

In efforts to discover better analgesics for the treatment of both acute and chronic pain, and to develop treatments for various neuropathic pain states, considerable research has been focused on the molecular mechanism of nociception. The response to heat, low extracellular pH (acidity), or capsaicin (the compound responsible for the hotness of hot peppers) is characterized by the persistent activation of nociceptors. It has been shown that both heat and capsaicin are capable of activating dorsal root ganglion and trigeminal ganglion neurons via an influx of cations. Additionally, moderately acidic conditions produce this response and can also potentiate the response of nociceptors to heat and capsaicin.

Capsaicin responses in isolated sensory neurons show dose-dependence and are also evoked by structural analogues of capsaicin that share a common vanilloid moiety. The term vanilloid receptor (VR) was coined to describe the neuronal membrane recognition site for capsaicin and such related irritant compounds. It was postulated that the VR is a nonselective cation channel with a preference for calcium. In 1989, resiniferatoxin (RTX), a natural product of certain *Euphorbia* plants, was recognized as an ultrapotent VR agonist. Specific binding of 3 H RTX provided the first unequivocal proof for the existence of a vanilloid receptor. The capsaicin response is competitively inhibited (and thereby antagonized) by another capsaicin analog, capsazepine and is also inhibited by the non-selective cation channel blocker ruthenium red. These antagonists bind to VR with no more than moderate affinity (i.e., with $K_i$ values of no lower than 140 uM).

Interest in characterizing VRs led to the cloning of a functional rat capsaicin receptor (VR1), from a rat dorsal root ganglion cDNA library. A human version of VR1 has also been described, and the term VR1 is used herein to refer to either or both.

The capsaicin receptor's channel opens in response to elevated temperatures (higher than about 45° C.). Capsaicin and related compounds, as well as protons are stimuli that lower the threshold channel opening, so that in the presence of any of these stimuli the capsaicin receptor can be opened even at room temperature.

Opening of the capsaicin receptor channel is followed by the release of inflammatory peptides from neurons expressing the receptor and other nearby neurons, increasing the pain response. After initial activation by capsaicin the capsaicin receptor undergoes a rapid desensitization, possibly via phosphorylation of intracellular sites of the receptor. Capsaicin and related VR1 agonist vanilloid compounds have enjoyed long pharmaceutical use as topical anaesthetics. While such compounds initially cause a strong burning sensation, receptor desensitization provides pain relief.

Localization of the capsaicin receptor in the dorsal root ganglion established this receptor as a leading target for analgesic discovery. Most currently marketed analgesic compounds act centrally, and often have side effects. Analgesic compounds that act peripherally are desirable for treating acute and chronic pain more effectively and with fewer side effects. Thus, compounds that interact with the capsaicin receptors, particularly antagonists of this receptor, which would not elicit the initial painful sensation of currently marketed capsaicin containing compounds, are desirable for the treatment of chronic and acute pain, itch, and urinary incontinence.

3. Description of Related Art

The vanilloid compounds capsaicin and Resiniferatoxin (RTX) act as potent and specific agonists of the capsaicin receptor. Capsazepine (which contains a phenyl ring with two oxygen atoms bound to two adjacent ring carbons and is therefore a capsaicin analog) acts as a moderate affinity competitive capsaicin receptor antagonist. Iodo-RTX is a capsaicin analog that has recently been reported to act as a high affinity antagonist. The inorganic dye, Ruthenium red, also antagonizes capsaicin responses of the receptor, albeit as a non-selective cation channel blocker. For an extensive review of vanilloid receptor ligands see Szallasi and Blumberg, (Pharmacological Reviews (1999) 51(3): 159–211).

SUMMARY OF THE INVENTION

This invention relates to VR1 receptor ligands, particularly VR1 receptor antagonists, and methods of using VR1 receptor antagonists for the treatment of neuropathic pain, peripheral-nerve-mediated pain, and pain, inflammatory and broncho-constriction symptoms resulting from exposure to capsacin-receptor-activating stimuli such as capsaicin and tear gas.

In one aspect the invention provides novel chemical compounds that act as capsaicin receptor modulatory agents, some of which exhibit antagonist potency greater than that of any previously described VR1 receptor antagonist. Compounds that act as capsaicin receptor antagonists and bind to capsaicin (preferably human VR1) receptors with $K_i$ values of less than 100 uM, as measured by a capsacin receptor binding assay, such as the assay given by Example 10, or that inhibit capsaicin activity in an assay for determination of capsaicin receptor antagonist effects (Example 11) with $EC_{50}$ values of less than or equal to 100 uM, are referred to herein as potent capsaicin receptor antagonists; such compounds that bind or antagonize with $K_i$ or $EC_{50}$ values of less than or equal to 10 uM are referred to herein as highly potent capsaicin receptor antagonists.

In an additional aspect, the invention provides methods of using the potent capsaicin receptor antagonist compounds of the invention for the treatment of symptoms resulting from exposure to painful capsaicin receptor activating stimuli. In particular, the invention provides methods of treating subjects who have been exposed to capsaicin or have been burnt by heat, light, tear gas, or acid exposure, the methods comprising administering to such subjects an effective amount of a potent capsaicin receptor antagonist, preferably a highly potent (high potency) capsaicin receptor antagonist, so that the subject's symptoms of pain or sensitivity are reduced. Preferred compounds of the invention provide pain relief without loss of consciousness, and preferably without sedation, in such subjects that is equal to or grater than the degree of pain relief that can be provided to such subjects by morphine without loss of consciousness. Highly preferred compounds provide such pain relief while causing only transient (i.e., lasting for no more than one half the time that pain relief lasts) or no sedation (see Example 16 for sedation assay). Subjects or patients referred to herein may be humans or non-human mammals including domestic companion animals (pets) and livestock animals, as discussed more fully below.

In yet another aspect the invention provides methods of treating of neuropathic pain based on the unexpected finding that capsaicin receptor antagonists can alleviate such pain.

This invention also provides aryl piperazines and related compounds that bind with high affinity and high selectivity to capsaicin receptors, including human capsaicin receptors, also known as VR1 receptors.

Thus, the invention provides novel compounds of Formula I, Formula II, Formula III, Formula IV, Formula V, Formula VI, or Formula VII, Formula VIII, Formula IX and Formulae A–F shown below (the "compounds of the invention," hereinafter Formulae I–IX and Formulae A–F), and pharmaceutical compositions comprising compounds of Formulae I–IX and Formulae A–F.

The invention further comprises methods of treating patients suffering from certain diseases or conditions, especially those involving pain or urinary incontinence, with an amount of a compound Formulae I–IX and Formulae A–F that is effective to improve the symptoms (e.g., reduce pain or reduce the frequency of urinary incontinence) of the disease or condition being treated.

Additionally this invention relates to the use of the compounds of the invention as reagents, standards, and probes for measurement, characterization and localization of capsaicin receptors, particularly VR1 receptors (e.g., in cells or tissues.

Accordingly, a broad aspect of the invention is directed to compounds of Formula I:

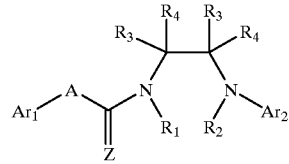

Formula I or the pharmaceutically acceptable salts thereof, wherein:

A is chosen from O, S, $NR_A$, $CR_BR_B{}'$, $NR_ACR_BR_B{}'$, $CR_BR_B{}'NR_A$, —$CR_A$=$CR_B$—, and $C_3H_4$; where $R_A$, $R_B$, and $R_B{}'$ are independently selected at each occurrence from hydrogen or alkyl;

Z is oxygen or sulfur;

$R_1$ and $R_2$ independently represent hydrogen or lower alkyl; or $R_1$ and $R_2$ are taken together to form a 5 to 8 membered nitrogen containing ring of the formula:

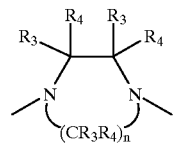

wherein n is 1, 2, or 3;

$R_3$ and $R_4$ are independently selected at each occurrence from the group consisting of hydrogen; halogen; hydroxy; amino; cyano; nitro; —COOH; —CHO; optionally substituted alkyl; optionally substituted alkenyl; optionally substituted alkynyl; optionally substituted alkoxy; optionally substituted mono or dialkylamino; optionally substituted alkylthio; optionally substituted alkyl ketone; optionally substituted alkylester; optionally substituted alkylsulfinyl; optionally substituted alkylsulfonyl; optionally substituted mono- or di-alkylcarboxamide; optionally substituted —S(O)$_n$NHalkyl; optionally substituted —S(O)$_n$N(alkyl)(alkyl); optionally substituted —NHC(=O)alkyl; optionally substituted —NC(=O)(alkyl)(alkyl); optionally substituted —NHS(O)$_n$alkyl; optionally substituted —NS(O)$_n$(alkyl)(alkyl); optionally substituted saturated or partially unsaturated heterocycloalkyl of from 5 to 8 atoms, which saturated or partially unsaturated heterocycloalkyl contains 1, 2, or 3 heteroatoms selected from N, O, and S; optionally substituted aryl having from 1 to 3 rings; or optionally substituted heteroaryl, said heteroaryl having from 1 to 3 rings, 5 to 8 ring members in each ring and, in at least one of said rings, from 1 to about 3 heteroatoms per ring selected from the group consisting of N, O, and S;

or any two $R_3$ and $R_4$ not attached to the same carbon may be joined to form an optionally substituted aryl ring; a saturated or partially unsaturated carbocyclic ring of from 5 to 8 members, which carbocyclic ring is optionally substituted; or a saturated, partially unsaturated, or aromatic heterocyclic ring of from 5 to 8 members, which heterocyclic ring is optionally substituted and contains 1, 2, or 3 heteroatoms selected from N, O, and S; and $Ar_1$ and $Ar_2$ are the same or different and independently represent optionally substituted cycloalkyl; an optionally substituted heterocycloalkyl ring of from 5 to 8 atoms, which heterocyloalkyl ring contains 1, 2, or 3 heteroatoms selected from N, O, and S; optionally substituted aryl having from 1 to 3 rings; or optionally substituted heteroaryl, said heteroaryl having from 1 to 3 rings, 5 to 8 ring members in each ring and, in at least one of said rings, from 1 to about 3 heteroatoms per ring selected from the group consisting of N, O, and S, and n is independently chosen at each occurrence from 0, 1, and 2.

In specific embodiments of the invention $R_1$ and $R_2$ are joined to form a 5 to 7-membered heterocycloalkyl ring, e.g. $R_1$ and $R_2$ may be joined to form a piperazine ring. This 5 to 7-membered heterocycloalkyl ring is preferably unsubstituted or substituted at one or two positions with a $C_{1-6}$ alkyl group, such as methyl or ethyl. The variable "Z" is preferably oxygen and the variable "A" is generally NH, CH=CH, or $CH_2NH$. $Ar_1$ and $Ar_2$ are preferably optionally substituted phenyl or optionally substituted pyridyl; optionally substituted 2-pyridyl is preferred for $Ar_2$. Substitutuents that may occur on $Ar_1$ and $Ar_2$ include, but are not limited to, butyl, isopropyl, trifluoromethyl, nitro, methyl, and halogen. Substitution at the 4 position of $Ar_1$ (when $Ar_1$ is phenyl or pyridyl) and substitution at the 3 position of $Ar_2$ (when $Ar_2$ is phenyl or pyridyl) are described in specific embodiments of the invention.

DETAILED DESCRIPTION OF THE INVENTION

The invention is particularly directed to compounds of Formula I, in which $R_1$ and $R_2$ independently represent hydrogen or lower alkyl, e.g., $C_{1-6}$ alkyl. Such compound will be referred to as compounds of Formula IA.

Preferred compounds and pharmaceutically acceptable salts of Formula IA are those wherein:

$R_3$ and $R_4$ are independently chosen at each occurrence from the group consisting of hydrogen, halogen, cyano, nitro, haloalkyl, haloalkoxy, hydroxy, amino, alkyl substituted with 0–2 $R_6$, alkenyl substituted with 0–2 $R_6$; alkynyl substituted with 0–2 $R_6$; alkoxy substituted with 0–2 $R_6$, —NH(alkyl) substituted with 0–2 $R_6$, —N(alkyl)(alkyl) where each alkyl is independently substituted with 0–2 $R_6$, —$XR_7$, and Y;

or any two $R_3$ and $R_4$ not attached to the same carbon may be joined to form an aryl ring substituted with 0–3 $R_6$, a saturated or partially unsaturated carbocyclic ring of from 5 to 8 members, which carbocyclic ring is substituted with 0–2 $R_6$, or a saturated, partially unsaturated, or aromatic heterocyclic ring of from 5 to 8 members, which heterocyclic ring is substituted with 0–2 $R_6$ and contains 1, 2, or 3 heteroatoms selected from N, O, and S; and $Ar_1$ and $Ar_2$ may be the same or different and are selected from the group consisting of cyclohexyl, cyclopentyl, piperidinyl, piperazinyl, phenyl, pyrrolyl, furanyl, thienyl, pyrazolyl, imidazolyl, thiazolyl, isothiazolyl, oxazolyl, isoxazolyl, oxadiazolyl, triazolyl, tetrazolyl, pyridyl, pyrimidyl, pyrazinyl, benzimidazolyl, naphthyl, indolyl, isoindolyl, benzofuranyl, isobenzofuranyl, benzo[b]thiophenyl, benz[d]isoxazolyl, quinolinyl, isoquinolinyl, cinnolinyl, quinazolinyl, and quinoxalinyl, each of which is optionally mono-, di-, or trisubstituted with $R_5$; or $Ar_1$ and $Ar_2$ may be the same or different and represent a bicyclic oxygen-containing group of the formula:

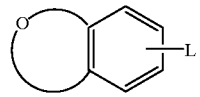

optionally mono-, di-, or trisubstituted with $R_5$, where L represents point of attachment and may be at any point on the benzene ring, and the oxygen-containing ring of the bicyclic oxygen-containing group consists of from 5 to 8 ring atoms, contains 1 or 2 oxygen atoms and remaining ring atoms are carbon;

$R_5$ is independently selected at each occurrence from the group consisting of halogen, cyano, nitro, haloalkyl, haloalkoxy, hydroxy, amino, alkyl substituted with 0–2 $R_6$, alkenyl substituted with 0–2 $R_6$, alkynyl substituted with 0–2 $R_6$, alkoxy substituted with 0–2 $R_6$, —NH (alkyl) substituted with 0–2 $R_6$, —N(alkyl)(alkyl) where each alkyl is independently substituted with 0–2 $R_6$, —$XR_7$, and Y;

$R_6$ is independently selected at each occurrence from the group consisting of halogen, hydroxy, cyano, alkyl, alkoxy, —NH(alkyl), —N(alkyl)(alkyl), —$S(O)_n$(alkyl), haloalkyl, haloalkoxy, CO(alkyl), CONH(alkyl), CON($alkyl_1$)($alkyl_2$) where $alkyl_1$ and $alkyl_2$ may be joined to form a heterocycloalkyl ring of from 5 to 8 ring atoms and containing 1, 2, or 3 heteroatoms selected from N, O, and S, —$XR_7$, and Y;

X is independently selected at each occurrence from the group consisting of —$CH_2$—, —$CHR_8$—, —O—, —$S(O)_n$—, —NH—, —$NR_8$—, —C(=O)—, —C(=O)O—, —C(=O)NH—, —C(=O)$NR_8$—, —$S(O)_nNH$—, —$S(O)_nNR_8$—, $NHC(=O)$—, —$NR_8C(=O)$—, —$NHS(O)_n$—, and —$NR_8S(O)_n$—;

$R_7$ and $R_8$ are independently selected at each occurrence from hydrogen, and straight, branched, and cyclic alkyl groups, and (cycloalkyl)alkyl groups, said straight, branched, and cyclic alkyl groups, and (cycloalkyl) alkyl groups consisting of 1 to 8 carbon atoms, and containing zero or one or more double or triple bonds, each of which 1 to 8 carbon atoms may be further substituted with one or more substituent(s) independently selected from oxo, hydroxy, halogen, amino, cyano, nitro, haloalkyl, haloalkoxy, —O(alkyl), —NH (alkyl), —N(alkyl)(alkyl), —NHC(O)(alkyl), —N(alkyl)C(O)(alkyl), —$NHS(O)_n$(alkyl), —$S(O)_n$(alkyl), —$S(O)_nNH$(alkyl), —$S(O)_nN(alkyl_3)(alkyl_4)$ where $alkyl_3$ and $alkyl_4$ may be joined to form a heterocycloalkyl ring consisting of from 5 to 8 ring atoms and containing 1, 2, or 3 heteroatoms selected from N, O, and S, and Y';

Y and Y' are independently selected at each occurrence from 3- to 8-membered carbocyclic or heterocyclic groups which are saturated, unsaturated, or aromatic, which may be further substituted with one or more substituents independently selected from halogen, oxo, hydroxy, amino, nitro, cyano, alkyl, alkoxy, haloalkyl, haloalkoxy, mono- or dialkylamino, and alkylthio; wherein said 3- to 8-memberered heterocyclic groups contain one or more heteroatom(s) independently selected from N, O, and S; and n is independently chosen at each occurrence from 0, 1, and 2.

Such compounds and pharmaceutically acceptable salts thereof, will be referred to as compounds of Formula IB.

The invention is further directed to compounds of Formula II:

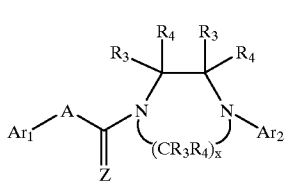

Formula II and the pharmaceutically acceptable salts thereof, wherein:
A, Z, $R_3$, $R_4$ are as defined for Formula I or for Formula IB; $Ar_1$ and $Ar_2$ are as defined for Formula I or for formula IB; and
x is 1 or 3.

Preferred compounds and salts of Formula II are those in which
$R_A$, $R_B$, and $R_B'$ (which are contained in the definition of A) are independently selected at each occurrence from hydrogen or $C_{1-6}$alkyl.

Other preferred compounds salts of Formula II are those in which Z is oxygen, and those in which Z is oxygen and A is NH.

The invention is further directed to compounds of Formula III:

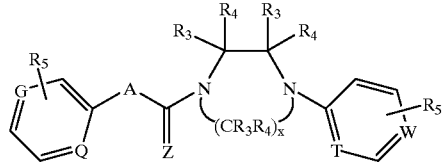

Formula III and the pharmaceutically acceptable salts thereof, wherein:
G, Q, T, and W are the same or different and represent N, CH, or $CR_5$, where $R_5$ is as defined for Formula IB;
$R_A$, $R_B$, and $R_B'$ are independently selected at each occurrence from hydrogen or $C_{1-6}$alkyl;
Z is oxygen or sulfur;
$R_3$ and $R_4$ are as defined for Formula I or for Formula IB; and
x is 1 or 3.

The invention also included compounds of Formula IV

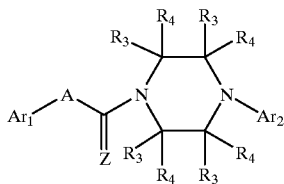

Formula IV and the pharmaceutically acceptable salts thereof, wherein:
Z is S or O (preferably O);
A, $R_3$, and $R_4$ is as defined for Formula I or Formula IB;
$Ar_1$ and $Ar_2$ may be the same or different and are selected from the group consisting of cyclohexyl, cyclopentyl, piperidinyl, piperazinyl, pyrrolyl, furanyl, thienyl, pyrazolyl, imidazolyl, thiazolyl, isothiazolyl, oxazolyl, isoxazolyl, oxadiazolyl, triazolyl, tetrazolyl, pyridyl, pyrimidyl, pyrazinyl, benzimidazolyl, naphthyl, indolyl, isoindolyl, benzofuranyl, isobenzofuranyl, benzo[b]thiophenyl, benz[d]isoxazolyl, quinolinyl, isoquinolinyl, cinnolinyl, quinazolinyl, and quinoxalinyl; wherein $Ar_1$ is optionally mono-, di-, or trisubstituted with $R_5$, and $Ar_2$ is optionally mono-, di-, or trisubstituted with $R_9$; or
$Ar_1$ and $Ar_2$ may be the same or different and represent a bicyclic oxygen-containing group as described for Formula IB,
$R_5$ is independently selected at each occurrence from the group consisting of cyano, nitro, haloalkyl, haloalkoxy, hydroxy, amino, alkyl substituted with 0–2 $R_6$, alkenyl substituted with 0–2 $R_6$, alkynyl substituted with 0–2 $R_6$, alkoxy substituted with 0–2 $R_6$, —NH(alkyl) substituted with 0–2 $R_6$, —N(alkyl)(alkyl) where each alkyl is independently substituted with 0–2 $R_6$, —$XR_7$, and Y;
$R_9$ is independently selected at each occurrence from the group consisting of cyano, nitro, haloalkoxy, hydroxy, amino, alkyl substituted with 0–2 $R_6$, alkenyl substituted with 0–2 $R_6$, alkynyl substituted with 0–2 $R_6$, alkoxy substituted with 0–2 $R_6$, —NH(alkyl) substituted with 0–2 $R_6$, —N(alkyl)(alkyl) where each alkyl is independently substituted with 0–2 $R_6$, —$XR_7$, and Y; and
$R_6$, $R_7$, $R_8$, X, Y and Y' are as defined for Formula IB.

Another embodiment of the invention is directed to compounds of Formula V:

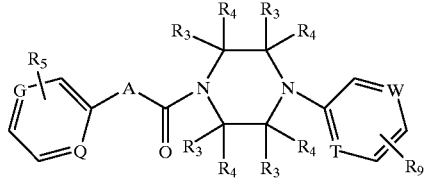

Formula V and the pharmaceutically acceptable salt thereof, wherein:
G, Q, T, and W are the same or different and are selected from the group consisting of N, CH, and $CR_5$, wherein T or W or both is N;
A, $R_3$, and $R_4$ are as defined for Formula I or for Formula IB (preferably A is —CH=CH—, —$CH_2$NH, NH, and $R_3$ and $R_4$ are hydrogen or $C_{1-6}$ alkyl);
Z is oxygen or sulfur (preferably oxygen);
$R_5$ represents 1 to 3 substituents and is independently selected at each occurrence from the group consisting of cyano, hydroxy, amino, $C_{3-6}$ alkyl substituted with 0–2 $R_6$, $C_{2-6}$ alkenyl substituted with 0–2 $R_6$, $C_{2-6}$ alkynyl substituted with 0–2 $R_6$, $C_{3-6}$ alkoxy substituted with 0–2 $R_6$, —NH($C_{1-6}$alkyl) substituted with 0–2 $R_6$, —N($C_{1-6}$alkyl)($C_{1-6}$alkyl) where each alkyl is independently substituted with 0–2 $R_6$, —$XR_7$, and Y;
$R_9$ represents 0 to 3 substituents and is independently selected at each occurrence from the group consisting of halogen, cyano, nitro, halo($C_{1-6}$)alkyl, halo($C_{1-6}$) alkoxy, hydroxy, amino, $C_{1-6}$alkyl substituted with 0–2 $R_6$, $C_{2-6}$alkenyl substituted with 0–2 $R_6$, $C_{2-6}$alkynyl substituted with 0–2 $R_6$, $C_{1-6}$alkoxy substituted with 0–2 $R_6$, —NH($C_{1-6}$alkyl) substituted with 0–2 $R_6$, —N($C_{1-6}$alkyl)($C_{1-6}$alkyl) where each $C_{1-6}$alkyl is independently substituted with 0–2 $R_6$, —$XR_7$, and Y;

$R_6$, $R_7$, $R_8$, X, Y, and Y' are as defined for Formula IB.

The invention is particularly directed to compounds and salts of Formula V wherein G and Q are selected from the group consisting of CH and $CR_5$.

The invention is also directed to compounds and salts of Formula V wherein G, Q, and W are independently selected at each occurrence from the group consisting of CH and $CR_5$; and T is N.

For compounds of Formula V, particularly preferred $R_6$ substituents are halogen, hydroxy, $C_{1-4}$ alkyl, $C_{1-4}$ alkoxy, —NH($C_{1-4}$alkyl), and —N($C_{1-4}$ alkyl)($C_{1-4}$ alkyl).

Still another embodiment of the invention is directed of compounds of Formula VI:

Formula VI

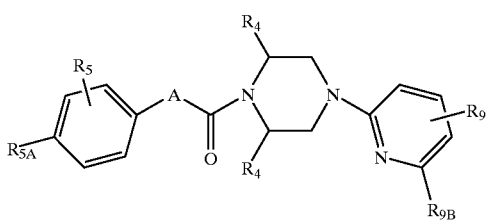

and the pharmaceutically acceptable salts thereof, wherein:

A is selected from the group consisting of NH, —CH=CH—, and $CH_2NH$;

$R_4$ is independently chosen from hydrogen and $C_{1-4}$ alkyl;

$R_5$ represents 0 to 2 substituents and is independently chosen at each occurrence from the group consisting of halogen, cyano, nitro, halo($C_{1-6}$)alkyl, halo($C_{1-6}$) alkoxy, hydroxy, amino, $C_{1-6}$alkyl substituted with 0–2 $R_6$, $C_{2-6}$alkenyl substituted with 0–2 $R_6$, $C_{2-6}$alkynyl substituted with 0–2 $R_6$, $C_{1-6}$alkoxy substituted with 0–2 $R_6$, —NH($C_{1-6}$alkyl) substituted with 0–2 $R_6$, —N($C_{1-6}$alkyl)($C_{1-6}$alkyl) where each $C_{1-6}$alkyl is independently substituted with 0–2 $R_6$;

$R_9$ represents 0 to 2 substituents and is independently chosen at each occurrence from the group consisting of halogen, cyano, nitro, halo($C_{1-6}$)alkyl, halo($C_{1-6}$) alkoxy, hydroxy, amino, $C_{1-6}$alkyl substituted with 0–2 $R_6$, $C_{2-6}$alkenyl substituted with 0–2 $R_6$, $C_{2-6}$alkynyl substituted with 0–2 $R_6$, $C_{1-6}$alkoxy substituted with 0–2 $R_6$, —NH($C_{1-6}$alkyl) substituted with 0–2 $R_6$, and —N($C_{1-6}$alkyl)($C_{1-6}$alkyl) where each $C_{1-6}$alkyl is independently substituted with 0–2 $R_6$;

$R_{5A}$ is independently selected from the group consisting of halogen, cyano, nitro, halo($C_{1-6}$)alkyl, halo($C_{1-6}$) alkoxy, hydroxy, amino, $C_{1-6}$ alkyl, $C_{1-6}$ alkoxy, —NH($C_{1-6}$ alkyl), and —N($C_{1-6}$ alkyl)($C_{1-6}$ alkyl);

$R_{9B}$ is independently selected from the group consisting of halogen, nitro, halo($C_{1-6}$)alkoxy, hydroxy, amino, $C_{1-6}$ alkyl, $C_{1-6}$ alkoxy, —NH($C_{1-6}$ alkyl), and —N($C_{1-6}$ alkyl)($C_{1-6}$ alkyl); and $R_6$ is independently selected at each occurrence the group consisting of halogen, hydroxy, $C_{1-4}$alkyl, $C_{1-4}$alkoxy, —NH($C_{1-4}$ alkyl), and —N($C_{1-4}$ alkyl)($C_{1-4}$ alkyl).

The invention is also directed to compounds of Formula VII:

Formula VII

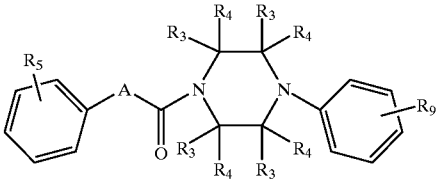

and the pharmaceutically acceptable salts thereof, wherein:

A, $R_3$, and $R_4$ are as defined for Formula I or for Formula IB;

$R_5$ is independently selected at each occurrence from the group consisting of cyano, nitro, haloalkyl, haloalkoxy, $C_{1-6}$ alkyl substituted with 0–2 $R_6$, $C_{2-6}$ alkenyl substituted with 0–2 $R_6$, $C_{2-6}$ alkynyl substituted with 0–2 $R_6$, $C_{1-6}$ alkoxy substituted with 0–2 $R_6$, —NH($C_{1-6}$ alkyl) substituted with 0–2 $R_6$, —N($C_{1-6}$ alkyl)($C_{1-6}$ alkyl) where each alkyl is independently substituted with 0–2 $R_6$, —$XR_7$, and Y;

$R_9$ represents 0–3 substituents and is independently selected at each occurrence from the group consisting of bromo, haloalkyl, haloalkoxy, hydroxy, $C_{2-6}$ alkyl substituted with 0–2 $R_6$, $C_{2-6}$ alkenyl substituted with 0–2 $R_6$, $C_{2-6}$ alkynyl substituted with 0–2 $R_6$, $C_{2-6}$ alkoxy substituted with 0–2 $R_6$, —NH($C_{2-6}$ alkyl) substituted with 0–2 $R_6$, —N($C_{2-6}$ alkyl)($C_{2-6}$ alkyl) where each $C_{2-6}$ alkyl is independently substituted with 0–2 $R_6$, —$XR_7$, and Y;

$R_6$, $R_7$, $R_8$, X, Y, and Y' are as defined for Formula IB.

Preferred compounds and salts of Formula VII include those wherein A is selected from NH, —CH=CH—, and $CH_2NH$; and $R_6$ is independently selected at each occurrence from the group consisting of halogen, hydroxy, $C_{1-4}$ alkyl, $C_{1-4}$ alkoxy, —NH($C_{1-4}$ alkyl), and —N($C_{1-4}$ alkyl)($C_{1-4}$ alkyl).

The invention includes compounds of Formula VIII:

Formula VIII

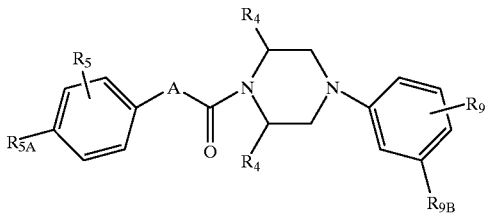

and the pharmaceutically acceptable salts thereof, wherein:

A is selected from the group consisting of NH, —CH=CH—, and $CH_2NH$ (NH is preferred);

$R_4$ is independently selected at each occurrence from hydrogen and $C_{1-4}$alkyl;

$R_5$ represents 0 to 2 substituents independently selected at each occurrence from the group consisting of halogen, cyano, nitro, halo($C_{1-6}$)alkyl, halo($C_{1-6}$)alkoxy, hydroxy, amino, $C_{1-6}$alkyl substituted with 0–2 $R_6$, $C_{2-6}$alkenyl substituted with 0–2 $R_6$, $C_{2-6}$alkynyl substituted with 0–2 $R_6$, $C_{1-6}$alkoxy substituted with 0–2 $R_6$, —NH($C_{1-6}$alkyl) substituted with 0–2 $R_6$, and —N($C_{1-6}$alkyl)($C_{1-6}$alkyl) where each $C_{1-6}$alkyl is independently substituted with 0–2 $R_6$;

$R_9$ represents 0 to 2 substituents and is independently selected at each occurrence from the group consisting of halogen, cyano, nitro, halo($C_{1-6}$)alkyl, halo($C_{1-6}$)alkoxy, hydroxy, amino, $C_{1-6}$alkyl substituted with 0–2 $R_6$, $C_{2-6}$alkenyl substituted with 0–2 $R_6$, $C_{2-6}$alkynyl substituted with 0–2 $R_6$, $C_{1-6}$alkoxy substituted with 0–2 $R_6$, —NH($C_{1-6}$alkyl) substituted with 0–2 $R_6$, and —N($C_{1-6}$alkyl)($C_{1-6}$alkyl) where each $C_{1-6}$alkyl is independently substituted with 0–2 $R_6$;

$R_{5A}$ is independently selected from the group consisting of halogen, cyano, nitro, trifluoromethyl, trifluoromethoxy, hydroxy, amino, $C_{1-6}$ alkyl, $C_{1-6}$ alkoxy, —NH($C_{1-6}$ alkyl), and —N($C_{1-6}$ alkyl)($C_{1-6}$ alkyl)

$R_{9B}$ is independently selected from the group consisting of trifluoromethoxy, hydroxy, $C_{2-6}$ alkyl, $C_{2-6}$ alkoxy, —NH($C_{2-6}$ alkyl), and —N($C_{2-6}$ alkyl)($C_{2-6}$ alkyl); and $R_6$ is independently selected at each occurrence from the group consisting of halogen, hydroxy, $C_{1-4}$ alkyl, $C_{1-4}$ alkoxy, —NH($C_{1-4}$ alkyl), and —N($C_{1-4}$ alkyl)($C_{1-4}$ alkyl).

Preferred compound of Formula VIII are those wherein one of $R_4$ is hydrogen and the other is methyl.

A particularly preferred embodiment of the invention includes compounds of Formula IX:

Formula IX

![Structure of Formula IX showing R5B, R5 on a benzene ring connected via A-C(=O)-N to a piperazine ring with R3, R4 substituents, connected to another N-pyridine ring with R9, R9B substituents]

and the pharmaceutically acceptable salts thereof, wherein:

A, $R_3$, and $R_4$ are as defined for Formula I or for Formula IB;

$R_5$ is selected from the group consisting of bromo, fluoro, iodo, halo($C_{1-6}$)alkyl, halo($C_{3-6}$)alkoxy, $C_{3-6}$ alkyl substituted with 0–3 $R_6$, $C_{2-6}$alkenyl substituted with 0–3 $R_6$, $C_{2-6}$alkynyl substituted with 0–3 $R_6$, $C_{3-6}$alkoxy substituted with 0–2 $R_6$, ($C_{3-8}$cycloalkyl)$C_{1-4}$alkyl, —NH($C_{1-6}$alkyl) substituted with 0–2 $R_6$, —N($C_{1-6}$alkyl)($C_{1-6}$alkyl) where each $C_{1-6}$alkyl is substituted with 0–2 $R_6$, Y, —(C=O)Y, —(CH$_2$)Y, and —(CH(CN))Y;

$R_9$ is selected from the group consisting of halogen, cyano, —N(SO$_2$C$_{1-6}$alkyl)(SO$_2$C$_{1-6}$alkyl), —SO$_2$NH$_2$, halo($C_{1-6}$)alkyl, halo($C_{1-6}$)alkoxy, $C_{1-6}$alkyl substituted with 0–2 $R_6$, $C_{2-6}$alkenyl substituted with 0–2 $R_6$, $C_{2-6}$alkynyl substituted with 0–2 $R_6$, $C_{1-6}$alkoxy substituted with 0–2 $R_6$, —NH($C_{1-6}$alkyl) substituted with 0–2 $R_6$, —N($C_{1-6}$alkyl)($C_{1-6}$alkyl) where each $C_{1-6}$alkyl is substituted with 0–2 $R_6$;

$R_{5B}$ and $R_{9B}$ each represent from 0 to 2 substituents and are independently selected at each occurrence from the group consisting of halogen, cyano, nitro, halo($C_{1-6}$)alkyl, halo($C_{1-6}$)alkoxy, hydroxy, amino, $C_{1-6}$alkyl substituted with 0–2 $R_6$, ($C_{3-8}$cycloalkyl)$C_{1-4}$alkyl substituted with 0–2 $R_6$, $C_{2-6}$alkenyl substituted with 0–2 $R_6$, $C_{2-6}$alkynyl substituted with 0–2 $R_6$, $C_{1-6}$alkoxy substituted with 0–2 $R_6$, —NH($C_{1-6}$alkyl) substituted with 0–2 $R_6$, and —N($C_{1-6}$alkyl)($C_{1-6}$alkyl) where each $C_{1-6}$alkyl is independently substituted with 0–2 $R_6$, and Y; and any two $R_5$ and $R_{5B}$ bound to adjacent atoms may be joined to form a $C_{3-8}$cycloalkyl group or a heterocycloalkyl group, each of which is optionally substituted by from 1 to 5 substituents independently chosen from cyano, halogen, hydroxy, $C_{1-4}$alkyl, $C_{1-4}$alkoxy, —NH($C_{1-4}$ alkyl), —N($C_{1-4}$alkyl)($C_{1-4}$alkyl), halo($C_{1-4}$)alkyl, and halo($C_{1-4}$)alkoxy, wherein the heterocycloalkyl group consists of from 4 to 8 atoms and contains 1, 2, or 3 heteroatoms selected from N, O, and S; and $R_6$, $R_7$, $R_8$, X, Y, and Y' are as defined for Formula IB.

Preferred compounds and salts of Formula IX are those wherein A is O or NR$_A$, wherein R$_A$ is hydrogen or methyl.

More preferred compounds and salts of Formula IX are those wherein

A is O or NRA, wherein R$_A$ is hydrogen or methyl; and $R_3$ and $R_4$ are independently chosen at each occurrence from the group consisting of hydrogen, halogen, cyano, nitro, halo($C_{1-6}$)alkyl, halo($C_{1-6}$)alkoxy, hydroxy, amino, $C_{1-6}$alkyl, $C_{2-6}$alkenyl, $C_{2-6}$alkynyl, $C_{1-6}$alkoxy, —NH($C_{1-6}$alkyl), and —N($C_{1-6}$alkyl)($C_{1-6}$alkyl).

Other preferred compounds and salts of Formula IX are those wherein:

A is O or NR$_A$, wherein R$_A$ is hydrogen or methyl;

$R_3$ is hydrogen; and $R_4$ is independently chosen at each occurrence from the group consisting of hydrogen, halogen, cyano, nitro, halo($C_{1-6}$)alkyl, halo($C_{1-6}$)alkoxy, hydroxy, amino, $C_{1-6}$alkyl, $C_{2-6}$alkenyl, $C_{2-6}$alkynyl, $C_{1-6}$alkoxy, —NH($C_{1-6}$alkyl), and —N($C_{1-6}$alkyl)($C_{1-6}$alkyl).

Still more preferred compounds and salts of Formula IX are those wherein

A is O, NR$_A$, wherein R$_A$ is hydrogen or methyl;

$R_3$ is hydrogen; and $R_4$ is independently chosen at each occurrence from hydrogen and $C_{1-6}$alkyl.

Another group of preferred compounds and salts of Formula IX is the group wherein A is NR$_A$, wherein R$_A$ is hydrogen or methyl;

$R_3$ is hydrogen; and $R_4$ is independently chosen at each occurrence from hydrogen, halo($C_{1-3}$)alkyl, and $C_{1-6}$alkyl, but more preferably $R_4$ is chosen from hydrogen and $C_{1-4}$ alkyl.

A particular class of compounds of Formula IX is represented by Formula IX-A:

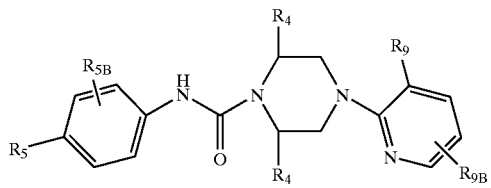

and the pharmaceutically acceptable salts thereof, wherein:

$R_5$, $R_{5B}$, $R_9$, and $R_{9B}$ are as defined for Formula IX; and $R_4$ is independently chosen at each occurrence from hydrogen and $C_{1-4}$alkyl.

Another class of compounds of Formula IX is represented by Formula IX-B:

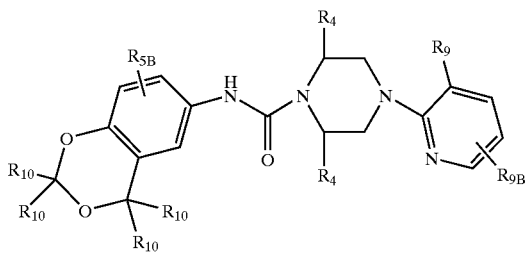

Formula IX-B and the pharmaceutically acceptably salts thereof, wherein:
$R_{5B}$ and $R_{9B}$ are independently chosen from hydrogen, halogen, cyano, nitro, halo($C_{1-2}$)alkyl, halo($C_{1-2}$)alkoxy, amino, $C_{1-4}$alkyl, and $C_{1-2}$alkoxy; and
$R_{10}$ is independently chosen at each occurrence from hydrogen, halogen, and $C_{1-4}$ alkyl.

Preferred compounds and salts of Formula IX-B are those wherein $R_9$ is selected from the group consisting of halogen, cyano, —N(SO$_2$CH$_3$)$_2$, —SO$_2$NH$_2$, halo($C_{1-3}$)alkyl, $C_{1-3}$alkoxy, —NH($C_{1-3}$alkyl), and —N($C_{1-3}$alkyl)($C_{1-3}$alkyl).

Other preferred compounds and salts of Formula IX-A and Formula IX-B are those wherein $R_{5B}$ and $R_{9B}$ are independently chosen from hydrogen, halogen, cyano, nitro, halo($C_{1-2}$)alkyl, halo($C_{1-2}$)alkoxy, amino, $C_{1-4}$alkyl, and $C_{1-2}$alkoxy.

Still other preferred compounds and salts of Formula IX-A and Formula IX-B are those wherein:
$R_{5B}$ represents 0 or 1 substituents chosen from halogen, cyano, nitro, halo($C_{1-2}$)alkyl, halo($C_{1-2}$)alkoxy, amino, $C_{1-4}$alkyl, and $C_{1-2}$alkoxy; and
$R_{9B}$ represents 0 or 1 substituents chosen from halogen, cyano, nitro, halo($C_{1-2}$)alkyl, and $C_{1-2}$alkyl, and $C_{1-2}$alkoxy.

The invention is further directed to compounds and salts of Formula IX-A and IX-B, wherein:
$R_9$ is selected from the group consisting of halogen, cyano, —N(SO$_2$CH$_3$)$_2$, —SO$_2$NH$_2$, halo($C_{1-3}$) alkyl, $C_{1-3}$alkoxy, —NH($C_{1-3}$alkyl), and —N($C_{1-3}$alkyl)($C_{1-3}$alkyl);
$R_{5B}$ represents 0 or 1 substituents chosen from halogen, cyano, nitro, halo($C_{1-2}$)alkyl, halo($C_{1-2}$)alkoxy, amino, $C_{1-4}$alkyl, and $C_{1-2}$alkoxy; and
$R_{9B}$ represents 0 or 1 substituents chosen from halogen, cyano, nitro, halo($C_{1-2}$)alkyl, and $C_{1-2}$alkyl, and $C_{1-2}$alkoxy.

For Formula IX-A, preferred substituents are
$R_5$ is selected from the group consisting of bromo, fluoro, iodo, halo($C_{1-6}$)alkyl, halo($C_{3-6}$)alkoxy, $C_{3-6}$alkyl substituted with 0–3 $R_6$, $C_{2-6}$ alkenyl substituted with 0–3 $R_6$, Y, —(C=O)Y, —(CH$_2$)Y, and —(CH(CN))Y;
$R_9$ is selected from the group consisting of halogen, cyano, —N(SO$_2$CH$_3$)$_2$, —SO$_2$NH$_2$, halo($C_{1-2}$)alkyl, $C_{1-3}$alkoxy, —NH($C_{1-6}$alkyl), and —N($C_{1-6}$alkyl)($C_{1-6}$alkyl);
$R_{5B}$ represents 0 or 1 substituents chosen from halogen, cyano, nitro, halo($C_{1-2}$)alkyl, halo($C_{1-2}$)alkoxy, amino, $C_{1-4}$alkyl, and $C_{1-2}$alkoxy; and
$R_{9B}$ represents 0 or 1 substituents chosen from halogen, cyano, nitro, halo($C_{1-2}$)alkyl, and $C_{1-2}$alkyl, and $C_{1-2}$alkoxy.

Particularly preferred definitions of $R_6$ for compounds and salts of this class are cyano, halogen, hydroxy, $C_{1-4}$alkyl, $C_{1-4}$alkoxy, —NH($C_{1-4}$alkyl), and —N($C_{1-4}$alkyl)($C_{1-4}$alkyl) and Y; where
Y is independently selected at each occurrence from $C_{3-8}$ cycloalkyl, piperidinyl, piperazinyl, tetrahydropyranyl, dihydropyranyl, morpholinyl, thiomorpholinyl, phenyl, pyridyl, pyrazinyl, pyrimidinyl, thiazolyl, thienyl, and imidazolyl, each of which may be further substituted with one or more substituents independently selected from halogen, oxo, hydroxy, amino, nitro, cyano, $C_{1-4}$alkyl, $C_{1-4}$alkoxy, halo($C_{1-4}$)alkyl, halo($C_{1-4}$)alkoxy, mono- or di($C_{1-4}$)alkylamino, and $C_{1-4}$alkylthio.

Particularly preferred definitions of $R_9$ and $R_{9B}$ for compounds of Formula IX-A are:
$R_9$ is cyano, trifluoromethyl, chloro, or iodo; and
$R_{9B}$ is hydrogen.

Particularly preferred definitions of $R_5$ for compounds of Formula IX-A are isopropyl, t-butyl, 2-butyl, trifluoromethyl, cyclopentyl, cyclohexyl, and heptafluoropropyl.

The invention is particularly directed to compounds and pharmaceutically acceptable salts of Formula IB, Formula II, Formula III, Formula IV, Formula V, Formula VII and Formula IX in which:

$R_A$, $R_B$, and $R_B'$ are independently selected at each occurrence from hydrogen and $C_{1-6}$alkyl; for the variables $R_3$, $R_4$, and $R_5$ haloalkyl is halo($C_{1-6}$)alkyl, i.e. a haloalkyl group having from 1 to 6 carbon atoms and from 1 to maximum allowable number of halogen substituents on those carbon atoms, haloalkoxy is halo($C_{1-6}$)alkoxy; alkyl is $C_{1-6}$alkyl, alkenyl is $C_{2-6}$alkenyl; alkynyl is $C_{2-6}$alkynyl; alkoxy is $C_{1-6}$alkoxy, —NH(alkyl) is —NH($C_{1-6}$alkyl), and —N(alkyl)(alkyl) is —N($C_{1-6}$alkyl)($C_{1-6}$alkyl), for the variables $R_6$, $R_7$, $R_8$, Y and Y' alkyl is $C_{1-4}$alkyl, alkoxy (or —O(alkyl) is $C_{1-4}$alkoxy (or —O($C_{1-4}$alkyl)), —NHalkyl (or monoalkylamino) is —NH($C_{1-4}$alkyl)(or mono($C_{1-4}$alkyl)amino), —N(alkyl)(alkyl) (also dialkylamino) is —N($C_{1-4}$alkyl)($C_{1-4}$alkyl)(also di ($C_{1-4}$alkyl) amino), —S (O)$_n$alkyl is —S(O)$_n$($C_{1-4}$alkyl), haloalkyl is halo($C_{1-4}$)alkyl, haloalkoxy is halo($C_{1-4}$)alkoxy, —CO(alkyl) is —CO($C_{1-4}$alkyl), —CONH(alkyl) is —CONH($C_{1-4}$alkyl), and —CON(alkyl)(alkyl) is —CON($C_{1-4}$alkyl$_1$)($C_{1-4}$alkyl$_2$); —NHC(O)(alkyl) is —NHC(O)($C_{1-4}$alkyl), —N(alkyl)C(O)(alkyl) is —N($C_{1-4}$alkyl)C(O)(alkyl), —NHS(O)$_n$(alkyl) is —NHS(O)$_n$($C_{1-4}$alkyl), —S(O)$_n$NH($C_{1-4}$alkyl), —S(O)$_n$N(alkyl)(alkyl) is —S(O)$_n$N($C_{1-4}$ alkyl)($C_{1-4}$alkyl);

and alkylthio is $C_{1-4}$alkylthio.

Preferred compounds and salts of Formula V, Formula VI, Formula VII and Formula IX are those wherein $R_3$ and $R_4$ are independently selected at each occurrence from the group consisting of hydrogen and $C_{1-6}$ alkyl. More preferred compounds and salts of Formula V are those wherein $R_3$ is hydrogen and the $R_4$ substituents present on the 3 and 5 positions of the piperazine ring are hydrogen and the $R_4$ substituents on the 2 and 6 position of the piperazine ring are independently hydrogen or $C_{1-4}$ alkyl. For this discussion the piperazine ring is numbered as follows:

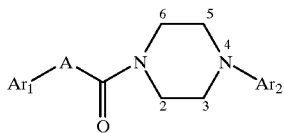

Even more preferred compounds and salts of Formula V are those wherein $R_4$ is methyl at the 2 position of the piperazine ring and $R_3$ and $R_4$ are hydrogen at all other positions.

The invention particularly includes compounds Formula A-1, Formula B-1, Formula C-1, Formula D-1, Formula E-1, and Formula F-1:

Formula A-1

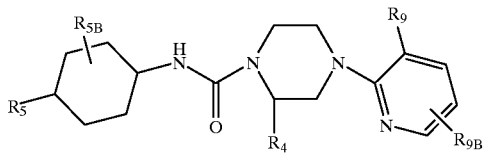

Formula B-1

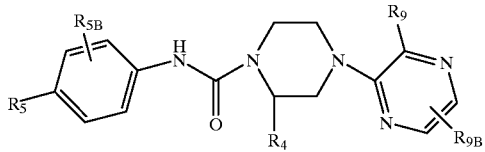

Formula C-1

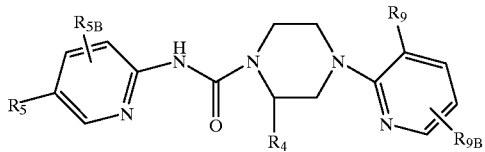

Formula D-1

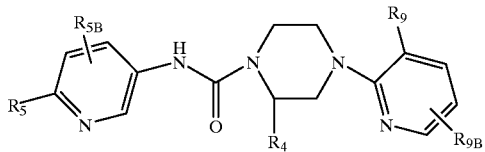

Formula E-1

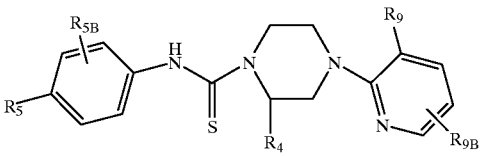

Formula F-1

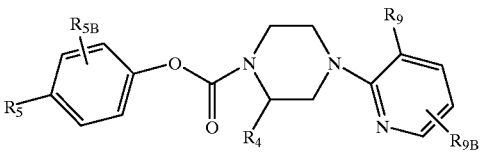

and the pharmaceutically acceptable salts of Formula A-1, Formula B-1, Formula C-1, Formula D-1, Formula E-1, and Formula F-1 wherein:

$R_5$ and $R_9$ are independently selected from the group consisting of halogen, cyano, nitro, halo($C_{1-6}$)alkyl, halo($C_{1-6}$)alkoxy, hydroxy, amino, $C_{1-6}$alkyl, $C_{2-6}$alkenyl, $C_{2-6}$alkynyl, $C_{1-6}$alkoxy, —NH($C_{1-6}$alkyl), —N($C_{1-6}$alkyl)($C_{1-6}$alkyl), and $C_{3-8}$ cycloalkyl; and $R_{5B}$ and $R_{9B}$ each represent up to 2 substituents independently selected at each occurrence from hydrogen, halogen, cyano, nitro, halo($C_{1-2}$)alkyl, halo($C_{1-2}$)alkoxy, hydroxy, amino, $C_{1-3}$alkyl, $C_{1-3}$alkoxy, —NH($C_{1-3}$alkyl), and —N($C_{1-6}$alkyl)($C_{1-6}$alkyl).

Especially preferred compounds and salts of Formula A-1, Formula B-1, Formula C-1, Formula D-1, Formula E-1, and Formula F-1 are those wherein:

$R_5$ is $C_{3-6}$ alkyl; $C_{3-6}$ alkoxy; halo($C_{1-3}$)alkyl, halo($C_{1-3}$) alkoxy, or $C_{3-8}$ cycloalkyl;

$R_9$ is chloro or trifluomethyl; and $R_{5B}$ and $R_{9B}$ are hydrogen.

Representative compounds of the invention are shown in Table I below:

TABLE I

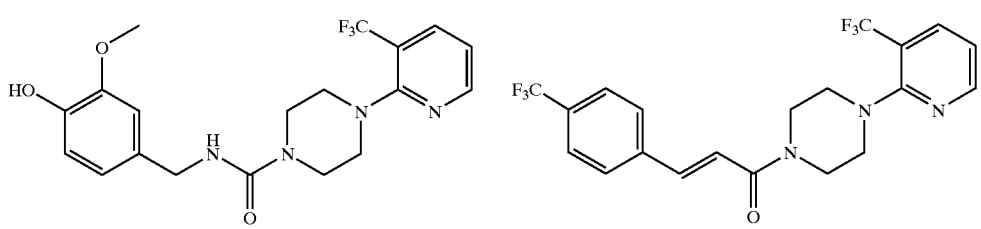

Compound 1                    Compound 2

TABLE I-continued

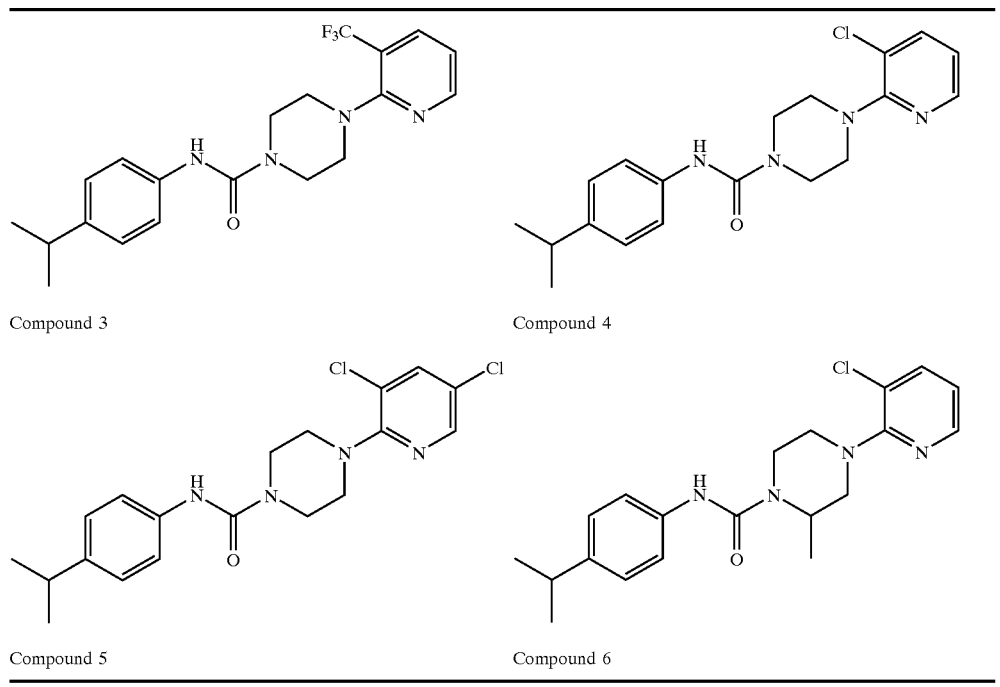

Compound 3

Compound 4

Compound 5

Compound 6

In one aspect invention relates to diaryl piperazines and related compounds that bind with high affinity to capsaicin receptors, including human capsaicin receptors. Compounds that bind with high affinity for the capsaicin receptor include compounds exhibit $K_i$ values of less than 10 uM, and preferably exhibit $K_i$ values of less than 1 uM, more preferably exhibit $K_i$ values of less than 100 nM, and most preferably exhibit $K_i$ values of less than 10 nM at the capsaicin receptors. This invention also includes diaryl piperazines that bind with high selectivity to capsaicin receptor. Compounds that exhibit high selectivity for the capsaicin receptor exhibit at least 20-fold, and preferably at least 100-fold greater affinity for the capsaicin receptor than for other cell surface receptors (e.g., NPY Y5 receptors, NPY Y1 receptors, $GABA_A$ receptors, MCH receptors, Bradykinin receptors, C5a receptors, androgen receptors, and the like).

Without wishing to be bound to any particular theory of operation, it is believed that the interaction of the compounds of Formulae I–IX and Formulae A–F with the capsaicin receptor results in the pharmaceutical utility of these compounds.

The invention further comprises methods of treating patients in need of such treatment with an amount of a compound of the invention sufficient to alter the symptoms of a disorder responsive to capsaicin receptor modulation. Thus, as used herein, the term treatement encompases both disease modifying treatment and symptomatic treatment.

The diseases and/or disorders that can also be treated using compounds and compositions according to the invention (which are examples of disorders responsive to capsaicin receptor modulation) include:

Chronic and acute pain conditions, including toothache, postherpetic neuralgia, diabetic neuropathy, postmastectomy pain syndrome, stump pain (and phantom limb pain), reflex sympathetic dystrophy, trigeminal neuralgia, oral neuropathic pain, osteoarthritis, rheumatoid arthritis, fibromyalgia, Guillain-Barre syndrome, meralgia paresthetica, "burning-mouth" syndrome, and pain due to bilateral peripheral neuropathy. Preferred pain conditions for treatment in accordance with the invention are neuropathic pain conditions, including causalgia (reflex sympathetic dystrophy—RSD, secondary to injury of a peripheral nerve; this type of pain is generally considered to be non-responsive or only partially responsive to conventional opioid analgesic regimens), neuritis—including, e.g., sciatic neuritis, peripheral neuritis, polyneuritis, optic neuritis, postfebrile neuritis, migrating neuritis, segmental neuritis, Gombault's neuritis, and neuronitis, and neuralgias—including those mentioned above and, e.g., cervicobrachial neuralgia, cranial neuralgia, geniculate neuralgia, glossopharyngial neuralgia, migranous neuralgia, idiopathic neuralgia, intercostals neuralgia, mammary neuralgia, mandibular joint neuralgia, Morton's neuralgia, nasociliary neuralgia, occipital neuralgia, red neuralgia, Sluder's neuralgia, splenopalatine neuralgia, supraorbital neuralgia and vidian neuralgia. Additional pain conditions that can be treated in accordance with the invention include headache—particularly those involving peripheral nerve activity including, e.g., sinus, cluster (i.e., migranous neuralgia, supra) and some tension and migraine headache conditions—, labor pains, Charcot's pains, gas pains, menstrual pain, root pain, homotopic pain and heterotopic pain—including cancer associated pain, pain (and inflammation) associated with venom exposure, e.g., due to snake bite, spider bite, or insect sting, and traumatic, e.g., post-surgical pain and burn pain. A preferred condition that can be treated in accordance with the invention is pain (as well as broncho-constriction and inflammation) due to exposure (e.g., via ingestion, inhalation, or eye contact) of mucous membranes to capsacin and related irritants such as tear gas, hot peppers, or pepper spray.

Itching conditions, including psoriatic pruritis, itch due to hemodyalisis, aguagenic pruritus, and itching associated with vulvar vestibulitis, contact dermatitis, insect bites and skin allergies.

Urinary incontenience, including detrusor hyperflexia of spinal origin and bladder hypersentivity.

The invention also provides pharmaceutical compositions comprising compounds of the invention, including packaged pharmaceutical compositions for treating disorders responsive to capsaicin receptor modulation. The packaged pharmaceutical compositions include a container holding a therapeutically effective amount of at least one capsaicin receptor modulator as described supra and instructions (e.g., labeling) indicating the contained capsaicin receptor ligand is to be used for treating a disorder responsive to capsaicin receptor modulation in the patient.

The present invention also pertains to methods of inhibiting the binding of vanilloid (capsaicin analog) compounds, such as capsaicin, olvanil and RTX, to capsaicin receptors, which methods involve contacting a compound of the invention with cells expressing capsaicin receptors, wherein the compound is present at a concentration sufficient to inhibit vanilloid binding to capsaicin receptors in vitro. The methods of the invention include inhibiting the binding of vanilloid compounds to capsaicin receptors in vivo, e.g., in a patient given an amount of a compound of Formulae I–IX and Formulae A–F that results in and in vivo concentration in a body fluid sufficient to inhibit the binding of capsaicin compounds to capsaicin receptors in vitro. In one embodiment, such methods are useful in treating the effects of tear gas, hot pepper or pepper spray exposure. The amount of a compound that would be sufficient to inhibit the binding of a vanilloid compound to the capsaicin receptor may be readily determined via a capsaicin receptor binding assay, such as the assay described in Example 10 or by an assay of capsaicin receptor antagonism e.g. as in Example 11. The capsaicin receptors used to determine in vitro binding may be obtained from a variety of sources, for example from preparations of mammalian dorsal root ganglion (DRG) or from cells expressing cloned rat or human capsaicin receptors.

The present invention also pertains to methods for altering the signal-transducing activity, particularly the calcium ion conductance, mediated by capsaicin receptors, said method comprising exposing cells expressing such receptors to a solution comprising a compound of the, wherein the compound is present in the solution at a concentration sufficient to specifically alter the calcium conductance activity in response to capsaicin or RTX in vitro in cells expressing capsaicin receptors, preferred cells for this purpose are those that express high levels of capsaicin receptors (i.e., equal to or greater than the number of capsaicin receptors per cell found in rat DRG cells). This method includes altering the signal-transducing activity of capsaicin receptors in vivo. Preferably such alterations are reductions of calcium flux. The amount of a compound that would be sufficient to alter the signal-transducing activity of capsaicin receptors may be determined in vitro via a capsaicin receptor signal transduction assay, such as the calcium mobilization (conductance, flux) assay described in Example 11. The amount of a compound that would be sufficient to alter the calcium conductance activity in response to capsaicin or RTX of capsaicin receptors may also be determined via an assay of capsaicin receptor mediated calcium conductance, such as an assay wherein the binding of capsaicin to a cell surface capsaicin receptor effects changes in the fluorescence of a calcium sensitive dye or in the expression of a calcium sensitive reporter gene.

The invention further provides:

A method of reducing the calcium conductance of a capsaicin receptor, which method comprises:

contacting a first solution comprising a fixed concentration of a capsaicin receptor agonist and a compound or salt of the invention with a cell expressing the capsaicin receptor, wherein the compound or salt is present in the solution at a concentration sufficient to produce a detectable reduction of the calcium mobilization effects of the capsaicin receptor agonist when tested in an in vitro assay in which cells expressing a capsaicin receptor are contacted with a second solution comprising the fixed concentration of capsaicin receptor agonist and the compound or salt and the same method wherein: the cell expressing the capsaicin receptor is a neuronal cell that is contacted in vivo in an animal, and wherein the first solution is a body fluid of said animal; or the animal is a human patient.

A pharmaceutical composition comprising a pharmaceutically acceptable carrier and a compound or salt of the invention; and a package comprising the pharmaceutical composition in a container and further comprising indicia comprising instructions for using the composition to either alleviate pain; or to treat a patient suffering from urinary incontinence or to alleviate symptoms of exposure to capsaicin or tear gas.

A compound or salt of the invention wherein, in an in vitro assay of capsaicin receptor antagonism, the compound or salt exhibits capsaicin receptor antagonist activity, but in an in vitro assay of capsaicin receptor agonism the compound does not exhibit detectable agonist activity.

A compound or salt of the invention wherein a dose of the compound or salt sufficient to provide analgesia in an animal model for determining pain relief does not produce sedation in an animal model assay of sedation.

A method of treating a mammal suffering from at least one symptom selected from the group consisting of symptoms of exposure to capsaicin, symptoms of burns or irritation due to exposure to heat, symptoms of burns or irritation due to exposure to light, symptoms of burns or irritation due to exposure to tear gas, and symptoms of burns or irritation due to exposure to acid, the method comprising administering to the mammal a therapeutic dose of a compound that:

a) is a high potency capsaicin receptor antagonist in an in vitro assay of capsaicin receptor antagonism,
b) exhibits no detectable agonist activity in an in vitro assay of capsaicin receptor agonism,
c) is not a capsaicin analog, and
d) when administered to an animal in an animal model assay of sedation, at five times the minimum dosage needed to provide analgesia in an animal model for determining pain relief, does not cause sedation, wherein the therapeutic dose contains an amount of the compound least one symptom and preferably wherein the compound is a compound of the invention.

A method of treating a mammal suffering from neuropathic pain, the method comprising administering to the mammal a therapeutic dose of a compound that is a capsaicin receptor antagonist, and in certain embodiments, wherein the compound is a compound of the invention.

A method of treating a mammal suffering from peripheral-nerve-mediated pain, e.g., neuropathic pain, the method comprising administering to the mammal a therapeutic dose of a compound that is a capsaicin receptor antagonist, wherein the compound:

a) is a high potency capsaicin receptor antagonist in an in vitro assay of capsaicin receptor antagonism, b) exhibits no detectable agonist activity in an in vitro assay of capsaicin receptor agonism,
c) is not a capsaicin analog, and
d) when administered to an animal in an animal model assay of sedation, at five times the minimum dosage needed to provide analgesia in an animal model for determining pain relief, does not cause sedation, wherein the therapeutic dose contains an amount of the compound that is effective to reduce the peripheral-nerve-mediated pain, and preferably wherein the pain is neuropathic pain and the compound is a compound of the invention, and preferably wherein the pain is associated with a condition selected from the group consisting of postmastectomy pain syndrome, stump pain, phantom limb pain, oral neuropathic pain, Charcot's pain, toothache, postherpetic neuralgia, diabetic neuropathy, reflex sympathetic dystrophy, trigeminal neuralgia, osteoarthritis, rheumatoid arthritis, fibromyalgia, Guillain-Barre syndrome, meralgia paresthetica, burning-mouth syndrome, bilateral peripheral neuropathy, causalgia, sciatic neuritis, peripheral neuritis, polyneuritis, optic neuritis, postfebrile neuritis, migrating neuritis, segmental neuritis, Gombault's neuritis, neuronitis, cervicobrachial neuralgia, cranial neuralgia, geniculate neuralgia, glossopharyngial neuralgia, migranous neuralgia, idiopathic neuralgia, intercostals neuralgia, mammary neuralgia, mandibular joint neuralgia, Morton's neuralgia, nasociliary neuralgia, occipital neuralgia, red neuralgia, Sluder's neuralgia, splenopalatine neuralgia, supraorbital neuralgia, vidian neuralgia, sinus headache, tension headache, labor, childbirth, intestinal gas, menstruation, cancer, and trauma.

A compound of the invention, wherein the compound is not addictive.

The capsaicin receptor ligands provided by this invention and labeled derivatives thereof are also useful as standards and reagents for determining the ability of a compound to bind to the capsaicin receptor and to act as an agonist, antagonist, inverse agonist, mixed agonist/antagonist or the like.

More particularly compounds of the invention may be used for demonstrating the presence of VR1 receptors or other capsaicin receptors in cell or tissue samples. This may be done by preparing a plurality of matched cell or tissue samples, at least one of which is prepared as an experimental sample and at least one of which is prepared as a control sample. The experimental sample is prepared by contacting (under conditions that permit binding of capsaicin or RTX to capsaicin receptors within cell and tissue samples) at least one of the matched cell or tissue samples that has not previously been contacted with any compound or salt of the invention with an experimental solution comprising the detectably-labeled preparation of the selected compound or salt at a first measured molar concentration. The control sample is prepared by in the same manner as the experimental sample and is incubated in a solution that contains the same ingredients as the experimental solution but that also contains an unlabelled preparation of the same compound or salt of the invention at a molar concentration that is greater than the first measured molar concentration.

The experimental and control samples are then washed (using the same wash conditions) to remove unbound detectably-labeled compound. The amount of detectably-labeled compound remaining bound to each sample is then measured and the amount of detectably-labeled compound in the experimental and control samples is compared. A comparison that indicates the detection of a greater amount of detectable label in the at least one washed experimental sample than is detected in any of the at least one washed control samples demonstrates the presence of capsaicin receptors in that experimental sample.

The detectably-labeled compound used in this procedure may be labeled with any detectable label, such as a radioactive label, a biological tag such as biotin (which can be detected by binding to detectably-labeled avidin), an enzyme (e.g., alkaline phosphatase, beta galactosidase, or a like enzyme that can be detected its activity in a calorimetric, luminescent, or like assay) or a directly or indirectly luminescent label. When tissue sections are used in this procedure and the detectably-labeled compound is radiolabeled, the bound, labeled compound may be detected autoradiographically to generate an autoradiogram. When autoradiography is used, the amount of detectable label in an experimental or control sample may be measured by viewing the autoradiograms and comparing the exposure density of matched regions of the autoradiograms.

Labeled derivatives the capsaicin receptor ligands provided by this invention are also useful as radiotracers for positron emission tomography (PET) imaging or for single photon emission computerized tomography (SPECT) to characterize and localize capsaicin receptors in vivo.

Definitions

The compounds herein described may have one or more asymmetric centers or planes. Compounds of the present invention containing an asymmetrically substituted atom may be isolated in optically active or racemic forms. It is well known in the art how to prepare optically active forms, such as by resolution of racemic forms (racemates), by asymmetric synthesis, or by synthesis from optically active starting materials. Resolution of the racemates can be accomplished, for example, by conventional methods such as crystallization in the presence of a resolving agent, or chromatography, using, for example a chiral HPLC column. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral (enantiomeric and diastereomeric), and racemic forms, as well as all geometric isomeric forms of a structure are intended, unless the specific stereochemistry or isomeric form is specifically indicated.

The term "substituted," as used herein, means that any one or more hydrogens on the designated atom is replaced with a selection from the indicated group, provided that the designated atom's normal valence is not exceeded, and that the substitution results in a stable compound. The present invention is intended to include all isotopes of atoms occurring in the present compounds. Isotopes include those atoms having the same atomic number but different mass numbers, By way of general example and without limitation, isotopes of hydrogen include tritium and deuterium. Isotopes of carbon include $^{11}C$, $^{13}C$, and $^{14}C$.

When any variable occurs more than one time in any constituent or formula for a compound, its definition at each occurrence is independent of its definition at every other occurrence. Thus, for example, if a group is shown to be substituted with 0–2 R*, then said group may optionally be substituted with up to two R* groups and R* at each occurrence is selected independently from the definition of R*. Also, combinations of substituents and/or variables are permissible only if such combinations result in stable compounds.

As indicated above, various substituents of the various formulae are "optionally substituted", including $Ar_1$, $Ar_2$, $R_3$ and $R_4$ of Formulae I–IX and Formulae A–F, and such substituents as recited in the sub-formulae such as Formula Ia and the like. When substituted, those substituents (e.g., $C_{1-6}$ alkyl, n, $Ar_1$, $Ar_2$, $R_1$, $R_2$, $R_3$, and $R_4$) may be substituted by other than hydrogen at one or more available positions, typically 1 to 3 or 4 positions, by one or more groups, such as, halogen such as fluoro, chloro, bromo and iodo; cyano; hydroxyl; nitro; azido; alkanoyl such as a $C_{1-6}$ alkanoyl group such as acyl and the like; carboxamido; alkyl groups including those groups having 1 to about 12 carbon atoms, or 1, 2, 3, 4, 5, or 6 carbon atoms; alkenyl and alkynyl groups including groups having one or more unsaturated linkages and from 2 to about 12 carbon, or 2, 3, 4, 5 or 6 carbon atoms; alkoxy groups having those having one or more oxygen linkages and from 1 to about 12 carbon atoms, or 1, 2, 3, 4, 5 or 6 carbon atoms; aryloxy such as phenoxy; alkylthio groups including those moieties having one or more thioether linkages and from 1 to about 12 carbon atoms, or 1, 2, 3, 4, 5 or 6 carbon atoms; alkylsulfinyl groups including those moieties having one or more sulfinyl linkages and from 1 to about 12 carbon atoms, or 1, 2, 3, 4, 5, or 6 carbon atoms; alkylsulfonyl groups including those moieties having one or more sulfonyl linkages and from 1 to about 12 carbon atoms, or 1, 2, 3, 4, 5, or 6 carbon atoms; aminoalkyl groups such as groups having one or more N atoms and from 1 to about 12 carbon atoms, or 1, 2, 3, 4, 5 or 6 carbon atoms; carbocyclic aryl having 6 or more carbons, particularly phenyl (e.g. an Ar group being a substituted or unsubstituted biphenyl moiety); arylalkyl having 1 to 3 separate or fused rings and from 6 to about 18 carbon ring atoms, with benzyl being a preferred group; arylalkoxy having 1 to 3 separate or fused rings and from 6 to about 18 carbon ring atoms, with O-benzyl being a preferred group; or a heteroaromatic or heteroalicyclic group having 1 to 3 separate or fused rings with 3 to about 8 members per ring and one or more N, O or S atoms, e.g. coumarinyl, quinolinyl, pyridyl, pyrazinyl, pyrimidyl, furyl, pyrrolyl, thienyl, thiazolyl, oxazolyl, imidazolyl, indolyl, benzofuranyl, benzothiazolyl, tetrahydrofuranyl, tetrahydropyranyl, piperidinyl, morpholino and pyrrolidinyl.

As used herein, "alkyl" is intended to include both branched, straight-chain, and cyclic alkyl groups, having the specified number of carbon atoms that may contain one or more double or triple bonds. "Lower alkyl" denotes an alkyl group having from 1 to about 6 carbon atoms. Examples of alkyl include, but are not limited to, methyl, ethyl, n-propyl, i-propyl, n-butyl, s-butyl, t-butyl, n-pentyl, and s-pentyl. Preferred alkyl groups are $C_1$–$C_6$ alkyl groups. Especially preferred alkyl groups are methyl, ethyl, propyl, butyl, 3-pentyl.

As used herein, "alkoxy", "$C_1$–$C_6$ alkoxy", or "lower alkoxy" in the present invention is meant an alkyl group attached through an oxygen bridge such as, for example, methoxy, ethoxy, propoxy, isopropoxy, n-butoxy, sec-butoxy, tert-butoxy, pentoxy, 2-pentyl, isopentoxy, neopentoxy, hexoxy, 2-hexoxy, 3-hexoxy, and 3-methylpentoxy. "Lower alkoxy" denotes an alkyl group having from 1 to about 6 carbon atoms.

"Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1). Examples of haloalkyl include, but are not limited to, trifluoromethyl, trichloromethyl, pentafluoroethyl, heptafluoropropyl, and pentachloroethyl.

As used herein, "carbocycle" or "carbocyclic ring" is intended to mean any stable 3- to 7-membered monocyclic or bicyclic or 7- to 13-membered bicyclic or tricyclic moeity, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, and tetrahydronaphthyl.

As used herein, the term "carbocyclic aryl" indicates aromatic groups containing only carbon. Such aromatic groups may be further substituted.

As used herein, the term "heterocyclic ring" is intended to mean a stable 5- to 7-membered monocyclic or bicyclic or 7- to 10-membered bicyclic heterocyclic ring which is saturated, partially unsaturated, or unsaturated (aromatic), and which consists of carbon atoms and from 1 to 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom that results in a stable structure. The heterocyclic rings described herein may be substituted on carbon or on a nitrogen atom if the resulting compound is stable. A nitrogen atom in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "heteroaryl" is intended to mean a stable 5- to 7-membered monocyclic or bicyclic or 7- to 10-membered bicyclic heterocyclic aromatic ring which consists of carbon atoms and from 1 to 4 heteroatoms independently selected from the group consisting of N, O and S. It is preferred that the total number of S and O atoms in the aromatic heterocycle. is not more than 1. The term "heterocycloalkyl" is intended to mean a stable 5- to 7-membered monocyclic or bicyclic or 7- to 10-membered bicyclic heterocyclic saturated ring which consists of carbon atoms and from 1 to 4 heteroatoms independently selected from the group consisting of N, O and S. Examples of heterocycles include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; -1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

Preferred heterocycles include, but are not limited to, pyrrolyl, furanyl, thienyl, pyrazolyl, imidazolyl, thiazolyl, isothiazolyl, oxazolyl, isoxazolyl, oxadiazolyl, triazolyl, tetrazolyl, pyridyl, pyrimidyl, pyrazinyl, benzimidazolyl, indolyl, isoindolyl, benzofuranyl, isobenzofuranyl, benzo[b]thiophenyl, benz[d]isoxazolyl, quinolinyl, isoquinolinyl, cinnolinyl, quinazolinyl, or quinoxalinyl,. Also included are fused ring and spiro compounds containing, for example, the above heterocycles.

The term "bicyclic oxygen-containing group" is meant to encompass a particular type of heteroaryl group of the formula:

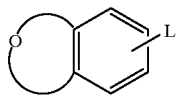

where L indicates the point of attachment of the group to the structure of Formulae I–IX and Formulae A–F. The heterocyclic oxygen-containing ring has a total of from 5 to 7 members, and is saturated or unsaturated. Either ring of the bicyclic oxygen-containing group may be further substituted.

Examples of bicyclic oxygen-containing groups include any or all of the following structures:

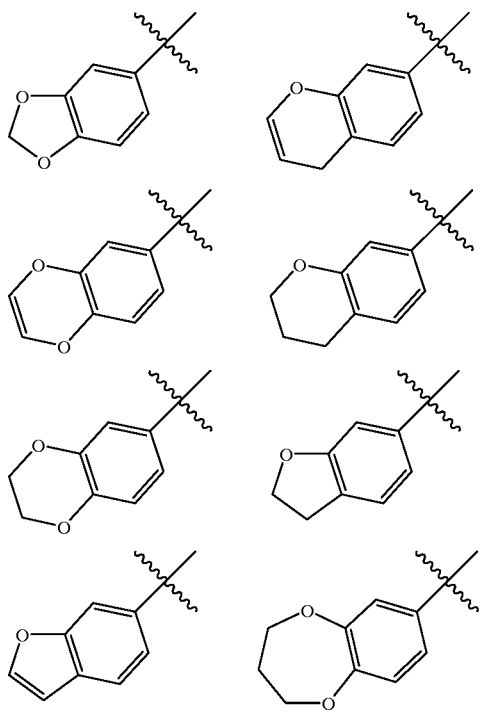

Pharmaceutical Preparations

Those skilled in the art will recognize various synthetic methodologies that may be employed to prepare non-toxic pharmaceutically acceptable prodrugs of the compounds encompassed by Formulae I–IX and Formulae A–F, which prodrugs are encompassed by the present invention. "Prodrugs" are intended to include any compounds that become compounds of Formulae I–IX and Formulae A–F when administered to a mammalian subject, e.g., upon metabolic processing of the prodrug. Examples of prodrugs include, but are not limited to, acetate, formate and benzoate and like derivatives of functional groups (such as alcohol or amine groups) in the compounds of Formulae I–IX and Formulae A–F. Those skilled in the art will recognize a wide variety of non-toxic pharmaceutically acceptable solvents that may be used to prepare solvates of the compounds of the invention, such as water, ethanol, mineral oil, vegetable oil, and dimethylsulfoxide.

The compounds of general Formulae I–IX and general Formulae A–F may be administered orally, topically, parenterally, e.g., by inhalation or spray or rectally in dosage unit formulations containing conventional non-toxic pharmaceutically acceptable carriers, adjuvants and vehicles. Oral administration in the form of a pill, capsule, elixir, syrup, lozenge, troche, or the like is particularly preferred. The term parenteral as used herein includes subcutaneous injections, intradermal, intravascular (e.g., intravenous), intramuscular, spinal, intrathecal injection or like injection or infusion techniques. In addition, there is provided a pharmaceutical formulation comprising a compound of general Formulae I–IX and general Formulae A–F and a pharmaceutically acceptable carrier. One or more compounds of general Formulae I–IX and general Formulae A–F may be present in association with one or more non-toxic pharmaceutically acceptable carriers and/or diluents and/or adjuvants and if desired other active ingredients. The pharmaceutical compositions containing compounds of general Formulae I–IX and general Formulae A–F may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl disterate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of general Formulae I–IX and general Formulae A–F may also be administered in the form of suppositories, e.g., for rectal or vaginal administration of the drug. These compositions can be prepared by mixing the drug with a suitable non-irritating excipient that is solid at ordinary temperatures but liquid at the rectal temperature and will therefore melt in the rectum to release the drug. Such materials are cocoa butter and polyethylene glycols.

Compounds of general Formulae I–IX and general Formulae A–F may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle where desirable.

Typical subjects to which compounds of the invention may be administered will be mammals, particularly primates, especially humans. For veterinary applications, a wide variety of subjects will be suitable, e.g. livestock such as cattle, sheep, goats, cows, swine and the like; poultry such as chickens, ducks, geese, turkeys, and the like; and other domesticated animals particularly pets (companion animals) such as dogs and cats. For diagnostic or research applications, a wide variety of mammals will be suitable subjects including rodents (e.g. mice, rats, hamsters), rabbits, primates, and swine such as inbred pigs and the like.

For administration to non-human animals, the composition may also be added to the animal feed or drinking water. It will be convenient to formulate these animal feed and drinking water compositions so that the animal takes in an appropriate quantity of the composition along with its diet. It will also be convenient to present the composition as a premix for addition to the feed or drinking water.

For systemic (as opposed to local or topical) administration, dosage levels of the order of from about 0.01 mg to about 140 mg per kilogram of body weight per day are useful in the treatment of pain, urinary incontinence, or other of the above-indicated conditions (about 0.05 mg to about 7 g per human patient per day). Preferred systemic doses for preferred high potency compounds of Formulae I–IX and Formulae A–F range from about 0.01 mg to about 50 mg per kilogram of body weight per subject per day, with oral doses generally being about 5–20 fold higher than intravenous doses. The most highly preferred compounds of the invention are orally active (e.g., provide a reduction of pain or a reduction of frequency of urinary incontinence) at doses ranging from 0.05 to 40 mg per kilogram of body weight per subject per day.

The amount of active ingredient that may be combined with the carrier materials to produce a single dosage form will vary depending upon the host treated and the particular mode of administration. Dosage unit forms will generally contain between from about 1 mg to about 500 mg of an active ingredient.

Frequency of dosage may also vary depending on the compound used and the particular disease treated. However, for treatment of most disorders, a dosage regimen (frequency of administration) of 4 times daily or less is preferred. For the treatment of chronic pain or urinary incontinence a dosage regimen of 2 times daily is more preferred and a frequency of administration of once a day is particularly preferred. For the treatment of acute pain a single dose that rapidly reaches effective concentrations is desirable.

It will be understood, however, that the specific dose level for any particular patient will depend upon a variety of factors including the activity of the specific compound employed, the age, body weight, general health, sex, diet, time of administration, route of administration, and rate of excretion, drug combination and the nature and severity of the particular disease or condition undergoing treatment.

Preferred compounds of the invention will have certain desirable pharmacological properties. For systemic administration such properties include, but are not limited to high oral bioavailability, such that the preferred oral dosages and dosage forms discussed above can provide therapeutically effective levels of the compound in vivo, low serum protein binding and low first pass hepatic metabolism. For all types of administration low toxicity, and desirable in vitro and in vivo half-lifes are desired. While penetration of the blood brain barrier for compounds used to treat CNS disorders is necessary, low brain levels of compounds used to treat peripheral disorders (such as urinary incontinence, or chronic or acute pain that does not originate from the CNS) are often preferred.

Laboratory assays may be used to predict these desirable pharmacological properties. The discussion that follows is supplemented by the detailed protocols of Example 16, infra. Assays used to predict bioavailability include transport across human intestinal cell monolayers, including Caco-2 cell monolayers. Toxicity to cultured hepatocytes may be used to predict compound toxicity, with non-toxic compounds being preferred. Penetration of the blood brain barrier of a compound in humans may be predicted from the brain levels of the compound in laboratory animals given the compound, e.g., intravenously.

Percentage of serum protein binding may be predicted from albumin binding assays. Examples of such assays are described in a review by Oravcová, et al. (Journal of Chromatography B (1996) volume 677, pages 1–27). Preferred compounds exhibit reversible serum protein binding. Preferably this binding is less than 99%, more preferably less than 95%, even more preferably less than 90%, and most preferably less than 80%.

Frequency of administration is generally inversely proportional to the in vivo half-life of a compound. In vivo half-lives of compounds may be predicted from the results of assays, e.g., in vitro assays of microsomal half-life as described by Kuhnz and Gieschen (*Drug Metabolism and Disposition*, 1998, volume 26, pages 1120–1127). Preferred half-lives are those allowing for a preferred frequency of administration.

Preparation of Compounds

The compounds of the present invention can be prepared in a number of ways well known to those skilled in the art of organic synthesis. By way of example, compounds of the present invention can be synthesized using the methods described below, together with synthetic methods known in the art of synthetic organic chemistry, or variations thereon as appreciated by those skilled in the art. Preferred methods include but are not limited to those methods described below. Compounds of the present invention i.e. urea or thiourea derivatives (VI) can be synthesized by following the steps outlined in Scheme 1.

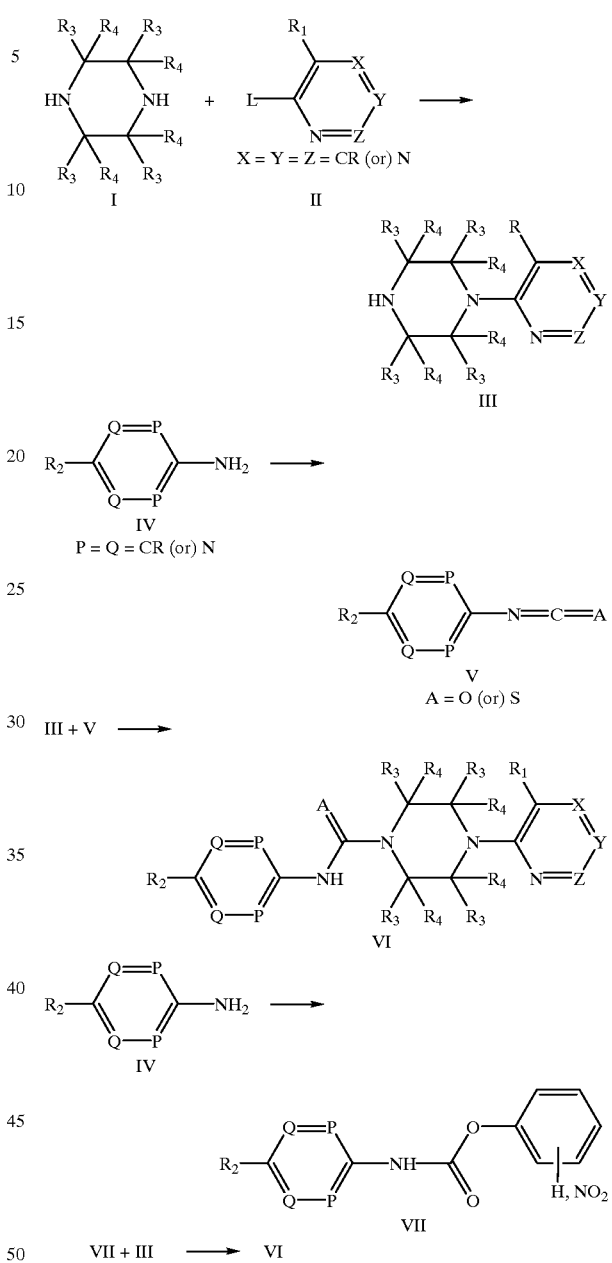

Scheme 1

Intermediate III can be obtained by treating I with II in the presence of a base (eg: $K_2CO_3$, $Cs_2CO_3$, $NR_1R_2R_3$, NaOR, KOR) in an inert solvent such as N,N-dialkylformamide, N,N-dialkylacetamide, dialkylethers, cyclic ethers, DMSO, N-methyl-2-pyrrolidinone at temperatures ranging from −78° C. to 200° C. Isocyanates or isothiocyanates of V can be obtained by treating compound of IV with phosgene, thiophosgene, carbonyldiimidazole in an inert solvent such as benzene, toluene at temperatures ranging from −78° C. to 200° C. The compound of present invention VI can be obtained by treating intermediates III with V in an organic solvent at temperatures −78° C. to 200° C. Alternatively compound of VI can be prepared by treatment of intermediate VII with III in the presence of base such as triethylamine in an inert solvent such as chloroform at temperatures ranging from −78° C. to 200° C.

Carbamates or thiocarbamates (X) of the present invention can be synthesized by following the steps outlined in Scheme 2.

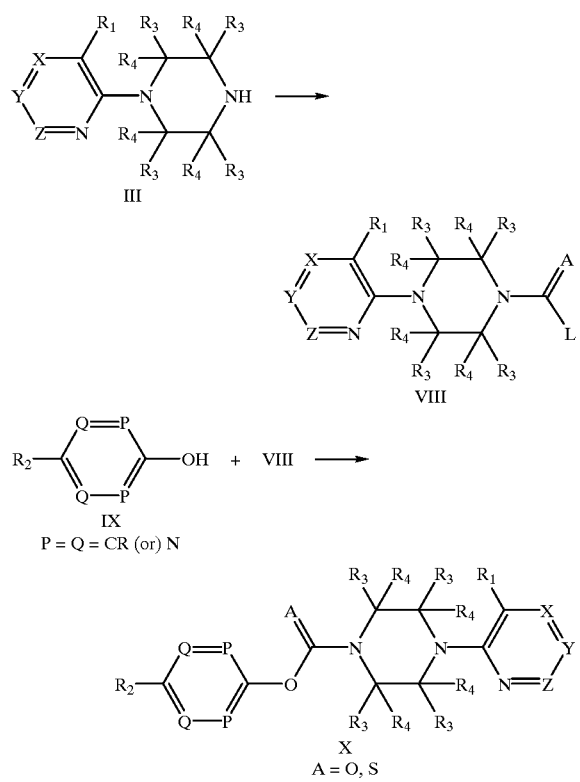

Intermediate III can be converted to VIII (A=O, S, L=halogen, imidazole) upon treatment with phosgene, thiophosgene or carbonyldiimidazoles. Compound of product X can be obtained by treatment with phenols (IX) with compound VIII in the presence of a base in an inert solvent at temperatures ranging from −78° C. to 200° C.

Those having skill in the art will recognize that the starting materials may be varied and additional steps employed to produce compounds encompassed by the present inventions, as demonstrated by the following examples. Unless otherwise specified all reagents and solvent are of standard commercial grade and are used without further purification.

The disclosures in this application of all articles and references, including patents, are incorporated herein by reference.

The invention is illustrated further by the following examples, which are not to be construed as limiting the invention in scope or spirit to the specific procedures described in them. Those having skill in the art will recognize that the starting materials may be varied and additional steps employed to produce compounds encompassed by the present inventions, as demonstrated by the following examples. In some cases, protection of certain reactive functionalities may be necessary to achieve some of the above transformations. In general, such need for protecting groups, as well as the conditions necessary to attach and remove such groups, will be apparent to those skilled in the art of organic synthesis.

EXAMPLES

Example 1

(R)-4-(3-Chloro-pyridin-2-yl)-2-methyl-piperazine-1-carboxylic acid (4-sec-butyl-phenyl)-amide Part A: Synthesis of (R)-1-(3-Chloro-pyridin-2-yl)-3-methyl-piperazine

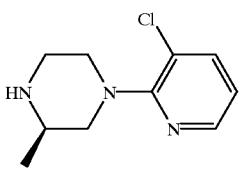

Dissolve 2,3-dichloropyridine (8.5 g, 0.057 moles) and (R)-(−)-2-methylpiperazine (5.75 g, 0.057 moles) in N,N-dimethylacetamide (125.0 mL) under nitrogen atmosphere. Add anhydrous powdered $K_2CO_3$ (23.75 g, 0.172 moles) to this mixture and stir at 135–140° C. for 48 h. New spot noticed in TLC (5% MeOH/CHCl$_3$/1% NEt$_3$) along with absence of starting materials. Cool the reaction mixture to room temperature, dilute with water (400 mL), extract with EtOAc (3×200 mL) and wash the combined organic extract with brine (2×150 mL). Dry over MgSO$_4$, concentrate under vacuum to afford crude product (20.0 g) as orange yellow liquid. Distil the crude under high vacuum to afford pyridylpiperazine derivative as yellow viscous oil (10 g, bp 112–115° C./0.1 torr). NMR (CDCl$_3$): δ 1.1–1.12 (d, 3H, J=1.6 Hz), 2.50–2.53 (t, 1H), 2.83–2.87 (m, 1H), 3.06–3.08 (m, 3H), 3.67–3.75 (m, 2H), 6.80–6.82(dd, 1H), 7.56–7.58 (dd, 1H), 8.17–8.18 (dd, 1H).

Part B: Synthesis of (4-sec-Butyl-phenyl)-carbamic acid phenyl ester

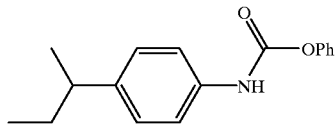

Dissolve 4-isobutylaniline (4.5 g, 0.03 moles) in pyridine (30 mL) under nitrogen at room temperature. Add drop wise phenyl chloroformate (3.75 mL, 0.03 moles) to the reaction mixture at room temperature. Stir the mixture for 3 days and new spot noticed in TLC (30% EtOAc/hexane). Evaporate the reaction mixture under vacuo, partition between EtOAc and water (200 mL), wash several times with brine, dry (MgSO$_4$) and concentrate in vacuo. Purify the crude by flash column chromatography on a silica gel using (10% EtOAc/hexanes) to afford white solid.

Part C: Title Compound

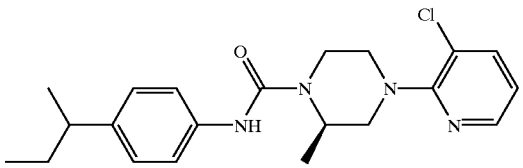

Dissolve Part A material of Example 1 (212 mg, 1.0 mmole) with Part B material of Example 1 (269 mg, 1.0 mmole) in CHCl$_3$ (10 mL) under nitrogen at room temperature. Add triethylamine (202 mg, 2.0 mmol) to the mixture and reflux for 4 hours. Cool the reaction mixture to room temperature, wash with 2N aq. NaOH, water and dry (MgSO$_4$). Evaporate the dried extract in vacuo and purify by flash column chromatography on a silica gel using CHCl$_3$ to afford white solid.

NMR (CDCl$_3$): δ 0.78–0.83 (t, 3H), 1.19–1.22 (d, 3H, J=2.2 Hz), 1.43–1.45 (d, 3H, J=2.3 Hz), 1.51–1.61 (m, 2H), 2.51–2.58 (m, 1H), 2.92–3.05 (m, 2H), 3.41–3.50 (m, 1H), 3.73–3.94 (m, 3H), 4.35 (m, 1H), 6.33 (bs, 1H), 6.86–6.90 (dd, 1H), 7.09–7.13 (m, 2H), 7.26–7.30 (m, 2H), 7.60–7.63 (dd, 1H), 8.18–8.20 (dd, 1H).

Example 2

(R)-(−)-4-(3-Chloro-pyridin-2-yl)-2-methyl-piperazine-1-carboxylic acid (4-trifluoromethyl-phenyl)-amide

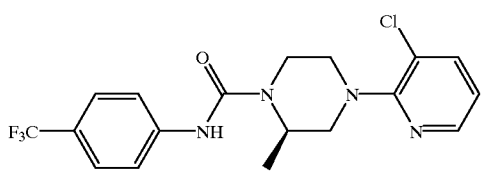

Dissolve Part A material of example 1 (0.2756 g, 1.3 mmoles) in toluene (1.5 mL) under nitrogen at room temperature. Add drop wise 4-trifluoromethylphenyl isocyanate (0.2431 g, 1.3 mmoles) dissolved in toluene (50 mL) to the mixture over a period of 30 mins and stir at room temperature for 3 hours. Evaporate the solvent from reaction mixture under vacuum to afford colorless oil. Crystallize the oil from 1:1 Et$_2$O/hexane (2.0 mL) to afford white solid.

NMR (CDCl$_3$): δ 1.45–1.47 (d, 3H, J=1.7 Hz), 2.97–3.01 (t, 1H), 3.06–3.10 (m, 1H), 3.47–3.50 (m, 1H), 3.75–3.85 (m, 2H), 3.92–3.95 (m, 1H), 4.37–4.38 (m, 1H), 6.59 (bs, 1H), 6.88–6.91 (dd, 1H), 7.52–7.56 (m, 4H), 7.61–7.63 (dd, 1H), 8.19–8.21 (dd, 1H).

Mass spectrum (ESI): 399.3 (M+H).

Analysis calcd. for C$_{18}$H$_{18}$ClF$_3$N$_4$O: C, 54.21; H, 4.55; Cl, 8.89; F, 14.29; N, 14.05. Found: C, 54.47; H, 4.36; Cl, 8.50; F, 14.99; N, 13.94.

Example 3

(R)-3-Chloro-pyridin-2-yl)-2-methyl-piperazine-1-carboxylic acid 4-tert-butyl-phenyl ester Part A: Synthesis of (R)-4-(3-Chloro-pyridin-2-yl)-2-methyl-piperazine-1-carbonyl chloride

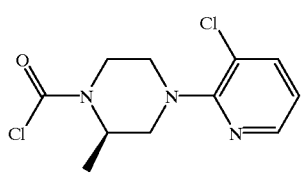

Dissolve Part A material of Example 1 (1.06 g, 5.0 mmole)) in CH$_2$Cl$_2$ (50 mL) and saturated NaHCO$_3$ (50 mL) under nitrogen at room temperature. Add drop wise 20% COCl$_2$ in toluene (5.0 mL) at room temperature and stir overnight. Separate the organic layer, extract the aq. layer with CH$_2$Cl$_2$ (2×15 mL) and dry (MgSO$_4$). Evaporate the organic layer under vacuo to afford yellow oil.

Part B: Title Compound

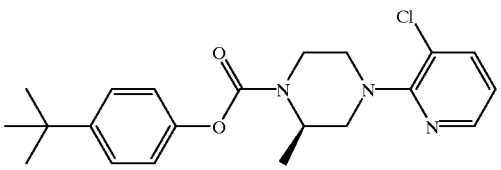

Dissolve Part A material of Example 3 (136 g, 0.5 mmole)) in pyridine (2.0 mL) under nitrogen at room temperature. Add 4-tert. butylphenol to the reaction mixture at room temperature and stir overnight. Evaporate the reaction mixture under vacuo, partition between water/CH$_2$Cl$_2$ (20 mL) and dry (MgSO$_4$). Evaporate the organic layer under vacuo and purify by flash column chromatography on silica gel using 15% EtOAc/hexane to afford colorless oil.

NMR (CDCl$_3$): δ 1.28–1.31 (3 S, 9H), 1.35–1.48 (m, 3H), 2.96–3.11 (m, 2H), 3.49 (m, 1H), 3.72–3.80 (m, 2H), 4.13–4.24 (m, 1H), 4.55–4.60 (m, 1H), 6.74–6.92 (m, 2H), 7.04–7.07 (m, 1H), 7.23–7.26 (m, 1H), 7.36–7.38 (m, 1H), 7.61–7.64 (m, 1H), 8.19–8.22 (m, 1H).

Mass spectrum (ESI): 388.2 (M+H).

Example 4

2-Methyl-4-(3-trifluoromethyl-pyridin-2-yl)-piperazine-1-carboxylic acid [4-(2,2,2-trifluoro-1-methyl-ethyl)-phenyl]-amide Part A: Synthesis of 3-Methyl-1-(3-trifluoromethyl-pyridin-2-yl)-piperazine

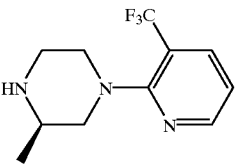

Dissolve 2-chloro-3-trifluoromethylpyridine (5.4 g, 0.03 moles) and (R)-(−)-2-methylpiperazine (3.0 g, 0.03 moles) in N,N-dimethylacetamide (100.0 mL) under nitrogen atmosphere. Add anhydrous powdered K$_2$CO$_3$ (12.4 g, 0.09 moles) to this mixture and stir at 135–140° C. for 24 h. New spot noticed in TLC (5% MeOH/CHCl$_3$/1% NEt$_3$) along with absence of starting materials. Cool the reaction mixture to room temperature, dilute with water (300 mL), extract with EtOAc (3×200 mL) and wash the combined organic extract with brine (2×150 mL). Dry over MgSO$_4$, concentrate under vacuum to afford crude product as orange yellow liquid. Purify by flash column chromatography using 1% MeOH/CHCl$_3$ to afford yellow viscous oil.

Part B: Synthesis of 4-(1-Trifluoromethyl-vinyl)-phenylamine

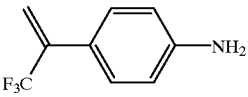

Dissolve 4-(4,4,5,5-tetramethyl-1,2,3-dioxaborolan-2-yl) aniline (2.19 g, 0.01 moles) and 2-Bromo-3,3,3-trifluoro-propene (2.61 g, 0.015 moles) in 1:1 THF/1,2-dimethoxyethane (30 mL) and cooled in an ice bath under nitrogen atmosphere. Add PdCl$_2$[(PPh$_3$)$_2$] (210 mg, 3 mol %) and AsPh₃ (459 mg, 15 mol %) to the reaction mixture followed by dropwise addition of 2.0 N Aq. NaOH (20 mL). Stirred the resultant mixture at room temp for 1 h followed by 70° C. for 15 h. Add additional 1.5 eq. of 2-Bromo-3,3,3-trifluoro-propene (2.61 g) to the reaction mixture and continued at 70° C. for 6 h. Evaporate the reaction mixture under vacuo, dissolve the residue in water/EtOAc (100 mL each), separate the organic layer, extract the aq. layer with EtOAc (2×100 mL), combine the organic layers and dry with MgSO4. Filter the dried extract, evaporate under vacuo and purify the crude by flash column chromatography on a silica gel using CHCl₃ to afford yellow oil.

Part C: Synthesis of 1-Isocyanato-4-(1-trifluoromethyl-vinyl)-benzene

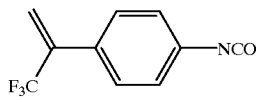

Cool 20% phosgene in toluene (5.0 mL) to −40° C. under N2 atmosphere. Dissolve Part B material of Example 4 (0.47 g, 2.5 mmoles) in toluene and add dropwise to the cooled stirred solution. Stir at −40° C. for 30 mins followed by room temperature for 1 h and then at reflux for 1 h. Concentrate in vacuo to afford orange yellow liquid.

Part D: Synthesis of 2-Methyl-4-(3-trifluoromethyl-pyridin-2-yl)-piperazine-1-carboxylic acid [4-(1-trifluoromethyl-vinyl)-phenyl]-amide

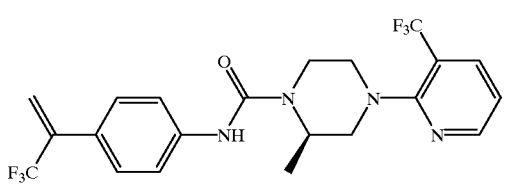

Dissolve Part A material of example 4 (0.123 g, 0.5 mmoles) in toluene (1.0 mL) under nitrogen at room temperature. Add drop wise Part C material of Example 4 (0.106 g, 0.5 mmoles) dissolved in toluene (1.0 mL) to the mixture over a period of 5 mins and stir at room temperature for 20 hours. Evaporate the solvent from reaction mixture under vacuum and purify by flash column chromatography using CHCl₃ to afford yellow oil.

Part E: Title Compound

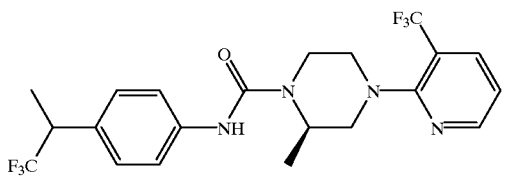

Dissolve Part D material of example 4 (0.120 g, 0.262 mmoles) in EtOH(25.0 mL) at room temperature. Add 5% Pd/C (30 mg) and hydrogenate at 5 atm. of H₂ for 5 hours at room temperature. Filter the catalyst, evaporate the solvent from reaction mixture under vacuum and purify by PTLC using 5% MeOH/CHCl₃ to afford yellow oil.

NMR (CDCl₃): δ 1.38–1.41 (d, 3H), 1.45–1.47 (d, 3H), 3.05–3.11 (m, 1H), 3.22–3.62 (m, 4H), 3.85–3.90 (m, 1H), 4.35–4.42 (m, 1H), 6.40 (s, 1H), 7.05–7.10 (m, 1H), 7.21–7.40 (m, 5H), 7.95–7.97 (d, 1H), 8.42–8.46 (d, 1H).

Mass spectrum (ESI): 461.3 (M+H).

Example 5

4-(3-Chloro-pyridin-2-yl)-2-methyl-piperazine-1-carboxylic acid [4-(2,2,2-trifluoro-1-methyl-ethyl)-phenyl]-amide Part A: Synthesis of 4-(2,2,2-Trifluoro-1-methyl-ethyl)-phenylamine

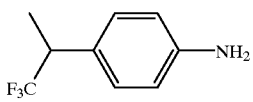

Dissolve Part B material of example 4 (0.375 g, 0.262 mmoles) in MeOH(25.0 mL) at room temperature. Add raney Ni (500 mg) and hydrogenate at 40 atm. of H₂ for 20 hours at room temperature. Filter the catalyst, evaporate the solvent from reaction mixture under vacuum and purify by flash column chromatography using CHCl₃ to afford yellow oil.

Part B: Synthesis of 1-Isocyanato-4-(2,2,2-trifluoro-1-methyl-ethyl)-benzene

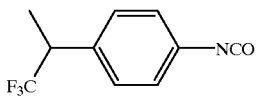

Cool 20% phosgene in toluene (2.0 mL) to −40° C. under N2 atmosphere. Dissolve Part A material of Example 5 (0.189 g, 1.0 mmole) in toluene and add drop wise to the cooled stirred solution. Stir at −40° C. for 30 mins followed by room temperature for 3 h and then at reflux for 18 h. Concentrate in vacuo to afford yellow liquid.

Part C: Title Compound

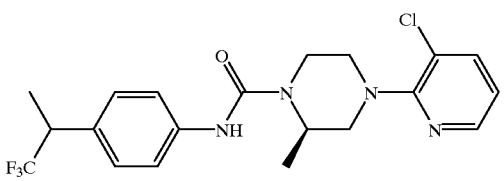

Dissolve Part A material of example 1 (0.169 g, 0.795 mmoles) in toluene (1.0 mL) under nitrogen at room temperature. Add drop wise Part B material of Example 5 (0.171 g, 0.795 mmoles) dissolved in toluene (1.0 mL) to the mixture over a period of 5 mins and stir at room temperature for 20 hours. Evaporate the solvent from reaction mixture under vacuum and purify by PTLC using 5% MeOH/CHCl₃ to afford white amorphous powder.

NMR (CDCl₃): δ 1.44–1.49 (2d, 6H), 2.94–3.11 (m, 2H), 3.36–3.51(m, 2H), 3.74–3.94 (m, 3H), 4.35–4.37 (m, 1H), 6.41 (s, 1H), 6.87–6.90 (dd, 1H), 7.23–7.26 (m, 2H), 7.36–7.38 (m, 2H), 7.60–7.63 (dd, 1H), 8.19–8.20 (dd, 1H).

Mass spectrum (ESI): 427.3 (M+H).

Example 6

(R)-4-(3-Chloro-pyridin-2-yl)-2-methyl-piperazine-1-carboxylic acid [4-(1,2,2,2-tetrafluoro-1-trifluoromethyl-ethyl)-phenyl]-amide Part A: Synthesis of 1-Isocyanato-4-(1,2,2,2-tetrafluoro-1-trifluoromethyl-ethyl)-benzene

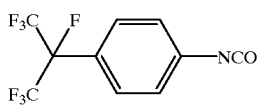

Cool 20% phosgene in toluene (20.0 mL) to −40° C. under N2 atmosphere. Dissolve 4-heptafluoroisopropylaniline (2.0 g, 7.7 mmoles; see: EP 1006102 for aniline preparation) in toluene (5.0 mL) and add drop wise to the cooled stirred solution. Stir at −40° C. for 30 mins followed by room temperature for 2 h and then at reflux for 4 h. Concentrate in vacuo to afford yellow liquid.

Part B: Title Compound

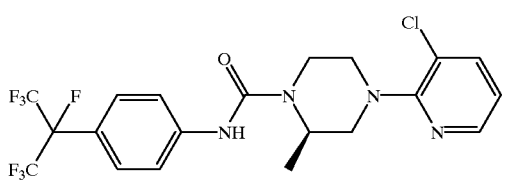

Dissolve Part A material of example 1 (0.106 g, 0.795 mmoles) in amtoluene (1.0 mL) under nitrogen at room temperature. Add drop wise Part A material of Example 6 (0.144 g, 0.5 mmoles) dissolved in toluene (1.0 mL) to the mixture over a period of 5 mins and stir at room temperature for 20 hours. Evaporate the solvent from reaction mixture under vacuum and purify by PTLC using 5% MeOH/CHCl₃ to afford white amorphous powder.

NMR (CDCl₃): δ 1.44–1.46 (d, 3H, J=1.6 Hz), 2.93–3.10 (m, 2H), 3.45–3.52(m, 1H), 3.74–3.78 (m, 2H), 3.91–3.94 (m, 1H), 4.37–4.38 (m, 1H), 6.60 (s, 1H), 6.87–6.90 (dd, 1H), 7.52–7.60 (m, 4H), 7.61–7.63 (m, 1H), 8.18–8.20(dd, 1H).

Mass spectrum (ESI): 499.2 (M+H).

Example 7

4-(3-Chloro-pyridin-2-yl)-2-methyl-piperazine-1-carbothioic acid (4-isopropyl-phenyl)-amide

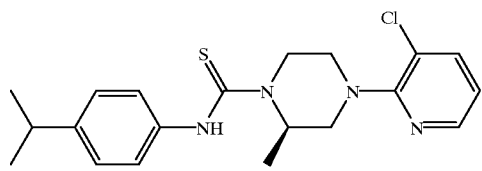

Dissolve Part A material of example 1 (0.212 g, 1.0 mmoles) in toluene (1.0 mL) under nitrogen at room temperature. Add drop wise 4-isopropylisothiocyanate (0.177 g, 0.5 mmoles) dissolved in toluene (1.0 mL) to the mixture over a period of 5 mins and stir at room temperature for 20 hours. Evaporate the solvent from reaction mixture under vacuum and purify by flash column chromatography using CHCl₃ to afford white solid (mp 49–51° C.).

NMR (CDCl₃): δ 1.22–1.25(d, 3H), 1.41–1.43 (d, 3H), 2.80–3.20 (m, 3H), 3.45–3.60(m, 1H), 3.65–3.80(m, 2H), 4.35–4.39 (m, 1H), 5.05–5.20 (m, 1H), 6.85–6.90 (s, 1H), 7.15–7.35 (m, 5H), 7.42–7.44(d, 1H), 8.18–8.20 (d, 1H).

Mass spectrum (ESI): 387.2 (M+H).

Example 8

Synthesis of 4-(3-Trifluoromethyl-2-pyridinyl)-N-(3-methoxy-4-hydroxyphenylmethyl)-1-piperazinecarboxamide

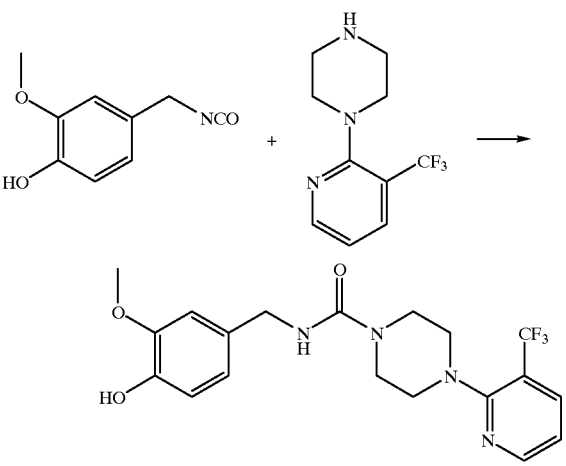

A quantity of 0.2 mL of a 0.2 M isocyante solution in dichloroethane is treated with 0.26 mL of a 0.2 mL solution of piperazine in 95:5 toluene: N-Methyl Morphine at 60° C. for 16 hr. The resulting reaction solution was cooled to room temperature. To the resulting solution is added 1 drop of amino propyl morpholine and warmed to 60° C. for an additional hour. The resulting mixture is cooled to room temperature and chromatographed SiO₂ with ethyl acetate to afford 10 mg 63% of the title compound (Compound 1). MS m/z 410.16 found: 411, 433 Na adduct. Capsaicin receceptor $K_i$: 366 nM

Example 9

Additional Compounds

Using variations of the methods given in Schemes 1 and 2, and Examples 1–8 that will be readily apparent to one skilled in the art of organic synthesis the compounds list in Tables II, III and IV are prepared. Commercial grade reagents are used without further purification in the preparation of these compound.

TABLE II

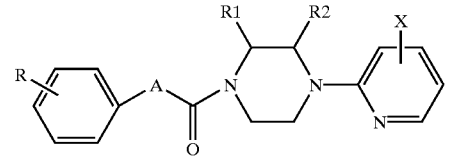

| Compound | R | R1 | R2 | A | X | Calc | Found | Activity | Chemical Name |
|---|---|---|---|---|---|---|---|---|---|
| 2 | 4-Butyl | H | H | NH | 3-NO2 | 383 | 384, 406 Na adduct | * | 4-(3-Nitro-2-pyridinyl)-N-[4-(n-butyl)phenyl]-1-piperazinecarboxamide |
| 3 | 4-Butyl | H | H | NH | 3-CF3 | 406 | 407, 429 Na adduct | * | 4-(3-Trifluoromethyl-2-pyridinyl)-N-[4-(n-butyl)phenyl]-1-piperazinecarboxamide |
| 4 | 4-Isopropyl | H | H | NH | 3-Me | 338 | 339, 361 Na adduct | * | 4-(3-Methyl-2-pyridinyl)-N-[4-(isopropyl)phenyl]-1-Piperazinecarboxamide |
| 5 | 4-Butyl | H | H | NH | 3-Me | 352 | 353, 375 Na adduct | NA | 4-(3-Methyl-2-pyridinyl)-N-[4-(n-butyl)phenyl]-1-piperazinecarboxamide |
| 6 | 4-Isopropyl | H | H | NH | 3-CF3 | 352 | 353, 375 Na adduct | * | 4-(3-Trifluoromethyl-2-pyridinyl)-N-[4-(isopropyl)phenyl]-1-piperazinecarboxamide |
| 7 | 4-Isopropyl | H | H | NH | 3-Cl, 5-CF3 | 427 | 427, 449 Na adduct | * | 4-(3-Chloro-5-trifluoromethyl-2-pyridinyl)-N-[4-(isopropyl)phenyl]-1-piperazinecarboxamide |
| 8 | 4-Isopropyl | H | H | NH | 3-Cl | 359 | 359, 381 Na adduct | * | 4-(3-Chloro-2-pyridinyl)-N-[4-(isopropyl)phenyl]-1-piperazinecarboxamide |
| 9 | 4-Isopropyl | H | H | NH | 3,5-diCl | 393 | 393, 415 Na adduct | * | 4-(3,5-Dichloro-2-pyridinyl)-N-[4-(isopropyl)phenyl]-1-piperazinecarboxamide |
| 10 | 4-Isopropyl | H | H | CH=CH | 3-CF3 | | | * | 1-(3-Methyl-2-pyridinyl)-3-(4-trifluoromethyl phenyl)-prop-2-en-1-one |
| 11 | 4-CF3 | H | H | CH=CH | 3-Me | | | * | 1-(3-Trifluoromethyl-2-pyridinyl)-3-(4-isopropylphenyl)-prop-2-en-1-one |
| 12 | 4-Isopropyl | H | H | NH | 3-CN | 349 | | * | 4-(3-Cyano-2-pyridinyl)-N-[4-(isopropyl)phenyl]-1-piperazinecarboxamide |
| 13 | 4-Isopropyl | Me | H | NH | 3-Cl | 373 | 373, 395 Na adduct | NA | 4-(3-Chloro-2-pyridinyl)-N-[4-(isopropyl)phenyl]-2-methyl-1-piperazinecarboxamide |
| 14 | 4-Isopropyl | R-Me | H | NH | 3-Cl | 373 | 373, 395 Na adduct | * | 4-(3-Chloro-2-pyridinyl)-N-[4-(isopropyl)phenyl]-1-piperazinecarboxamide |
| 15 | 4-Isopropyl | S-Me | H | NH | 3-Cl | 373 | 373, 395 Na adduct | NA | 4-(3-Chloro-2-pyridinyl)-N-[4-(isopropyl)phenyl]-2-methylthio-1-piperazinecarboxamide |
| 16 | 4-CF3 | H | H | NH | 3,5-diCl | 373 | | NA | 4-(3,5-Dichloro-2-pyridinyl)-N-[4-(isopropyl)phenyl]-1-piperazinecarboxamide |

*indicates a Ki value of less than 4 uM in a Capsaicin receptor binding assay
A Capsaicin receptor binding assay is described in example 10
NA = Not available
Mass spec data are collected using a MicroMass 60 series (Beverly, MA) LC-MS TOF spectrometer in the electrospray mode.
LC conditions: YMC-pack pro C18 column, 33 × 4.6 ID, Particle size: S-5 μm 120A, supplied by WATERS, Milford, MA 95%–5% gradient, 2 min gradient time, flow rate 3.5 ml/min, Mobile Phase:A: 0.05% TFA in H2O/MeOH (95:5 v/v)B: 0.05% TFA IN MeOH/H2O(95:5 v/v), 1 ul injection volumn.

TABLE III

| Cmp. # | STRUCTURE | IUPAC Name | EC50 |
|---|---|---|---|
| 17 | 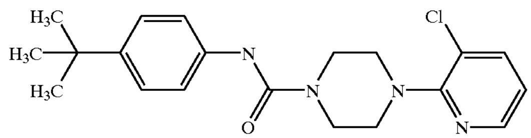 | N-(4-tert-butylphenyl)-4-(3-chloropyrdin-2-yl)piperazine-1-carboxamide | * |
| 18 | 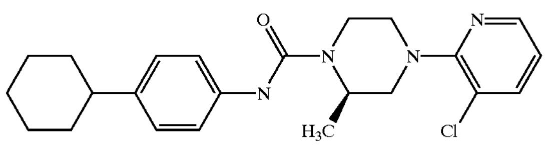 | (2R)-4-(3-chloropyridin-2-yl)-N-(4-cyclohexylphenyl)-2-methylpiperazine-1-carboxamide | * |
| 19 | 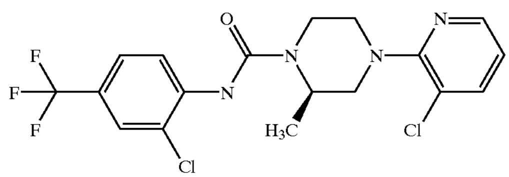 | (2R)-4-(3-chloropyridin-2-yl)-N-[2-chloro-4-(trifluoromethyl)phenyl]-2-methylpiperazine-1-carboxamide | * |
| 20 | 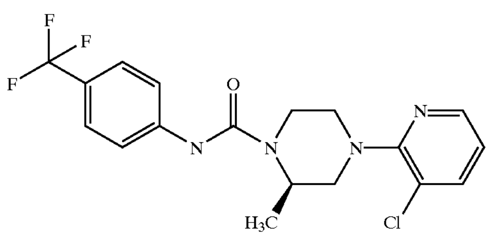 | (2R)-4-(3-chloropyridin-2-yl)-2-methyl-N-[4-(trifluoromethyl)phenyl]piperazine-1-carboxamide | * |
| 21 | 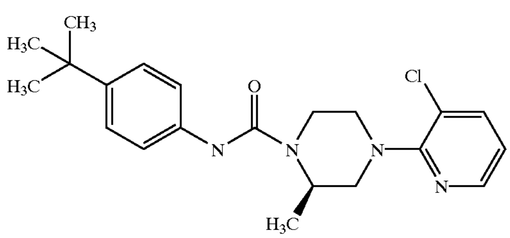 | (2R)-N-(4-tert-butylphenyl)-4-(3-chlorpyridin-2-yl)-2-methylpiperazine-1-carboxamide | * |
| 22 | 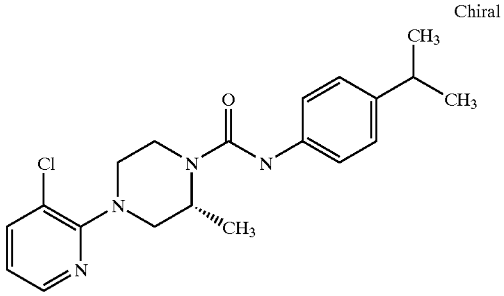 | (2R)-4-(3-chloropyridin-2-yl)-N-(4-isopropylphenyl)-2-methylpiperazine-1-carboxamide | * |
| 23 | 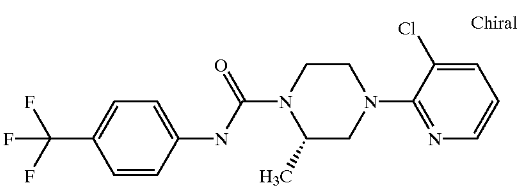 | (2S)-4-(3-chloropyridin-2-yl)-N-(4-trifluoromethylphenyl)-2-methylpiperazine-1-carboxamide | * |

TABLE III-continued

| Cmp. # | STRUCTURE | IUPAC Name | EC50 |
|---|---|---|---|
| 24 | 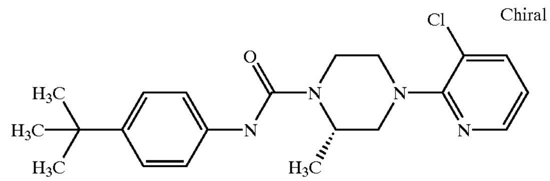 | (2S)-N-(4-tert-butylphenyl)-4-(3-chloropyridin-2-yl)-2-methylpiperazine-1-carboxamide | * |
| 25 | 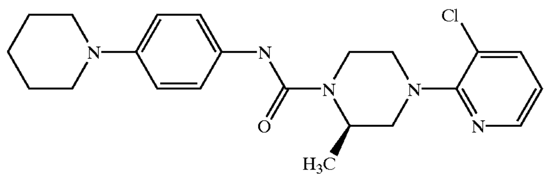 | (2S)-4-(3-chloropyridin-2-yl)-N-(4-isopropylphenyl)-2-methylpiperazine-1-carboxamide | * |
| 26 | 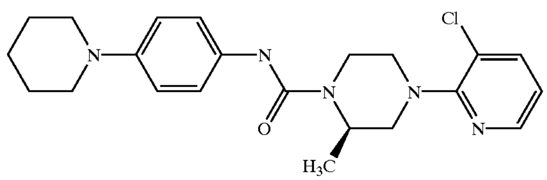 | (2R)-4-(3-chloropyridin-2-yl)-2-methyl-N-(4-piperidin-1-ylphenyl)piperazine-1-carboxamide | * |
| 27 | 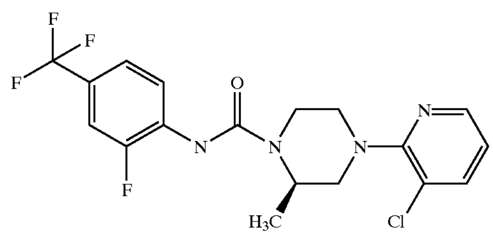 | (2R)-4-(3-chloropyridin-2-yl)-N-[2-fluoro-4-(trifluoromethyl)phenyl]-2-methylpiperazine-1-carboxamide | * |
| 28 | 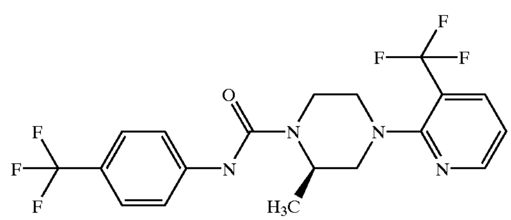 | (2R)-2-methyl-N-[4-(trifluoromethyl)phenyl]-4-[3-(trifluoromethyl)pyridin-2-yl]piperazine-1-carboxamide | * |
| 29 | 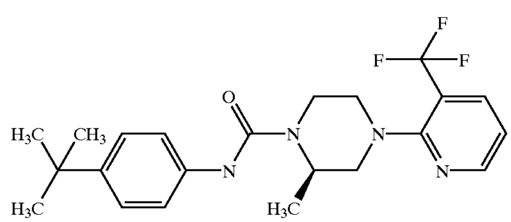 | (2R)-N-(4-tert-butylphenyl)-2-methyl-4-[3-(trifluoromethyl)pyridin-2-yl]piperazine-1-carboxamide | * |
| 30 | 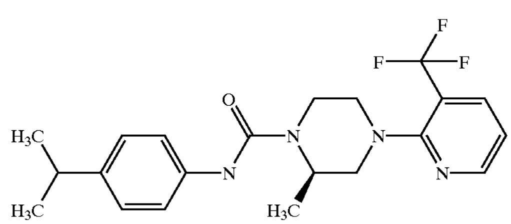 | (2R)-N-(4-isopropylphenyl)-2-methyl-4-[3-(trifluoromethyl)pyridin-2-yl]piperazine-1-carboxamide | * |

TABLE III-continued

| Cmp. # | STRUCTURE | IUPAC Name | EC50 |
|---|---|---|---|
| 31 | 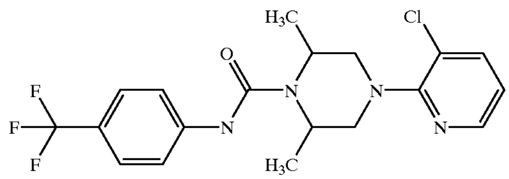 | 4-(3-chloropyridin-2-yl)-2,6-dimethyl-N-[4-(trifluoromethyl)phenyl]piperazine-1-carboxamide | * |
| 32 | 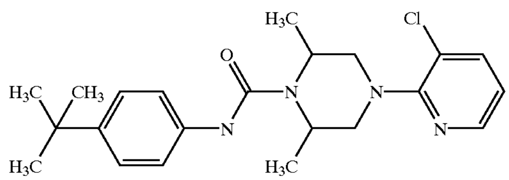 | N-(4-tert-butylphenyl)-4-(3-chloropyridin-2-yl)-2,6-dimethylpiperazine-1-carboxamide | * |
| 33 | 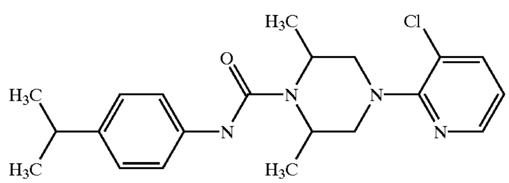 | 4-(3-chloropyridin-2-yl)-N-(4-isopropylphenyl)-2,6-dimethylpiperazine-1-carboxamide | * |
| 34 | 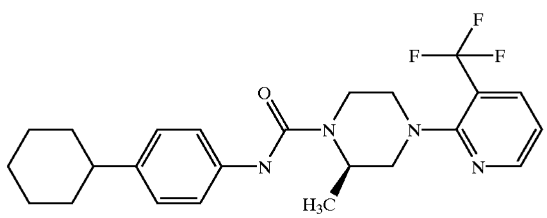 | (2R)-N-(4-cyclohexylphenyl)-2-methyl-4-[3-(trifluoromethyl)pyridin-2-yl]piperazine-1-carboxamide | * |
| 35 | 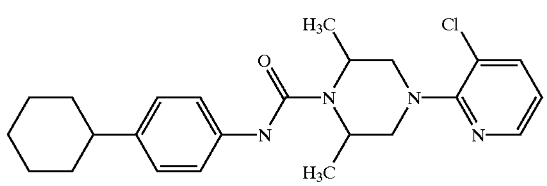 | 4-(3-chloropyridin-2-yl)-N-(4-cyclohexylphenyl)-2,6-dimethylpiperazine-1-carboxamide | * |
| 36 | 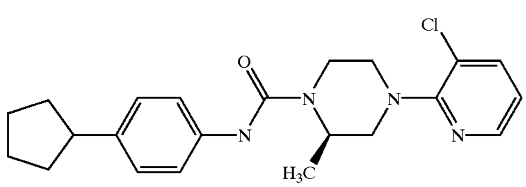 | (2R)-4-(3-chloropyridin-2-yl)-N-(4-cyclopentylphenyl)-2-methylpiperazine-1-carboxamide | * |
| 37 | 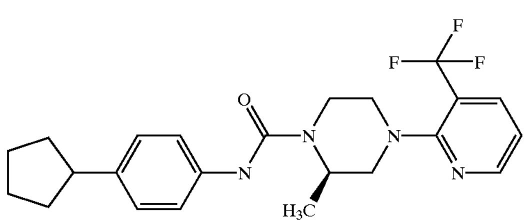 | (2R)-N-(4-cyclopentylphenyl)-2-methyl-4-[3-(trifluoromethyl)pyridin-2-yl]piperazine-1-carboxamide | * |

TABLE III-continued

| Cmp. # | STRUCTURE | IUPAC Name | EC50 |
|---|---|---|---|
| 38 | 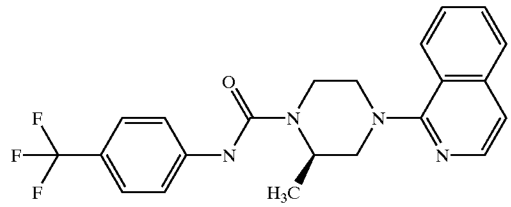 | (2R)-4-isoquinolin-1-yl-2-methyl-N-[4-(trifluoromethyl)phenyl]piperazine-1-carboxamide | * |
| 39 | 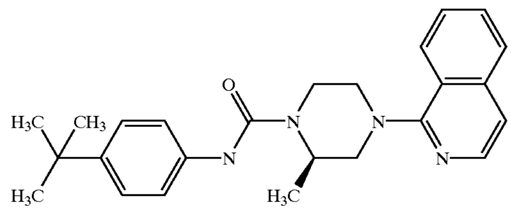 | (2R)-N-(4-tert-butylphenyl)-4-isoquinolin-1-yl-2-methylpiperazine-1-carboxamide | * |
| 40 | 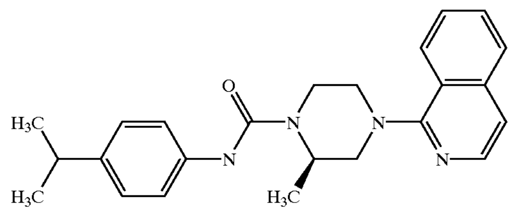 | (2R)-N-(4-isopropylphenyl)-4-isoquinolin-1-yl-2-methylpiperazine-1-carboxamide | * |
| 41 | 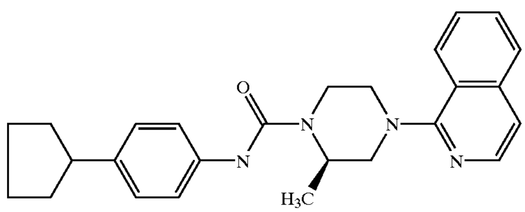 | (2R)-N-(4-cyclopentylphenyl)-4-isoquinolin-1-yl-2-methylpiperazine-1-carboxamide | * |
| 42 | 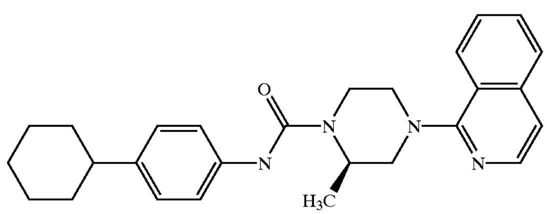 | (2R)-N-(4-cyclohexylphenyl)-4-isoquinolin-1-yl-2-methylpiperazine-1-carboxamide | * |
| 43 | 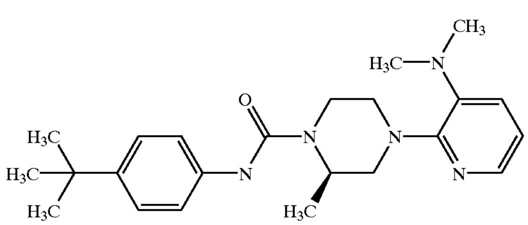 | (2R)-N-(4-tert-butylphenyl)-4-[3-(dimethylamino)pyridin-2-yl]-2-methylpiperazine-1-carboxamide | * |
| 44 | 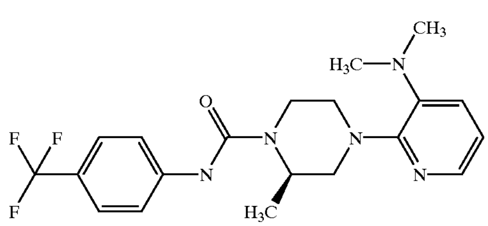 | (2R)-4-[3-(dimethylamino)pyridin-2-yl]-2-methyl-N-[4-trifluoromethyl)phenyl]piperazine-1-carboxamide | * |

TABLE III-continued

| Cmp. # | STRUCTURE | IUPAC Name | EC50 |
|---|---|---|---|
| 45 | 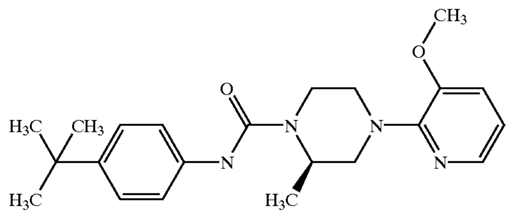 | (2R)-N-(4-tert-butylphenyl)-4-(3-methoxypyridin-2-yl)-2-methylpiperazine-1-carboxamide | * |
| 46 | 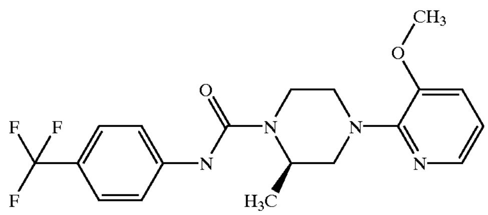 | (2R)-4-(3-methoxypyridin-2-yl)-2-methyl-N-[4-(trifluoromethyl)phenyl]piperazine-1-carboxamide | |
| 47 | 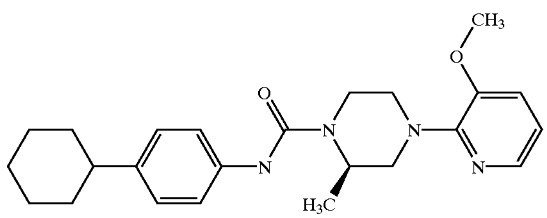 | (2R)-N-(4-cyclohexylphenyl)-4-(3-methoxypyridin-2-yl)-2-methylpiperazine-1-carboxamide | * |
| 48 | 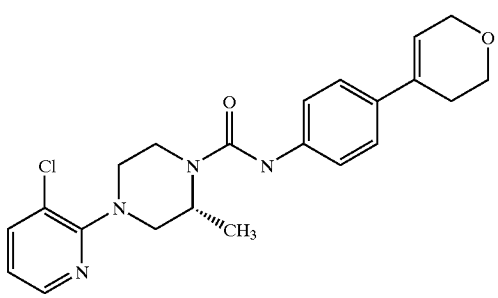 | (2R)-4-(3-chloropyridin-2-yl)-N-[4-(3,6-dihydro-2H-pyran-4-yl)phenyl]-2-methylpiperazine-1-carboxamide | * |
| 49 | 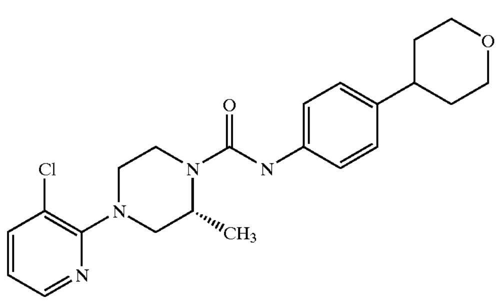 | (2R)-4-(3-chloropyridin-2-yl)-2-methyl-N-(4-tetrahydro-2H-pyran-4-ylphenyl)piperazine-1-carboxamide | * |
| 50 | 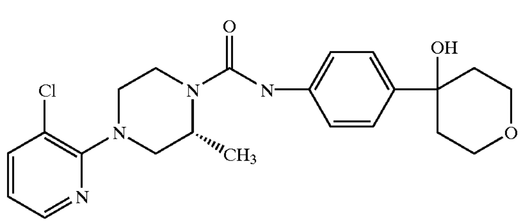 | (2R)-4-(3-chloropyridin-2-yl)-N-[4-(4-hydroxytetrahydro-2H-pyran-4-yl)phenyl]-2-methylpiperazine-1-carboxamide | * |

TABLE III-continued

| Cmp. # | STRUCTURE | IUPAC Name | EC50 |
|---|---|---|---|
| 51 | 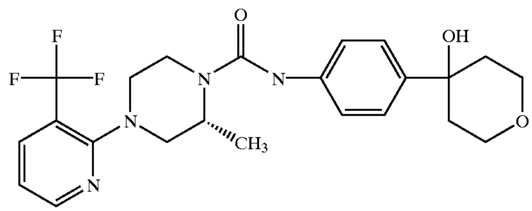 | (2R)-N-[4-(4-hydroxytetrahydro-2H-pyran-4-yl)phenyl]-2-methyl-4-[3-(trifluoromethyl)pyridin-2-yl]piperazine-1-carboxamide | * |
| 52 | 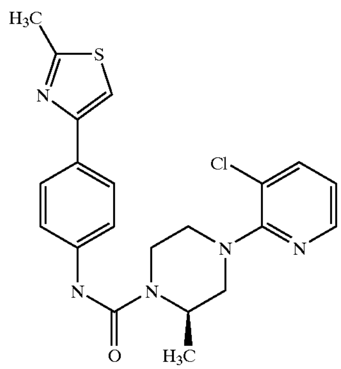 | (2R)-4-(3-chloropyridin-2-yl)-2-methyl-N-[4-(2-methyl-1,3-thiazol-4-yl)phenyl]piperazine-1-carboxamide | * |
| 53 | 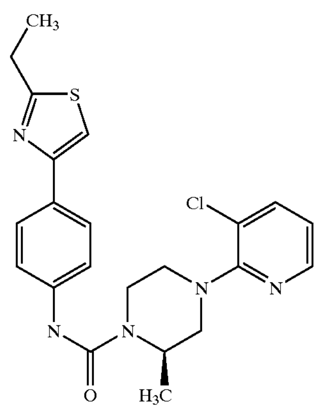 | (2R)-4-(3-chloropyridin-2-yl)-N-[4-(2-ethyl-1,3-thiazol-4-yl)phenyl]-2-methylpiperazine-1-carboxamide | * |
| 54 | 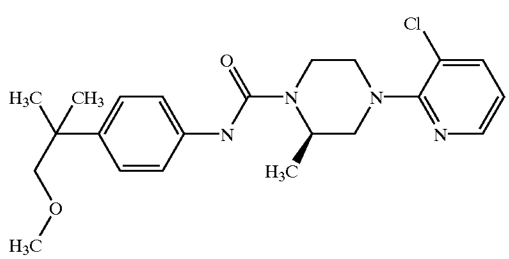 | (2R)-4-(3-chloropyridin-2-yl)-N-[4-(2-methoxy-1,1-dimethylethyl)phenyl]-2-methylpiperazine-1-carboxamide | * |
| 55 | 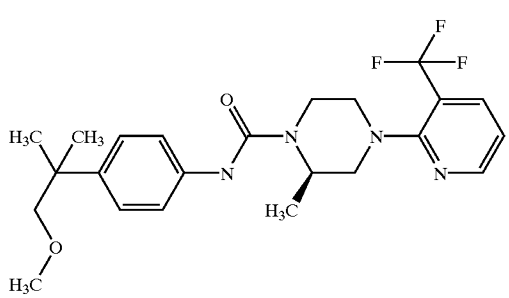 | (2R)-N-[4-(2-methoxy-1,1-dimethylethyl)phenyl]-2-methyl-4-[3-(trifluoromethyl)pyridin-2-yl]piperazine-1-carboxamide | * |

TABLE III-continued

| Cmp. # | STRUCTURE | IUPAC Name | EC50 |
|---|---|---|---|
| 56 | 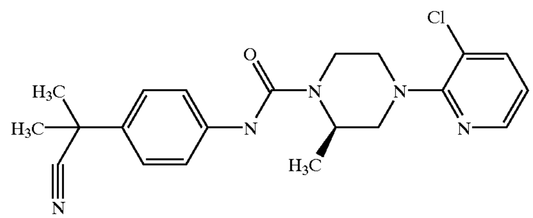 | (2R)-4-(3-chloropyridin-2-yl)-N-[4-(1-cyano-1-methylethyl)phenyl]-2-methylpiperazine-1-carboxamide | * |
| 57 | 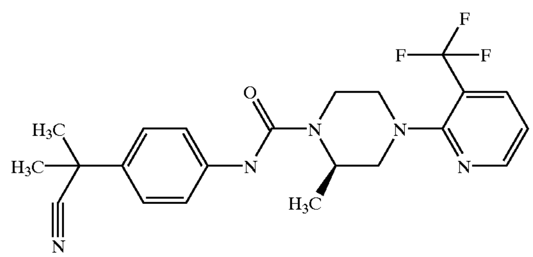 | (2R)-N-[4-(1-cyano-1-methylethyl)phenyl]-2-methyl-4-[3-(trifluoromethyl)pyridin-2-yl]piperazine-1-carboxamide | * |
| 58 | 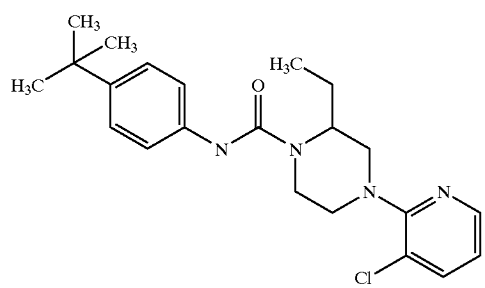 | N-(4-tert-butylphenyl)-4-(3-chloropyridin-2-yl)-2-ethylpiperazine-1-carboxamide | * |
| 59 | 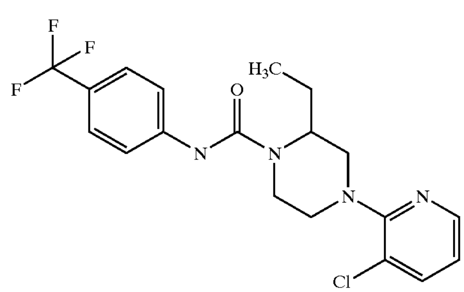 | 4-(3-chloropyridin-2-yl)-2-ethyl-N-[4-(trifluoromethyl)phenyl]piperazine-1-carboxamide | * |
| 60 | 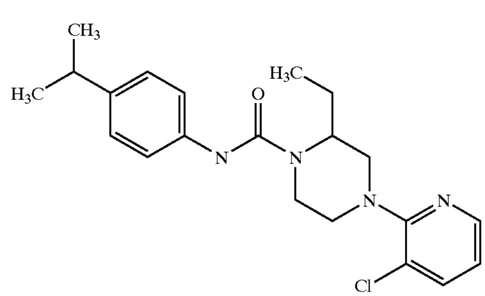 | 4-(3-chloropyridin-2-yl)-2-ethyl-N-(4-isopropylphenyl)piperazine-1-carboxamide | * |

TABLE III-continued

| Cmp. # | STRUCTURE | IUPAC Name | EC50 |
|---|---|---|---|
| 61 | 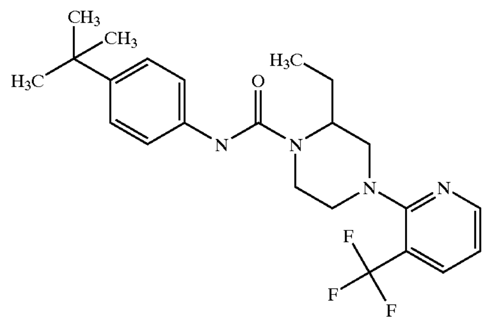 | N-(4-tert-butylphenyl)-2-ethyl-4-[3-(trifluoromethyl)pyridin-2-yl]piperazine-1-carboxamide | * |
| 62 | 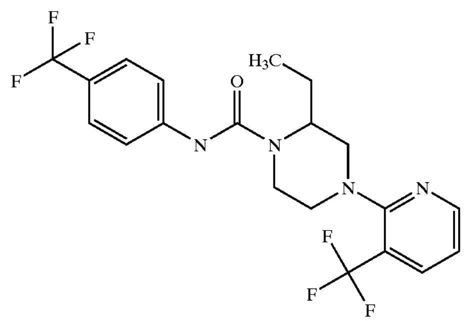 | 2-ethyl-N-[4-(trifluoromethyl)phenyl]-4-[3-(trifluoromethyl)pyridin-2-yl]piperazine-1-carboxamide | * |
| 63 | 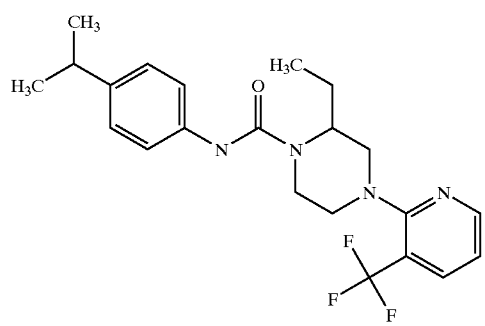 | 2-ethyl-N-(4-isopropylphenyl)-4-[3-(trifluoromethyl)pyridin-2-yl]piperazine-1-carboxamide | * |
| 64 | 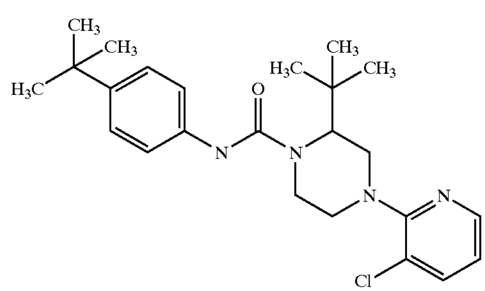 | 2-tert-butyl-N-(4-tert-butylphenyl)-4-(3-chloropyridin-2-yl)piperazine-1-carboxamide | * |
| 65 | 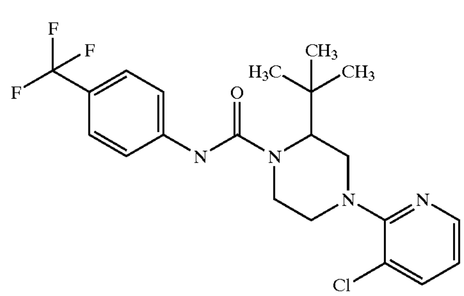 | 2-tert-butyl-4-(3-chloropyridin-2-yl)-N-[4-(trifluoromethyl)phenyl]piperazine-1-carboxamide | * |

TABLE III-continued

| Cmp. # | STRUCTURE | IUPAC Name | EC50 |
|---|---|---|---|
| 66 | 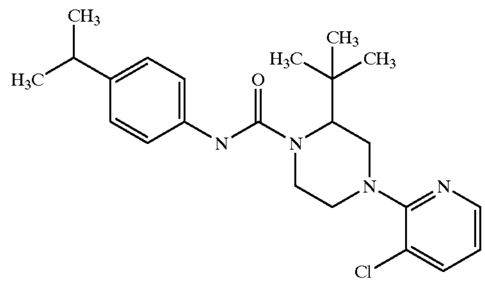 | 2-tert-butyl-4-(3-chloropyridin-2-yl)-N-(4-isopropylphenyl)piperazine-1-carboxamide | |
| 67 | 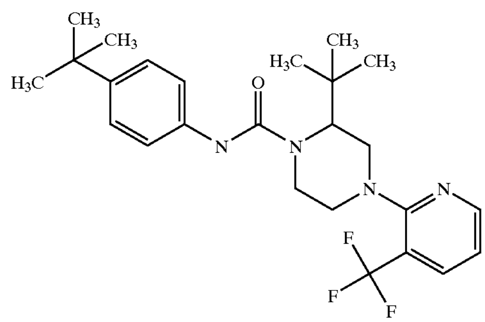 | 2-tert-butyl-N-(4-tert-butyl-N-(4-tert-butylphenyl)-4-[3-(trifluoromethyl)pyridin-2-yl]piperazine-1-carboxamide | |
| 68 | 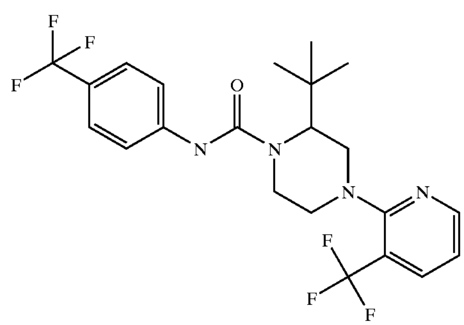 | 2-tert-butyl-N-[4-(trifluoromethyl)phenyl]-4-[3-(trifluoromethyl)pyridin-2-yl]piperazine-1-carboxamide | * |
| 69 | 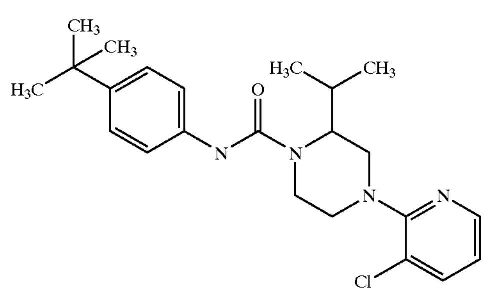 | N-(4-tert-butylphenyl)-4-(3-chloropyridin-2-yl)-2-isopropylpiperazine-1-carboxamide | * |
| 70 | 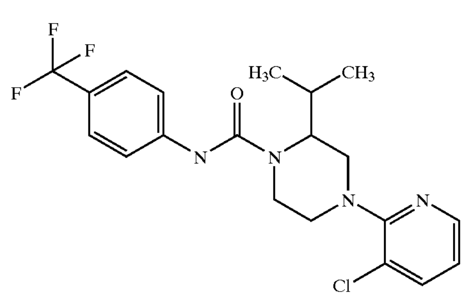 | 4-(3-chloropyridin-2-yl)-2-isopropyl-N-[4-(trifluoromethyl)phenyl]piperazine-1-carboxamide | |

TABLE III-continued

| Cmp. # | STRUCTURE | IUPAC Name | EC50 |
|---|---|---|---|
| 71 | 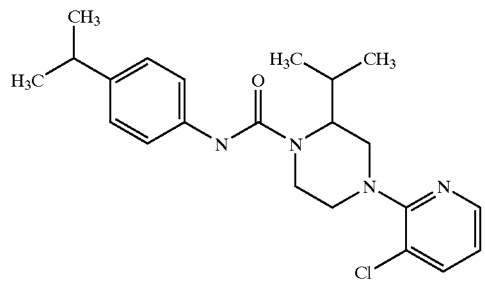 | 4-(3-chloropyridin-2-yl)-2-isopropyl-N-(4-isopropylphenyl)piperazine-1-carboxamide | |
| 72 | 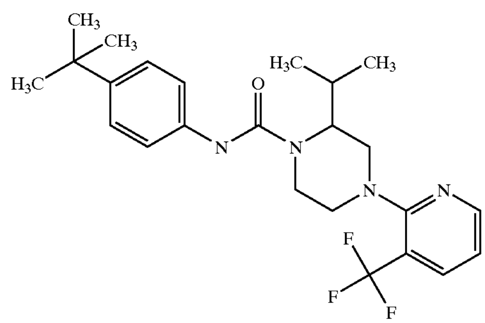 | N-(4-tert-butylphenyl)-2-isopropyl-4-[3-(trifluoromethyl)pyridin-2-yl]piperazine-1-carboxamide | * |
| 73 | 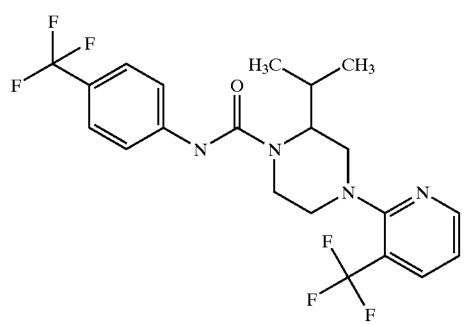 | 2-isopropyl-N-[4-(trifluoromethyl)phenyl]-4-[3-(trifluoromethyl)pyridin-2-yl]piperazine-1-carboxamide | * |
| 74 | 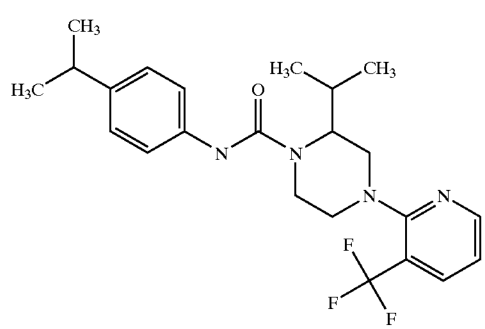 | 2-isopropyl-N-(4-isopropylphenyl)-4-[3-(trifluoromethyl)pyridin-2-yl]piperazine-1-carboxamide | * |
| 75 | 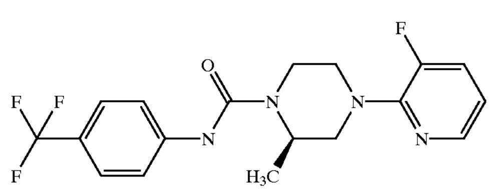 | (2R)-4-(3-fluoropyridin-2-yl)-2-methyl-N-[4-(trifluoromethyl)phenyl]piperazine-1-carboxamide | * |

TABLE III-continued

| Cmp. # | STRUCTURE | IUPAC Name | EC50 |
|---|---|---|---|
| 76 | 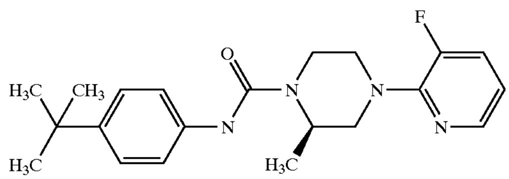 | (2R)-N-(4-tert-butylphenyl)-4-(3-fluoropyridin-2-yl)-2-methylpiperazine-1-carboxamide | * |
| 77 | 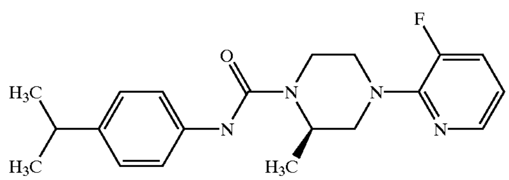 | (2R)-4-(3-fluoropyridin-2-yl)-N-(4-isopropylphenyl)-2-methylpiperazine-1-carboxamide | * |
| 78 | 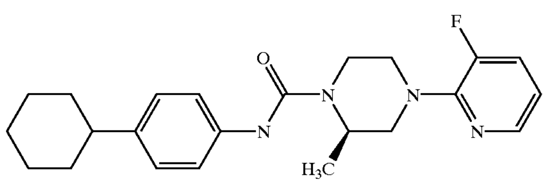 | (2R)-N-(4-cyclohexylphenyl)-4-(3-fluoropyridin-2-yl)-2-methylpiperazine-1-carboxamide | * |
| 79 | 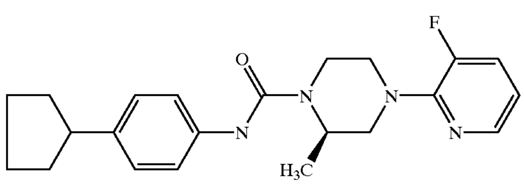 | (2R)-N-(4-cyclopentylphenyl)-4-(3-fluoropyridin-2-yl)-2-methylpiperazine-1-carboxamide | * |
| 80 | 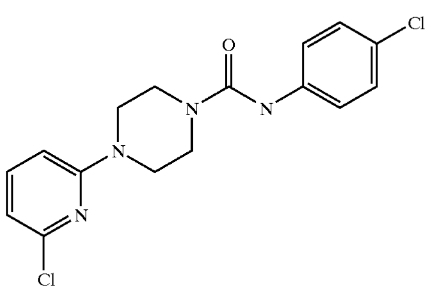 | N-(4-chlorophenyl)-4-(6-chloropyridin-2-yl)piperazine-1-carboxamide | |
| 81 | 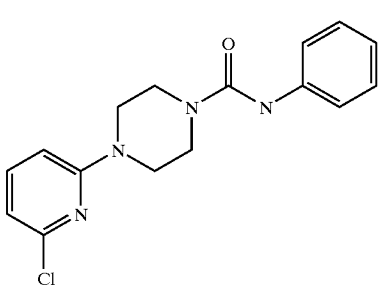 | 4-(6-chloropyridin-2-yl)-N-phenylpiperazine-1-carboxamide | |

TABLE III-continued

| Cmp. # | STRUCTURE | IUPAC Name | EC50 |
|---|---|---|---|
| 82 | 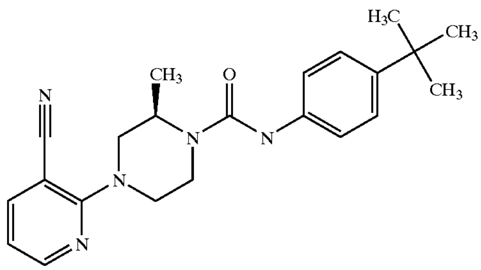 | (2R)-N-(4-tert-butylphenyl)-4-(3-cyanopyridin-2-yl)-2-methylpiperazine-1-carboxamide | * |
| 83 | 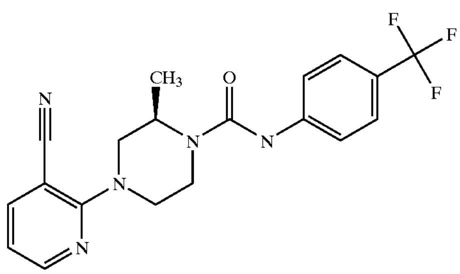 | (2R)-4-(3-cyanopyridin-2-yl)-2-methyl-N-[4-(trifluoromethyl)phenyl]piperazine-1-carboxamide | * |
| 84 | 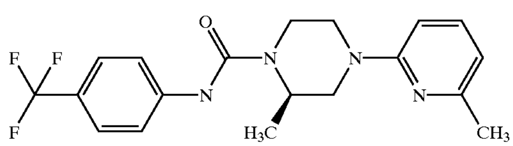 | (2R)-2-methyl-4-(6-methylpyridin-2-yl)-N-[4-(trifluoromethyl)phenyl]piperazine-1-carboxamide | |
| 85 | 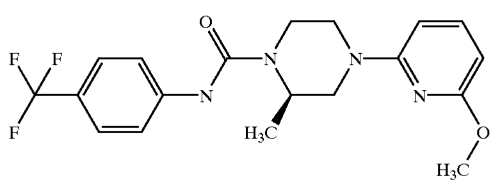 | (2R)-4-(6-methoxypyridin-2-yl)-2-methyl-N-[4-(trifluoromethyl)phenyl]piperazine-1-carboxamide | |
| 86 | 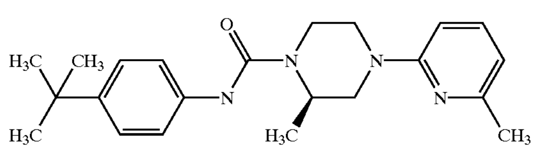 | (2R)-N-(4-tert-butylphenyl)-2-methyl-4-(6-methylpyridin-2-yl)piperazine-1-carboxamide | * |
| 87 | 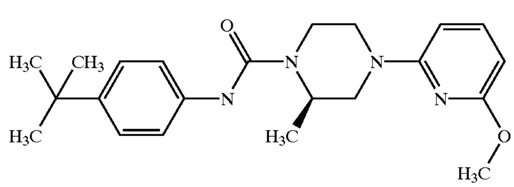 | (2R)-N-(4-tert-butylphenyl)-4-(6-methoxypyridin-2-yl)-2-methylpiperazine-1-carboxamide | |
| 88 | 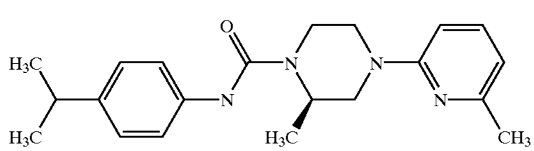 | (2R)-N-(4-isopropylphenyl)-2-methyl-4-(6-methylpyridin-2-yl)piperazine-1-carboxamide | |
| 89 | 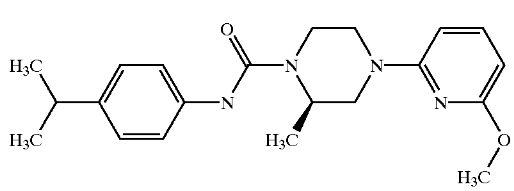 | (2R)-N-(4-isopropylphenyl)-4-(6-methoxypyridin-2-yl)-2-methylpiperazine-1-carboxamide | |

TABLE III-continued

| Cmp. # | STRUCTURE | IUPAC Name | EC50 |
|---|---|---|---|
| 90 | 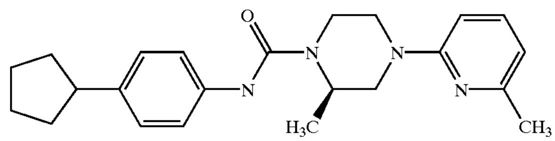 | (2R)-N-(4-cyclopentylphenyl)-2-methyl-4-(6-methylpyridin-2-yl)piperazine-1-carboxamide | |
| 91 | 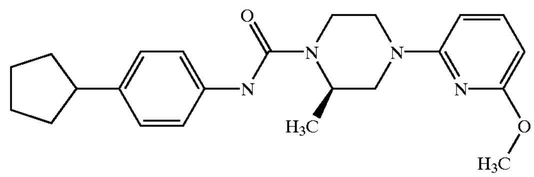 | (2R)-N-(4-cyclopentylphenyl)-4-(6-methoxypyridin-2-yl)-2-methylpiperazine-1-carboxamide | |

TABLE IV

| Cpd. # | STRUCTURE | IUPAC Name | EC50 |
|---|---|---|---|
| 93 | 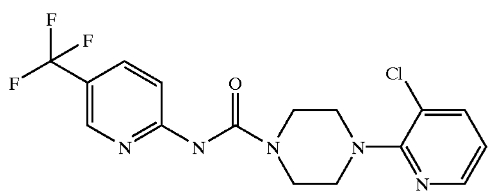 | 4-(3-chloropyridin-2-yl)-N-[5-(trifluoromethyl)pyridin-2-yl]piperazine-1-carboxamide | * |
| 94 | 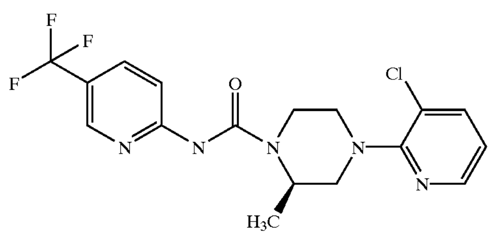 | (2R)-4-(3-chloropyridin-2-yl)-2-methyl-N-[5-(trifluoromethyl)pyridin-2-yl]piperazine-1-carboxamide | * |
| 95 | 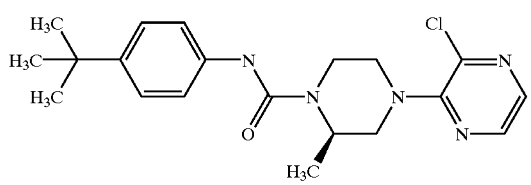 | (2R)-N-(4-tert-butylphenyl)-4-(3-chloropyrazin-2-yl)-2-methylpiperazine-1-carboxamide | * |
| 96 | 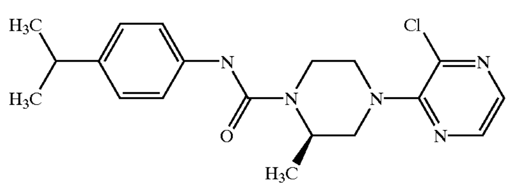 | (2R)-4-(3-chloropyrazin-2-yl)-N-(4-isopropylphenyl)-2-methylpiperazine-1-carboxamide | * |
| 97 | 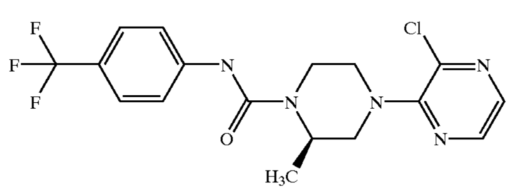 | (2R)-4-(3-chloropyrazin-2-yl)-2-methyl-N-[4-(trifluoromethyl)phenyl]piperazine-1-carboxamide | * |

TABLE IV-continued

| Cpd. # | STRUCTURE | IUPAC Name | EC50 |
|---|---|---|---|
| 98 | 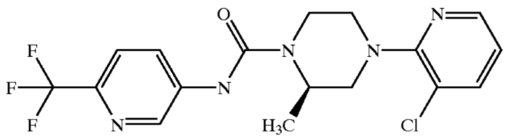 | (2R)-4-(3-chloropyridin-2-yl)-2-methyl-N-[6-(trifluoromethyl)pyridin-3-yl]piperazine-1-carboxamide | * |
| 99 | 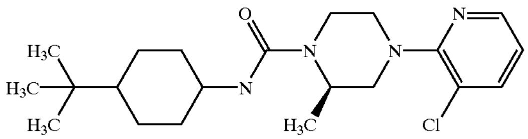 | (2R)-N-(4-tert-butylcyclohexyl)-4-(3-chloropyridin-2-yl)-2-methylpiperazine-1-carboxamide | * |
| 100 | 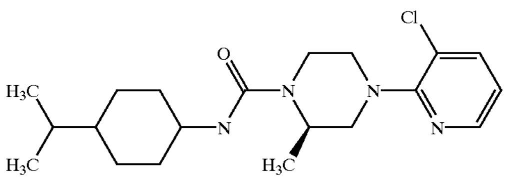 | (2R)-4-(3-chloropyridin-2-yl)-N-(4-isopropylcyclohexyl)-2-methylpiperazine-1-carboxamide | * |
| 101 | 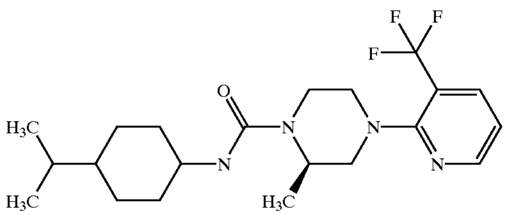 | (2R)-N-(4-isopropylcyclohexyl)-2-methyl-4-[3-(trifluoromethyl)pyridin-2-yl]piperazine-1-carboxamide | * |
| 102 | 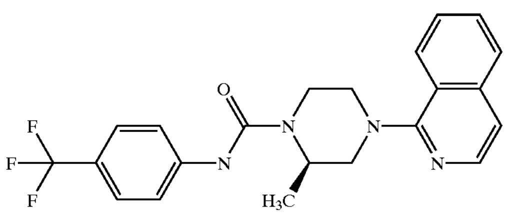 | (2R)-4-isoquinolin-1-yl-2-methyl-N-[4-(trifluoromethyl)phenyl]piperazine-1-carboxamide | |
| 103 | 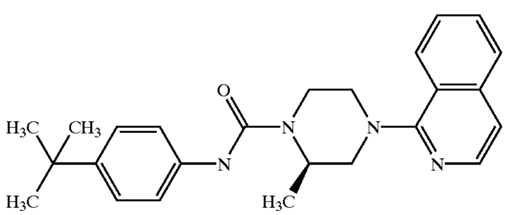 | (2R)-N-(4-tert-butylphenyl)-4-isoquinolin-1-yl-2-methylpiperazine-1-carboxamide | |
| 104 | 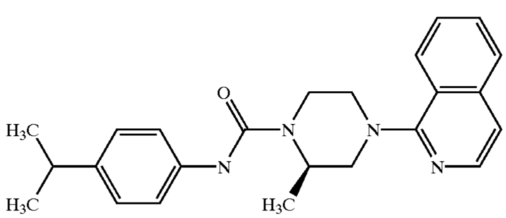 | (2R)-N-(4-isopropylphenyl)-4-isoquinolin-1-yl-2-methylpiperazine-1-carboxamide | |
| 105 | 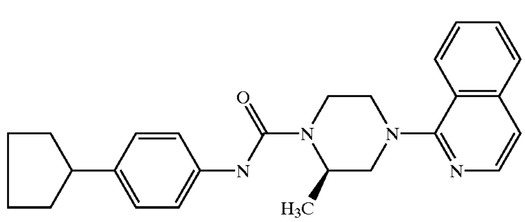 | (2R)-N-(4-cyclopentylphenyl)-4-isoquinolin-1-yl-2-methylpiperazine-1-carboxamide | |

TABLE IV-continued

| Cpd. # | STRUCTURE | IUPAC Name | EC50 |
|---|---|---|---|
| 106 | 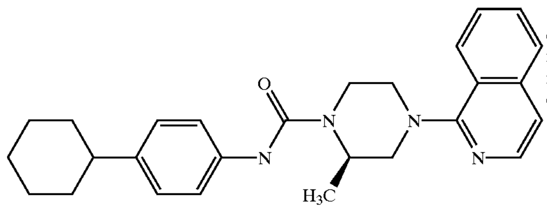 | (2R)-N-(4-cyclohexylphenyl)-4-isoquinolin-1-yl-2-methylpiperazine-1-carboxamide | |

TABLE V

| Cmp # | Structure | Name | EC50 |
|---|---|---|---|
| 107 | 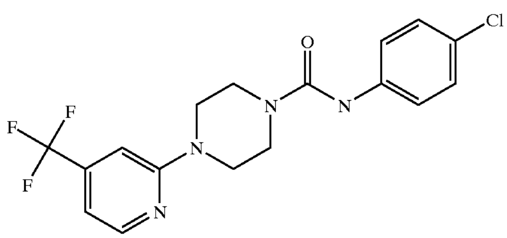 | N-(4-chlorophenyl)-4-[4-(trifluoromethyl)pyridin-2-yl]piperazine-1-carboxamide | * |
| 108 | 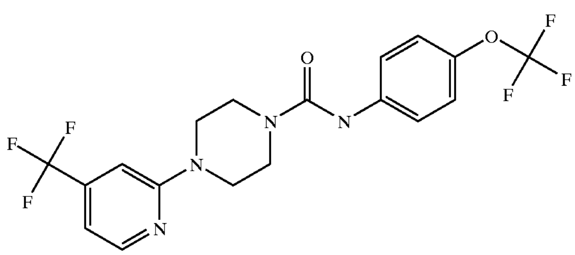 | N-[4-*trifluoromethoxy)phenyl]-4-[4-(trifluoromethyl)pyririn-2-yl]piperazine-1-carboxamide | * |
| 109 | 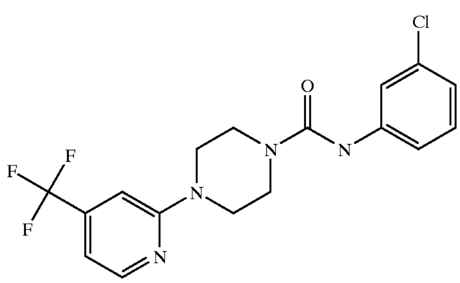 | N-(3-chlorophenyl)-4-[4-(trifluoromethyl)pyridin-2-yl]piperazine-1-carboxamide | * |
| 110 | 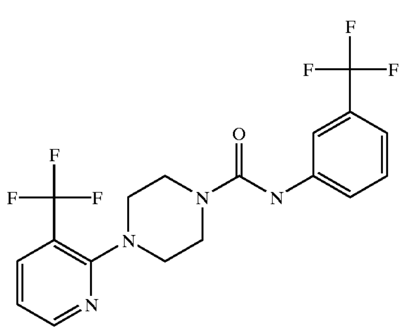 | N-[3-(trifluoromethyl)phenyl]-4-[3-(trifluoromethyl)pyridin-2-yl]piperazine-1-carboxamide | * |

TABLE V-continued

| Cmp # | Structure | Name | EC50 |
|---|---|---|---|
| 111 | 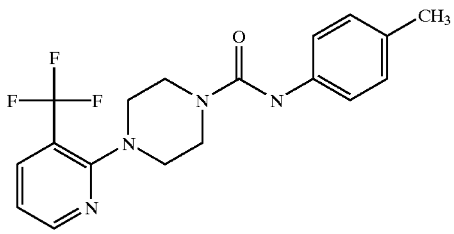 | N-(4-methylphenyl)-4-[3-(trifluoromethyl)pyridin-2-yl]piperazine-1-carboxamide | |
| 112 | 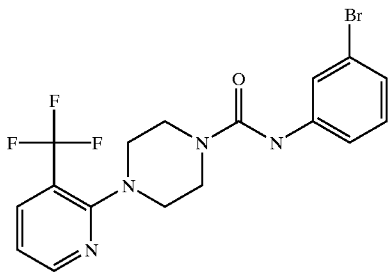 | N-(3-bromophenyl)-4-[3-(trifluoromethyl)pyridin-2-yl]piperazine-1-carboxamide | |
| 113 | 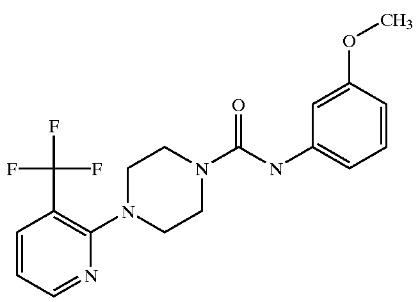 | N-(3-methoxyphenyl)-4-[3-(trifluoromethyl)pyridin-2-yl]piperazine-1-carboxamide | * |
| 114 | 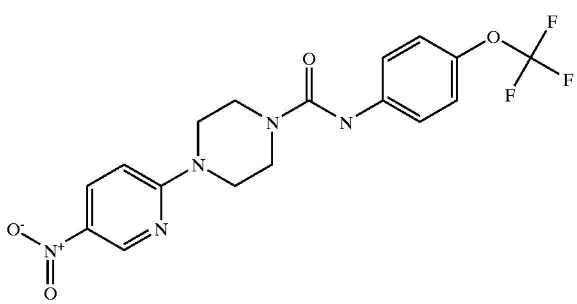 | 4-(5-nitropyridin-2-yl)-N-[4-(trifluoromethoxy)phenyl]piperazine-1-carboxamide | |
| 115 | 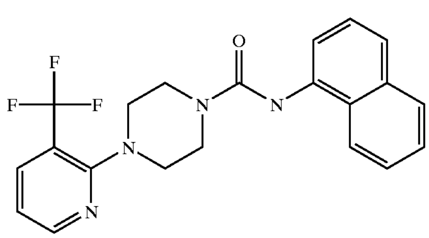 | N-(1-naphthyl)-4-[3-(trifluoromethyl)pyridin-2-yl]piperazine-1-carboxamide | |

TABLE V-continued

| Cmp # | Structure | Name | EC50 |
|---|---|---|---|
| 116 | 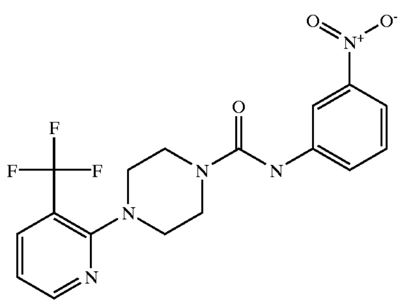 | N-(3-nitrophenyl)-4-[3-(trifluoromethyl)pyridin-2-yl]piperazine-1-carboxamide | * |
| 117 | 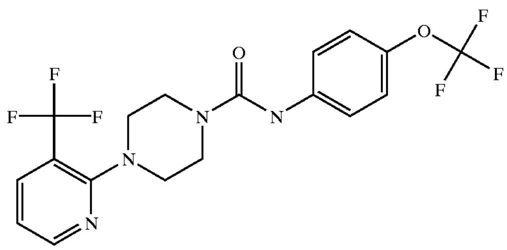 | N-[4-(trifluoromethoxy)phenyl]-4-[3-(trifluoromethyl)pyridin-2-yl]piperazine-1-carboxamide | * |
| 118 | 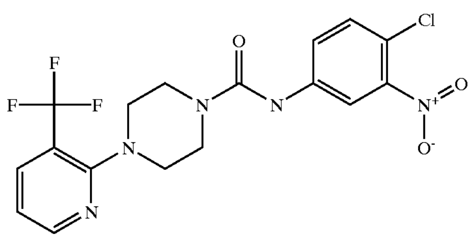 | N-(4-chloro-3-nitrophenyl)-4-[3-(trifluoromethyl)pyridin-2-yl]piperazine-1-carboxamide | * |
| 119 | 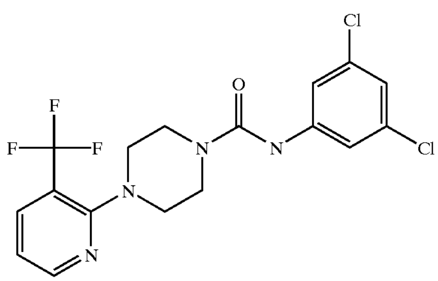 | N-(3,5-dichlorophenyl)-4-[3-(trifluoromethyl)pyridin-2-yl]piperazine-1-carboxamide | * |
| 120 | Chiral | (2R)-4-(3-chloropyridin-2-yl)-N-[4-[cyano(phenyl)methyl]phenyl]-2-methylpiperazine-1-carboxamide | * |
| 121 | Chiral | (2R)-4-(3-chloropyridin-2-yl)-2-methyl-N-[3-methyl-4-(trifluoromethyl)phenyl]piperazine-1-carboxamide | * |

TABLE V-continued

| Cmp # | Structure | Name | EC50 |
|---|---|---|---|
| 122 | 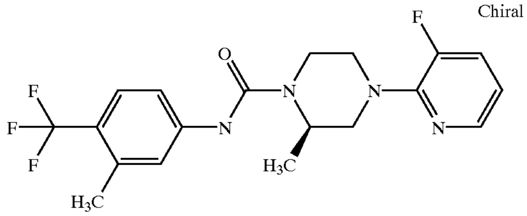 | (2R)-4-(3-fluoropyridin-2-yl)-2-methyl-N-[3-methyl-4-(trifluoromethyl)phenyl]piperazine-1-carboxamide | * |
| 123 | 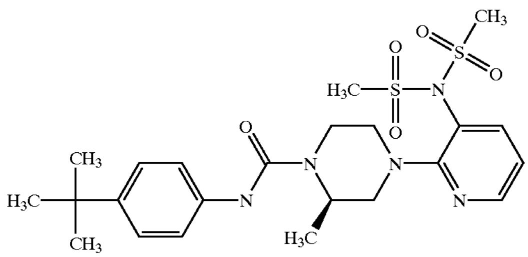 | (2R)-4-{3-[bis(methylsulfonyl)amino]pyridin-2-yl}-N-(4-tert-butylphenyl)-2-methylpiperazine-1-carboxamide | * |
| 124 | 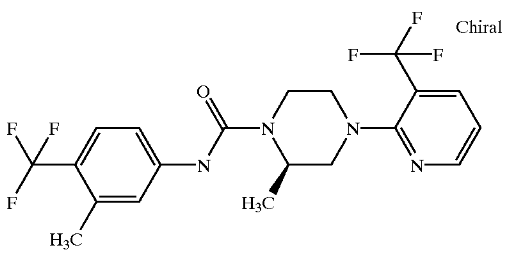 | (2R)-2-methyl-N-[3-methyl-4-(trifluoromethyl)phenyl]-4-[3-(trifluoromethyl)pyridin-2-yl]piperazine-1-carboxamide | * |
| 125 | 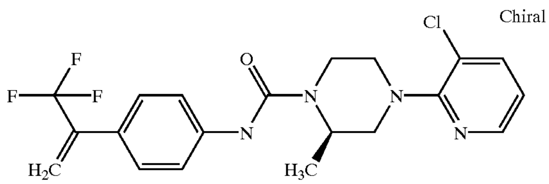 | (2R)-4-(3-chloropyridin-2-yl)-2-methyl-N-{4-[1-(trifluoromethyl)vinyl]phenyl}piperazine-1-carboxamide | * |
| 126 | 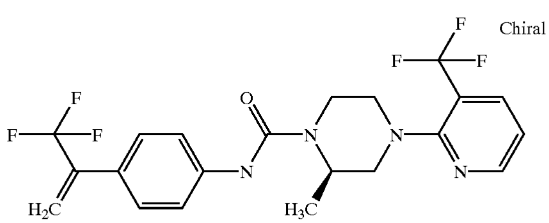 | (2R)-2-methyl-4-[3-(trifluoromethyl)pyridin-2-yl]-N-{4-[1-(trifluoromethyl)vinyl]phenyl}piperazine-1-carboxamide | * |
| 127 | 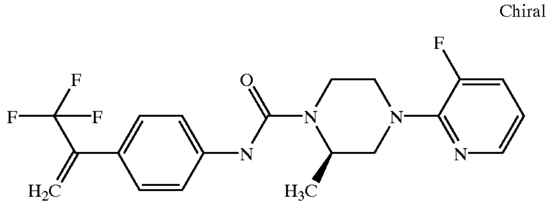 | (2R)-4-(3-fluoropyridin-2-yl)-2-methyl-N-{4-[1-(trifluoromethyl)vinyl]phenyl}piperazine-1-carboxamide | * |

TABLE V-continued

| Cmp # | Structure | Name | EC50 |
|---|---|---|---|
| 128 | Chiral | (2R)-N-(4-sec-butylphenyl)-4-(3-fluoropyridin-2-yl)-2-methylpiperazine-1-carboxamide | * |
| 129 | Chiral | (2R)-2-methyl-N-[4-(2,2,2-trifluoro-1-methylethyl)phenyl]-4-[3-(trifluoromethyl)pyridin-2-yl]piperazine-1-carboxamide | * |
| 130 | Chiral | (2R)-4-(3-fluoropyridin-2-yl)-2-methyl-N-[4-(2,2,2-trifluoro-1-methylethyl)phenyl]piperazine-1-carboxamide | * |
| 131 | Chiral | (2R)-4-(3-chloro-5-nitropyridin-2-yl)-2-methyl-N-[4-(trifluoromethyl)phenyl]piperazine-1-carboxamide | * |
| 132 | Chiral | (2R)-4-(5-amino-3-chloropyridin-2-yl)-2-methyl-N-[4-(trifluoromethyl)phenyl]piperazine-1-carboxamide | * |
| 133 | Chiral | (2R)-4-(3-fluoropyridin-2-yl)-N-[3-fluoro-4-(trifluoromethyl)phenyl]-2-methylpiperazine-1-carboxamide | * |

TABLE V-continued

| Cmp # | Structure | Name | | EC50 |
|---|---|---|---|---|
| 134 | 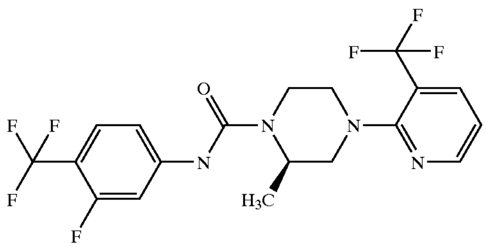 | Chiral | (2R)-N-[3-fluoro-4-(trifluoromethyl)phenyl]-2-methyl-4-[3-(trifluoromethyl)pyridin-2-yl]piperazine-1-carboxamide | * |
| 135 | 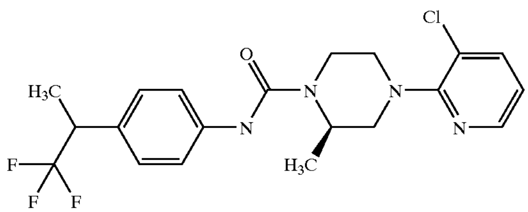 | Chiral | (2R)-4-(3-chloropyridin-2-yl)-2-methyl-N-[4-(2,2,2-trifluoro-1-methylethyl)phenyl]piperazine-1-carboxamide | * |
| 136 | 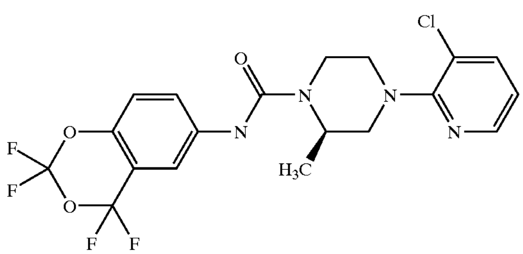 | Chiral | (2R)-4-(3-chlorpyridin-2-yl)-2-methyl-N-(2,2,4,4-tetrafluoro-4H-1,3-benzodioxin-6-yl)piperazine-1-carboxamide | * |
| 137 | 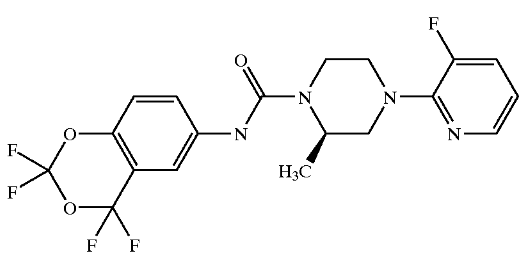 | Chiral | (2R)-4-(3-fluoropyridin-2-yl)-2-methyl-N-(2,2,4,4-tetrafluoro-4H-1,3-benzodioxin-6-yl)piperazine-1-carboxamide | * |
| 138 | 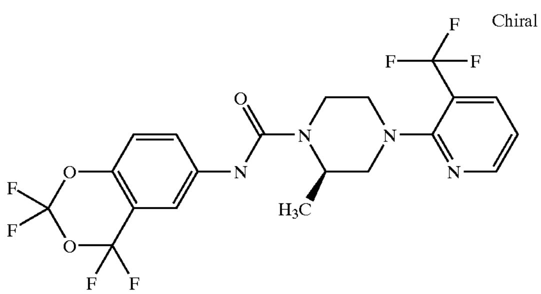 | Chiral | (2R)-2-methyl-N-(2,2,4,4-tetrafluoro-4H-1,3-benzodioxin-6-yl)-4-[3-(trifluoromethyl)pyridin-2-yl]piperazine-1-carboxamide | * |

TABLE V-continued

| Cmp # | Structure | Name | EC50 |
|---|---|---|---|
| 139 | Chiral | (2R)-4-[3-(aminosulfonyl)pyridin-2-yl]-N-(4-tert-butylphenyl)-2-methylpiperazine-1-carboxamide | * |
| 140 | Chiral | (2R)-N-(4-benzoylphenyl)-4-(3-chloropyridin-2-yl)-2-methylpiperazine-1-carboxamide | * |
| 141 | Chiral | (2R)-4-(3-chloropyridin-2-yl)-N-(4-iodophenyl)-2-methylpiperazine-1-carboxamide | * |
| 142 | Chiral | (2R)-4-(3-chloropyridin-2-yl)-N-(9H-flouren-2-yl)-2-methylpiperazine-1-carboxamide | * |
| 143 | Chiral | (2R)-N-(9H-fluoren-2-yl)-2-methyl-4-[3-(trifluoromethyl)pyridin-2-yl]piperazine-1-carboxamide | * |

TABLE V-continued

| Cmp # | Structure | Name | | EC50 |
|---|---|---|---|---|
| 144 | 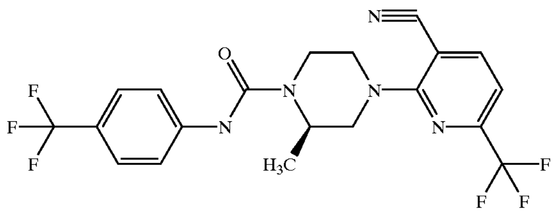 | Chiral | (2R)-4-[3-cyano-6-(trifluoromethyl)pyridin-2-yl]-2-methyl-N-[4-(trifluoromethyl)phenyl]piperazine-1-carboxamide | |
| 145 | 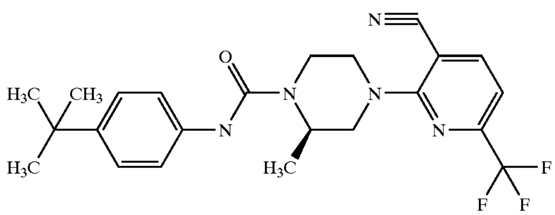 | Chiral | (2R)-N-(4-tert-butylphenyl)-4-[3-cyano-6-(trifluoromethyl)pyridin-2-yl]-2-methylpiperazine-1-carboxamide | |
| 146 | 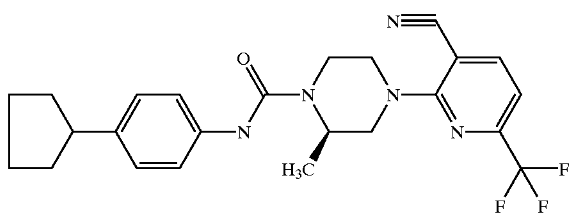 | Chiral | (2R)-4-[3-cyano-6-(trifluoromethyl)pyridin-2-yl]-N-(4-cyclopentylphenyl)-2-methylpiperazine-1-carboxamide | |
| 147 | 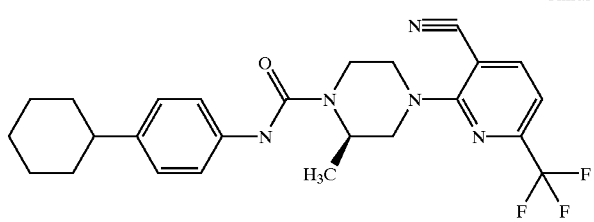 | Chiral | (2R)-4-[3-cyano-6-(trifluoromethyl)pyridin-2-yl]-N-(4-cyclohexylphenyl)-2-methylpiperazine-1-carboxamide | |
| 148 | 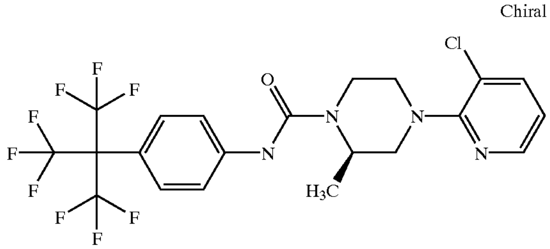 | Chiral | (2R)-4-(3-chloropyridin-2-yl)-2-methyl-N-{4-[2,2,2-trifluoro-1,1-bis(trifluoromethyl)-ethyl]phenyl}piperazine-1-carboxamide | * |
| 149 | 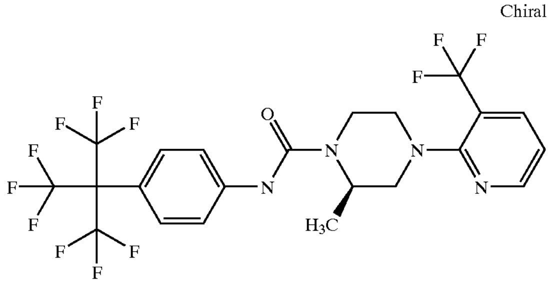 | Chiral | (2R)-2-methyl-N-{4-[2,2,2-trifluoro-1,1-bis(trifluoromethyl)-ethyl]phenyl}-4-[3-(trifluoromethyl)pyridin-2-yl]piperazine-1-carboxamide | * |

TABLE V-continued

| Cmp # | Structure | Name | EC50 |
|---|---|---|---|
| 150 | Chiral | (2R)-4-(3-chloropyridin-2-yl)-N-(3-iodophenyl)-2-methylpiperazine-1-carboxamide | * |
| 151 | Chiral | (2R)-4-(3-fluoropyridin-2-yl)-N-(3-iodophenyl)-2-methylpiperazine-1-carboxamide | * |
| 152 | Chiral | (2R)-N-(4-butylphenyl)-4-(3-chloropyridin-2-yl)-2-methylpiperazine-1-carboxamide | * |
| 153 | 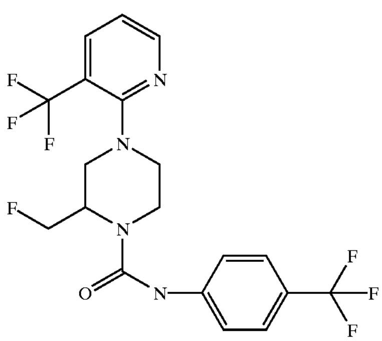 | 2-(fluoromethyl)-N-[4-(trifluoromethyl)phenyl]-4-[3-(trifluoromethyl)pyridin-2-yl]piperazine-1-carboxamide | * |
| 154 | Chiral | (2R)-4-(3-chloropyridin-2-yl)-2-methyl-N-[4-methyl-4-(trifluoromethyl)phenyl]piperazine-1-carboxamide | * |

TABLE V-continued

| Cmp # | Structure | Name | EC50 |
|---|---|---|---|
| 155 | 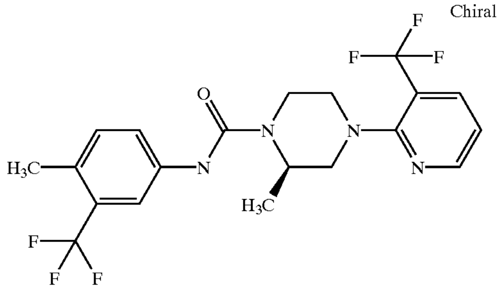 | (2R)-2-methyl-N-[4-methyl-3-(trifluoromethyl)phenyl]-4-[3-(trifluoromethyl)pyridin-2-yl]piperazine-1-carboxamide | * |
| 156 | 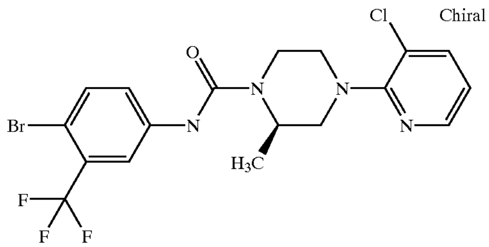 | (2R)-N-[4-bromo-3-(trifluoromethyl)phenyl]-4-(3-chloropyridin-2-yl)-2-methylpiperazine-1-carboxamide | * |
| 157 | 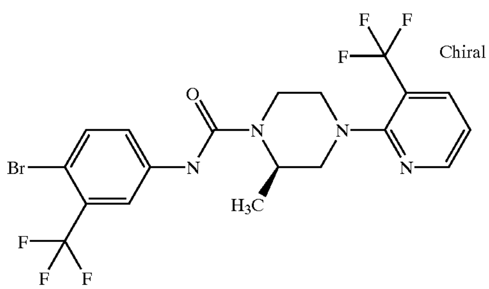 | (2R)-N-[4-bromo-3-(trifluoromethyl)phenyl]-2-methyl-4-[3-(trifluoromethyl)pyridin-2-yl]piperazine-1-carboxamide | * |
| 158 | 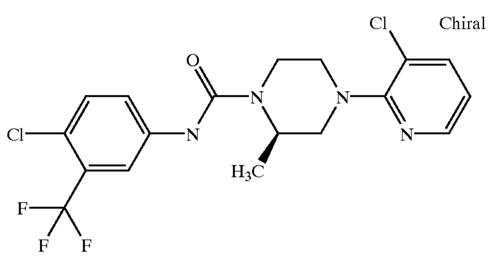 | (2R)-4-(3-chloropyridin-2-yl)-N-[4-chloro-3-(trifluoromethyl)phenyl]-2-methylpiperazine-1-carboxamide | * |
| 159 | 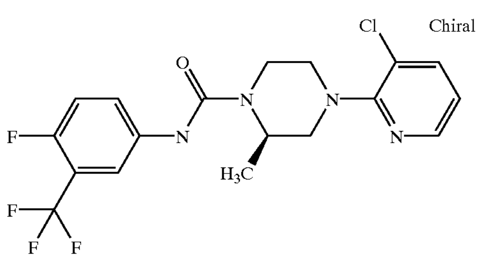 | (2R)-4-(3-chlorpyridin-2-yl)-N-[4-fluoro-3-(trifluoromethyl)phenyl]-2-methylpiperazine-1-carboxamide | * |

TABLE V-continued

| Cmp # | Structure | Name | EC50 |
|---|---|---|---|
| 160 | 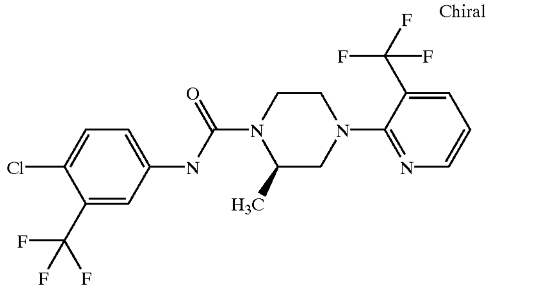 | (2R)-N-[4-chloro-3-(trifluoromethyl)phenyl]-2-methyl-4-[3-(trifluoromethyl)pyridin-2-yl]piperazine-1-carboxamide | * |
| 161 | 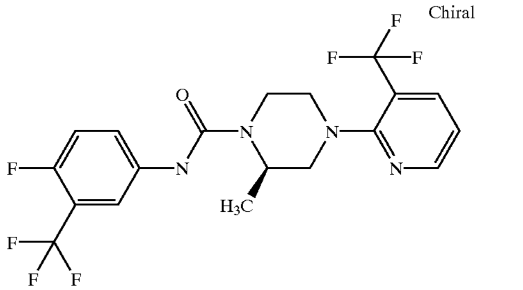 | (2R)-N-[4-fluoro-3-(trifluoromethyl)phenyl]-2-methyl-4-[3-(trifluoromethyl)pyridin-2-yl]piperazine-1-carboxamide | * |
| 162 | 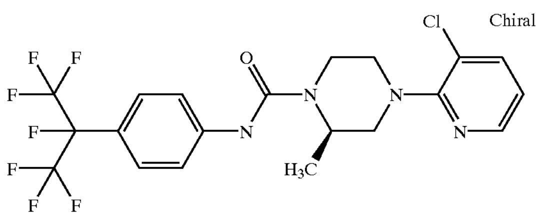 | (2R)-4-(3-chloropyridin-2-yl)-2-methyl-N-{4-[1,2,2,2-tetrafluoro-1-(trifluoromethyl)ethyl]phenyl}piperazine-1-carboxamide | * |
| 163 | 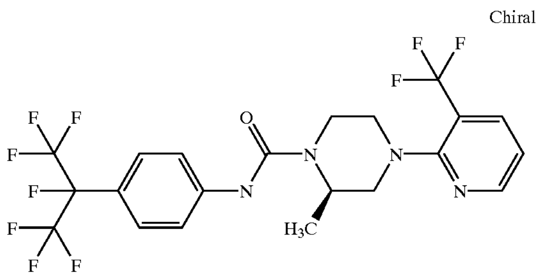 | (2R)-2-methyl-N-{4-[1,2,2,2-tetrafluoro-1-(trifluoromethyl)ethyl]phenyl}-4-[3-(trifluoromethyl)pyridin-2-yl]piperazine-1-carboxamide | * |

TABLE VI

| Cmp. # | Structure | NAME | EC50 |
|---|---|---|---|
| 164 | | (2R)-4-(3-chloropyrazin-2-yl)-2-methyl-N-{4-[1,2,2,2-tetrafluoro-1-(trifluoromethyl)ethyl]phenyl}piperazine-1-carboxamide | * |

## TABLE VI-continued

| Cmp. # | Structure | NAME | EC50 |
|---|---|---|---|
| 165 | 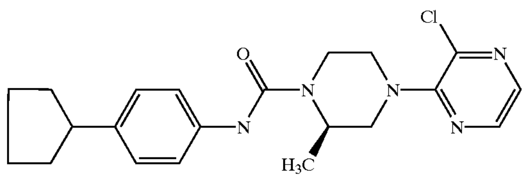 | Chiral (2R)-4-(3-chloropyrazin-2-yl)-2-methyl-N-{4-cyclopentyl-phenyl}piperazine-1-carboxamide | * |
| 166 | 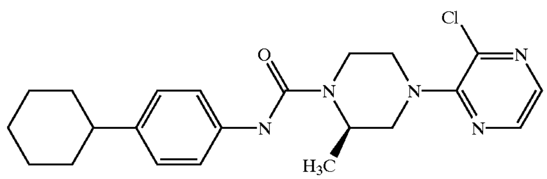 | Chiral (2R)-4-(3-chloropyrazin-2-yl)-2-methyl-N-{4-cyclohexyl-phenyl}piperazine-1-carboxamide | * |
| 167 | 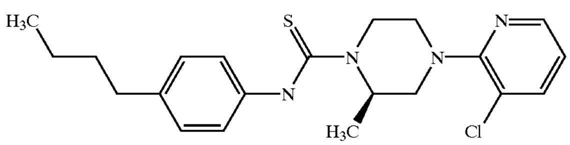 | Chiral | * |
| 168 | 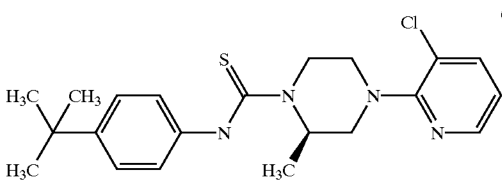 | Chiral | * |
| 169 | 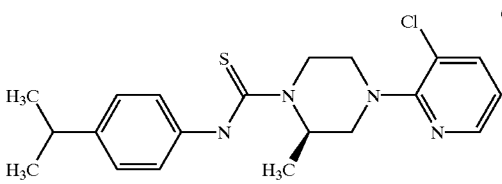 | Chiral | * |
| 170 | 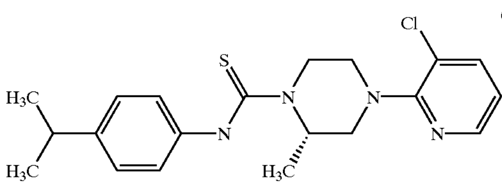 | Chiral | * |
| 171 | 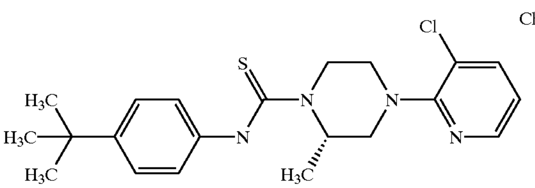 | Chiral | * |

TABLE VI-continued

| Cmp. # | Structure | NAME | EC50 |
|---|---|---|---|
| 172 | 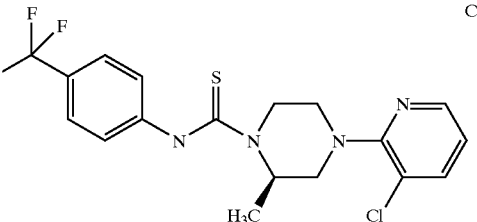 Chiral | | * |
| 173 | 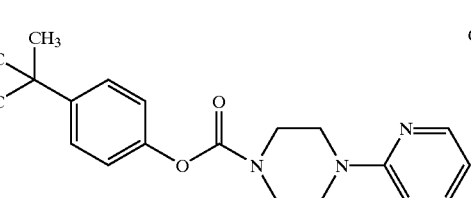 Chiral | | * |
| 174 | 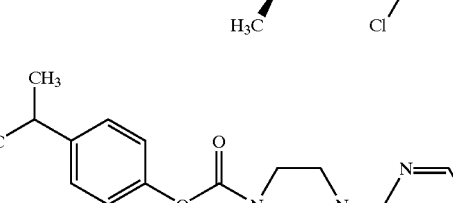 Chiral | | * |

*in Table III —Table VI indicates a EC50 value of less than 1 uM in an antagonist assay for Capsaicin receptor mediated calcium mobilization.
An assay for Capsaicin receptor mediated calcium mobilization is described in example 11

Example 10
Capsaicin Receptor Binding Assay

The following assay is a standard assay of capsaicin receptor binding that may be used to determine the binding affinity of compounds for the capsaicin (VR1) receptor.

Materials

[$^3$H]Resiniferatoxin (RTX; 37 Ci/mmol) was synthesized by and obtained from the Chemical Synthesis and Analysis Laboratory, National Cancer Institute-Frederick Cancer Research and Development Center, Frederick, Md. [$^3$H] RTX may also be obtained from commercial vendors, e.g., Amersham Pharmacia Biotech, Inc. 800 Centennial Avenue, P.O. Box 1327, Piscataway, N.J. 08855 (code TRK 1069). Nonradioactive RTX may be purchased from Alexis Corp. (San Diego, Calif.) and capsazepine from RBI (Natick, Mass).

Molecular Biology

A cDNA encoding the full length human capsaicin receptor (SEQ ID NO:1 or SEQ ID NO:2) is subcloned in the appropriate orientation for expression into an expression vector such as pcDNA3.1 (Invitrogen, Carlsbad, Calif.) or pUHG102-3 (Clontech, Palo Alto, Calif.) for recombinant expression in mammalian cells.

Cell Culture

Human embryonic kidney (HEK293) cells are transfected with a pcDNA3.1 expression consrtuct encoding the full length human capsaicin receptor (i.e. containing either the nucleotide sequence of SEQ ID NO:1 and SEQ ID NO:2) using standard methods. These transfected cells are selected for two weeks in media containing G418 (400 ug/ml) and then maintained as a pool of stably transfected cells.

pUHG102 VR1 expression plasmids are transfected into Chinese Hamster Ovary (CHO) cells containing the pTet Off Regulator plasmid (Clontech). In these cells, expression of the pUHG plasmid is repressed in the presence of tetracycline but is induced upon removal of the antibiotic. Stable clones are isolated in culture medium containing puromycin (10 ug/ml) and maintained in medium supplemented with tetracycline (1 ug/ml) Cells utilized for assays are grown in culture medium without antibiotic for 48–72 hours prior to use. For radioligand binding experiments, cells are seeded in T175 cell culture flasks in media without antibiotics and grown to approximately 90% confluency. The flasks are then washed with PBS and harvested in PBS containing 5 mM EDTA. The cells are pelleted by gentle centrifugation and stored at −80° C. until assayed.

Membrane Preparations

Previously frozen cells are disrupted with the aid of a tissue homogenizer in ice-cold HEPES homogenization buffer (5 mM KCl 5, 5.8 mM NaCl, 0.75 mM CaCl$_2$, 2 mM MgCl$_2$, 320 mM sucrose, and 10 mM HEPES pH 7.4). Tissue homogenates are first centrifuged for 10 min at 1000×g (4° C.) to remove the nuclear fraction and debris and then the supernatant from the first centrifugation is further centrifuged for 30 min at 35,000×g (4° C.) to obtain a partially purified membrane fraction. Membranes are resuspended in the HEPES homogenization buffer prior to being assayed. An aliquot of this membrane homogenate is used to determine protein concentration via the Bradford method (BIO-RAD Protein Assay Kit, #500-0001, BIO-RAD, Hercules, Calif.).

Radioligand Binding

Binding studies with [$^3$H]RTX are carried out essentially according to a published protocol (Szallasi and Blumberg, 1992, *J. Pharmacol. Exp. Ter.* 262: 883–888) in which non-specific RTX binding is reduced by adding bovine alpha, acid glycoprotein (100 ug per tube) after the binding reaction has been terminated. The homogenate is centrifuged as before and resuspended to a protein concentration of 333 ug/ml in homogenization buffer. Binding assay mixtures were set up on ice and contained [$^3$H]RTX (specific activity 2200 mCi/ml), 2 ul non-radioactive ligands test compound, 0.25 mg/ml bovine serum albumin (Cohn fraction V), and 5×10$^4$–1×10$^5$ VR1-transfected cells. The final volume was adjusted to 500 ul (competition binding assays) or 1,000 ul (saturation binding assays) with the ice-cold HEPES homogenization buffer solution (pH 7.4) described above. Non-specific binding was defined as that occurring in the presence of 1 uM non-radioactive RTX. For saturation binding, [$^3$H]RTX was added in the concentration range of 7–1,000 pM, using 1 to 2 dilutions. Typically 11 concentration points are collected per saturation binding curve.

Competition binding assays were performed in the presence of 60 pM [$^3$H]RTX and various concentrations of competing ligands. The binding reactions are initiated by transferring the assay mixtures into a 37° C. water bath and are terminated following a 60 min incubation period by cooling the tubes on ice. Membrane-bound RTX is separated from free, as well as any alpha$_1$-acid glycoprotein-bound RTX, by filtration onto WALLAC glass fiber filters (PERKIN-ELMER, Gaithersburg, Md.) which are pre-soaked with 1.0% PEI (polyethyleneimine) for 2 hours prior to use. Filters are allowed to dry overnight then counted in a WALLAC 1205 BETA PLATE counter after addition of WALLAC BETA SCINT scintillation fluid.

Equilibrium binding parameters were determined by fitting the allosteric Hill equation to the measured values with the aid of the computer program FIT P (Biosoft, Ferguson, Mo.) as described previously (Szallasi, et al. (1993) *J. Pharmacol. Exp. Ther.* 266:678–683)).

Though compounds exhibiting K$_i$ values for capsaicin receptors of greater than 1 uM are generally less preferred as pharmaceutical agents, useful compounds of the invention exhibit K$_i$ values for capsaicin receptors of less than 4 uM, more preferred compounds exhibit K$_i$ values of less than 1 uM, even more preferred compounds exhibit K$_i$ values of less than 100 nM, more highly preferred compounds exhibit K$_i$ values of less than 50 nM, even more highly preferred compounds exhibit K$_i$ values of less than 25 nM and the most preferred compounds of the invention yield K$_i$ values of less than or about equal to 10 nM in this assay.

Example 11

Calcium Mobilization Assay

The following assay can be used to monitor the response of cells capsaicin receptors to capsaicin and other vanilloid ligands of the capsaicin receptor. The assay can also be used to determine if test compounds act as agonists or antagonists of capsaicin receptors.

Cells transfected with expression plasmids (as described in Example 10) and thereby expressing the human capsaicin receptor are seeded and grown to 70–90% confluency in FALCON black-walled, clear-bottomed 96-well plates (#3904, BECTON-DICKINSON, Franklin Lakes, N.J.). The culture media are emptied from the 96 well plates and FLUO-3 AM calcium sensitive dye (Molecular Probes, Eugene, Oreg.) is added to each well (dye solution: 1 mg FLUO-3 AM, 440 uL DMSO and 440 ul 20% pluronic acid in DMSO, diluted 1:4, 50 ul diluted solution per well). Plates are covered with aluminum foil and incubated at 37° C. for 1–2 hours in an environment containing 5% $CO_2$. After the incubation the dye is emptied from the plates, and the cells are washed once with Krebs-Ringer HEPES (KRH) buffer (25 mM HEPES, 5 mM KCl, 0.96 mM $NaH_2PO_4$, 1 MM $MgSO_4$, 2 mM $CaCl_2$, 5 mM glucose, 1 mM probenecid, pH 7.4), and resuspended in KRH buffer.

Agonist (e.g., olvanil, capsaicin, or RTX)-induced calcium mobilization is monitored using either FLUOROSKAN ASCENT (Labsystems, Franklin, Mass.) or FLIPR (fluorometric imaging plate reader system, Molecular Devices, Sunnyvale, Calif.) instruments. Similarly, varying concentrations of the antagonists ruthenium red or capsazepine are added to cells concurrently with agonist (e.g., 25–50 nM capsaicin). For agonist-induced calcium responses, data obtained between 30 and 60 seconds after agonist application are used to generate the EC$_{50}$ values. KALEIDAGRAPH software (Synergy Software, Reading, Pa.) was utilized to fit the data to the equation:

$$y=a*(1/(1+(b/x)^c))$$

to determine the EC$_{50}$ for the response. In this equation, y is the maximum fluorescence signal, x is the concentration of the agonist or antagonist, a is the E$_{max}$, b corresponds to the EC$_{50}$ or IC$_{50}$ value, and finally, c is the Hill coefficient.

Assay for Determination of Capsaicin Receptor Antagonist Effects

In order to measure the ability of a test compound to antagonize (inhibit) the response of cells expressing capsaicin receptors to capsaicin or other vanilloid agonist, the EC$_{50}$ of capsaicin is first determined.

An additional 20 ul of KRH buffer and 1 ul DMSO is added to each well of cells, prepared as described above. 100 ul capsaicin in KRH buffer is automatically transferred by the FLIPR instrument to each well. An 8-point concentration response curve, with final capsaicin concentrations of 1 nM to 3 uM, is used to determine capsaicin EC$_{50}$.

Test compounds are dissolved in DMSO, diluted in 20 ul KRH buffer so that the final concentration of test compounds in the assay well is between 1 uM and 5 uM, and added to cells prepared as described above. The 96 well plates containing prepared cells and test compounds are incubated in the dark, at room temperature for 0.5–6 hours. It is important that the incubation not continue beyond 6 hours. Just prior to determining the fluorescence response, 100 ul capsaicin in KRH buffer at twice the EC$_{50}$ concentration determined from the concentration response curve is automatically added by the FLIPR instrument to each well of the 96 well plate for a final sample volume of 200 ul and a final capsaicin concentration equal to the EC$_{50}$. The final concentration of test compounds in the assay wells is between 1 uM and 5 uM. Typically cells exposed to one EC$_{50}$ of capsaicin exhibit a fluorescence response of about 10,000 Relative Fluorescence Units. Antagonists of the capsaicin receptor decrease this response by about 20%, preferably by about 50%, and most preferably by at least 80% as compared to matched control. The concentration of antagonist required to provide a 50% decrease is the EC$_{50}$ for the antagonist (also referred to as the IC$_{50}$).

Equilibrium binding parameters may be determined as described in Example 10.

Assay for Determination of Capsaicin Receptor Agonist Effects

The ability of a compound to act as an agonist of the capsaicin receptor may be determined by measuring the fluorescence response of cells expressing capsaicin receptors, using the methods described above, in the absence of capsaicin, RTX, or other known capsaicin receptor agonists. Compounds that cause cells to exhibit fluorescence above background are capsaicin receptor agonists. Highly preferred compounds of the invention are antagonists that are essentially free of agonist activity as demonstrated by the absence of detectable agonist activity in such an assay at compound concentrations below 4 nM, more preferably at concentrations below 10 uM and most preferably at concentrations less than or equal to 100 uM.

Example 12
NPY Y5 Receptor Binding Assay

The following assay is a standard assay for NPY Y5 (neuropeptide Y receptor 5) receptor binding that may be used to determine the affinity of compounds for the NPY Y5 receptor. Expression of a recombinant human Y5 receptor in cultured cells and receptor binding assays using of membranes prepared from such cells has been described previously, e.g. in U.S. Pat. No. 5,602,024 at columns 17–20. U.S. Pat. No. 5,602,024 is hereby incorporated by reference for its teachings regarding a recombinant human Y5 receptor, expression of this receptor in cultured cells, and receptor binding assays using membranes prepared from such cells.

Cell Culture

Baculovirus-infected Sf9 cells expressing recombinant human NPY Y5 receptors are harvested at 48 hrs.

Membrane Preparation

Sf9 cell pellets are resuspended in lysis buffer (20 mM Tris-HCL, 5 mM EDTA, 0.5 ug/ml leupeptin, 2 ug/ml Aprotinin, 200 uM PMSF, pH 7.4) and homogenized using a POLYTRON homogenizer (setting 3 for 25–30 seconds). The homogenate was centrifuged (536×g/10 minutes/4° C.) to pellet the nuclei. The supernatant containing isolated membranes are decanted to a clean centrifuge tube, centrifuged (48,000×g/30 minutes, 4° C.) and resuspended in 30 ml homogenization buffer. This centrifugation and resuspension step is repeated twice. The final pellet is resuspended in ice cold Dulbecco's PBS containing 5 mM EDTA and stored in aliquots at −80° C. until needed. The protein concentration of the resulting membrane preparation is measured using the Bradford Protein assay, as described in Example 3. By this measure, a 1-liter culture of cells typically yields 100–125 mg of total membrane protein.

Thawed Sf9 membranes are washed with PBS and resuspended by Dounce homogenization (tight pestle) in binding buffer (50 mM Tris-HCl, 5 mM KCl, 120 mM NaCl, 2 mM $CaCl_2$, 0.1% BSA, pH 7.4).

For competition binding analysis, membranes (10–25 ug) in 150 ul binding buffer are added to polypropylene tubes or 96-well deepwell plates containing [$^{125}$I]PYY (porcine, NEN, Boston, Mass.)/GTP. Final concentration of [$^{125}$]PYY is 30–35 pM/assay well; final concentration of GTP is 100 uM/well. Nonspecific binding is determined in the presence of 1 uM NPY (human, American Peptide Co., Sunnyvale, Calif.) and accounts for less than 10% of total binding. Test compounds at a concentration of 1–4 uM in 2 ul DMSO are added to the assay mixtures. Final assay volume is 250 ul. For competition analysis test compounds are added at concentrations ranging from $10^{-12}$ to $10^{-6}$ M. Typically 11 concentration points are collected per saturation binding curve. Following a 2-hour incubation at room temperature, the assay reactions are terminated by rapid vacuum filtration. Samples are filtered over presoaked (in polyethyleneimine for 2 hours prior to use) GF/C WHATMAN filters and rinsed 2 times with 5 mls cold binding buffer without BSA. Remaining bound radioactivity is quantified by gamma counting. Ki values may be determined by the method described in Example 10.

Preferred compounds of the invention exhibit 10-fold greater affinity for the capsaicin receptor than for the chimeric NPY Y5 receptor, more preferred compounds of the invention also exhibit 100-fold greater affinity for the capsaicin receptor than for the chimeric NPY Y5 receptor, and still more preferred compounds of the invention also exhibit 1000-fold greater affinity for the capsaicin receptor than for the chimeric NPY Y5 receptor. Most highly preferred compounds of the invention do not exhibit detectable binding at the NPY 5 receptor.

Example 13
Preparation of Radiolabeled Probe Compounds of the Invention

The compounds of the invention are prepared as radiolabeled probes by carrying out their synthesis using precursors comprising at least one atom that is a radioisotope. The radioisotope is preferably selected from of at least one of carbon (preferably $^{14}$C), hydrogen (preferably $^{3}$H), sulfur (preferably $^{35}$S), or iodine (preferably $^{125}$I). Such radiolabeled probes are conveniently synthesized by a radioisotope supplier specializing in custom synthesis of radiolabeled probe compounds. Such suppliers include Amersham Corporation, Arlington Heights, Ill.; Cambridge Isotope Laboratories, Inc. Andover, Mass.; SRI International, Menlo Park, Calif.; Wizard Laboratories, West Sacramento, Calif.; ChemSyn Laboratories, Lexena, Kans.; American Radiolabeled Chemicals, Inc., St. Louis, Mo.; and Moravek Biochemicals Inc., Brea, Calif.

Tritium labeled probe compounds are also conveniently prepared catalytically via platinum-catalyzed exchange in tritiated acetic acid, acid-catalyzed exchange in tritiated trifluoroacetic acid, or heterogeneous-catalyzed exchange with tritium gas. Such preparations are also conveniently carried out as a custom radiolabeling by any of the suppliers listed in the preceding paragraph using the compound of the invention as substrate. In addition, certain precursors may be subjected to tritium-halogen exchange with tritium gas, tritium gas reduction of unsaturated bonds, or reduction using sodium borotritide, as appropriate.

Examples 14a and 14b
Preparation of Radiolabeled Aryl Piperazine Capsaicin Receptor Ligands Example 14a Scheme 3

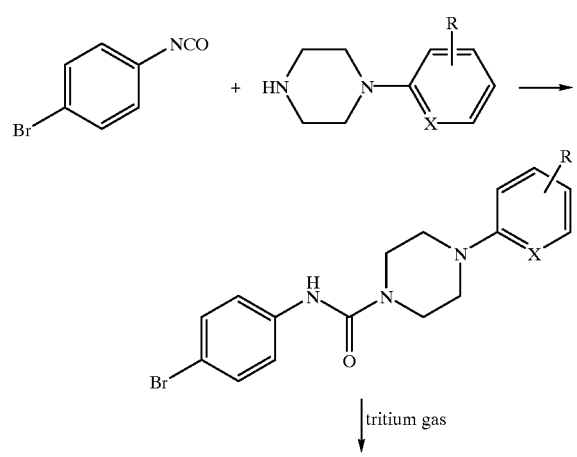

-continued

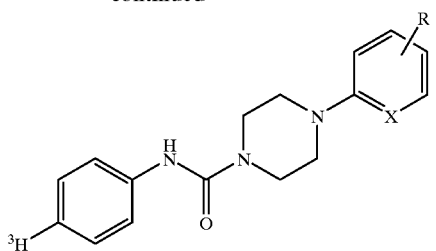

Example 14b

Scheme 4

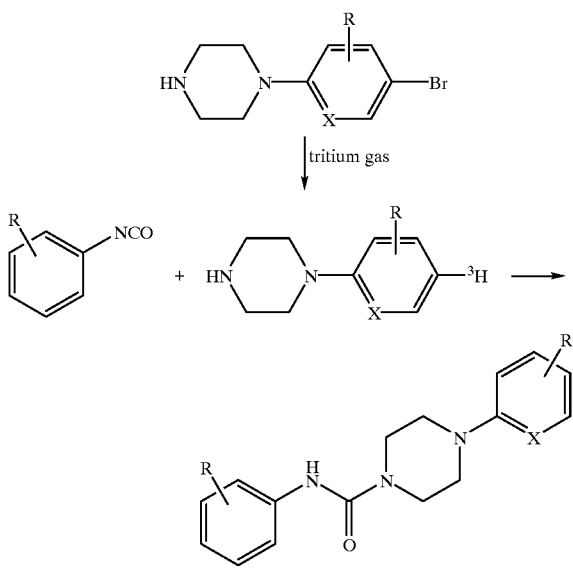

Example 15
Receptor Autoradiography

Receptor autoradiography (receptor mapping) is carried out in vitro as described by Kuhar in sections 8.1.1 to 8.1.9 of Current Protocols in Pharmacology (1998) John Wiley & Sons, New York, using radiolabeled compounds of the invention prepared as described in the preceding Example.

Example 16
Additional Aspects of Preferred Compounds of the Invention

The most preferred compounds of the invention are suitable for pharmaceutical use in treating human patients. Accordingly, such preferred compounds are non-toxic. They do not exhibit single or multiple dose acute or long-term toxicity, mutagenicity (e.g., as determined in a bacterial reverse mutation assay such as an Ames test), teratogenicity, tumorogenicity, or the like, and rarely trigger adverse effects (side effects) when administered at therapeutically effective dosages.

Preferably, administration of such preferred compounds of the invention at certain doses (i.e., doses yielding therapeutically effective in vivo concentrations or preferably doses of 0.01, 0.05. 0.1, 0.5, 1, 5, 10, 40, or 50 mg/kg administered parenterally or prefrerably orally) does not result in prolongation of heart QT intervals (i.e., as determined by electrocardiography, e.g., in guinea pigs, minipigs or dogs). When administered daily for 5 or preferably ten days, such doses of such preferred compounds also do not cause liver enlargement resulting in an increase of liver to body weight ratio of more than 100%, preferably not more than 75% and more preferably not more than 50% over matched controls in laboratory rodents (e.g., mice or rats). In another aspect such doses of such preferred compounds also preferably do not cause liver enlargement resulting in an increase of liver to body weight ratio of more than 50%, preferably preferably not more than 25%, and more preferably not more than 10% over matched untreated controls in dogs or other non-rodent mammals.

In yet another aspect such doses of such preferred compounds also preferably do not promote the release of liver enzymes (e.g., ALT, LDH, or AST) from hepatocytes in vivo. Preferably such doses do not elevate serum levels of such enzymes by more than 100%, preferably not by more than 75% and more preferably not by more than 50% over matched untreated controls in vivo in laboratory rodents. Similarly, concentrations (in culture media or other such solutions that are contacted and incubated with cells in vitro) equivalent to two, fold, preferably five-fold, and most preferably ten-fold the minimum in vivo therapeutic concentration do not cause release of any of such liver enzymes from hepatocytes in vitro into culture medium above baseline levels seen in media from untreated cells.

Because side effects are often due to undesirable receptor activation or antagonism, preferred compounds of the invention exert their receptor-modulatory effects with high selectivity. This means that they do not bind to certain other receptors (other than capsaicin receptors) with high affinity, but rather only bind to, activate, or inhibit the activity of such other receptors with affinity constants of greater than 100 nanomolar, preferably greater than 1 micromolar (uM), more preferably greater than 10 uM and most preferably greater than 100 uM. Such receptors preferably are selected from the group including ion channel receptors, including sodium ion channel receptors, neurotransmitter receptors such as alpha- and beta-adrenergic receptors, muscarinic receptors (particularly m1, m2, and m3 receptors), dopamine receptors, and metabotropic glutamate receptors; and also include histamine receptors and cytokine receptors, e.g., interleukin receptors, particularly IL-8 receptors. The group of other receptors to which preferred compounds do not bind with high affinity also includes $GABA_A$ receptors, bioactive peptide receptors (including NPY and VIP receptors), neurokinin receptors, bradykinin receptors (e.g., BK1 receptors and BK2 receptors), and hormone receptors (including androgen receptors, thyrotropin releasing hormone receptors and melanocyte-concentrating hormone receptors).

Example 16a
Sodium Ion Channel and Anti-Androgen Activity Criteria

Preferred compounds of the invention do not exhibit significant activity as sodium ion channel blockers, exhibiting less than 15 percent inhibition, and more preferably less than 10 percent inhibition, of sodium channel specific ligand (e.g., batrachotoxin, tetrodotoxin, or saxitoxin) binding when present at a concentration of 4 uM or less.

Preferred compounds of the invention do not exhibit significant androgen bioactivity, more preferably they do not exhibit significant androgen antagonist activity, e.g., in vivo, in a Hershberger assay, or in vitro, in an assay such as that described by Nellemann et al., *Toxicology* 2001, 163(1): 29–38. Preferred compounds of the invention exhibit less than a 15% inhibition, more preferably less than a 10%, and most preferably less than 5% inhibition of androgen receptor activation in this in vitro assay when present at concentrations of 4 uM or less.

By significant activity is meant results varying from control at the p<0.1 level or more preferably at the p<0.05 level of significance as measured using a standard parametric assay of statistical significance such as a student's T test.

Example 16b

Microsomal in vitro Half-life

Compound half-life values ($t_{1/2}$ values) may be determined via the following standard liver microsomal half-life assay. Pooled Human liver microsomes are obtained from XenoTech LLC, 3800 Cambridge St., Kansas City, Kan. 66103 (catalog # H0610). Such liver microsomes may also be obtained, e.g., from In Vitro Technologies, Baltimore, Md. 21227, or from Tissue Transformation Technologies, Edison, N.J. 08837. Reactions are preformed as follows:

Reagents

Phosphate buffer: 19 mL 0.1 M $NaH_2PO_4$, 81 mL 0.1 $Na_2HPO_4$, adjusted to pH 7.4 with $H_3PO_4$.

CoFactor Mixture: 16.2 mg NADP, 45.4 mg Glucose-6-phosphate in 4 mL 100 mM $MgCl_2$.

Glucose-6-phosphate dehydrogenase: 214.3 ul glucose-6-phosphate dehydrogenase suspension (Boehringer-Manheim catalog no. 0737224, distributed by Roche Molecular Biochemicals, Indianapolis, Ind. 46250) is diluted into 1285.7 ul distilled water.

Starting Reaction Mixture: 3 mL CoFactor Mixture, 1.2 mL Glucose-6-phosphate dehydrogenase.

Reaction 6 test reactions are prepared, each containing 25 ul microsomes, 5 ul of a 100 uM solution of test compound, and 399 ul 0.1 M phosphate buffer. A seventh reaction is prepared as a positive control containing 25 ul microsomes, 399 ul 0.1 M phosphate buffer, and 5 ul of a 100 uM solution of a compound with known metabolic properties (e.g. DIAZEPAM or CLOZEPINE). Reactions are preincubated at 39° C. for 10 minutes. 71 ul Starting Reaction Mixture is added to 5 of the 6 test reactions and to the positive control, 71 ul 100 mM $MgCl_2$ is added to the sixth test reaction, which is used as a negative control. At each time point (0, 1, 3, 5, and 10 minutes) 75 ul of each reaction mix is pipetted into a well of a 96-well deep-well plate containing 75 ul ice-cold acetonitrile. Samples are vortexed and centrifuged 10 minutes at 3500 rpm (Sorval T 6000D centrifuge, H1000B rotor). 75 ul of supernatant from each reaction is transferred to a well of a 96-well plate containing 150 ul of a 0.5 uM solution of a compound with a known LCMS profile (internal standard) per well. LCMS analysis of each sample is carried out and the amount of unmetabolized test compound is measured as AUC, compound concentration vs time is plotted, and the $t_{1/2}$ value of the test compound is extrapolated.

Preferred compounds of the invention exhibit in vitro $t_{1/2}$ values of greater than 10 minutes and less than 4 hours. Most preferred compounds of the invention exhibit in vitro half-life values of between 30 minutes and 1 hour in human liver microsomes.

Example 16c

MDCK Toxicity Assay

Compounds causing acute cytotoxicity will produce a substantial decrease of ATP production by Madin Darby canine kidney (MDCK) cells in the following assay. Preferred compounds of the invention will not.

MDCK cells, ATCC no. CCL-34 (American Type Culture Collection, Manassas, Va.) are maintained in sterile conditions following the instructions in the ATCC production information sheet. The PACKARD, (Meriden, Conn.) ATP-LITE-M Luminescent ATP detection kit, product no. 6016941, allows measurement ATP production in MDCK cells.

Prior to assay 1 ul of test compound or control sample is pipetted into PACKARD (Meriden, Conn.) clear bottom 96-well plates. Test compounds and control samples are diluted in DMSO to give final concentration in the assay of 10 micromolar, 100 micromolar, or 200 micromolar. Control samples are drug or other compounds having known toxicity properties.

Confluent MDCK cells are trypsinized, harvested, and diluted to a concentration of $0.1 \times 10^6$ cells/ml with warm (37° C.) VITACELL Minimum Essential Medium Eagle (ATCC catalog #30–2003). 100 ul of cells in medium is pipetted into each of all but five wells of each 96-well plate. Warm medium without cells (100 ul) is pipetted in the remaining five wells of each plate to provide standard curve control wells. These wells, to which no cells are added, are used to determine the standard curve. The plates are then incubated at 37° C. under 95% $O_2$, 5% $CO_2$ for 2 hours with constant shaking. After incubation, 50 ul of mammalian cell lysis solution is added per well, the wells are covered with PACKARD TOPSEAL stickers, and plates are shaken at approximately 700 rpm on a suitable shaker for 2 minutes.

During the incubation, PACKARD ATP LITE-M reagents are allowed to equilibrate to room temperature. Once equilibrated the lyophilized substrate solution is reconstituted in 5.5 mls of substrate buffer solution (from kit). Lyophilized ATP standard solution is reconstituted in deionized water to give a 10 mM stock. For the five control wells, 10 ul of serially diluted PACKARD standard is added to each of the five standard curve control wells to yield a final concentration in each subsequent well of 200 nM, 100 nM, 50 nM, 25 nM, and 12.5 nM.

PACKARD substrate solution (50 ul) is added to all wells. Wells are covered with PACKARD TOPSEAL stickers, and plates are shaken at approximately 700 rpm on a suitable shaker for 2 minutes. A white PACKARD sticker is attached to the bottom of each plate and samples are dark adapted by wrapping plates in foil and placing in the dark for 10 minutes. Luminescence is then measured at 22° C. using a luminescence counter, e.g. PACKARD TOPCOUNT Microplate Scintillation and Luminescense Counter or TECAN SPECTRAFLUOR PLUS.

Luminescence values at each drug concentration are compared to the values computed from the standard curve for that concentration. Preferred test compounds exhibit luminescence values 80% or more of the standard, or preferably 90% or more of the standard, when a 10 micromolar (uM) concentration of the test compound is used. When a 100 uM concentration of the test compound is used, preferred test compounds exhibit luminescence values 50% or more of the standard, or more preferably 80% or more of the standard. Luminescence values less than 50% of the standard indicate a substantial decrease of ATP production.

Example 18

Animal Models for Determining Pain Relief and Sedation

The following experimental protocols can be used to determine the degree of pain relief and sedation provided by compounds of the invention, e.g., in comparison to pain relief and sedation provided by morphine or pain relief by ibuprofen.

Example 18a

CFA Arthritis Model

Male SD rats are injected with 200 ml of CFA (0.1 mg heat killed and dried M. tuberculosis/ml) in the hind paw (100 ml on the dorsal and 100 ml on the plantar surface of the paw) essentially as described by Bertorelli R, Corradini L, Rafiq K, Tupper J, Calo G, Ongini E., *Br J Pharmacol.* 1999 128(6):1252–8 and by Stein C, Millan M J, Herz A. *Pharmacol Biochem Behav.* 1988 31(2):455–51.

Rats are tested for thermal (as described by Hargreaves K, Dubner R, Brown F, Flores C, Joris J. Pain. 1988 32(1):77–88) and mechanical (as described by Tal M, Eliav E. Pain. March 1996; 64(3):511–8) sensitivities on days 5, 6, and 7. Baseline data should be obtained for each animal prior to CFA injection.

On day 7, animals are treated orally with a compound of the invention, morphine or vehicle (2% vitamin E-TPGS) 1 hour prior to testing. Note: an oral dose of 5 mg/kg morphine has sedative effects.

Results are conveniently expressed as % of Maximum Potential Efficacy (MPE). 0% MPE is defined as analgesic effect of vehicle, 100% MPE is defined as an animal's return to baseline level of thermal or mechanical sensitivity.

Example 18b

Mechanical Allodynia

This assay determines the effectiveness of compounds of Formulae I–IX and Formulae A–F in relieving at least one of the symptoms in an in vivo model of pain produced by spinal nerve ligation, namely mechanical allodynia.

Tactile allodynia is induced in rats using the procedures described by Bennet and Xie, Pain 1988, 33:87–107. Rats are anesthetized, e.g., with an intraperitoneal dose of pentobarbital sodium (65 mg/kg) with additional doses of anesthetic given as needed. The lateral aspect of each rat's hind limb is shaved and disinfected. Using aseptic technique, an incision is made on the lateral aspect of the hind limb at the mid-thigh level. The biceps femoris is bluntly dissected to expose the sciatic nerve. On one hind limb of each rat, four loosely tied ligatures are made around the sciatic nerve approximately 1–2 millimeters apart. On the other side of each rat, an identical dissection is performed except that the sciatic nerve is not ligated. The muscle is closed with a continuous suture pattern, and the skin is closed with wound clips or sutures.

Mechanical sensitivity is assessed using a procedure described by Chaplan et al. J. Neurosci. Methods 1994, 53:55–63. A series of Von Frey filaments of varying rigidity strength (typically eight filaments in the series) are applied to the plantar surface of the hind paw ipsilaterial to the ligations with just enough force to bend the filament. The filaments are held in this position for no more than three seconds or until a positive allodynic response is displayed by the rat. A positive allodynic response consists of lifting the affected paw followed immediately by licking or shaking of the paw. The order and frequency with which the individual filaments are applied are determined by using Dixon up-down method. Testing is initiated with the middle hair of the series with subsequent filaments being applied in consecutive fashion, ascending or descending, depending on whether a negative or positive response, respectively, is obtained with the initial filament.

Certain preferred compounds of Formulae I–IX and Formulae A–F are effective in reversing mechanical allodynia-like symptoms (i.e., rats treated with effective amounts of such compounds will require stimulation with a Von Frey filament of higher rigidity strength to provoke a positive allodynic response as compared to control untreated or vehicle treated rats) when tested by this method.

Example 18c

Cold Allodynia

This assay determines the effectiveness of compounds in relieving one of the symptoms of neuropathic pain produced by unilateral mononeuropathy, namely cold allodynia.

Unilateral mononeuropathy is produced in rats using the Chronic Constriction Injury model performed essentially as described by Bennet and Xie, Pain 1988, 33:87–107. Rats are anesthetized. The lateral aspect of each rat's hind limb is shaved and disinfected. Using aseptic technique, an incision is made on the lateral aspect of the hind limb at the mid-thigh level. The biceps femoris is bluntly dissected to expose the sciatic nerve. On one hind limb of each rat, four loosely tied ligatures are made around the sciatic nerve approximately 1–2 millimeters apart. On the other side of each rat, an identical dissection is performed except that the sciatic nerve is not ligated. The muscle is closed with a continuous suture pattern, and the skin is closed with wound clips or sutures.

Rats demonstrating unilateral mononeuropathy are assessed for acute and chronic cold allodynia sensitivity. Each rat is placed individually into a chamber with a metal plate about 6 cm from the bottom. This chamber is filled with ice water to a depth of about 2.5 cm above the metal plate, with the temperature of the bath maintained at about zero to four degrees C throughout the experiment. A timer is started, and the rat's response latency is measured to the nearest tenth of a second. A "response" is defined as a rapid withdrawal of the ligated hindpaw completely out of the water while the animal is stationary and not pivoting. An exaggerated limp while the animal is walking is not scored as a response. Maximum immersion time is 20 seconds with a 20-minute interval between trials. The screening criteria are 1) the average of two trials is less than or equal to 13 seconds, and 2) there is consistency across the two trial scores. Animals are screened for hypersensitivity to cold on post-surgery days 4 through 10, and selected for inclusion in drug-response studies based on the criteria described above. The pre-dose screening values are used as the animal's baseline cold allodynia scores. For acute studies, the animals are tested for cold allodynia at 1, 3, and sometimes 5 hours post-dose.

Although this acute cold allodynia assay is generally less preferred for demonstrating efficacy of compounds of the invention, when tested in this assay, certain preferred compounds of Formulae I–IX and Formulae A–F demonstrate anti-allodynic effects (increases in response latency) at doses of less than 50 mg/kg.

Example 18d

Mechanical Hyperalgesia

This assay determines the effectiveness of compounds in relieving one of the symptoms of neuropathic pain produced by unilateral mononeuropathy, namely mechanical hyperalgesia.

A chronic constriction injury is produced by loosely ligating the right common sciatic nerve as described by Bennet and Xie, Pain 1988, 33:87–107. The left common sciatic nerve is visualized, but not manipulated to produce sham conditions.

The rats having a chronic constriction injury are assessed for mechanical hyperalgesia to a pin-prick stimulus as described by Koch et al. Analgesia 1996, 2(3), 157–164. Rats are placed in individual compartments of a cage with a warmed, perforated metal floor. Hindpaw withdrawal duration is measured after a mild pinprick to the plantar surface of the ligated and sham hindpaws.

Preferred compounds of the invention produce a reduction of mechanical hyperalgesia (i.e., a reduction in the duration of hindpaw withdrawal) elicited by a pin-prick stimulus in rats with a chronic constriction injury at doses of 50 mg/kg or less when tested by this method.

Example 18e
Thermal Hyperalgesia

This assay determines the effectiveness of compounds in relieving one of the symptoms of neuropathic pain produced by unilateral mononeuropathy, namely thermal hyperalgesia.

Rats having had surgery as described in Example 18d are assessed for thermal hyperalgesia sensitivity at least 10 days post-surgery. The rats are placed beneath inverted cages upon an elevated glass platform and a radiant heat source beneath the glass is aimed at the plantar hindpaw.

The duration of time before the hindpaw is withdrawn from the floor is measured to the nearest tenth of a second. The cutoff time for the heat stimulus is 20 seconds, and the light is calibrated such that this stimulus duration does not burn or blister the skin. Preferably about four latency measurements are taken for each hindpaw in each test session, alternating left and right hindpaws, with 5-minute intervals between tests. The times to withdrawal of each side are averaged and a difference score is obtained.

Preferred compounds of the invention produce an increase in the average time to withdrawal after oral administration of 50 mg/kg or less in this model.

Example 18f
Sedation

Sedation may be determined using the method described by Fitzgerald et al., *Toxicology* 1988, 49(2–3)433–9. Preferred compounds of the invention do not produce reproducible or significant sedation at intravenous doses of less than 25 mg/kg (preferably less than 10 mg/kg) or at oral doses of less than 140 mg/kg (preferably less than 50 mg/kg).

What is claimed is:

1. A compound of the formula:

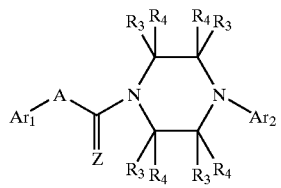

or a pharmaceutically acceptable salt thereof, wherein:

A is absent or is selected from the group consisting of O, S, $NR_A$, $NR_A CR_B R_B'$, $CR_B R_B' NR_A$, $—CR_A = CR_B—$, and $C_3H_4$; where $R_A$, $R_B$, and $R_B'$ are independently selected at each occurrence from hydrogen or alkyl;

Z is oxygen or sulfur;

each $R_3$ and $R_4$ independently
  (a) selected from the group consisting of hydrogen; halogen; hydroxy; amino; cyano; nitro; —COOH; —CHO, optionally substituted alkyl; optionally substituted alkenyl; optionally substituted alkynyl; optionally substituted alkoxy; optionally substituted alkylthio; optionally substituted alkyl ketone; optionally substituted alkylester; optionally substituted alkylsulfinyl; optionally substituted alkylsulfonyl; optionally substituted mono- or di-alkylcarboxamide; optionally substituted $—S(O)_n$NHalkyl; optionally substituted $—S(O)_n$N(alkyl)(alkyl); optionally substituted —NHC(=O)alkyl; optionally substituted —NC(=O)(alkyl)(alkyl); optionally substituted $—NHS(O)_n$alkyl; optionally substituted $—NS(O)_n$(alkyl)(alkyl); optionally substituted saturated heterocyclic ring or partially unsaturated heterocycle of from 5 to 8 atoms, which saturated heterocyclic ring or partially unsaturated heterocycloalkyl contains 1, 2, or 3 heteroatoms selected from N, O, and S; optionally substituted aryl having from 1 to 3 rings; or optionally substituted heteroaryl, said heteroaryl having from 1 to 3 rings, 5 to 8 ring members in each ring and, in at least one of said rings, from 1 to about 3 heteroatoms per ring independently selected from the group consisting of N, O, and S; or (b) joined to a $R_3$ and $R_4$ not attached to the same carbon may be joined to form an optionally substituted aryl ring, a saturated or partially unsaturated carbocyclic ring of from 5 to 8 members, which carbocyclic ring is optionally substituted, or a saturated, partially unsaturated, or aromatic heterocyclic ring of from 5 to 8 members, which heterocyclic ring is optionally substituted and contains 1, 2, or 3 heteroatoms selected from N, O, and S;

$Ar_1$ is selected from the group consisting of:
  (a) cyclohexyl, cyclopentyl, piperidinyl, piperazinyl, phenyl, pyrrolyl, furanyl, thienyl, pyrazolyl, imidazolyl, thiazolyl, isothiazolyl, oxazolyl, isoxazolyl, oxadiazolyl, triazolyl, tetrazolyl, pyridyl, pyrimdyl, pyrazinyl, benzimidazolyl naphthyl, indolyl, isoindolyl, benzfuranyl, isobenzofuranyl, benzo[b]thiophenyl, benz[d]isoxazoly, quinolinyl, isoquinolinyl, cinnolinyl, quinazolinyl, and quinoxalinyl, each of which is optionally mono-, di-, or trisubstituted with $R_5$; and
  (b) bicyclic oxygen-containing groups of the formula:

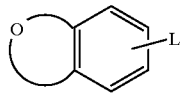

optionally mono-, di-, or trisubstituted with $R_5$, where L represents point of attachment and may be at any point on the benzene ring, and the oxygen-containing ring of the bicyclic oxygen-containing group consists of from 5 to 8 ring atoms, contains 1 or 2 oxygen atoms and remaining ring atoms are carbon;

$Ar_2$ is selected from the group consisting of:
  (a) cyclohexyl, cyclopentyl, piperidinyl, piperazinyl, pyrrolyl, furanyl thienyl, pyrazolyl, imidazolyl, thiazolyl, isothiazolyl, oxazolyl, isoxazolyl, oxadiazolyl, triazolyl, tetrazolyl, pyridyl, pyrimdyl, benzimidazolyl, naphthyl, indolyl, isoindolyl, benzofuranyl, isobenzofuranyl, benzo[b]thiophenyl, benz[d]isoxazoly, quinolinyl, isoquinolinyl, cinnolinyl, quinazolinyl, and quinoxalinyl, each of which is optionally mono-, di-, or trisubstituted with $R_5$; and
  (b) bicyclic oxygen-containing groups of the formula:

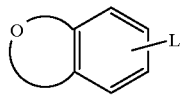

optionally mono-, di-, or trisubstituted with $R_5$, where L represents point of attachment and may be at any point on the benzene ring, and the oxygen-containing ring of the bicyclic oxygen-containing group consists of from 5 to 8 ring atoms, contains 1 or 2 oxygen atoms and remaining ring atoms are carbon;

$R_5$ is independently selected at each occurence from the group consisting of halogen, nitro, halo($C_{1-6}$)alkyl, halo($C_{1-6}$)alkoxy, hydroxy, amino, $C_{1-6}$alkyl substituted with 0–2 $R_6$, $C_{2-6}$alkenyl substituted with 0–2 $R_6$, $C_{2-6}$alkynyl substituted with 0–2 $R_6$, $C_{1-6}$alkoxy and Y;

$R_6$ is independently selected at each occurence from the group consisting of halogen, hydroxy, cyano $C_{1-4}$alkyl, $C_{1-4}$alkoxy, —S(O)$_n$($C_{1-4}$alkyl), halo($C_{1-4}$)alkly, halo($C_{1-4}$)alkoxy, CO($C_{1-4}$alkyl), CONH($C_{1-4}$alkyl), CON($C_{1-4}$alkyl$_1$)($C_{1-4}$alkyl$_2$) where alkyl$_1$ and alkyl$_2$ may be joined to form a saturated heterocyclic ring of from 5 to 8 ring atoms and containing 1, 2, or 3 heteroatoms independently selected from N, O, and S, —XR$_7$, and Y;

X is independently selected at each occurence from the group consisting of —CH$_2$—, —CHR$_8$—, —O—, —S(O)$_n$—, —NH—, —NR$_8$—, —C(=O)—, —C(=O)O—, —C(=O)NH—, —C(=O)NR$_8$—, —S(O)$_n$NH—, —S(O)$_n$NR$_8$—, NHC(=O)—, —NR$_8$C(=O)—, —NHS(O)$_n$—, and —NR$_8$S(O)$_n$—;

$R_7$ and $R_8$ are independently selected at each occurrence from hydrogen, and straight, branched, and cyclic alkyl groups, and (cycloalkyl)alkyl groups, said straight, branched, and cyclic alkyl groups, and (cycloalkyl) alkyl groups consisting of 1 to 8 carbon atoms, and containing zero or one or more double or triple bonds, each of which 1 to 8 carbon atoms is unsubsitituted or substituted with one or more substituent(s) independently selected from oxo, hydroxy, halogen, amino, cyano, nitro, haloalkyl, haloalkoxy, —O(alkyl), —NH(alkyl), —N(alkyl)(alkyl), —NHC(O)(alkyl), —N(alkyl)C(O)(alkyl), —NHS(O)$_n$(alkyl), —S(O)$_n$(alkyl), —S(O)$_n$NH(alkyl), —S(O)$_n$N(alkyl$_3$)(alkyl$_4$) where alkyl$_3$ and alkyl$_4$ are opitionally joined to form a saturated heterocyclic ring consisting of from 5 to 8 ring atoms and containing 1, 2, or 3 heteroatoms independently selected from N, O, and S, and Y';

Y and Y' are independently selected at each occurrence from 3- to 8-membered carbocyclic or heterocyclic groups which are saturated, unsaturated, or aromatic, which may be further substituted with one or more substituents independently selected from halogen, oxo, hydroxy, amino, nitro, cyano, alkyl, alkoxy, haloalkyl, haloalkoxy, mono- or dialkylamino, and alkylthio;

wherein said 3- to 8-memberered heterocyclic groups contain one or more heteroatom(s) independently selected from N, O, and S;

n is independently chosen at each occurrence from 0, 1, and 2.

2. A compound or salt according to claim 1, wherein:

$R_A$, $R_B$, and $R_B$' are independently selected at each occurrence from hydrogen and $C_{1-6}$alkyl;

each $R_3$ and $R_4$ is independently (a) chosen from the group consisting of hydrogen halogen, cyano, nitro, halo($C_{1-6}$)alkyl, halo($C_{1-6}$) alkoxy, hydroxy, amino, $C_{1-6}$alkyl substituted with 0–2 $R_6$, $C_{2-6}$alkenyl substituted with 0–2 $R_6$; $C_{2-6}$alkynyl substituted with 0–2 $R_6$; $C_{1-6}$alkoxy substituted with 0–2 $R_6$, —NH($C_{1-6}$alkyl) substituted with 0–2 $R_6$, —N($C_{1-6}$alkyl)($C_{1-6}$alkyl) where each $C_{1-6}$alkyl is independently substituted with 0–2 $R_6$, —XR$_7$, and Y; or (b) joined to a $R_3$ or $R_4$ not attached to the same carbon to form an aryl ring substituted with 0–3 $R_6$, a saturated or partially unsaturated carbocyclic ring of from 5 to 8 members, which carbocyclic ring is substituted with 0–2 $R_6$, or a saturated, partially unsaturated, or aromatic heterocyclic ring of from 5 to 8 members, which heterocyclic ring is substituted with 0–2 $R_6$ and contains 1, 2, or 3 heteroatoms independently selected from N, O, and S;

$R_7$ and $R_8$ are independently selected at each occurrence from hydrogen, and straight, branched, and cyclic alkyl groups, and (cycloalkyl)alkyl groups, said straight, branched, and cyclic alkyl groups, and (cycloalkyl) alkyl groups consisting of 1 to 8 carbon atoms, and containing zero or one or more double or triple bonds, each of which 1 to 8 carbon atoms is unsubsitituted or substituted with one or more substituent(s) independently selected from oxo, hydroxy, halogen, amino, cyano, nitro, haloalkyl, haloalkoxy, —O(alkyl), —NH(alkyl), —N(alkyl)(alkyl), —NHC(O)($C_{1-4}$alkyl), —N($C_{1-4}$alkyl)C(O)($C_{1-4}$alkyl), —NHS(O)$_n$($C_{1-4}$alkyl), —S(O)$_n$($C_{1-4}$alkyl), —S(O)$_n$NH($C_{1-4}$alkyl), —S(O)$_n$N($C_{1-4}$alkyl$_3$)($C_{1-4}$alkyl$_4$) where $C_{1-4}$alkyl$_3$ and $C_{1-4}$alkyl$_4$ are opitionally joined to form a saturated heterocyclic ring consisting of from 5 to 8 ring atoms and containing 1, 2, or 3 heteroatoms independently selected from N, O, and S, and Y'; and Y and Y' are independently selected at each occurrence from 3- to 8-membered carbocyclic or heterocyclic groups which are saturated, unsaturated, or aromatic, which are unsubsitiuted or substituted with one or more substituents independently selected from halogen, oxo, hydroxy, amino, nitro, cyano, $C_{1-4}$alkyl, $C_{1-4}$alkoxy, halo($C_{1-4}$)alkyl, halo($C_{1-4}$)alkoxy, mono- or di($C_{1-4}$) alkylamino, and $C_{1-4}$alkylthio;

wherein said 3- to 8-memberered heterocyclic groups contain one or more heteroatom(s) independently selected from N, O, and S.

3. A compound or salt according to claim 1, wherein Z is oxygen.

4. A compound of the formula:

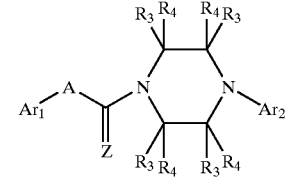

or a pharmaceutically acceptable salt thereof, wherein:

A is absent or is selected from the group consisting of O, S, NR$_A$, CR$_B$R$_B$', NR$_A$CR$_B$R$_B$', CR$_B$ R$_B$'NR$_A$, —CR$_A$=CR$_B$—, and C$_3$H$_4$; where R$_A$, R$_B$, and R$_B$' are independently selected at each occurrence from hydrogen or alkyl;

each $R_3$ and $R_4$ is independently;

(a) selected from the group consisting of hydrogen; halogen; hydroxy; amino; cyano; nitro; —COOH; —CHO, optionally substituted alkyl; optionally substituted alkenyl; optionally substituted alkynyl; optionally substituted alkoxy; optionally substituted mono or dialkylamino; optionally substituted alkylthio; optionally substituted alkyl ketone; optionally substituted alkylester; optionally substituted alkylsulfinyl; optionally substituted alkylsulfonyl; optionally substituted mono- or di-alkylcarboxamide; optionally substituted —S(O)$_n$NHalkyl; optionally substituted —S(O)$_n$N(alkyl)(alkyl); optionally substituted —NHC(=O)alkyl; optionally substituted —NC(=O)(alkyl)(alkyl); optionally substituted —NHS(O)$_n$alkyl; optionally substituted —NS(O)$_n$(alkyl)(alkyl); optionally substituted saturated heterocyclic ring or partially unsaturated heterocycle of from 5 to 8 atoms, which saturated heterocyclic ring or partially unsaturated heterocycloalkyl contains 1, 2, or 3 heteroatoms selected from N, O, and S; optionally substituted aryl having from 1 to 3 rings; or optionally substituted heteroaryl, said heteroaryl having from 1 to 3 rings, 5 to 8 ring members in each ring and, in at least one of said rings, from 1 to about 3 heteroatoms per ring independently selected from the group consisting of N, O, and S; or (b) joined to a $R_3$ and $R_4$ not attached to the same carbon to form an optionally substituted aryl ring, a saturated or partially unsaturated carbocyclic ring of from 5 to 8 members, which carbocyclic ring is optionally substituted, or a saturated, partially unsaturated, or aromatic heterocyclic ring of from 5 to 8 members, which heterocyclic ring is optionally substituted and contains 1, 2, or 3 heteroatoms independently selected from N, O, and S;

$Ar_1$ is selected from the group consisting of:
(a) cyclohexyl, cyclopentyl, piperidinyl, piperazinyl, pyrrolyl, furanyl thienyl, pyrazolyl, imidazolyl, thiazolyl, isothiazolyl, oxazolyl, isoxazolyl, oxadiazolyl, triazolyl, tetrazolyl, pyridyl, pyrimidyl, pyrazinyl, benzimidazolyl, naphthyl, indolyl, isoindolyl, benzofuranyl, isobenzofuranyl, benzo[b]thiophenyl, benz[d]isoxazoly, quinolinyl, isoquinolinyl, cinnolinyl, quinazolinyl, and quinoxalinyl; wherein $Ar_1$ is optionally mono-, di-, or trisubstituted with $R_5$, and $Ar_2$ is optionally mono-, di-, or trisubstituted with $R_9$;

$Ar_1$ is selected from the group consisting of: cyclohexyl, cyclopentyl, piperidinyl, piperazinyl, pyrrolyl, furanyl, thienyl, pyrazolyl, imidazolyl, thiazolyl, isothiazolyl, oxazolyl, isoxazolyl, oxadiazolyl, triazolyl, tetrazolyl, pyridyl, pyrim1dyl, benzimidazolyl, naphthyl, indolyl, isoindolyl, benzofuranyl, isobenzofuranyl, benzo[b]thiophenyl, benz[d]isoxazoly, quinolinyl, isoquinolinyl, cinnolinyl, quinazolinyl, and quinoxalinyl; wherein $Ar_1$ is optionally mono-, di-, or trisubstituted with $R_5$, and $Ar_2$ is optionally mono-, di-, or trisubstituted with $R_9$; and (b) groups of the formula:

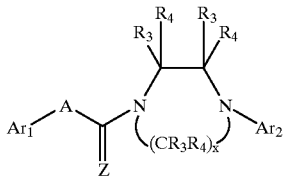

optionally mono-, di-, or trisubstituted with $R_5$, where L represents point of attachment and may be at any point on the benzene ring, and the oxygen-containing ring of the bicyclic oxygen-containing group consists of from 5 to 8 ring atoms, contains 1 or 2 oxygen atoms and remaining ring atoms are carbon;

$R_5$ is independently selected at each occurence from the group consisting of cyano, nitro, haloalkyl, haloalkoxy, hydroxy, amino, alky substituted with 0–2 $R_6$, alkenyl substituted with 0–2 $R_6$, alkynyl substituted with 0–2 $R_6$, alkoxy and Y;

$R_9$ is independently selected at each occurrence from the group consisting of nitro, haloalkoxy, hydroxy, amino, alkyl substituted with 0–2 $R_6$, alkenyl substituted with 0–2 $R_6$, alkynyl substituted with 0–2 $R_6$, alkoxy substituted with 0–2 $R_6$, and Y;

$R_6$ is independently selected at each occurrence from the group consisting of halogen, hydroxy, cyano, alkyl, alkoxy, —S(O)$_n$(alkyl), haloalkyl, haloalkoxy, CO(alkyl), CONH(alkyl), CON(alkyl$_1$)(alkyl$_2$) where alkyl$_1$ and alkyl$_2$ may be joined to from a saturated heterocyclic ring of from 5 to 8 ring atoms and containing 1, 2, or 3 heteroatoms independently selected from N, O, and S, —XR$_7$, and Y;

X is independently selected at each occurence from the group consisting of —CH$_2$—, —CHR$_8$—, —O—, —S(O)$_n$—, —NH—, —NR$_8$—, —C(=O)—, —C(=O)O—, —C(=O)NH—, —C(=O)NR$_8$—, —S(O)$_n$NH—, —S(O)$_n$NR$_8$—, NHC(=O)—, —NR$_8$C(=O)—, —NHS(O)$_n$—, and —NR$_8$S(O)$_n$—;

$R_7$ and $R_8$ are independently selected at each occurrence from hydrogen, and straight, branched, and cyclic alkyl groups, and (cycloalkyl)alkyl groups, said straight, branched, and cyclic alkyl groups, and (cycloalkyl)alkyl groups consisting of 1 to 8 carbon atoms, and containing zero or one or more double or triple bonds, each of which 1 to 8 carbon atoms is unsubstituted or substituted with one or more substituent(s) independently selected from oxo, hydroxy, halogen, amino, cyano, nitro, haloalkyl, haloalkoxy, —O(alkyl), —NH(alkyl), —N(alkyl)(alkyl), —NHC(O)(alkyl), —N(alkyl)C(O)(alkyl), —NHS(O)$_n$(alkyl), —S(O)$_n$(alkyl), —S(O)$_n$NH(alkyl), —S(O)$_n$N(alkyl$_3$)(alkyl$_4$) where alkyl$_3$ and alkyl$_4$ are opitionally joined to form a saturated heterocyclic ring consisting of from 5 to 8 ring atoms and containing 1, 2, or 3 heteroatoms independently selected from N, O, and S, and Y';

Y and Y' are independently selected at each occurrence from 3- to 8-membered carbocyclic or heterocyclic groups which are saturated, unsaturated, or aromatic, which are unsubstituted or substituted with one or more substituents independently selected from halogen, oxo, hydroxy, amino, nitro, cyano, alkyl, alkoxy, haloalkyl, haloalkoxy, mono- or dialkylamino, and alkylthio;

wherein said 3- to 8-memberered heterocyclic groups contain one or more heteroatom(s) independently selected from N, O, and S;

n is independently chosen at each occurrence from 0, 1, and 2.

5. A compound of the formula:

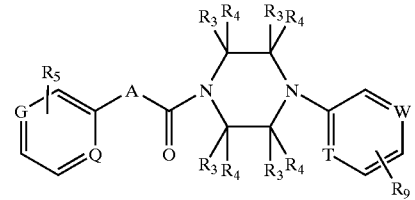

or a pharmaceutically acceptable salt thereof, wherein:
G, Q, T, and W are the same or different and are selected from the group consisting of N, CH, and CR$_5$, wherein T or W or both is N;

A is absent or is selected from the group consisting of O, S, $NR_A$, $CR_BR_B'$, $NR_ACR_BR_B'$, $CR_B$ $R_B'NR_A$, —$CR_A$=$CR_B$—, and $C_3H_4$; where $R_A$, $R_B$, and $R_B'$ are independently selected at each occurrence from hydrogen alkyl;

Z is oxygen or sulfur;

each $R_3$ and $R_4$ is independently
(a) selected from the group consisting of hydrogen; halogen; hydroxy; amino; cyano; nitro; —COOH; —CHO, optionally substituted $C_{1-6}$alkyl; optionally substituted $C_{2-6}$alkenyl; optionally substituted $C_{2-6}$alkynyl; optionally substituted $C_{1-6}$alkoxy; optionally substituted mono or di($C_{1-6}$)alkylamino; optionally substituted $C_{1-6}$alkylthio; optionally substituted $C_{1-6}$alkyl ketone; optionally substituted $C_{1-6}$alkylester; optionally substituted $C_{1-6}$alkylsulfinyl; optionally substituted $C_{1-6}$alkylsulfonyl; optionally substituted mono- or di($C_{1-6}$)alkylcarboxamide; optionally substituted —$S(O)_n$NH$C_{1-6}$alkyl; optionally substituted —$S(O)_n$ N($C_{1-6}$alkyl)($C_{1-6}$alkyl); optionally substituted —NHC(=O)$C_{1-6}$alkyl; optionally substituted —NC(=O)($C_{1-6}$alkyl)($C_{1-6}$alkyl); optionally substituted —NHS(O)$_n$$C_{1-6}$alkyl; optionally substituted —NS(O)$_n$($C_{1-6}$alkyl)($C_{1-6}$alkyl); optionally substituted saturated heterocyclic ring or partially unsaturated heterocycle of from 5 to 8 atoms, which saturated heterocyclic ring or partially unsaturated heterocycle contains 1, 2, or 3 heteroatoms independently selected from N, O, and S; optionally substituted aryl having from 1 to 3 rings; and optionally substituted heteroaryl, said heteroaryl having from 1 to 3 rings, 5 to 8 ring members in each ring and, in at least one of said rings, from 1 to about 3 heteroatoms per ring independently selected from the group consisting of N, O, and S; or
(b) joined to a $R_3$ and $R_4$ not attached to the same carbon may be joined to form an optionally substituted aryl ring; a saturated or partially unsaturated carbocyclic ring of from 5 to 8 members, which carbocyclic ring is optionally substituted; or a saturated, partially unsaturated, or aromatic heterocyclic ring of from 5 to 8 members, which heterocyclic ring is optionally substituted and contains 1, 2, or 3 heteroatoms selected from N, O, and S;

$R_5$ represents 1 to 3 substituents independently selected at each occurrence from the group consisting of cyano, hydroxy, amino, $C_{3-6}$ alkyl substituted with 0–2 $R_6$, $C_{2-6}$ alkenyl substituted with 0–2 $R_6$, $C_{2-6}$ alkynyl substituted with 0–2 $R_6$, $C_{3-6}$alkoxy, —NH($C_{1-6}$alkyl) substituted with 0–2 $R_6$, —N($C_{1-6}$alkyl)($C_{1-6}$alkyl) where each alkyl is independently substituted with 0–2 $R_6$, —$XR_7$, and Y;

$R_9$ represents 0 to 3 substituents and is independently selected at each occurrence from the group consisting of halogen, nitro, halo($C_{1-6}$)alkyl, halo($C_{1-6}$)alkoxy, hydroxy, amino, $C_{1-6}$alkyl substituted with 0–2 $R_6$, $C_{2-6}$alkenyl substituted with 0–2 $R_6$, $C_{2-6}$alkynyl substituted with 0–2 $R_6$, $C_{1-6}$alkoxy substituted with 0–2 $R_6$; and Y;

$R_6$ is independently selected at each occurrence from the group consisting of halogen, hydroxy, cyano, $C_{1-4}$alkyl, $C_{1-4}$alkoxy, —$S(O)_n$($C_{1-4}$alkyl), halo($C_{1-4}$)alkyl, halo($C_{1-4}$) alkoxy, CO($C_{1-4}$alkyl), CONH($C_{1-4}$alkyl), CON($C_{1-4}$alkyl$_1$)($C_{1-4}$alkyl$_2$) where alkyl$_1$ and alkyl$_2$ may be joined to form a saturated heterocyclic ring of from 5 to 8 ring atoms and containing 1, 2, or 3 heteroatoms independently selected from N, O, and S, —$XR_7$, and Y;

X is independently selected at each occurrence from the group consisting of —$CH_2$—, —$CHR_8$—, —O—, —$S(O)_n$—, —NH—, —$NR_8$—, —C(=O)—, —C(=O)O—, —C(=O)NH—, —C(=O)$NR_8$—, —$S(O)_n$NH—, —$S(O)_n$$NR_8$—, NHC(=O)—, —$NR_8$C(=O)—, —NHS(O)$_n$—, and —$NR_8$S(O)$_n$—;

$R_7$ and $R_8$ are independently selected at each occurrence from hydrogen, and straight, branched, and cyclic alkyl groups, and (cycloalkyl)alkyl groups, said straight, branched, and cyclic alkyl groups, and (cycloalkyl) alkyl groups consisting of 1 to 8 carbon atoms, and containing zero or one or more double or triple bonds, each of which 1 to 8 carbon atoms is unsubsitituted or substituted with one or more substituent(s) independently selected from oxo, hydroxy, halogen, amino, cyano, nitro, haloalkyl, haloalkoxy, —O($C_{1-4}$alkyl), —NH($C_{1-4}$alkyl), —N($C_{1-4}$alkyl)($C_{1-4}$alkyl), —NHC(O)($C_{1-4}$alkyl), —N($C_{1-4}$alkyl)C(O)($C_{1-4}$alkyl), —NHS(O)$_n$($C_{1-4}$alkyl), —S(O)$_n$($C_{1-4}$alkyl), —S(O)$_n$NH($C_{1-4}$alkyl), —S(O)$_n$N($C_{1-4}$alkyl$_3$)($C_{1-4}$alkyl$_4$) where $C_{1-4}$alkyl$_3$ and $C_{1-4}$alkyl$_4$ are opitionally joined to form a saturated heterocyclic ring consisting of from 5 to 8 ring atoms and containing 1, 2, or 3 heteroatoms independently selected from N, O, and S, and Y';

Y and Y' are independently selected at each occurrence from 3- to 8-membered carbocyclic or heterocyclic groups which are saturated, unsaturated, or aromatic, which are unsubstituted or substituted with one or more substituents independently selected from halogen, oxo, hydroxy, amino, nitro, cyano, $C_{1-4}$alklyl, $C_{1-4}$alkoxy, halo($C_{1-4}$)alklyl, halo($C_{1-4}$)alkoxy, mono- or di($C_{1-4}$) alklylamino, and $C_{1-4}$alklthio;

wherein said 3- to 8-membered heterocyclic group contain one or more heteroatom(s) independently selected from N, O, and S; and n is independently chosen at each occurrence from 0, 1, and 2.

6. A compound according to claim 5, which 4-(3-Chloro-2-pyridinyl)-N-[4(isopropyl)phenyl]-2- methylthio-1-piperazinecarboxamide, or a pharmaceutically acceptable salt thereof.

7. A compound according to claim 5, wherein $R_3$ and $R_4$ are independently selected at each occurrence from the group consisting of hydrogen and $C_{1-6}$alkyl.

8. A compound according to claim 7, wherein G and Q are selected from the group consisting of CH and $CR_5$.

9. A compound according to claim 7, wherein G, Q, and W are independently selected at each occurrence from the group consisting of CH and $CR_5$; and T is N.

10. A compound according to claim 9 wherein $R_3$ and $R_4$ are hydrogen; and A is selected from the group consisting of NH, —CH=CH—, and —$CH_2$NH—.

11. A compound or salt according to claim 10, wherein $R_6$ is independently selected at each occurrence from the group consisting of halogen, hydroxy, $C_{1-4}$ alkyl, $C_{1-4}$ alkoxy, —NH($C_{1-4}$alkyl), and —N($C_{1-4}$ alkyl)($C_{1-4}$ alkyl).

12. A compound according to claim 10, which is 4-(3-Trifluoromethyl-2-pyridinyl)-N-(3-methoxy-4-hydroxyphenylmethyl)-1-piperazinecarboxamide, or a pharmaceutically acceptable salt thereof.

13. A compound according to claim 10, which is 4-(3-Nitro-pyridinyl)-N-[4-(n-butyl)phenyl]-1-piperazinecarboxamide, or a pharmaceutically acceptable salt thereof.

14. A compound according to claim 10, which is 4-(3-Trifluoromethyl-2-pyridinyl)-N-[4-(n-butyl)phenyl]-1-piperazinecarboxamide, or a pharmaceutically acceptable salt thereof.

15. A compound according to claim 10, which is 4-(3-Methyl-2-pyridinyl)-N-[4-(isopropyl)phenyl]-1-piperazinecarboxamide, or a pharmaceutically acceptable salt thereof.

16. A compound according to claim 10, which is 4-(3-Methyl-2-pyridinyl)-N-[4-(n-butyl)phenyl]-1-piperazinecarboxamide, or a pharmaceutically acceptable salt thereof.

17. A compound according to claim 10, which is 4-(3-Chloro-5-trifluoromethyl-2-pyridinyl)-N-[4-(isopropyl)phenyl]-1-piperazinecarboxamide, or a pharmaceutically acceptable salt thereof.

18. A compound according to claim 10, which is 4-(3-Chloro-2-pyridinyl)-N-[4-(isopropyl)phenyl]-1-piperazinecarboxamide, or a pharmaceutically acceptable salt thereof.

19. A compound according to claim 10, which is 4-(3,5-Dichloro-2-pyridinyl)-N-[4-(isopropyl)phenyl]-1-piperazinecarboxamide, or a pharmaceutically acceptable salt thereof.

20. The compound according to claim 9, which is 4-(3-Chloro-2-pyridinyl)-N-[4-(isopropyl)phenyl]-2-methyl-1-piperazinecarboxamide.

21. A compound of the formula:

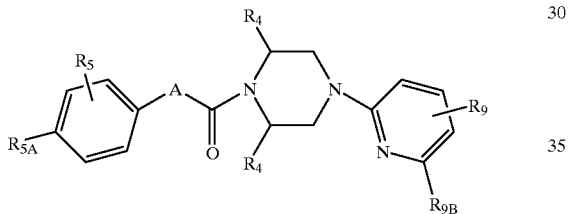

or a pharmaceutically acceptable salt thereof, wherein:

A is selected from the group consisting of NH, —CH═CH—, and CH$_2$NH;

R$_4$ is independently chosen from hydrogen and C$_{1-4}$ alkyl;

R$_5$ represents 0 to 2 substituents independently chosen at each occurrence from the group consisting of halogen, cyano, nitro, halo(C$_{1-6}$)alkyl, halo(C$_{1-6}$)alkoxy, hydroxy, amino, C$_{1-6}$alkyl substituted with 0–2 R$_6$, C$_{2-6}$alkenyl substituted with 0–2 R$_6$, C$_{2-6}$alkynyl substituted with 0–2 R$_6$, C$_{1-6}$alkoxy, —NH(C$_{1-6}$alkyl) substituted with 0–2 R$_6$, and —N(C$_{1-6}$alkyl)(C$_{1-6}$alkyl) where each C$_{1-6}$alkyl is independently substituted with 0–2 R$_6$;

R$_9$ represents 0 to 2 substituents and is independently chosen at each occurrence from the group consisting of halogen, nitro, halo(C$_{1-6}$)alkyl, halo(C$_{1-6}$)alkoxy, hydroxy, amino, C$_{1-6}$alkyl substituted with 0–2 R$_6$, C$_{2-6}$alkenyl substituted with 0–2 R$_6$, C$_{2-6}$alkynyl substituted with 0–2 R$_6$, and C$_{1-6}$alkoxy substituted with 0–2 R$_6$;

R$_{5A}$ is independently selected from the group consisting of halogen, cyano, nitro, halo(C$_{1-6}$)alkyl, halo(C$_{1-6}$)alkoxy, hydroxy, amino, C$_{1-6}$ alkyl, C$_{1-6}$ alkoxy, —NH(C$_{1-6}$ alkyl), and —N(C$_{1-6}$ alkyl)(C$_{1-6}$ alkyl)

R$_{9B}$ is independently selected from the group consisting of halogen, nitro, halo(C$_{1-6}$)alkoxy, hydroxy, amino, C$_{1-6}$ alkyl, and C$_{1-6}$ alkoxy; and R$_6$ is independently selected at each occurrence the group consisting of halogen, hydroxy, C$_{1-4}$alkyl, C$_{1-4}$alkoxy, —NH(C$_{1-4}$ alkyl), and —N(C$_{1-4}$ alkyl)(C$_{1-4}$ alkyl).

22. A compound of the formula:

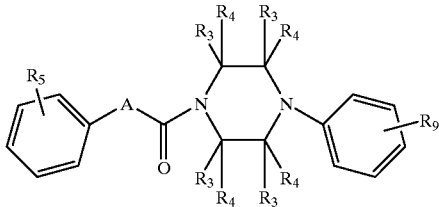

or a pharmaceutically acceptable salt thereof, wherein:

A is selected from the group consisting of a single bond, S, NR$_A$, NR$_A$CHR$_B$, CHR$_B$NR$_A$, —CR$_A$═CR$_B$—, and C$_3$H$_4$; where R$_A$ and R$_B$ are independently selected at each occurrence from the group consisting of hydrogen and alkyl;

each R$_3$ and R$_4$ is independently (a) selected from the group consisting of hydrogen; halogen; hydroxy; amino; cyano; nitro; —COOH; —CHO, optionally substituted alkyl; optionally substituted alkenyl; optionally substituted alkynyl; optionally substituted alkoxy; optionally substituted mono or dialkylamino; optionally substituted alkylthio; optionally substituted alkyl ketone; optionally substituted alkylester; optionally substituted alkylsulfinyl; optionally substituted alkylsulfonyl; optionally substituted mono- or di-alkylcarboxamide; optionally substituted —S(O)$_n$NHalkyl; optionally substituted —S(O)$_n$N(alkyl)(alkyl); optionally substituted —NHC(═O)alkyl; optionally substituted —NC(═O)(alkyl)(alkyl); optionally substituted —NHS(O)$_n$alkyl; optionally substituted —NS(O)$_n$(alkyl)(alkyl); optionally substituted saturated heterocyclic ring or partially unsaturated heterocycle of from 5 to 8 atoms, which saturated heterocyclic ring or partially unsaturated heterocycle contains 1, 2, or 3 heteroatoms independently selected from N, O, and S; optionally substituted aryl having from 1 to 3 rings; and optionally substituted heteroaryl, said heteroaryl having from 1 to 3 rings, 5 to 8 ring members in each ring and, in at least one of said rings, from 1 to about 3 heteroatoms per ring independently selected from the group consisting of N, O, and S; or (b) joined to a R$_3$ or R$_4$ not attached to the same carbon to form an optionally substituted aryl ring; a saturated or partially unsaturated carbocyclic ring of from 5 to 8 members, which carbocyclic ring is optionally substituted; or a saturated, partially unsaturated, or aromatic heterocyclic ring of from 5 to 8 members, which heterocyclic ring is optionally substituted and contains 1, 2, or 3 heteroatoms independently selected from N, O, and S;

R$_5$ represents 0–3 substituents independently selected at each occurrence from the group consisting of cyano, nitro, haloalkyl, haloalkoxy, C$_{2-6}$ alkenyl substituted with 0–2 R$_6$, and C$_{2-6}$ alkynyl substituted with 0–2 R$_6$;

R$_9$ represents 0–3 substituents independently selected at each occurrence from the group consisting of bromo, haloalkyl, haloalkoxy, hydroxy, C$_{2-6}$ alkyl substituted with 0–2 R$_6$, C$_{2-6}$ alkenyl substituted with 0–2 R$_6$, C$_{2-6}$ alkynyl substituted with 0–2 R$_6$, and C$_{2-6}$ alkoxy;

$R_6$ is independently selected at each occurrence from the group consisting of halogen, hydroxy, cyano, alkyl, alkoxy, —S(O)$_n$(alkyl), haloalkyl, haloalkoxy, CO(alkyl), CONH(alkyl), CON(alkyl$_1$)(alkyl$_2$) where alkyl$_1$ and alkyl$_2$ may be joined to form a saturated heterocyclic ring of from 5 to 8 ring atoms and containing 1, 2, or 3 heteroatoms independently selected from N, O, and S, —XR$_7$, and Y;

X is independently selected at each occurrence from the group consisting of —CH$_2$—, —CHR$_8$—, —O—, —S(O)$_n$—, —NH—, —NR$_8$—, —C(=O)—, —C(=O)O—, —C(=O)NH—, —C(=O)NR$_8$—, —S(O)$_n$NH—, —S(O)$_n$NR$_8$—, NHC(=O)—, —NR$_8$C(=O)—, —NHS(O)$_n$—, and —NR$_8$S(O)$_n$—;

$R_7$ and $R_8$ are independently selected at each occurrence from straight, branched, and cyclic alkyl groups, and (cycloalkyl)alkyl groups, said straight, branched, and cyclic alkyl groups, and (cycloalkyl)alkyl groups consisting of 3 to 8 carbon atoms, and containing zero or one or more double or triple bonds, each of which 3 to 8 carbon atoms is unsubstituted or substituted with one or more substituent(s) independently selected from oxo, hydroxy, halogen, amino, cyano, nitro, haloalkyl, haloalkoxy, —O(alkyl), —NH(alkyl), —N(alkyl)(alkyl), —NHC(O)(alkyl), —N(alkyl)C(O)(alkyl), —NHS(O)$_n$(alkyl), —S(O)$_n$(alkyl), —S(O)$_n$NH(alkyl), —S(O)$_n$N(alkyl$_3$)(alkyl$_4$) where alkyl$_3$ and alkyl$_4$ are optionally joined to form a saturated heterocyclic ring consisting of from 5 to 8 ring atoms and containing 1, 2, or 3 heteroatoms independently selected from N, O, and S, and Y';

Y and Y' are independently selected at each occurrence from 3- to 8-membered carbocyclic or heterocyclic groups which are saturated, unsaturated, or aromatic, which are unsubstituted or substituted with one or more substituents independently selected from halogen, oxo, hydroxy, amino, nitro, cyano, alkyl, alkoxy, haloalkyl, haloalkoxy, mono- or dialkylamino, and alkylthio;

wherein said 3- to 8-membered heterocyclic groups contain one or more heteroatom(s) independently selected from N, O, and S; and n is independently chosen at each occurrence from 0, 1, and 2.

23. A compound or salt according to claim 22 in which $R_3$ and $R_4$ are independently selected at each occurrence from the group consisting of hydrogen and $C_{1-6}$ alkyl.

24. A compound or salt according to claim 22, wherein A is selected from the group consisting of NH, —CH=CH—, and CH$_2$NH; $R_3$ is hydrogen and $R_4$ is independently chosen at each occurrence from hydrogen and methyl; and $R_6$ is independently selected at each occurrence from the group consisting of halogen, hydroxy, $C_{1-4}$ alkyl, $C_{1-4}$ alkoxy, —NH($C_{1-4}$ alkyl), and —N($C_{1-4}$ alkyl)($C_{1-4}$ alkyl).

25. A compound of the formula:

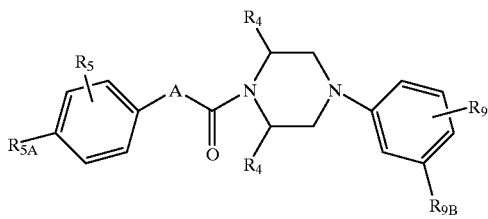

or a pharmaceutically acceptable salt thereof, wherein:

A is selected from the group consisting of NH, —CH=CH—, and CH$_2$NH;

$R_4$ is independently selected at each occurrence from hydrogen and $C_{1-4}$alkyl;

$R_5$ represents 0 to 2 substituents independently selected at each occurrence from the group consisting of halogen, cyano, nitro, halo($C_{1-6}$)alkyl, halo($C_{1-6}$)alkoxy, amino, $C_{2-6}$alkenyl substituted with 0–2 $R_6$, and $C_{2-6}$alkynyl substituted with 0–2 $R_6$;

$R_9$ represents 0 to 2 substituents and is independently selected at each occurrence from the group consisting of halogen, nitro, halo($C_{1-6}$)alkyl, halo($C_{1-6}$)alkoxy, hydroxy, amino, $C_{1-6}$alkyl substituted with 0–2 $R_6$, $C_{2-6}$alkenyl substituted with 0–2 $R_6$, $C_{2-6}$alkynyl substituted with 0–2 $R_6$, and $C_{1-6}$alkoxy substituted with 0–2 $R_6$;

$R_{5A}$ is independently selected from the group consisting of halogen, cyano, nitro, trifluoromethyl, trifluoromethoxy, hydroxy, amino, $C_{1-6}$ alkyl, $C_{1-6}$ alkoxy, —NH($C_{1-6}$ alkyl), and —N($C_{1-6}$ alkyl)($C_1$–$C_6$ alkyl);

$R_{9B}$ is independently selected from the group consisting of trifluoromethoxy, hydroxy, $C_{2-6}$ alkyl, and $C_{2-6}$ alkoxy; and $R_6$ is independently selected at each occurrence from the group consisting of halogen, hydroxy, $C_{1-4}$ alkyl, and $C_{1-4}$ alkoxy.

26. A compound of the formula:

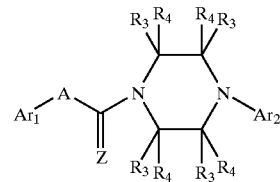

or a pharmaceutically acceptable salt thereof, wherein the compound or pharmaceutically acceptable salt thereof exhibits an EC50 or $K_i$ of 1 micromolar or less in a standard assay of capsaicin receptor mediated calcium mobilization; and wherein A is absent or is selected from the group consisting of O, S, NR$_A$, NR$_A$CR$_B$R$_B$', CR$_B$R$_B$'NR$_A$, —CR$_A$=CR$_B$—, and C$_3$H$_4$; where R$_A$, R$_B$, and R$_B$' are independently selected at each occurrence from hydrogen and $C_{1-6}$ alkyl;

Z is oxygen or sulfur;

each $R_3$ and $R_4$ is independently
  (a) selected from the group consisting of hydrogen, halogen, cyano, nitro, halo($C_{1-6}$)alkyl, halo($C_{1-6}$)alkoxy, hydroxy, amino, $C_{1-6}$alkyl substituted with 0–2 $R_6$, $C_{2-6}$alkenyl substituted with 0–2 $R_6$; $C_{2-6}$alkynyl substituted with 0–2 $R_6$; $C_{1-6}$alkoxy substituted with 0–2 $R_6$, —NH($C_{1-6}$alkyl) substituted with 0–2 $R_6$, —N($C_{1-6}$alkyl)($C_{1-6}$alkyl) where each $C_{1-6}$alkyl is independently substituted with 0–2 $R_6$, —XR$_7$, and Y; or
  (b) joined to a $R_3$ or $R_4$ not attached to the same carbon to form an aryl ring substituted with 0–3 $R_6$, a saturated or partially unsaturated carbocyclic ring of from 5 to 8 members, which carbocyclic ring is substituted with 0–2 $R_6$, or a saturated, partially unsaturated, or aromatic heterocyclic ring of from 5 to 8 members, which heterocyclic ring is substituted with 0–2 $R_6$ and contains 1, 2, or 3 heteroatoms independently selected from N, O, and S;

Ar₁ is selected from the group consisting of:
(a) cyclohexyl, cyclopentyl, piperidinyl, piperazinyl, phenyl, pyrrolyl, furanyl, thienyl, pyrazolyl, imidazolyl, thiazolyl, isothiazolyl, oxazolyl, isoxazolyl, oxadiazolyl, triazolyl, tetrazolyl, pyridyl, pyrimidyl, pyrazinyl, benzimidazolyl, naphthyl, indolyl, isoindolyl, benzofuranyl, isobenzofuranyl, benzo[b]thiophenyl, benz[d]isoxazolyl, quinolinyl, isoquinolinyl, cinnolinyl, quinazolinyl, and quinoxalinyl, each of which is optionally mono-, di-, or trisubstituted with R₅; and
(b) bicyclic oxygen-containing groups of the formula:

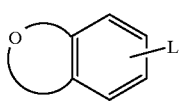

optionally mono-, di-, or trisubstituted with R₅, where L represents point of attachment and may be at any point on the benzene ring, and the oxygen-containing ring of the bicyclic oxygen-containing group consists of from 5 to 8 ring atoms, contains 1 or 2 oxygen atoms and remaining ring atoms are carbon;

Ar₂ is selected from the group consisting of:
(a) cyclohexyl, cyclopentyl, piperidinyl, piperazinyl, pyrrolyl, furanyl, thienyl, pyrazolyl, imidazolyl, thiazolyl, isothiazolyl, oxazolyl, isoxazolyl, oxadiazolyl, triazolyl, tetrazolyl, pyridyl, pyrimidyl, benzimidazolyl, naphthyl, indolyl, isoindolyl, benzofuranyl, isobenzofuranyl, benzo[b]thiophenyl, benz[d]isoxazolyl, quinolinyl, isoquinolinyl, cinnolinyl, quinazolinyl, and quinoxalinyl, each of which is optionally mono-, di-, or trisubstituted with R₅; and
(b) bicyclic oxygen-containing groups of the formula:

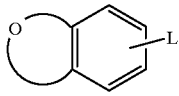

optionally mono-, di-, or trisubstituted with R₅, where L represents point of attachment and may be at any point on the benzene ring, and the oxygen-containing ring of the bicyclic oxygen-containing group consists of from 5 to 8 ring atoms, contains 1 or 2 oxygen atoms and remaining ring atoms are carbon;

R₅ is independently selected at each occurrence from the group consisting of halogen, nitro, halo($C_{1-6}$)alkyl, halo($C_{1-6}$)alkoxy, hydroxy, amino, $C_{1-6}$alkyl substituted with 0–2 $R_6$, $C_{2-6}$alkenyl substituted with 0–2 $R_6$, $C_{2-6}$alkynyl substituted with 0–2 $R_6$, $C_{1-6}$alkoxy and Y;

R₆ is independently selected at each occurrence from the group consisting of halogen, hydroxy, cyano, $C_{1-4}$alkyl, $C_{1-4}$alkoxy, —S(O)$_n$($C_{1-4}$alkyl), halo($C_{1-4}$)alkyl, halo($C_{1-4}$)alkoxy, CO($C_{1-4}$alkyl), CONH($C_{1-4}$alkyl), CON($C_{1-4}$alkyl$_1$)($C_{1-4}$alkyl$_2$) where alkyl$_1$ and alkyl$_2$ may be joined to form a saturated heterocyclic ring of from 5 to 8 ring atoms and containing 1, 2, or 3 heteroatoms independently selected from N, O, and S, —XR₇, and Y;

X is independently selected at each occurrence from the group consisting of —CH₂—, —CHR₈—, —O—, —S(O)$_n$—, —NH—, —NR₈—, —C(=O)—, —C(=O)O—, —C(=O)NH—, —C(=O)NR₈—, —S(O)$_n$NH—, —S(O)$_n$NR₈—, NHC(=O)—, —NR₈C(=O)—, —NHS(=O)$_n$—, and —NR₈S(O)$_n$—;

R₇ and R₈ are independently selected at each occurrence from hydrogen, and straight, branched, and cyclic alkyl groups, and (cycloalkyl)alkyl groups, said straight, branched, and cyclic alkyl groups, and (cycloalkyl)alkyl groups consisting of 1 to 8 carbon atoms, and containing zero or one or more double or triple bonds, each of which 1 to 8 carbon atoms is unsubstituted or substituted with one or more substituent(s) independently selected from oxo, hydroxy, halogen, amino, cyano, nitro, haloalkyl, haloalkoxy, —O($C_{1-4}$alkyl), —NH($C_{1-4}$alkyl), —NH($C_{1-4}$alkyl)($C_{1-4}$alkyl), —NHC(O)($C_{1-4}$alkyl), —NH($C_{1-4}$alkyl)C(O)($C_{1-4}$alkyl), —NHS(O)$_n$($C_{1-4}$alkyl), —S(O)$_n$($C_{1-4}$alkyl), —S(O)$_n$NH($C_{1-4}$alkyl), —S(O)$_n$N($C_{1-4}$alkyl$_3$)($C_{1-4}$alkyl$_4$) where $C_{1-4}$alkyl$_3$ and $C_{1-4}$alkyl$_4$ are optionally joined to form a saturated heterocyclic ring consisting of from 5 to 8 ring atoms and containing 1, 2, or 3 heteroatoms independently selected from N, O, and S, and Y';

Y and Y' are independently selected at each occurrence from 3- to 8-membered carbocyclic or heterocyclic groups which are saturated, unsaturated, or aromatic, which may be further substituted with one or more substituents independently selected from halogen, oxo, hydroxy, amino, nitro, cyano, $C_{1-4}$alkyl, $C_{1-4}$alkoxy, halo($C_{1-4}$)alkyl, halo($C_{1-4}$)alkoxy, mono- or di($C_{1-4}$)alkylamino, and $C_{1-4}$alkylthio;

wherein said 3- to 8-membered heterocyclic groups contain one or more heteroatom(s) independently selected from N, O, and S; and n is independently chosen at each occurrence from 0, 1, and 2.

27. A compound of the Formula A, Formula B, Formula C, Formula D, Formula E, or Formula F:

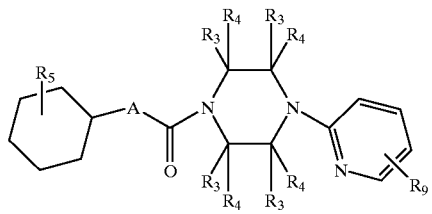

Formula A

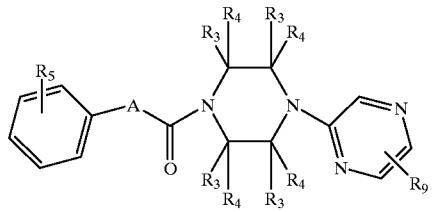

Formula B

-continued

Formula C

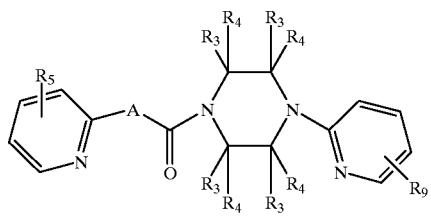

Formula D

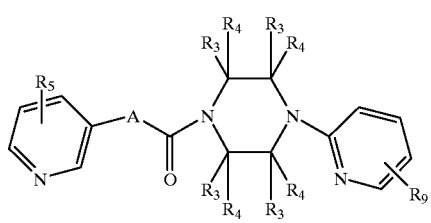

Formula E

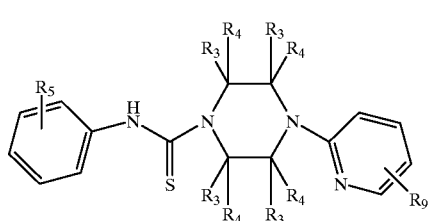

Formula F

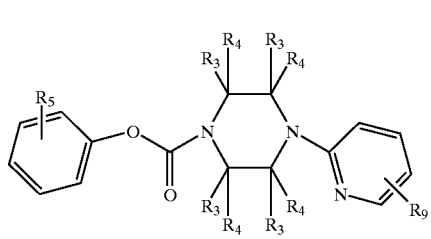

or a pharmaceutically acceptable salt of Formula A, Formula B, Formula C, Formula D, Formula E, or Formula F, wherein A represents NH or O;

each $R_3$ and $R_4$ is independently
- (a) selected from the group consisting of hydrogen, halogen, cyano, nitro, halo($C_{1-6}$)alkyl, halo($C_{1-6}$)alkoxy, hydroxy, amino, $C_{1-6}$alkyl substituted with 0–2 $R_6$, $C_{2-6}$alkenyl substituted with 0–2 $R_6$; $C_{2-6}$alkynyl substituted with 0–2 $R_6$; $C_{1-6}$alkoxy substituted with 0–2 $R_6$, —NH($C_{1-6}$alkyl) substituted with 0–2 $R_6$, —N($C_{1-6}$alkyl)($C_{1-6}$alkyl) where each $C_{1-6}$alkyl is independently substituted with 0–2 $R_6$, —$XR_7$, and Y; or
- (b) joined to a $R_3$ or $R_4$ not attached to the same carbon to form an aryl ring substituted with 0–3 $R_6$, a saturated or partially unsaturated carbocyclic ring of from 5 to 8 members, which carbocyclic ring is substituted with 0–2 $R_6$, or a saturated, partially unsaturated, or aromatic heterocyclic ring of from 5 to 8 members, which heterocyclic ring is substituted with 0–2 $R_6$ and contains 1, 2, or 3 heteroatoms independently selected from N, O, and S;

$R_5$ represents from 1 to 3 substituents independently selected at each occurrence from the group consisting of halogen, cyano, nitro, halo($C_{1-6}$)alkyl, halo($C_{1-6}$)alkoxy, hydroxy, amino, $C_{1-6}$alkyl substituted with 0–2 $R_6$, $C_{2-6}$alkenyl substituted with 0–2 $R_6$, $C_{2-6}$alkynyl substituted with 0–2 $R_6$, $C_{1-6}$alkoxy, —NH($C_{1-6}$alkyl) substituted with 0–2 $R_6$, —N($C_{1-6}$alkyl)($C_{1-6}$alkyl) where each $C_{1-6}$alkyl is independently substituted with 0–2 $R_6$, —$XR_7$, and Y;

$R_9$ represents from 1 to 3 substituents independently selected at each occurrence from the group consisting of halogen, cyano, nitro, halo($C_{1-6}$)alkyl, halo($C_{1-6}$)alkoxy, hydroxy, amino, $C_{1-6}$alkyl substituted with 0–2 $R_6$, $C_{2-6}$alkenyl substituted with 0–2 $R_6$, $C_{2-6}$alkynyl substituted with 0–2 $R_6$, $C_{1-6}$alkoxy substituted with 0–2 $R_6$, and Y;

$R_6$ is independently selected at each occurrence from the group consisting of halogen, hydroxy, cyano, $C_{1-4}$alkyl, $C_{1-4}$alkoxy, —S(O)$_n$($C_{1-4}$alkyl), halo($C_{1-4}$)alkyl, halo($C_{1-4}$)alkoxy, CO($C_{1-4}$alkyl), CONH($C_{1-4}$alkyl), CON($C_{1-4}$alkyl$_1$)($C_{1-4}$alkyl$_2$) where alkyl$_1$ and alkyl$_2$ may be joined to form a saturated heterocyclic ring of from 5 to 8 ring atoms and containing 1, 2, or 3 heteroatoms independently selected from N, O, and S, —$XR_7$, and Y;

X is independently selected at each occurrence from the group consisting of —CH$_2$—, —CHR$_8$—, —O—, —S(O)$_n$—, —NH—, —NR$_8$—, —C(=O)—, —C(=O)O—, —C(=O)NH—, —C(=O)NR$_8$—, and —NR$_8$S(O)$_n$—;

$R_7$ and $R_8$ are independently selected at each occurrence from hydrogen, and straight, branched, and cyclic alkyl groups, and (cycloalkyl)alkyl groups, said straight, branched, and cyclic alkyl groups, and (cycloalkyl)alkyl groups consisting of 1 to 8 carbon atoms, and containing zero or one or more double or triple bonds, each of which 1 to 8 carbon atoms is unsubstituted or substituted with one or more substituent(s) independently selected from oxo, hydroxy, halogen, amino, cyano, nitro, haloalkyl, haloalkoxy, —O($C_{1-4}$alkyl), —NH($C_{1-4}$alkyl), —N($C_{1-4}$alkyl)($C_{1-4}$alkyl), —NHC(O)($C_{1-4}$alkyl), —N($C_{1-4}$alkyl)C(O)($C_{1-4}$alkyl), —NHS(O)$_n$($C_{1-4}$alkyl), —S(O)$_n$($C_{1-4}$alkyl), —S(O)$_n$NH($C_{1-4}$alkyl), —S(O)$_n$N($C_{1-4}$alkyl$_3$)($C_{1-4}$alkyl$_4$) where $C_{1-4}$alkyl$_3$ and $C_{1-4}$alkyl$_4$ are optionally joined to form a saturated heterocyclic ring consisting of from 5 to 8 ring atoms and containing 1, 2, or 3 heteroatoms independently selected from N, O, and S, and Y';

Y and Y' are independently selected at each occurrence from 3- to 8-membered carbocyclic or heterocyclic groups which are saturated, unsaturated, or aromatic, which may be further substituted with one or more substituents independently selected from halogen, oxo, hydroxy, amino, nitro, cyano, $C_{1-4}$alkyl, $C_{1-4}$alkoxy, halo($C_{1-4}$)alkyl, halo($C_{1-4}$)alkoxy, mono- or di($C_{1-4}$) alkylamino, and $C_{1-4}$alkylthio;

wherein said 3- to 8-membered heterocyclic groups contain one or more heteroatom(s) independently selected from N, O, and S; and n is independently chosen at each occurrence from 0, 1, and 2.

28. A compound or salt according to claim 27, wherein A represents NH.

29. A compound or salt according to claim 27, wherein:
A represents NH; and
$R_3$ and $R_4$ are independently chosen at each occurrence from the group consisting of hydrogen, halogen, cyano, nitro, halo($C_{1-6}$)alkyl, halo($C_{1-6}$)alkoxy, hydroxy, amino, $C_{1-6}$alkyl, $C_{2-6}$alkenyl, $C_{2-6}$alkynyl, $C_{1-6}$alkoxy substituted with 0–2 $R_6$, —NH($C_{1-6}$alkyl), and —N($C_{1-6}$ alkyl)($C_{1-6}$alkyl).

30. A compound or salt according to claim 27, wherein:

A represents NH;

$R_3$ represents hydrogen; and $R_4$ is independently chosen at each occurrence from hydrogen and $C_{1-6}$ alkyl.

31. A compound or salt according to claim 27, wherein:

A represents NH;

$R_3$ represents hydrogen; and $R_4$ is independently chosen at each occurrence from hydrogen and methyl.

32. A compound or salt according to claim 27, wherein:

A represents NH;

$R_3$ represents hydrogen;

$R_4$ is independently chosen at each occurrence from hydrogen and methyl; and represents from 1 to 3 substituents independently selected at each occurrence from the group consisting of halogen, cyano, nitro, halo($C_{1-6}$)alkyl, halo($C_{1-6}$) alkoxy, hydroxy, amino, $C_{1-6}$alkyl, $C_{2-6}$alkenyl, $C_{2-6}$alkynyl, $C_{1-6}$alkoxy, —NH($C_{1-6}$alkyl), —N($C_{1-6}$alkyl)($C_{1-6}$alkyl), and $C_{3-8}$ cycloalkyl; and $R_9$ represents from 1 to 3 substituents independently selected at each occurrence from the group consisting of halogen, nitro, halo($C_{1-6}$)alkyl, halo($C_{1-6}$)alkoxy, hydroxy, amino, $C_{1-6}$alkyl, $C_{2-6}$alkenyl, $C_{2-6}$alkynyl, $C_{1-6}$alkoxy, and $C_{3-8}$ cycloalkyl.

33. A compound or salt of the Formula A-1

Formula A-1

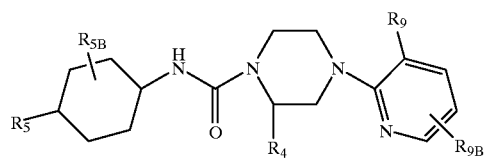

wherein $R_4$ is hydrogen or methyl;

$R_5$ and $R_9$ are independently selected from the group consisting of halogen, cyano, nitro, halo($C_{1-6}$)alkyl, halo($C_{1-6}$)alkoxy, hydroxy, amino, $C_{1-6}$alkyl, $C_{2-6}$alkenyl, $C_{2-6}$alkynyl, $C_{1-6}$alkoxy, —NH($C_{1-6}$alkyl), —N($C_{1-6}$alkyl)($C_{1-6}$alkyl), and $C_{3-8}$ cycloalkyl; and $R_{5B}$ and $R_{9B}$ each represent from 0 to 2 substituents independently selected at each occurrence from hydrogen, halogen, cyano, nitro, halo($C_{1-2}$)alkyl, halo ($C_{1-2}$)alkoxy, hydroxy, amino, $C_{1-3}$alkyl, $C_{1-3}$alkoxy, —NH($C_{1-3}$alkyl), and —N($C_{1-6}$alkyl)($C_{1-6}$alkyl).

34. A compound or salt according to claim 33, wherein:

$R_5$ is $C_{3-6}$ alkyl; $C_{3-6}$ alkoxy; halo($C_{1-3}$)alkyl, halo($C_{1-3}$) alkoxy, or $C_{3-8}$ cycloalkyl;

$R_9$ is chloro or trifluoromethyl; and $R_{5B}$ and $R_{9B}$ are hydrogen.

35. A compound or salt of Formula B-1:

Formula B-1

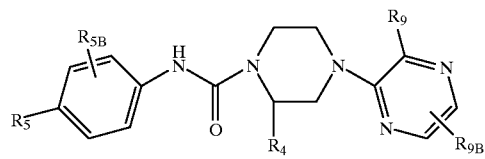

wherein $R_4$ is hydrogen or methyl;

$R_5$ and $R_9$ are independently selected from the group consisting of halogen, cyano, nitro, halo($C_{1-6}$)alkyl, halo($C_{1-6}$)alkoxy, hydroxy, amino, $C_{1-6}$alkyl, $C_{2-6}$alkenyl, $C_{2-6}$alkynyl, $C_{1-6}$alkoxy, —NH($C_{1-6}$ alkyl), —N($C_{1-6}$alkyl)($C_{1-6}$alkyl), and $C_{3-8}$ cycloalkyl; and $R_{5B}$ and $R_{9B}$ each represent from 0 to 2 substituents independently selected at each occurrence from hydrogen, halogen, cyano, nitro, halo($C_{1-2}$)alkyl, halo ($C_{1-2}$)alkoxy, hydroxy, amino, $C_{1-3}$alkyl, $C_{1-3}$alkoxy, —NH($C_{1-3}$alkyl), and —N($C_{1-6}$alkyl)($C_{1-6}$alkyl).

36. A compound or salt according to claim 35, wherein:

$R_5$ is $C_{3-6}$alkyl; $C_{3-6}$ alkoxy; halo($C_{1-3}$)alkyl, halo($C_{1-3}$) alkoxy, or $C_{3-8}$ cycloalkyl;

$R_9$ is chloro or trifluoromethyl; and $R_{5B}$ and $R_{9B}$ are hydrogen.

37. A compound or salt of Formula C-1:

Formula C-1

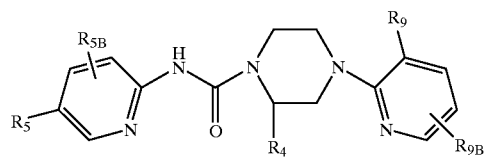

wherein:

$R_4$ is hydrogen or methyl;

$R_5$ and $R_9$ are independently selected from the group consisting of halogen, cyano, nitro, halo($C_{1-6}$)alkyl, halo($C_{1-6}$)alkoxy, hydroxy, amino, $C_{1-6}$alkyl, $C_{2-6}$alkenyl, $C_{2-6}$alkynyl, $C_{1-6}$alkoxy, —NH($C_{1-6}$ alkyl), —N($C_{1-6}$alkyl)($C_{1-6}$alkyl), and $C_{3-8}$ cycloalkyl; and $R_{5B}$ and $R_{9B}$ each represent from 0 to 2 substituents independently selected at each occurrence from hydrogen, halogen, cyano, nitro, halo($C_{1-2}$)alkyl, halo ($C_{1-2}$)alkoxy, hydroxy, amino, $C_{1-3}$alkyl, $C_{1-3}$alkoxy, —NH($C_{1-3}$alkyl), and —N($C_{1-6}$alkyl)($C_{1-6}$alkyl).

38. A compound or salt according to claim 37, wherein:

$R_5$ is $C_{3-6}$ alkyl; $C_{3-6}$ alkoxy; halo($C_{1-3}$)alkyl, halo($C_{1-3}$) alkoxy, or $C_{3-8}$ cycloalkyl;

$R_9$ is chloro or trifluoromethyl; and $R_{5B}$ and $R_{9B}$ are hydrogen.

39. A compound or salt according to claim 32 of Formula D-1:

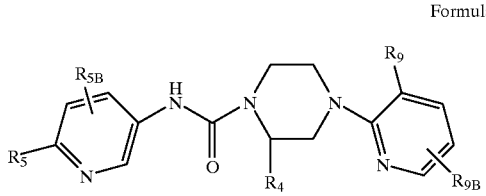

Formula D-1 wherein:

$R_5$ is selected from the group consisting of halogen, cyano, nitro, halo($C_{1-6}$)alkyl, halo($C_{1-6}$)alkoxy, hydroxy, amino, $C_{1-6}$alkyl, $C_{2-6}$alkenyl, $C_{2-6}$alkynyl, $C_{1-6}$alkoxy, —NH($C_{1-6}$alkyl), —N($C_{1-6}$alkyl)($C_{1-6}$alkyl), and $C_{3-8}$ cycloalkyl;

$R_9$ is selected from the group consisting of halogen, cyano, nitro, halo($C_{1-6}$)alkyl, halo($C_{1-6}$)alkoxy, hydroxy, amino, $C_{1-6}$alkyl, $C_{2-6}$alkenyl, $C_{2-6}$alkynyl, $C_{1-6}$alkoxy, and $C_{3-8}$ cycloalkyl; and $R_{5B}$ and $R_{9B}$ each represent from 0 to 2 substituents independently selected at each occurrence from hydrogen, halogen, cyano, nitro, halo($C_{1-2}$)alkyl, halo($C_{1-2}$)alkoxy, hydroxy, amino, $C_{1-3}$alkyl, $C_{1-3}$alkoxy, —NH($C_{1-3}$alkyl), and —N($C_{1-6}$alkyl)($C_{1-6}$alkyl).

40. A compound or salt according to claim 39, wherein:

$R_5$ is $C_{3-6}$ alkyl; $C_{3-6}$ alkoxy; halo($C_{1-3}$)alkyl, halo($C_{1-3}$)alkoxy, or $C_{3-8}$ cycloalkyl;

$R_9$ is chloro or trifluoromethyl; and $R_{5B}$ and $R_{9B}$ are hydrogen.

41. A compound or salt of Formula E-1:

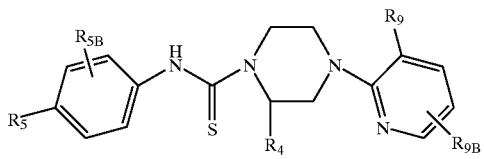

Formula E-1 wherein:

$R_4$ is hydrogen or methyl;

$R_5$ and $R_9$ are independently selected from the group consisting of halogen, cyano, nitro, halo($C_{1-6}$)alkyl, halo($C_{1-6}$)alkoxy, hydroxy, amino, $C_{1-6}$alkyl, $C_{2-6}$alkenyl, $C_{2-6}$alkynyl, $C_{1-6}$alkoxy, —NH($C_{1-6}$alkyl), —N($C_{1-6}$alkyl)($C_{1-6}$alkyl), and $C_{3-8}$ cycloalkyl; and $R_{5B}$ and $R_{9B}$ each represent from 0 to 2 substituents independently selected at each occurrence from hydrogen, halogen, cyano, nitro, halo($C_{1-2}$)alkyl, halo($C_{1-2}$)alkoxy, hydroxy, amino, $C_{1-3}$alkyl, $C_{1-3}$alkoxy, —NH($C_{1-3}$alkyl), and —N($C_{1-6}$alkyl)($C_{1-6}$alkyl).

42. A compound or salt according to claim 41, wherein:

$R_5$ is $C_{3-6}$ alkyl; $C_{3-6}$ alkoxy; halo($C_{1-3}$)alkyl, halo($C_{1-3}$)alkoxy, or $C_{3-8}$ cycloalkyl;

$R_9$ is chloro or trifluoromethyl; and $R_{5B}$ and $R_{9B}$ are hydrogen.

43. A compound of salt of Formula F-1:

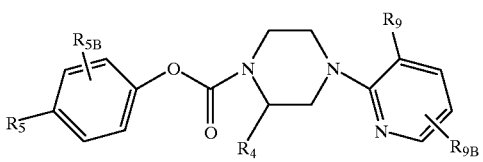

Formula F-1 wherein:

$R_4$ is hydrogen or methyl;

$R_5$ and $R_9$ are independently selected from the group consisting of halogen, cyano, nitro, halo($C_{1-6}$)alkyl, halo($C_{1-6}$)alkoxy, hydroxy, amino, $C_{1-6}$alkyl, $C_{2-6}$alkenyl, $C_{2-6}$alkynyl, $C_{1-6}$alkoxy, —NH($C_{1-6}$alkyl), —N($C_{1-6}$alkyl)($C_{1-6}$alkyl), and $C_{3-8}$ cycloalkyl; and $R_{5B}$ and $R_{9B}$ each represent from 0 to 2 substituents independently selected at each occurrence from hydrogen, halogen, cyano, nitro, halo($C_{1-2}$)alkyl, halo($C_{1-2}$)alkoxy, hydroxy, amino, $C_{1-3}$alkyl, $C_{1-3}$alkoxy, —NH($C_{1-3}$alkyl), and —N($C_{1-6}$alkyl)($C_{1-6}$alkyl).

44. A compound or salt according to claim 42, wherein:

$R_5$ is $C_{3-6}$ alkyl; $C_{3-6}$ alkoxy; halo($C_{1-3}$)alkyl, halo($C_{1-3}$)alkoxy, or $C_{3-8}$ cycloalkyl;

$R_9$ is chloro or trifluoromethyl; and $R_{5B}$ and $R_{9B}$ are hydrogen.

45. A compound of the Formula:

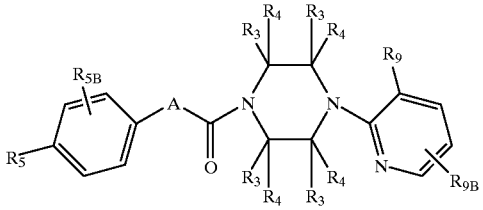

or a pharmaceutically acceptable salt thereof, wherein:

A is absent or is selected from the group consisting of O, S, $NR_A$, $CR_BR_B'$, $NR_ACR_BR_B'$, $CR_BR_B'NR_A$, —$CR_A$=$CR_B$—, and $C_3H_4$; where $R_A$, $R_B$, and $R_B'$ are independently selected at each occurrence from hydrogen and $C_{1-6}$ alkyl;

each $R_3$ and $R_4$ is independently (a) selected from the group consisting of hydrogen, halogen, cyano, nitro, halo($C_{1-6}$)alkyl, halo($C_{1-6}$)alkoxy, hydroxy, amino, $C_{1-6}$alkyl substituted with 0–2 $R_6$, $C_{2-6}$alkenyl substituted with 0–2 $R_6$; $C_{2-6}$alkynyl substituted with 0–2 $R_6$; $C_{1-6}$alkoxy substituted with 0–2 $R_6$, —NH($C_{1-6}$alkyl) substituted with 0–2 $R_6$, —N($C_{1-6}$alkyl)($C_{1-6}$alkyl) where each $C_{1-6}$alkyl is independently substituted with 0–2 $R_6$, —$XR_7$, and Y; or (b) joined to a $R_3$ or $R_4$ not attached to the same carbon to form an aryl ring substituted with 0–3 $R_6$, a saturated or partially unsaturated carbocyclic ring of from 5 to 8 members, which carbocyclic ring is substituted with 0–2 $R_6$, or a saturated, partially unsaturated, or aromatic heterocyclic ring of from 5 to 8 members, which heterocyclic ring is substituted with 0–2 $R_6$ and contains 1, 2, or 3 heteroatoms independently selected from N, O, and S;

$R_5$ is selected from the group consisting of bromo, fluoro, iodo, halo($C_{1-6}$)alkyl, halo($C_{3-6}$)alkoxy, $C_{3-6}$alkyl substituted with 0–3 $R_6$, $C_{2-6}$alkenyl substituted with 0–3 $R_6$, $C_{2-6}$alkynyl substituted with 0–3 $R_6$, $C_{3-6}$alkoxy, ($C_{3-8}$cycloalkyl)$C_{1-4}$alkyl, —NH($C_{1-6}$alkyl) substituted with 0–2 R, —N($C_{1-6}$alkyl)($C_{1-6}$alkyl) where each $C_{1-6}$alkyl is substituted with 0–2 $R_6$, Y, —(C=O)Y, —(CH$_2$)Y, and —(CH(CN))Y;

$R_9$ is selected from the group consisting of halogen, cyano, —N(SO$_2$C$_{1-6}$alkyl)(SO$_2$C$_{1-6}$alkyl), —SO$_2$NH$_2$, halo($C_{1-6}$)alkyl, halo($C_{1-6}$)alkoxy, $C_{1-6}$alkyl substituted with 0–2 $R_6$, $C_{2-6}$alkenyl substituted with 0–2 $R_6$, $C_{2-6}$alkynyl substituted with 0–2 $R_6$, and $C_{1-6}$alkoxy substituted with 0–2 $R_6$;

$R_{5B}$ represents from 0 to 2 substituents independently selected at each occurrence from the group consisting of (a) halogen, cyano, nitro, halo($C_{1-6}$)alkyl, halo($C_{1-6}$)alkoxy, hydroxy, amino, $C_{1-6}$alkyl substituted with 0–2 $R_6$, ($C_{3-8}$cycloalkyl)$C_{1-4}$alkyl substituted with 0–2 $R_6$, $C_{2-6}$alkenyl substituted with 0–2 $R_6$, $C_{2-6}$alkynyl substituted with 0–2 $R_6$, $C_{1-6}$alkoxy, —NH($C_{1-6}$alkyl) substituted with 0–2 $R_6$, —N($C_{1-6}$alkyl)($C_{1-6}$alkyl) where each $C_{1-6}$alkyl is independently substituted with 0–2 $R_6$, and Y; and (b) groups that are joined to $R_5$ to form a $C_{3-8}$cycloalkyl group or a saturated heterocyclic ring or partially unsaturated heterocycle, each of which is optionally substituted by from 1 to 5 substituents independently chosen from cyano, halogen, hydroxy, $C_{1-4}$alkyl, $C_{1-4}$alkoxy, —NH($C_{1-4}$alkyl), —N($C_{1-4}$alkyl)($C_{1-4}$alkyl) halo($C_{1-4}$)alkyl, and halo($C_{1-4}$)alkoxy, wherein the saturated heterocyclic ring or partially unsaturated heterocycle contains from 4 to 3 ring atoms of which 1, 2, or 3 are heteroatoms independently selected from N, O, and S;

$R_{9B}$ represents from 0 to 2 substituents independently selected at each occurrence from halogen, cyano, nitro, halo($C_{1-6}$)alkyl, halo($C_{1-6}$)alkoxy, hydroxy, amino, $C_{1-6}$alkyl substituted with 0–2 $R_6$, ($C_{3-8}$cycloalkyl)$C_{1-4}$alkyl substituted with 0–2 $R_6$, $C_{2-6}$alkenyl substituted with 0–2 $R_6$, $C_{2-6}$alkynyl substituted with 0–2 $R_6$, $C_{1-6}$alkoxy substituted with 0–2 $R_6$, and Y;

$R_6$ is independently selected at each occurrence from the group consisting of cyano, halogen, hydroxy, $C_{1-4}$alkyl, $C_{1-4}$alkoxy, —S(O)$_n$($C_{1-4}$alkyl), halo($C_{1-4}$)alkyl, halo($C_{1-4}$)alkoxy, CO($C_{1-4}$alkyl), CONH($C_{1-4}$alkyl), CON($C_{1-4}$alkyl$_1$)($C_{1-4}$alkyl$_2$) where alkyl$_1$ and alkyl$_2$ may be joined to form a saturated heterocyclic ring of from 5 to 8 ring atoms and containing 1, 2, or 3 heteroatoms independently selected from N, O, and S, —XR$_7$, and Y;

X is independently selected at each occurrence from the group consisting of —CH$_2$—, —CHR$_8$—, —O—, —S(O)$_n$—, —NH—, —NR$_8$—, —C(=O)—, —C(=O)NH—, —C(=O)NH$_8$—, —S(=O)$_n$NH—, —S(O)$_n$NR$_8$—, NHC(=O)—, —NR$_8$C(=O)—, —NHS(O)$_n$—, and —NH$_8$S(O)$_n$—;

$R_7$ and $R_8$ are independently selected at each occurrence from hydrogen, and straight, branched, and cyclic alkyl groups, and (cycloalkyl)alkyl groups, said straight, branched, and cyclic alkyl groups, and (cycloalkyl)alkyl groups consisting of 1 to 8 carbon atoms, and containing zero or one or more double or triple bonds, each of which 1 to 8 carbon atoms may be further substituted with one or more substituent(s) independently selected from oxo, hydroxy, halogen, amino, cyano, nitro, haloalkyl, haloalkoxy, —O($C_{1-4}$alkyl), NH($C_{1-4}$alkyl), —N($C_{1-4}$alkyl)($C_{1-4}$alkyl) —NHC(O)($C_{1-4}$alkyl), —N($C_{1-4}$alkyl)C(O)($C_{1-4}$alkyl) —NHS(O)$_n$ ($C_{1-4}$alkyl), —S(O)$_n$($C_{1-4}$alkyl), —S(O)$_n$NH($C_{1-4}$alkyl), —S(O)$_n$N($C_{1-4}$alkyl$_3$)($C_{1-4}$alkyl$_4$) where $C_{1-4}$alkyl$_3$ and $C_{1-4}$alkyl$_4$ are optionally joined to form a saturated heterocyclic ring consisting of from 5 to 8 ring atoms and containing 1, 2, or 3 heteroatoms independently selected from N, O, and S, and Y';

Y and Y' are independently selected at each occurrence from 3- to 8-membered carbocyclic or heterocyclic groups which are saturated, unsaturated, or aromatic, which may be further substituted with one or more substituents independently selected from halogen, oxo, hydroxy, amino, nitro, cyano, $C_{1-4}$alkyl, $C_{1-4}$alkoxy, halo($C_{1-4}$)alkyl, halo($C_{1-4}$)alkoxy, mono- or di($C_{1-4}$)alkylamino, and $C_{1-4}$alkylthio; wherein said 3- to 8-membered heterocyclic groups contain one or more heteroatom(s) independently selected from N, O, and S; and n is independently chosen at each occurrence from 0, 1, and 2.

46. A compound or salt according to claim 45, wherein:

A as O or NR$_A$, wherein R$_A$ is hydrogen or methyl.

47. A compound or salt according to claim 45, wherein:

A is O or NR$_A$, wherein R$_A$ is hydrogen or methyl; and $R_3$ and $R_4$ are independently chosen at each occurrence from the group consisting of hydrogen, halogen, cyano, nitro, halo($C_{1-6}$)alkyl, halo($C_{1-6}$)alkoxy, hydroxy, amino, $C_{1-6}$alkyl, $C_{2-6}$alkenyl, $C_{2-6}$alkynyl, $C_{1-6}$alkoxy, —NH($C_{1-6}$alkyl), and —N($C_{1-6}$alkyl)($C_{1-6}$alkyl).

48. A compound or salt according to claim 45, wherein:

A is O or NR$_A$, wherein R$_A$ is hydrogen or methyl;

$R_3$ is hydrogen; and $R_4$ is independently chosen at each occurrence from the group consisting of hydrogen, halogen, cyano, nitro, halo($C_{1-6}$)alkyl, halo($C_{1-6}$)alkoxy, hydroxy, amino, $C_{1-6}$alkyl, $C_{2-6}$alkenyl, $C_{2-6}$alkynyl, $C_{1-6}$alkoxy, —NH($C_{1-6}$alkyl), and —N($C_{1-6}$alkyl)($C_{1-6}$alkyl).

49. A compound or salt according to claim 45, wherein:

A is O or NR$_A$, wherein R$_A$ is hydrogen or methyl;

$R_3$ is hydrogen; and $R_4$ is independently chosen at each occurrence from hydrogen and $C_{1-6}$alkyl.

50. A compound or salt according to claim 45, wherein:

A is NR$_A$, wherein R$_A$ is hydrogen or methyl;

$R_3$ is hydrogen; and $R_4$ is independently chosen at each occurrence from hydrogen, halo($C_{1-3}$)alkyl, and $C_{1-6}$alkyl.

51. A compound or salt according to claim 45, wherein:

A is NR$_A$, wherein R$_A$ is hydrogen or methyl;

$R_3$ is hydrogen; and $R_4$ is independently chosen at each occurrence from hydrogen and $C_{1-4}$alkyl.

52. A compound or salt according to claim 45 of the Formula:

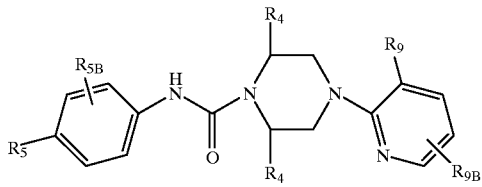

wherein:

R$_4$ is independently chosen at each occurrence from hydrogen and C$_{1-4}$alkyl.

53. A compound or salt according to claim 52 of the formula:

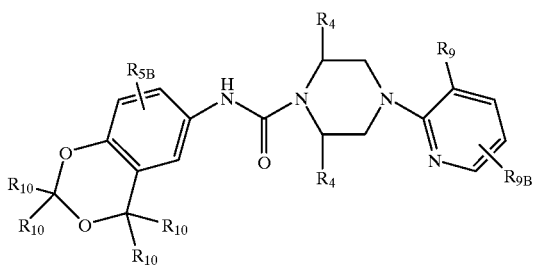

wherein

R$_{5B}$ and R$_{9B}$ are independently chosen from hydrogen, halogen, cyano, nitro, halo(C$_{1-2}$)alkyl, halo(C$_{1-2}$) alkoxy, amino, C$_{1-4}$alkyl, and C$_{1-2}$alkoxy; and R$_{10}$ is independently chosen at each occurrence from hydrogen, halogen, and C$_{1-4}$ alkyl.

54. A compound or salt according to claim 53 wherein:

R$_9$ is selected from the group consisting of halogen, cyano, —N(SO$_2$CH$_3$)$_2$, —SO$_2$NH$_2$, halo(C$_{1-3}$)alkyl, and C$_{1-3}$alkoxy.

55. A compound or salt according to claim 52, wherein:

R$_{5B}$ and R$_{9B}$ are independently chosen from hydrogen, halogen, cyano, nitro, halo(C$_{1-2}$)alkyl, halo(C$_{1-2}$) alkoxy, amino, C$_{1-4}$alkyl, and C$_{1-2}$alkoxy.

56. A compound or salt according to claim 52, wherein:

R$_{5B}$ represents 0 or 1 substituents chosen from halogen, cyano, nitro, halo(C$_{1-2}$alkyl, halo(C$_{1-2}$)alkoxy, amino, C$_{1-4}$alkyl, and C$_{1-2}$alkoxy; and R$_{9B}$ represents 0 or 1 substituents chosen from halogen, cyano, nitro, halo(C$_{1-2}$)alkyl, and C$_{1-2}$alkyl, and C$_{1-2}$alkoxy.

57. A compound or salt according to claim 52, wherein:

R$_9$ is selected from the group consisting of halogen, cyano, —N(SO$_2$CH$_3$)$_2$, —SO$_2$NH$_2$, halo(C$_{1-3}$)alkyl, and C$_{1-3}$alkoxy;

R$_{5B}$ represents 0 or 1 substituents chosen from halogen, cyano, nitro, halo(C$_{1-2}$)alkyl, halo(C$_{1-2}$)alkoxy, amino, C$_{1-4}$alkyl, and C$_{1-2}$alkoxy; and R$_{9B}$ represents 0 or 1 substituents chosen from halogen, cyano, nitro, halo(C$_{1-2}$)alkyl, C$_{1-2}$alkyl, and C$_{1-2}$alkoxy.

58. A compound or salt according to claim 52, wherein:

R$_5$ is selected from the group consisting of bromo, fluoro, iodo, halo(C$_{1-6}$)alkyl, halo(C$_{3-6}$)alkoxy, C$_{3-6}$alkyl substituted with 0–3 R$_6$, C$_{2-6}$alkenyl substituted with 0–3 R$_6$, Y, —(C=O)Y, —(CH$_2$)Y, and —(CH(CN))Y;

R$_9$ is selected from the group consisting of halogen, cyano, —N(SO$_2$CH$_3$)$_2$, —SO$_2$NH$_2$, halo(C$_{1-2}$alkyl, C$_{1-3}$alkoxy;

R$_{5B}$ represents 0 or 1 substituents chosen from halogen, cyano, nitro, halo(C$_{1-2}$)alkyl, halo(C$_{1-2}$)alkoxy, amino, C$_{1-4}$alkyl, and C$_{1-2}$alkoxy; and R$_{9B}$ represents 0 or 1 substituents chosen from halogen, cyano, nitro, halo(C$_{1-2}$)alkyl, C$_{1-2}$alkyl, and C$_{1-2}$alkoxy.

59. A compound or salt according to claim 58, wherein:

R$_6$ is independently selected at each occurrence from the group consisting of cyano, halogen, hydroxy, C$_{1-4}$alkyl, C$_{1-4}$alkoxy, —NH(C$_{1-4}$alkyl), and —N(C$_{1-4}$alkyl)(C$_{1-4}$alkyl) and Y; and Y is independently selected at each occurrence from C$_{3-8}$ cycloalkyl, piperidinyl, piperazinyl, tetrahydropyranyl, dihydropyranyl, morpholinyl, thiomorpholinyl, phenyl, pyridyl, pyrazinyl, pyrimidinyl, thiazolyl, thienyl, and imidazolyl, each of which may be further substituted with one or more substituents independently selected from halogen, oxo, hydroxy, amino, nitro, cyano, C$_{1-4}$alkyl, C$_{1-4}$alkoxy, halo(C$_{1-4}$)alkyl, halo(C$_{1-4}$) alkoxy, mono- or di(C$_{1-4}$)alkylamino, and C$_{1-4}$alkylthio.

60. A compound or salt according to claim 58, wherein:

R$_9$ is cyano, trifluoromethyl, chloro, or iodo; and

R$_{9B}$ is hydrogen.

61. A compound according to claim 45, which is N-(4-tert-butylphenyl)-4-(3-chloropyridin-2-yl)piperazine-1-carboxamide, or a pharmaceutically acceptable salt thereof.

62. A compound according to claim 45, which is (2R)-4-(3-chloropyridin-2-yl)-N-(4-cyclohexylphenyl)-2-methylpiperazine-1-carboxamide, or a pharmaceutically acceptable salt thereof.

63. A compound according to claim 45, which is (2R)-4-(3-chloropyridin-2-yl)-2-methyl-N-[4-(trifluoromethyl) phenyl]piperazine-1-carboxamide, or a pharmaceutically acceptable salt thereof.

64. A compound according to claim 45, which is (2R)-N-(4-tert-butylphenyl)-4-(3-chloropyridin-2-yl)-2-methylpiperazine-1-carboxamide, or a pharmaceutically acceptable salt thereof.

65. A compound according to claim 45, which is (2R)-4-(3-chloropyridin-2-yl)-N-(4-isopropylphenyl)-2-methylpiperazine-1-carboxamide, or a pharmaceutically acceptable salt thereof.

66. A compound according to claim 45, which is (2S)-4-(3-chloropyridin-2-yl)-N-(4-trifluoromethylphenyl)-2-methylpiperazine-1-carboxamide, or a pharmaceutically acceptable salt thereof.

67. A compound according to claim 45, which is (2S)-N-(4-tert-butylphenyl)-4-(3-chloropyridin-2-yl)-2-methylpiperazine-1-carboxamide, or a pharmaceutically acceptable salt thereof.

68. A compound according to claim 45, which is (2S)-4-(3-chloropyridin-2-yl)-N-(4-isopropylphenyl)-2-methylpiperazine-1-carboxamide, or a pharmaceutically acceptable salt thereof.

69. A compound according to claim 45, which is (2R)-4-(3-chloropyridin-2-yl)-2-methyl-N-(4-piperidin-1-ylphenyl) piperazine-1-carboxamide, or a pharmaceutically acceptable salt thereof.

70. A compound according to claim 45, which is (2R)-4-(3-chloropyridin-2-yl)-N-[2-fluoro-4-(trifluoromethyl) phenyl]-2-methylpiperazine-1-carboxamide, or a pharmaceutically acceptable salt thereof.

71. A compound according to claim 45, which is (2R)-2-methyl-N-[4-(trifluoromethyl)phenyl]-4-[3-(trifluoromethyl)pyridin-2-yl]piperazine-1-carboxamide, or a pharmaceutically acceptable salt thereof.

72. A compound according to claim 45, which is (2R)-N-(4-tert-butylphenyl)-2-methyl-4-[3-(trifluoromethyl)pyridin-2-yl]piperazine-1-carboxamide, or a pharmaceutically acceptable salt thereof.

73. A compound according to claim 45, which is (2R)-N-(4-isopropylphenyl)-2-methyl-4-[3-(trifluoromethyl)pyridin-2-yl]piperazine-1-carboxamide, or a pharmaceutically acceptable salt thereof.

74. A compound according to claim 45, which is 4-(3-chloropyridin-2-yl)-2,6-dimethyl-N-[4-(trifluoromethyl)phenyl]piperazine-1-carboxamide, or a pharmaceutically acceptable salt thereof.

75. A compound according to claim 45, which is N-(4-tert-butylphenyl)-4-(3-chloropyridin-2-yl)-2,6-dimethylpiperazine-1-carboxamide, or a pharmaceutically acceptable salt thereof.

76. A compound according to claim 45, which is 4-(3-chloropyridin-2-yl)-N-(4-isopropylphenyl)-2,6-dimethylpiperazine-1-carboxamide, or a pharmaceutically acceptable salt thereof.

77. A compound according to claim 45, which is (2R)-N-(4-cyclohexylphenyl)-2-methyl-4-[3-(trifluoromethyl)pyridin-2-yl]piperazine-1-carboxamide, or a pharmaceutically acceptable salt thereof.

78. A compound according to claim 45, which is 4-(3-chloropyridin-2-yl)-N-(4-cyclohexylphenyl)-2,6-dimethylpiperazine-1-carboxamide, or a pharmaceutically acceptable salt thereof.

79. A compound according to claim 45, which is (2R)-4-(3-chloropyridin-2-yl)-N-(4-cyclopentylphenyl)-2-methylpiperazine-1-carboxamide, or a pharmaceutically acceptable salt thereof.

80. A compound according to claim 50, which is (2R)-N-(4-cyclopentylphenyl)-2-methyl-4-[3-(trifluoromethyl)pyridin-2-yl]piperazine-1-carboxamide, or a pharmaceutically acceptable salt thereof.

81. A compound according to claim 45, which is (2R)-N-(4-tert-butylphenyl)-4-(3-methoxypyridin-2-yl)-2-methylpiperazine-1-carboxamide, or a pharmaceutically acceptable salt thereof.

82. A compound according to claim 45, which is (2R)-4-(3-methoxypyridin-2-yl)-2-methyl-N-[4-(trifluoromethyl)phenyl]piperazine-1-carboxamide, or a pharmaceutically acceptable salt thereof.

83. A compound according to claim 45, which is (2R)-N-(4-cyclohexylphenyl)-4-(3-methoxypyridin-2-yl)-2-methylpiperazine-1-carboxamide, or a pharmaceutically acceptable salt thereof.

84. A compound according to claim 45, which is (2R)-4-(3-chloropyridin-2-yl)-N-[4-(3,6-dihydro-2H-pyran-4-yl)phenyl]-2-methylpiperazine-1-carboxamide, or a pharmaceutically acceptable salt thereof.

85. A compound according to claim 45, which is (2R)-4-(3-chloropyridin-2-yl)-2-methyl-N-(4-tetrahydro-2H-pyran-4-ylphenyl)piperazine-1-carboxamide, or a pharmaceutically acceptable salt thereof.

86. A compound according to claim 45, which is (2R)-4-(3-chloropyridin-2-yl)-N-[4-(4-hydroxytetrahydro-2H-pyran-4-yl)phenyl]-2-methylpiperazine-1-carboxamide, or a pharmaceutically acceptable salt thereof.

87. A compound according to claim 45, which is (2R)-N-[4-(4-hydroxytetrahydro-2H-pyran-4-yl)phenyl]-2-methyl-4-[3-(trifluoromethyl)pyridin-2-yl]piperazine-1-carboxamide, or a pharmaceutically acceptable salt thereof.

88. A compound according to claim 45, which is (2R)-4-(3-chloropyridin-2-yl)-2-methyl-N-[4-(2-methyl-1,3-thiazol-4-yl)phenyl]piperazine-1-carboxamide, or a pharmaceutically acceptable salt thereof.

89. A compound according to claim 45, which is (2R)-4-(3-chloropyridin-2-yl)-N-[4-(2-ethyl-1,3-thiazol-4-yl)phenyl]-2-methylpiperazine-1-carboxamide, or a pharmaceutically acceptable salt thereof.

90. A compound according to claim 45, which is (2R)-4-(3-chloropyridin-2-yl)-N-[4-(2-methoxy-1,1-dimethylethyl)phenyl]-2-methylpiperazine-1-carboxamide, or a pharmaceutically acceptable salt thereof.

91. A compound according to claim 45, which is (2R)-N-[4-(2-methoxy-1,1-dimethylethyl)phenyl]-2-methyl-4-[3-(trifluoromethyl)pyridin-2-yl]piperazine-1-carboxamide, or a pharmaceutically acceptable salt thereof.

92. A compound according to claim 45, which is (2R)-4-(3-chloropyridin-2-yl)-N-[4-(1-cyano-1-methylethyl)phenyl]-2-methylpiperazine-1-carboxamide, or a pharmaceutically acceptable salt thereof.

93. A compound according to claim 45, which is (2R)-N-[4-(1-cyano-1-methylethyl)phenyl]-2-methyl-4-[3-(trifluoromethyl)pyridin-2-yl]piperazine-1-carboxamide, or a pharmaceutically acceptable salt thereof.

94. A compound according to claim 45, which is N-(4-tert-butylphenyl)-4-(3-chloropyridin-2-yl)-2-ethylpiperazine-1-carboxamide, or a pharmaceutically acceptable salt thereof.

95. A compound according to claim 45, which is 4-(3-chloropyridin-2-yl)-2-ethyl-N-[4-(trifluoromethyl)phenyl]piperazine-1-carboxamide, or a pharmaceutically acceptable salt thereof.

96. A compound according to claim 45, which is 4-(3-chloropyridin-2-yl)-2-ethyl-N-(4-isopropylphenyl)piperazine-1-carboxamide, or a pharmaceutically acceptable salt thereof.

97. A compound according to claim 45, which is N-(4-tert-butylphenyl)-2-ethyl-4-[3-(trifluoromethyl)pyridin-2-yl]piperazine-1-carboxamide, or a pharmaceutically acceptable salt thereof.

98. A compound according to claim 45, which is 2-ethyl-N-[4-(trifluoromethyl)phenyl]-4-[3-(trifluoromethyl)pyridin-2-yl]piperazine-1-carboxamide, or a pharmaceutically acceptable salt thereof.

99. A compound according to claim 45, which is 2-ethyl-N-(4-isopropylphenyl)-4-[3-(trifluoromethyl)pyridin-2-yl]piperazine-1-carboxamide, or a pharmaceutically acceptable salt thereof.

100. A compound according to claim 45, which is 2-tert-butyl-N-(4-tert-butylphenyl)-4-(3-chloropyridin-2-yl)piperazine-1-carboxamide, or a pharmaceutically acceptable salt thereof.

101. A compound according to claim 45, which is 2-tert-butyl-N-[4-(trifluoromethyl)phenyl]-4-[3-(trifluoromethyl)pyridin-2-yl]piperazine-1-carboxamide, or a pharmaceutically acceptable salt thereof.

102. A compound according to claim 45, which is N-(4-tert-butylphenyl)-4-(3-chloropyridin-2-yl)-2-isopropylpiperazine-1-carboxamide, or a pharmaceutically acceptable salt thereof.

103. A compound according to claim 45, which is N-(4-tert-butylphenyl)-2-isopropyl-4-[3-(trifluoromethyl)pyridin-2-yl]piperazine-1-carboxamide, or a pharmaceutically acceptable salt thereof.

104. A compound according to claim 45, which is 2-isopropyl-N-[4-(trifluoromethyl)phenyl]-4-[3-(trifluoromethyl)pyridin-2-yl]piperazine-1-carboxamide, or a pharmaceutically acceptable salt thereof.

105. A compound according to claim 45, which is 2-isopropyl-N-(4-isopropylphenyl)-4-[3-(trifluoromethyl)pyridin-2-yl]piperazine-1-carboxamide, or a pharmaceutically acceptable salt thereof.

106. A compound according to claim 45, which is (2R)-4-(3-fluoropyridin-2-yl)-2-methyl-N-[4-(trifluoromethyl)phenyl]piperazine-1-carboxamide, or a pharmaceutically acceptable salt thereof.

107. A compound according to claim 45, which is (2R)-N-(4-tert-butylphenyl)-4-(3-fluoropyridin-2-yl)-2-methylpiperazine-1-carboxamide, or a pharmaceutically acceptable salt thereof.

108. A compound according to claim 45, which is (2R)-4-(3-fluoropyridin-2-yl)-N-(4-isopropylphenyl)-2-methylpiperazine-1-carboxamide, or a pharmaceutically acceptable salt thereof.

109. A compound according to claim 45, which is (2R)-N-(4-cyclohexylphenyl)-4-(3-fluoropyridin-2-yl)-2-methylpiperazine-1-carboxamide, or a pharmaceutically acceptable salt thereof.

110. A compound according to claim 45, which is (2R)-N-(4-cyclopentylphenyl)-4-(3-fluoropyridin-2-yl)-2-methylpiperazine-1-carboxamide, or a pharmaceutically acceptable salt thereof.

111. A compound according to claim 45, which is (2R)-N-(4-tert-butylphenyl)-4-(3-cyanopyridin-2-yl)-2-methylpiperazine-1-carboxamide, or a pharmaceutically acceptable salt thereof.

112. A compound according to claim 45, which is (2R)-4-(3-cyanopyridin-2-yl)-2-methyl-N-[4-(trifluoromethyl)phenyl]piperazine-1-carboxamide, or a pharmaceutically acceptable salt thereof.

113. A compound according to claim 45, which is (2R)-4-(3-chloropyridin-2-yl)-N-{4-[cyano(phenyl)methyl]phenyl}-2-methylpiperazine-1-carboxamide, or a pharmaceutically acceptable salt thereof.

114. A compound according to claim 45, which is (2R)-4-(3-chloropyridin-2-yl)-2-methyl-N-[3-methyl-4-(trifluoromethyl)phenyl]piperazine-1-carboxamide, or a pharmaceutically acceptable salt thereof.

115. A compound according to claim 45, which is (2R)-4-(3-fluoropyridin-2-yl)-2-methyl-N-[3-methyl-4-(trifluoromethyl)phenyl]piperazine-1-carboxamide, or a pharmaceutically acceptable salt thereof.

116. A compound according to claim 45, which is (2R)-4-{3-[bis(methylsulfonyl)amino]pyridin-2-yl}-N-(4-tert-butylphenyl)-2-methylpiperazine-1-carboxamide, or a pharmaceutically acceptable salt thereof.

117. A compound according to claim 45, which is (2R)-2-methyl-N-[3-methyl-4-(trifluoromethyl)phenyl]-4-[3-(trifluoromethyl)pyridin-2-yl]piperazine-1-carboxamide, or a pharmaceutically acceptable salt thereof.

118. A compound according to claim 45, which is (2R)-4-(3-chloropyridin-2-yl)-2-methyl-N-{4-[1-(trifluoromethyl)vinyl]phenyl}piperazine-1-carboxamide, or a pharmaceutically acceptable salt thereof.

119. A compound according to claim 45, which is (2R)-2-methyl-4-[3-(trifluoromethyl)pyridin-2-yl]-N-{4-[1-(trifluoromethyl)vinyl]phenyl}piperazine-1-carboxamide, or a pharmaceutically acceptable salt thereof.

120. A compound according to claim 45, which is (2R)-4-(3-fluoropyridin-2-yl)-2-methyl-N-{4-[1-(trifluoromethyl)vinyl]phenyl}piperazine-1-carboxamide, or a pharmaceutically acceptable salt thereof.

121. A compound according to claim 45, which is (2R)-N-(4-sec-butylphenyl)-4-(3-fluoropyridin-2-yl)-2-methylpiperazine-1-carboxamide, or a pharmaceutically acceptable salt thereof.

122. A compound according to claim 45, which is (2R)-2-methyl-N-[4-(2,2,2-trifluoro-1-methylethyl)phenyl]-4-[3-(trifluoromethyl)pyridin-2-yl]piperazine-1-carboxamide, or a pharmaceutically acceptable salt thereof.

123. A compound according to claim 45, which is (2R)-4-(3-fluoropyridin-2-yl)-2-methyl-N-[4-(2,2,2-trifluoro-1-methylethyl)phenyl]piperazine-1-carboxamide, or a pharmaceutically acceptable salt thereof.

124. A compound according to claim 45, which is (2R)-4-(3-chloro-5-nitropyridin-2-yl)-2-methyl-N-[4-(trifluoromethyl)phenyl]piperazine-1-carboxamide, or a pharmaceutically acceptable salt thereof.

125. A compound according to claim 45, which is (2R)-4-(5-amino-3-chloropyridin-2-yl)-2-methyl-N-[4-(trifluoromethyl)phenyl]piperazine-1-carboxamide, or a pharmaceutically acceptable salt thereof.

126. A compound according to claim 45, which is (2R)-4-(3-fluoropyridin-2-yl)-N-[3-fluoro-4-(trifluoromethyl)phenyl]-2-methylpiperazine-1-carboxamide, or a pharmaceutically acceptable salt thereof.

127. A compound according to claim 45, which is (2R)-N-[3-fluoro-4-(trifluoromethyl)phenyl]-2-methyl-4-[3-(trifluoromethyl)pyridin-2-yl]piperazine-1-carboxamide, or a pharmaceutically acceptable salt thereof.

128. A compound according to claim 45, which is (2R)-4-(3-chloropyridin-2-yl)-2-methyl-N-[4-(2,2,2-trifluoro-1-methylethyl)phenyl]piperazine-1-carboxamide, or a pharmaceutically acceptable salt thereof.

129. A compound according to claim 45, which is (2R)-4-(3-chloropyridin-2-yl)-2-methyl-N-(2,2,4,4-tetrafluoro-4H-1,3-benzodioxin-6-yl)piperazine-1-carboxamide, or a pharmaceutically acceptable salt thereof.

130. A compound according to claim 45, which is (2R)-4-(3-fluoropyridin-2-yl)-2-methyl-N-(2,2,4,4-tetrafluoro-4H-1,3-benzodioxin-6-yl)piperazine-1-carboxamide, or a pharmaceutically acceptable salt thereof.

131. A compound according to claim 45, which is (2R)-2-methyl-N-(2,2,4,4-tetrafluoro-4H-1,3-benzodioxin-6-yl)-4-[3-(trifluoromethyl)pyridin-2-yl]piperazine-1-carboxamide, or a pharmaceutically acceptable salt thereof.

132. A compound according to claim 45, which is (2R)-4-[3-(aminosulfonyl)pyridin-2-yl]-N-(4-tert-butylphenyl)-2-methylpiperazine-1-carboxamide, or a pharmaceutically acceptable salt thereof.

133. A compound according to claim 45, which is (2R)-N-(4-benzoylphenyl)-4-(3-chloropyridin-2-yl)-2-methylpiperazine-1-carboxamide, or a pharmaceutically acceptable salt thereof.

134. A compound according to claim 45, which is (2R)-4-(3-chloropyridin-2-yl)-N-(4-iodophenyl)-2-methylpiperazine-1-carboxamide, or a pharmaceutically acceptable salt thereof.

135. A compound according to claim 45, which is (2R)-4-(3-chloropyridin-2-yl)-2-methyl-N-{4-[2,2,2-trifluoro-1,1-bis(trifluoromethyl)ethyl]phenyl}piperazine-1-carboxamide, or a pharmaceutically acceptable salt thereof.

136. A compound according to claim 45, which is (2R)-2-methyl-N-{4-[2,2,2-trifluoro-1,1-bis(trifluoromethyl)ethyl]phenyl}-4-[3-(trifluoromethyl)pyridin-2-yl]piperazine-1-carboxamide, or a pharmaceutically acceptable salt thereof.

137. A compound according to claim 45, which is (2R)-N-(4-butylphenyl)-4-(3-chloropyridin-2-yl)-2-methylpiperazine-1-carboxamide, or a pharmaceutically acceptable salt thereof.

138. A compound according to claim 45, which is 2-(fluoromethyl)-N-[4-(trifluoromethyl)phenyl]-4-[3-

(trifluoromethyl)pyridin-2-yl]piperazine-1-carboxamide, or a pharmaceutically acceptable salt thereof.

139. A compound according to claim 45, which is (2R)-N-[4-bromo-3-(trifluoromethyl)phenyl]-4-(3-chloropyridin-2-yl)-2-methylpiperazine-1-carboxamide, or a pharmaceutically acceptable salt thereof.

140. A compound according to claim 45, which is (2R)-N-[4-bromo-3-(trifluoromethyl)phenyl]-2-methyl-4-[3-(trifluoromethyl)pyridin-2-yl]piperazine-1-carboxamide, or a pharmaceutically acceptable salt thereof.

141. A compound according to claim 45, which is (2R)-4-(3-chloropyridin-2-yl)-N-[4-fluoro-3-(trifluoromethyl)phenyl]-2-methylpiperazine-1-carboxamide, or a pharmaceutically acceptable salt thereof.

142. A compound according to claim 45, which is (2R)-N-[4-fluoro-3-(trifluoromethyl)phenyl]-2-methyl-4-[3-(trifluoromethyl)pyridin-2-yl]piperazine-1-carboxamide, or a pharmaceutically acceptable salt thereof.

143. A compound according to claim 45, which is (2R)-4-(3-chloropyridin-2-yl)-2-methyl-N-{4-[1,2,2,2-tetrafluoro-1-(trifluoromethyl)ethyl]phenyl}piperazine-1-carboxamide, or a pharmaceutically acceptable salt thereof.

144. A compound according to claim 45, which is (2R)-2-methyl-N-{4-[1,2,2,2-tetrafluoro-1-(trifluoromethyl)ethyl]phenyl}-4-[3-(trifluoromethyl)pyridin-2-yl]piperazine-1-carboxamide, or a pharmaceutically acceptable salt thereof.

145. A compound according to claim 35, which is (2R)-N-(4-tert-butylphenyl)-4-(3-chloropyrazin-2-yl)-2-methylpiperazine-1-carboxamide, or a pharmaceutically acceptable salt thereof.

146. A compound according to claim 35, which is (2R)-4-(3-chloropyrazin-2-yl)-N-(4-isopropylphenyl)-2-methylpiperazine-1-carboxamide, or a pharmaceutically acceptable salt thereof.

147. A compound according to claim 35, which is (2R)-4-(3-chloropyrazin-2-yl)-2-methyl-N-[4-(trifluoromethyl)phenyl]piperazine-1-carboxamide, or a pharmaceutically acceptable salt thereof.

148. A compound according to claim 35, which is (2R)-4-(3-chloropyrazin-2-yl)-2-methyl-N-{4-[1,2,2,2-tetrafluoro-1-(trifluoromethyl)ethyl]phenyl}piperazine-1-carboxamide, or a pharmaceutically acceptable salt thereof.

149. A compound according to claim 35, which is (2R)-4-(3-chloropyrazin-2-yl)-2-methyl-N-{4-cyclopentylphenyl}piperazine-1-carboxamide, or a pharmaceutically acceptable salt thereof.

150. A compound according to claim 35, which is (2R)-4-(3-chloropyrazin-2-yl)-2-methyl-N-{4-cyclohexylphenyl}piperazine-1-carboxamide, or a pharmaceutically acceptable salt thereof.

151. A compound according to claim 37, which is 4-(3-chloropyridin-2-yl)-N-[5-(trifluoromethyl)pyridin-2-yl]piperazine-1-carboxamide, or a pharmaceutically acceptable salt thereof.

152. A compound according to claim 37, which is (2R)-4-(3-chloropyridin-2-yl)-2-methyl-N-[5-(trifluoromethyl)pyridin-2-yl]piperazine-1-carboxamide, or a pharmaceutically acceptable salt thereof.

153. A compound according to claim 37, which is (2R)-4-(3-chloropyridin-2-yl)-2-methyl-N-[6-(trifluoromethyl)pyridin-3-yl]piperazine-1-carboxamide, or a pharmaceutically acceptable salt thereof.

154. A compound of the Formula:

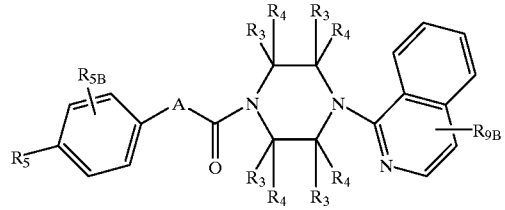

or a pharmaceutically acceptable salt thereof, wherein:
A is absent or is selected from the group consisting of O, S, $NR_A$, $CR_BR_B'$, $NR_ACR_BR_B'$, $CR_BR_B'NR_A$, —$CR_A$=$CR_B$—, and $C_3H_4$; where $R_A$, $R_B$, and $R_B'$ are independently selected at each occurrence from hydrogen and $C_{1-6}$ alkyl;

$R_3$ and $R_4$ are independently chosen at each occurrence from the group consisting of hydrogen, halogen, cyano, nitro, halo($C_{1-6}$)alkyl, halo($C_{1-6}$)alkoxy, hydroxy, amino, $C_{1-6}$alkyl, $C_{2-6}$alkenyl, $C_{2-6}$alkynyl, $C_{1-6}$alkoxy, —NH($C_{1-6}$alkyl), and —N($C_{1-6}$alkyl)($C_{1-6}$alkyl);

$R_5$ is selected from the group consisting of halogen, halo($C_{1-6}$)alkyl, $C_{3-6}$alkyl substituted with 0–3 $R_6$, $C_{2-6}$alkenyl substituted with 0–3 $R_6$, ($C_{3-8}$cycloalkyl)$C_{1-4}$alkyl substituted with 0–3 $R_6$, and Y;

$R_{5B}$ and $R_{9B}$ each represent from 0 to 2 substituents and are independently chosen from halogen, cyano, nitro, halo($C_{1-2}$)alkyl, halo($C_{1-2}$)alkoxy, amino, $C_{1-4}$alkyl, and $C_{1-2}$alkoxy;

$R_6$ is independently selected at each occurrence from the group consisting of cyano, halogen, hydroxy, $C_{1-4}$alkyl, $C_{1-4}$alkoxy, —NH($C_{1-4}$alkyl), —N($C_{1-4}$alkyl)($C_{1-4}$alkyl) and Y;

Y is independently selected at each occurrence from $C_{3-8}$ cycloalkyl, piperidinyl, piperazinyl, tetrahydropyranyl, dihydropyranyl, morpholinyl, thiomorpholinyl, phenyl, pyridyl, pyrazinyl, pyrimidinyl, thiazolyl, thienyl, and imidazolyl, each of which may be further substituted with one or more substituents independently selected from halogen, oxo, hydroxy, amino, nitro, cyano, $C_{1-4}$alkyl, $C_{1-4}$alkoxy, halo($C_{1-4}$)alkyl, halo($C_{1-4}$)alkoxy, mono- or di($C_{1-4}$)alkylamino, and $C_{1-4}$alkylthio.

155. A compound or salt according to claim 154 of the Formula:

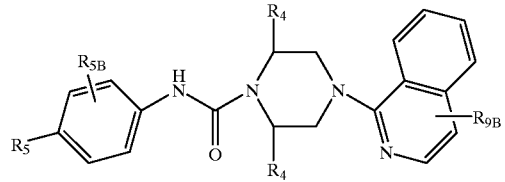

wherein
$R_4$ is independently selected at each occurrence from hydrogen and $C_{1-4}$alkyl.

156. A compound or salt according to claim 155, wherein:
$R_5$ is selected from the group consisting of halo($C_{1-6}$)alkyl, $C_{3-6}$alkyl, ($C_{3-8}$cycloalkyl)$C_{1-4}$alkyl, and Y;

$R_{5B}$ and $R_{9B}$ each represent from 0 to 1 substituents and are independently chosen from halogen, cyano, nitro, halo($C_{1-2}$)alkyl, halo($C_{1-2}$)alkoxy, amino, $C_{1-4}$alkyl, and $C_{1-2}$alkoxy;

Y is selected from C$_{3-8}$ cycloalkyl, piperidinyl, piperazinyl, tetrahydropyranyl, dihydropyranyl, morpholinyl, thiomorpholinyl, phenyl, pyridyl, pyrazinyl, pyrimidinyl, thiazolyl, thienyl, and imidazolyl.

157. A compound according to claim 154, which is (2R)-4-isoquinolin-1-yl-2-methyl-N-[4-(trifluoromethyl)phenyl]piperazine-1-carboxamide, or a pharmaceutically acceptable salt thereof.

158. A compound according to claim 154, which is (2R)-N-(4-tert-butylphenyl)-4-isoquinolin-1-yl-2-methylpiperazine-1-carboxamide, or a pharmaceutically acceptable salt thereof.

159. A compound according to claim 154, which is (2R)-N-(4-isopropylphenyl)-4-isoquinolin-1-yl-2-methylpiperazine-1-carboxamide, or a pharmaceutically acceptable salt thereof.

160. A compound according to claim 154, which is (2R)-N-(4-cyclopentylphenyl)-4-isoquinolin-1-yl-2-methylpiperazine-1-carboxamide, or a pharmaceutically acceptable salt thereof.

161. A compound according to claim 154, which is (2R)-N-(4-cyclohexylphenyl)-4-isoquinolin-1-yl-2-methylpiperazine-1-carboxamide, or a pharmaceutically acceptable salt thereof.

162. A compound of the Formula:

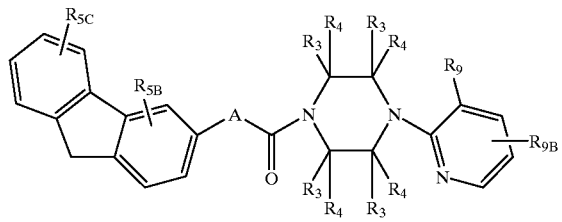

or a pharmaceutically acceptable salt thereof, wherein:

A is absent or is selected from the group consisting of O, S, NR$_A$, CR$_B$R$_B$', NR$_A$CR$_B$R$_B$', CR$_B$R$_B$'NR$_A$, —CR$_A$=CR$_B$—, and C$_3$H$_4$; where R$_A$, R$_B$, and R$_B$' are independently selected at each occurrence from hydrogen and C$_{1-6}$ alkyl;

R$_3$ and R$_4$ are independently chosen at each occurrence from the group consisting of hydrogen, halogen, cyano, nitro, halo(C$_{1-6}$)alkyl, halo(C$_{1-6}$)alkoxy, hydroxy, amino, C$_{1-6}$alkyl, C$_{2-6}$alkenyl, C$_{2-6}$alkynyl, C$_{1-6}$alkoxy, —NH(C$_{1-6}$alkyl), and —N(C$_{1-6}$alkyl)(C$_{1-6}$alkyl);

R$_{5B}$, R$_{5C}$, and R$_{9B}$ each represent from 0 to 2 substituents and are independently chosen from halogen, cyano, nitro, halo(C$_{1-2}$)alkyl, halo(C$_{1-2}$)alkoxy, amino, C$_{1-4}$alkyl, and C$_{1-2}$alkoxy; and R$_9$ is selected from the group consisting of halogen, cyano, —N(SO$_2$CH$_3$)$_2$, —SO$_2$NH$_2$, halo(C$_{1-3}$)alkyl, C$_{1-3}$alkoxy, —NH(C$_{1-3}$alkyl), and —N(C$_{1-3}$alkyl)(C$_{1-3}$alkyl).

163. A compound or salt according to claim 162 of the Formula:

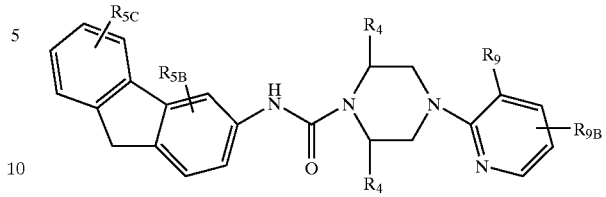

wherein

R$_4$ is independently selected at each occurrence from hydrogen and C$_{1-4}$alkyl.

164. A compound or salt according to claim 163, wherein:

R$_9$ is selected from the group consisting of halogen and halo(C$_{1-2}$)alkyl; and R$_{5B}$ and R$_{9B}$ each represent from 0 to 1 substituents and are independently chosen from halogen, cyano, nitro, halo(C$_{1-2}$)alkyl, halo(C$_{1-2}$)alkoxy, amino, C$_{1-4}$alkyl, and C$_{1-2}$alkoxy.

165. A compound according to claim 162, which is (2R)-4-(3-chloropyridin-2-yl)-N-(9H-fluoren-2-yl)-2-methylpiperazine-1-carboxamide, or a pharmaceutically acceptable salt thereof.

166. A compound according to claim 162, which is (2R)-N-(9H-fluoren-2-yl)-2-methyl-4-[3-(trifluoromethyl)pyridin-2-yl]piperazine-1-carboxamide, or a pharmaceutically acceptable salt thereof.

167. A compound according to claim 33, which is (2R)-N-(4-tert-butylcyclohexyl)-4-(3-chloropyridin-2-yl)-2-methylpiperazine-1-carboxamide, or a pharmaceutically acceptable salt thereof.

168. A compound according to claim 33, which is (2R)-4-(3-chloropyridin-2-yl)-N-(4-isopropylcyclohexyl)-2-methylpiperazine-1-carboxamide, or a pharmaceutically acceptable salt thereof.

169. A compound according to claim 33, which is (2R)-N-(4-isopropylcyclohexyl)-2-methyl-4-[3-(trifluoromethyl)pyridin-2-yl]piperazine-1-carboxamide, or a pharmaceutically acceptable salt thereof.

170. A compound or salt of claim 45 wherein the compound or salt is not addictive.

171. A compound of the Formula:

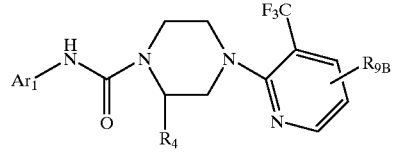

or a pharmaceutically acceptable salt thereof wherein:

R$_4$ is methyl or hydrogen;

R$_{9B}$ represents 0–2 substituents independently chosen from: halogen, cyano, nitro, halo(C$_{1-2}$)alkyl, halo(C$_{1-2}$)alkoxy, amino, C$_{1-4}$alkyl, and C$_{1-2}$alkoxy; and Ar$_1$ is 2,4-dichlorphenyl or 3-nitro-4-chlorophenyl.

172. A compound of the Formula:

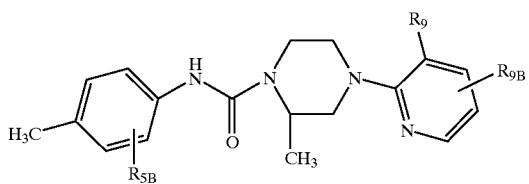

or a pharmaceutically acceptable salt thereof wherein:

$R_9$ is chloro or trifluoromethyl; and $R_{5B}$ and $R_{9B}$ independently represent from 0–2 substituents on each of the rings on which they occur and are independently chosen from: halogen, cyano, nitro, halo$(C_{1-2})$alkyl, halo$(C_{1-2})$alkoxy, amino, $C_{1-4}$alkyl, and $C_{1-2}$alkoxy.

173. A pharmaceutical composition comprising a pharmaceutically acceptable carrier and a compound or salt according to claim 1.

174. A package comprising a pharmaceutical composition of claim 173 in a container and further comprising indicia comprising instructions for using the composition to alleviate pain.

175. A package comprising a pharmaceutical composition of claim 173 in a container and further comprising indicia comprising instructions for using the composition to alleviate symptoms of exposure to capsaicin or tear gas.

176. A compound or salt of claim 1 wherein, in an in vitro assay of capsaicin receptor antagonism, the compound or salt exhibits capsaicin receptor antagonist activity, but in an in vitro assay of capsaicin receptor agonism the compound does not exhibit detectable agonist activity.

177. A compound or salt of claim 1 wherein a dose of the compound or salt that is twice the minimum dose sufficient to provide analgesia in an animal model for determining pain relief does not produce sedation in an animal model assay of sedation.

178. 4-(3-Chloro-2-pyridinyl)-N-[4-(isopropyl)phenyl]-1-piperazinecarboxamide or a pharmaceutically acceptable salt thereof.

179. (2R)-N-(4-tert-butylphenyl)-4-[3-(dimethylamino)pyridin-2-yl]-2-methylpiperazine-1-carboxamide or a pharmaceutically acceptable salt thereof.

180. (2R)-4-[3-(dimethylamino)pyridin-2-yl]-2-methyl-N-[4-(trifluoromethyl)phenyl]piperazine-1-carboxamide or a pharmaceutically acceptable salt thereof.

181. A pharmaceutical composition comprising a pharmaceutically acceptable carrier and a compound or salt according to claim 22.

182. A compound or salt of claim 22 wherein, in an in vitro assay of capsaicin receptor antagonism, the compound or salt exhibits capsaicin receptor antagonist activity, but in an in vitro assay of capsaicin receptor agonism the compound does not exhibit detectable agonist activity.

183. A compound or salt of claim 22 wherein a dose of the compound or salt that is twice the minimum dose sufficient to provide analgesia in an animal model for determining pain relief does not produce sedation in an animal model assay of sedation.

184. A package comprising a pharmaceutical composition of claim 181 in a container and further comprising indicia comprising instructions for using the composition to alleviate pain.

185. A package comprising a pharmaceutical composition of claim 181 in a container and further comprising indicia comprising instructions for using the composition to alleviate symptoms of exposure to capsaicin or tear gas.

* * * * *

(12) EX PARTE REEXAMINATION CERTIFICATE (5857th)
United States Patent
Bakthavatchalam et al.

(10) Number: US 6,723,730 C1
(45) Certificate Issued: Aug. 14, 2007

(54) CAPSAICIN RECEPTOR LIGANDS

(75) Inventors: Rajagopal Bakthavatchalam, Wilmington, DE (US); Alan Hutchinson, Madison, CT (US); Robert W. DeSimone, Durham, CT (US); Kevin J. Hodgetts, Killingworth, CT (US); James E. Krause, Madison, CT (US); Geoffrey G. White, Guilford, CT (US)

(73) Assignee: Neurogen Corporation, Branford, CT (US)

Reexamination Request:
No. 90/007,394, Jan. 26, 2005

Reexamination Certificate for:
Patent No.: 6,723,730
Issued: Apr. 20, 2004
Appl. No.: 09/910,442
Filed: Jul. 20, 2001

Related U.S. Application Data
(60) Provisional application No. 60/280,223, filed on Mar. 30, 2001, provisional application No. 60/230,726, filed on Sep. 7, 2000, and provisional application No. 60/219,529, filed on Jul. 20, 2000.

(51) Int. Cl.
| | |
|---|---|
| C07D 405/00 | (2006.01) |
| C07D 405/12 | (2006.01) |
| C07D 241/00 | (2006.01) |
| C07D 241/20 | (2006.01) |
| C07D 213/00 | (2006.01) |
| C07D 213/74 | (2006.01) |
| C07D 217/22 | (2006.01) |
| C07D 213/75 | (2006.01) |
| C07D 417/12 | (2006.01) |
| C07D 417/00 | (2006.01) |

(52) U.S. Cl. .............. 514/284; 206/570; 514/354; 514/356; 514/357; 514/400; 514/405; 544/235; 544/284; 544/353; 544/355; 544/356; 544/357; 544/360; 544/363; 544/364; 544/365; 544/368; 544/369; 544/370; 544/371; 544/372; 544/376; 544/379; 544/389; 544/390; 544/391

(58) Field of Classification Search .............. None
See application file for complete search history.

(56) References Cited

U.S. PATENT DOCUMENTS

| | | | | |
|---|---|---|---|---|
| 4,439,606 A | * | 3/1984 | Du et al. | 544/356 |
| 4,459,296 A | | 7/1984 | Ancher et al. | 424/244 |
| 4,659,710 A | | 4/1987 | Sato et al. | 514/234 |
| 5,021,438 A | | 6/1991 | Junge et al. | 514/373 |
| 5,780,472 A | * | 7/1998 | Cho et al. | 514/253.12 |
| 5,840,720 A | | 11/1998 | Chen | 544/230.5 |
| 5,849,732 A | * | 12/1998 | Suzuki et al. | 514/217.11 |

FOREIGN PATENT DOCUMENTS

| | | | |
|---|---|---|---|
| EP | 0 407 200 A1 | | 1/1991 |
| EP | 0 882 717 A1 | | 12/1998 |
| EP | 0 974 573 A1 | | 1/2000 |
| WO | WO 98/00402 A1 | * | 1/1998 |
| WO | WO 98/20867 A1 | | 5/1998 |
| WO | WO 99/07672 A1 | * | 2/1999 |

* cited by examiner

Primary Examiner—Evelyn M. Huang

(57) ABSTRACT

Disclosed are diaryl piperazines and related compounds of the following Formula:

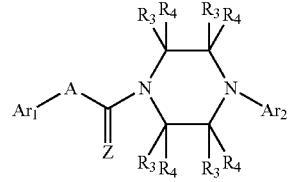

wherein the variables are as defined in the specification. These compounds are selective modulators of capsaicin receptors, including human capsaicin receptors, that are, therefore, useful in the treatment of a chronic and acute pain conditions, itch and urinary incontinence. Methods of treatment of such disorders and well as packaged pharmaceutical compositions are also provided. Compounds of the invention are also useful as probes for the localization of capsaicin receptors and as standards in assays for capsaicin receptor binding and capsaicin receptor mediated cation conductance. Methods of using the compounds in receptor localization studies are given.

US 6,723,730 C1

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 105, between lines 33 and 34:

```
                      SEQUENCE LISTING

<160> NUMBER OF SEQ ID NOS: 2

<210> SEQ ID NO 1
<211> LENGTH: 4203
<212> TYPE: DNA
<213> ORGANISM: Homo sapiens

<400> SEQUENCE: 1
ccgaagggcg tccacagcga ctcctgctat gcagggcagc tgctgccagg gccgggcccg      60
ggaccccacg gaggcgggga gaccactctt ctcccacacg agcccagctc tcccttcgag     120
tagcaaccgc cttcaagctc acaagcaccc gtgggcctgg ggtgtgcctg cgtctagctg     180
gttgcacact gggccacaga ggatccagca aggatgaaga aatggagcag cacagacttg     240
ggggcagctg cggacccact ccaaaaggac acctgcccag accccctgga tggagaccct     300
aactccaggc cacctccagc caagcccagg ctctccacgg ccaagagccg cacccggctc     360
tttgggaagg gtgactcgga ggaggctttc ccggtggatt gccctcacga ggaaggtgag     420
ctggactcct gcccgaccat cacagtcagc cctgttatca ccatccagag gccaggagac     480
ggccccaccg gtgccaggct gctgtcccag gactctgtcg ccgccagcac cgagaagacc     540
ctcaggctct atgatcgcag gagtatcttt gaagccgttg ctcagaataa ctgccaggat     600
ctggagagcc tgctgctctt cctgcagaag agcaagaagc acctcacaga caacgagttc     660
aaagaccctg agacagggaa gacctgtctg ctgaaagcca tgctcaacct gcacgacgga     720
cagaacacca ccatccccct gctcctggag atcgcgcggc aaacggacag cctgaaggag     780
cttgtcaacg ccagctacac ggacagctac tacaaggcc agacagcact gcacatcgcc     840
atcgagagac gcaacatggc cctggtgacc ctcctggtgg agaacggagc agacgtccag     900
gctgcggccc atggggactt ctttaagaaa accaagggc ggcctggatt ctacttcggt     960
gaactgcccc tgtccctggc cgcgtgcacc aaccagctgg gcatcgtgaa gttcctgctg    1020
cagaactcct ggcagacggc cgacatcagc gccagggact cggtgggcaa cacggtgctg    1080
cacgccctgg tggaggtggc cgacaacacg gccgacaaca cgaagtttgt gacgagcatg    1140
tacaatgaga ttctgatgct gggggccaaa ctgcacccga cgctgaagct ggaggagctc    1200
accaacaaga agggaatgac gccgctggct ctggcagctg gaccgggaa gatcggggtc    1260 ttggcctata ttctccagcg ggagatccag gagcccgagt gcaggcacct gtccaggaag    1320
ttcaccgagt gggcctacgg gcccgtgcac tcctcgctgt acgacctgtc ctgcatcgac    1380
acctgcgaga agaactcggt gctggaggtg atcgcctaca gcagcagcga gaccctaat    1440 cgccacgaca tgctcttggt ggagccgctg aaccgactcc tgcaggacaa gtgggacaga    1500
ttcgtcaagc gcatcttcta cttcaacttc ctggtctact gcctgtacat gatcatcttc    1560
accatggctc cctactacag gcccgtggat ggcttgcctc cctttaagat ggaaaaaatt    1620
ggagactatt tccgagttac tggagagatc ctgtctgtgt taggaggagt ctacttcttt    1680
```

-continued

```
ttccgaggga ttcagtattt cctgcagagg cggccgtcga tgaagaccct gtttgtggac      1740
agctacagtg agatgctttt ctttctgcag tcactgttca tgctggccac cgtggtgctg      1800
tacttcagcc acctcaagga gtatgtggct tccatggtat tctccctggc cttgggctgg      1860
accaacatgc tctactacac ccgcggtttc cagcagatgg gcatctatgc cgtcatgata      1920
gagaagatga tcctgagaga cctgtgccgt ttcatgtttg tctacatcgt cttcttgttc      1980
gggttttcca cagcggtggt gacgctgatt gaagacggga agaatgactc cctgccgtct      2040
gagtccacgt cgcacaggtg gcgggggcct gcctgcaggc cccccgatag ctcctacaac      2100
agcctgtact ccacctgcct ggagctgttc aagttcacca tcggcatggg cgacctggag      2160
ttcactgaga actatgactt caaggctgtc ttcatcatcc tgctgctggc ctatgtaatt      2220
ctcacctaca tcctcctgct caacatgctc atcgccctca tgggtgagac tgtcaacaag      2280
atcgcacagg agagcaagaa catctggaag ctgcagagag ccatcaccat cctggacacg      2340
gagaagagct tccttaagtg catgaggaag gccttccgct caggcaagct gctgcaggtg      2400
gggtacacac ctgatggcaa ggacgactac cggtggtgct tcagggtgga cgaggtgaac      2460
tggaccacct ggaacaccaa cgtgggcatc atcaacgaag acccgggcaa ctgtgagggc      2520
gtcaagcgca ccctgagctt ctccctgcgg tcaagcagag tttcaggcag acactggaag      2580
aactttgccc tggtccccct tttaagagag gcaagtgctc gagataggca gtctgctcag      2640
cccgaggaag tttatctgcg acagttttca gggtctctga agccagagga cgctgaggtc      2700
ttcaagagtc ctgccgcttc cggggagaag tgaggacgtc acgcagacag cactgtcaac      2760
actgggcctt aggagacccc gttgccacgg ggggctgctg agggaacacc agtgctctgt      2820
cagcagcctg gcctggtctg tgcctgccca gcatgttccc aaatctgtgc tggacaagct      2880
gtgggaagcg ttcttggaag catggggagt gatgtacatc caaccgtcat tgtccccaag      2940
tgaatctcct aacagacttt caggttttta ctcactttac taaacagtgt ggatggtcag      3000
tctctactgg gacatgttag gcccttgttt tctttgattt tattcttttt tttgagacag      3060
aatttcactc ttctcgccca ggctggaatg cagtggcaca attttggctc cctgcaacct      3120
ccgcctcctg gattccagca attctcctgc ctcggcttcc caagtagctg ggattacagg      3180
cacgtgccac catgtctggc taattttttg tattttttta atagatatgg ggtttcgcca      3240
tgttggccag gctggtctcg aactcctgac ctcaggtgat ccgcccacct cggcctccca      3300
aagtgctggg attacaggtg tgagcctcca cacctggctg ttttctttga ttttattctt      3360 ttttttttt ttctgtgaga cagagtttca ctcttgttgc ccaggctgga gtgcagtggt      3420
gtgatcttgg ctcactgcaa cctctgcctc ccgggttcaa gcgattcttc tgcttcagtc      3480
tcccaagtag cttggattac aggtgagcac taccacgccc ggctaatttt tgtattttta      3540
atagagacgg ggtttcacca tgttggccag gctggtctcg aactcttgac ctcaggtgat      3600
ctgcccgcct tggcctccca aagtgctggg attacaggtg tgagccgctg cgctcggcct      3660
tctttgattt tatattatta ggagcaaaag taaatgaagc ccaggaaaac acctttggga      3720
acaaactctt cctttgatgg aaaatgcaga ggcccttcct ctctgtgccg tgcttgctcc      3780
tcttacctgc ccggggtggtt tgggggtgtt ggtgttccct ccctgagaa gatggggag       3840 gctgtcccac tcccagctct ggcagaatca agctgttgca gcagtgcctt cttcatcctt      3900
ccttacgatc aatcacagtc tccagaagat cagctcaatt gctgtgcagg ttaaaactac      3960
agaaccacat cccaaaggta cctggtaaga atgtttgaaa gatcttccat ttctaggaac      4020
```

-continued

| | | | |
|---|---|---|---|
| cccagtcctg | cttctccgca | atggcacatg | cttccactcc atccatactg gcatcctcaa | 4080 |
| ataaacagat | atgtatwcat | ataaaaaaaa | aaaaaaaaaa aaaaaaaaac tcgagagtac | 4140 |
| ttctagagcg | ccgcgggcc | catcgatttt | ccacccgggt ggggtaccag gtaaggtgcc | 4200 |
| aac | | | | 4203 |

<210> SEQ ID NO 2
<211> LENGTH: 4182
<212> TYPE: DNA
<213> ORGANISM: Homo sapiens

<400> SEQUENCE: 2

| | | | | |
|---|---|---|---|---|
| tgctagtgca | gggcagctgc | tgccagggcc | gggcccggga | ccccacggag gcggggagac | 60 |
| cactcttctc | ccacacgagc | ccagctctcc | cttcgagtag | caaccgcctt caagctcaca | 120 |
| agcacccgtg | ggcctggggt | gtgcctgcgt | ctagctggtt | gcacactggg ccacagagga | 180 |
| tccagcaagg | atgaagaaat | ggagcagcac | agacttgggg | gcagctgcgg acccactcca | 240 |
| aaaggacacc | tgcccagacc | cctggatggg | agaccctaac | tccaggccac ctccagccaa | 300 |
| gccccagctc | tccacggcca | agagccgcac | ccggctcttt | gggaagggtg actcggagga | 360 |
| ggctttcccg | gtggattgcc | ctcacgagga | aggtgagctg | gactcctgcc cgaccatcac | 420 |
| agtcagccct | gttatcacca | tccagaggcc | aggagacggc | cccaccggtg ccaggctgct | 480 |
| gtcccaggac | tctgtcgccg | ccagcaccga | aagaccctc | aggctctatg atcgcaggag | 540 |
| tatctttgaa | gccgttgctc | agaataactg | ccaggatctg | gagagcctgc tgctcttcct | 600 |
| gcagaagagc | aagaagcacc | tcacagacaa | cgagttcaaa | gaccctgaga cagggaagac | 660 |
| ctgtctgctg | aaagccatgc | tcaacctgca | cgacggacag | aacaccacca tcccctgct | 720 |
| cctggagatc | gcgcggcaaa | cggacagcct | gaaggagctt | gtcaacgcca gctacacgga | 780 |
| cagctactac | aagggccaga | cagcactgca | catcgccatc | gagagacgca acatggccct | 840 |
| ggtgaccctc | ctggtggaga | acggagcaga | cgtccaggct | gcggcccatg gggacttctt | 900 |
| taagaaaacc | aaagggcggc | ctggattcta | cttcggtgaa | ctgcccctgt ccctggccgc | 960 |
| gtgcaccaac | cagctgggca | tcgtgaagtt | cctgctgcag | aactcctggc agacggccga | 1020 |
| catcagcgcc | agggactcgg | tgggcaacac | ggtgctgcac | gccctggtgg aggtggccga | 1080 |
| caacacggcc | gacaacacga | gtttgtgac | gagcatgtac | aatgagattc tgatgctggg | 1140 |
| ggccaaactg | cacccgacgc | tgaagctgga | ggagctcacc | aacaagaagg gaatgacgcc | 1200 |
| gctggctctg | gcagctggga | ccgggaagat | cggggtcttg | gcctatattc tccagcggga | 1260 |
| gatccaggag | cccgagtgca | ggcacctgtc | caggaagttc | accgagtggg cctacgggcc | 1320 |
| cgtgcactcc | tcgctgtacg | acctgtcctg | catcgacacc | tgcgagaaga actcggtgct | 1380 |
| ggaggtgatc | gcctacagca | gcagcgagac | ccctaatcgc | cacgacatgc tcttggtgga | 1440 |
| gccgctgaac | cgactcctgc | aggacaagtg | ggacagattg | tcaagcgca tcttctactt | 1500 |
| caacttcctg | gtctactgcc | tgtacatgat | catcttcacc | atggctgcct actacaggcc | 1560 |
| cgtggatggc | ttgcctccct | taagatgga | aaaaattgga | gactatttcc gagttactgg | 1620 |
| agagatcctg | tctgtgttag | gaggagtcta | cttctttttc | cgagggattc agtatttcct | 1680 |
| gcagaggcgg | ccgtcgatga | agaccctgtt | tgtggacagc | tacagtgaga tgcttttctt | 1740 |
| tctgcagtca | ctgttcatgc | tggccaccgt | ggtgctgtac | ttcagccacc tcaaggagta | 1800 |
| tgtggcttcc | atggtattct | ccctggcctt | gggctggacc | aacatgctct actacacccg | 1860 |
| cggtttccag | cagatgggca | tctatgccgt | catgatagag | aagatgatcc tgagagacct | 1920 |

-continued

```
gtgccgtttc atgtttgtct acatcgtctt cttgttcggg ttttccacag cggtggtgac    1980
gctgattgaa gacgggaaga atgactccct gccgtctgag tccacgtcgc acaggtggcg    2040 gggggcctgcc tgcaggcccc ccgatagctc ctacaacagc ctgtactcca cctgcctgga    2100
gctgttcaag ttcaccatcg gcatgggcga cctggagttc actgagaact atgacttcaa    2160
ggctgtcttc atcatcctgc tgctggccta tgtaattctc acctcatccc tcctgctcaa    2220
catgctcatc gccctcatgg gtgagactgt caacaagatc gcacaggaga gcaagaacat    2280
ctggaagctg cagagagcca tcaccatcct ggacacggag aagagcttcc ttaagtgcat    2340
gaggaaggcc ttccgctcag gcaagctgct gcaggtgggg tacacacctg atggcaagga    2400
cgactaccgg tggtgcttca gggtggacga ggtgaactgg accacctgga acaccaacgt    2460
gggcatcatc aacgaagacc cggcaactg tgagggcgtc aagcgcaccc tgagcttctc    2520
cctgcggtca gcagagtttt caggcagaca ctggaagaac tttgccctgg tccccctttt    2580
aagagaggca agtgctcgag ataggcagtc tgctcagccc gaggaagttt atctgcgaca    2640
gttttcaggg tctctgaagc cagaggacgt tgaggtcttc aagagtcctg ccgcttccgg    2700
ggagaagtga ggacgtcacg cagacagcac tgtcaacact gggccttagg agaccccgtt    2760
gccacggggg gctgctgagg gaacaccagt gctctgtcag cagcctggcc tggtctgtgc    2820
ctgcccagca tgttcccaaa tctgtgctgg acaagctgtg ggaagcgttc ttggaagcat    2880
ggggagtgat gtacatccaa ccgtcactgt ccccaagtga atctcctaac agactttcag    2940 gttttttactc actttactaa acagtgtgga tggtcagtct ctactgggac atgttaggcc    3000
cttgttttct tgatttat tctttttttt gagacagaat ttcactcttc tcgcccaggc    3060
tggaatgcag tggcacaatt ttggctccct gcaacctccg cctcctggat tccagcaatt    3120
ctcctgcctc ggcttcccaa gtagctggga ttacaggcac gtgccaccat gtctggctaa    3180 tttttttgtat ttttttaata gatatggggt ttcgccatgt tggccaggct ggtctcgaac    3240
tcctgacctc aggtgatccg cccacctcgg cctcccaaag tgctgggatt acaggtgtga    3300
gcctccacac ctggctgttt tctttgattt tattctttt ttttttttct gtgagacaga    3360 gttttcactct tgttgcccag gctggagtgc agtggtgtga tcttggctca ctgcaacctc    3420
tgcctcccgg gttcaagcga ttcttctgct tcagtctccc aagtagcttg gattacaggt    3480
gagcactacc acgcccggct aatttttgta tttttaatag agacggggtt tcaccatgtt    3540
ggccaggctg gtctcgaact cttgacctcg ggtgatctgc cgccttggc ctcccaaagt    3600 gctgggatta caggtgtgag ccgctgcgct cggccttctt tgattttata ttattaggag    3660
caaaagtaaa tgaagcccag gaaaacacct ttgggaacaa actcttcctt tgatggaaaa    3720
tgcagaggcc cttcctctct gtgccgtgct tgctcctctt acctgcccgg tggtttggg    3780 ggtgttggtg tttcctcccct ggagaagatg ggggaggctg tcccactccc agctctggca    3840
gaatcaagct gttgcagcag tgccttcttc atccttcctt acgatcaatc acagtctcca    3900
gaagatcagc tcaattgctg tgcaggttaa aactacagaa ccacatccca aaggtacctg    3960
gtaagaatgt ttgaaagatc ttccatttct aggaacccca gtcctgcttc tccgcaatgg    4020
cacatgcttc cactccatcc atactggcat cctcaaataa acagatatgt atacatataa    4080
aaaaaaaaaa aaaaaaaaaa aaaaactcga gagtacttct agagcggccg cgggcccatc    4140
gattttccac ccgggtgggg taccaggtaa gtgtacccaa tc                      4182
```

AS A RESULT OF REEXAMINATION, IT HAS BEEN DETERMINED THAT:

The patentability of claims 25, 33–38, 43, 45–153, 162–172 and 178–180 is confirmed.

Claims 21–24, 40–42 and 154–156 are cancelled.

Claims 1, 4–5, 10, 26, 27, 32, 39, 44, 157–161 and 181–183 are determined to be patentable as amended.

Claims 2–3, 6–9, 11–20, 28–31, 173–177 and 184–185, dependent on an amended claim, are determined to be patentable.

New claim 186 is added and determined to be patentable.

1. A compound of the formula:

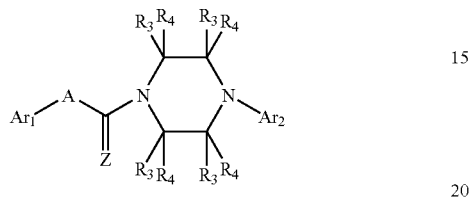

or a pharmaceutically acceptable salt thereof, wherein:

A is absent or is selected from the group consisting of O, S, NR$_A$, NR$_A$CR$_B$R$_B$', CR$_B$R$_B$'NR$_A$, [—CR$_A$=CR$_B$—,] and C$_3$H$_4$; where R$_A$, R$_B$, and R$_B$' are independently selected at each occurrence from hydrogen and alkyl;

Z is oxygen or sulfur;

each R$_3$ and R$_4$ independently
  (a) selected from the group consisting of hydrogen; halogen; hydroxy; amino; cyano; nitro; —COOH; —CHO; optionally substituted alkyl; optionally substituted alkenyl; optionally substituted alkynyl; optionally substituted alkoxy; optionally substituted mono or dialkylamino; optionally substituted alkylthio; optionally substituted alkyl ketone; optionally substituted alkylester; optionally substituted alkylsulfinyl; optionally substituted alkylsulfonyl; optionally substituted mono- or di-alkylcarboxamide; optionally substituted —S(O)$_n$NHalkyl; optionally substituted —S(O)$_n$N(alkyl)(alkyl); optionally substituted —NHC(=O)alkyl; optionally substituted —NC(=O)(alkyl)(alkyl); optionally substituted —NHS(O)$_n$alkyl; optionally substituted —NS(O)$_n$(alkyl)(alkyl); optionally substituted saturated heterocyclic ring or partially unsaturated heterocycle or from 5 to 8 atoms, which saturated hetercyclic ring of partially unsaturated heterocycle contains 1, 2, or 3 heteroatoms independently selected from N, O, and S; optionally substituted aryl having from 1 to 3 rings; and optionally substituted heteroaryl, said heteroaryl having from 1 to 3 rings, 5 to 8 ring members in each ring and, in at least one of said rings, from 1 to about 3 heteroatoms per ring independently selected from the group consisting of N, O, and S; or
  (b) joined to a R$_3$ or R$_4$ not attached to the same carbon to form an optionally substituted aryl ring, a saturated or partially unsaturated carbocyclic ring of from 5 to 8 members, which carbocyclic ring is optionally substituted, or a saturated, partially unsaturated, or aromatic heterocyclic ring of from 5 to 8 members, which heterocyclic ring is optionally substituted and contains 1, 2, or 3 heteroatoms selected from N, O, and S;

Ar$_1$ is selected from the group consisting of:
  (a) cyclohexyl, cyclopentyl, piperidinyl, piperazinyl, phenyl, pyrrolyl, furanyl, thienyl, pyrazolyl, imidazolyl, thiazolyl, isothiazolyl, oxazolyl, isoxazolyl, oxadiazolyl, triazolyl, tetrazolyl, [pyridyl, pyrimdyl] *pyrimidyl*, pyrazinyl, benzimidazolyl, naphthyl, indolyl, isoindolyl, benzofuranyl, isobenzofuranyl, benzo[b]thiophenyl, benz[d]isoxazolyl, quinolinyl, isoquinolinyl, cinnolinyl, quinazolinyl, and quinoxalinyl, each of which is optionally mono-, [di, or trisubstituted] *or disubstituted* with R$_5$; and
  (b) bicyclic oxygen-containing groups of the formula:

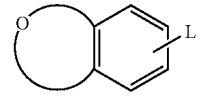

optionally mono-, di-, or trisubstituted with R$_5$, where L represents point of attachment and may be at any point on the benzene ring, and the oxygen-containing ring of the bicyclic oxygen-containing group consists of from 5 to 8 ring atoms, contains 1 or 2 oxygen atoms and remaining ring atoms are carbon;

Ar$_2$ is selected from the group consisting of:
  (a) cyclohexyl, cyclopentyl, piperidinyl, piperazinyl, pyrrolyl, furanyl, thienyl, pyrazolyl, imidazolyl, [thiazolyl,] isothiazolyl, oxazolyl, isoxazolyl, oxadiazolyl, triazolyl, tetrazolyl, pyridyl, [pyrimdyl, benzimidazolyl, naphthyl, indolyl] *pyrimidyl*, isoindolyl, benzofuranyl, isobenzofuranyl, benzo[b]thiophenyl, *and* benz[d]isoxazolyl, [quinolinyl, isoquinolinyl, cinnolinyl, quinazolinyl, and quinoxalinyl,] each of which is optionally mono-, di-, or trisubstituted with R$_5$; and
  (b) bicyclic oxygen-containing groups of the formula:

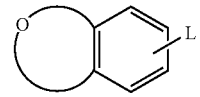

optionally mono-, di-, or trisubstituted with R$_5$, where L represents point of attachment and may be at any point on the benzene ring, and the oxygen-containing ring of the bicyclic oxygen-containing group consists of from 5 to 8 ring atoms, contains 1 or 2 oxygen atoms and remaining ring atoms are carbon;

R$_5$ is independently selected at each occurrence from the group consisting of halogen, nitro, halo(C$_{1-6}$)alkyl, halo(C$_{1-6}$)alkoxy, hydroxy, amino, C$_{1-6}$alkyl substituted with 0–2 R$_6$, C$_{2-6}$alkenyl substituted with 0–2 R$_6$, C$_{2-6}$alkynyl substituted with 0–2 R$_6$, C$_{1-6}$alkoxy and Y;

R$_6$ is independently selected at each occurrence from the group consisting of halogen, hydroxy, cyano, C$_{1-4}$alkyl, C$_{1-4}$alkoxy, —S(O)$_n$(C$_{1-4}$alkyl), halo(C$_{1-4}$)alkyl, halo(C$_{1-4}$)alkoxy, CO(C$_{1-4}$alkyl), CONH(C$_{1-4}$alkyl), CON(C$_{1-4}$alkyl$_1$)(C$_{1-4}$alkyl$_2$) where alkyl$_1$ and alkyl$_2$ may be joined to form a saturated heterocyclic ring of from 5 to 8 ring atoms and containing 1, 2, or 3 heteroatoms independently selected from N, O, and S, —XR$_7$, and Y;

X is independently selected at each occurrence from the group consisting of —CH$_2$—, —CHR$_8$—, —O—, —S(O)$_n$—, —NH—, —NR$_B$—, —C(=O)—, —C(=O)O—, —C(=O)NH—, —C(=O)NR$_B$—, —S(O)$_n$NH—, —S(O)$_n$NR$_B$—, NHC(=O)—, —NR$_B$C(=O)—, —NHS(O)$_n$—, and —NR$_B$S(O)$_n$—;

R$_7$ and R$_8$ are independently selected at each occurrence from hydrogen, and straight, branched, and cyclic alkyl groups, and (cycloalkyl)alkyl groups, said straight, branched, and cyclic alkyl groups, and (cycloalkyl) alkyl groups consisting of 1 to 8 carbon atoms, and containing zero or one or more double or triple bonds, each of which 1 to 8 carbon atoms is unsubstituted or substituted with one or more substituent(s) independently selected from oxo, hydroxy, halogen, amino, cyano, nitro, haloalkyl, haloalkoxy, —O(alkyl), —NH(alkyl), —N(alkyl)(alkyl), —NHC(O)(alkyl), —N(alkyl)C(O)(alkyl), —NHS(O)$_n$(alkyl), —S(O)$_n$(alkyl), —S(O)$_n$NH(alkyl), —S(O)$_n$N(alkyl$_3$)(alkyl$_4$) where alkyl$_3$ and alkyl$_4$ are optionally joined to form a saturated heterocyclic ring consisting or from 5 to 8 ring atoms and containing 1, 2, or 3 heteroatoms independently selected from N, O, and S, and Y';

Y and Y' are independently selected at each occurrence from 3- to 8-membered carbocyclic or heterocyclic groups which are saturated, unsaturated, or aromatic, which may be further substituted with one or more substituents independently selected from halogen, oxo, hydroxy, amino, nitro, cyano, alkyl, alkoxy, haloalkyl, haloalkoxy, mono- or dialkylamio, and alkylthio;

wherein said 3- to 8-membered heterocyclic groups contain one or more heteroatom(s) independently selected from N, O, and S; and n is independently chosen at each occurrence from 0, 1, and 2.

4. A compound of the formula:

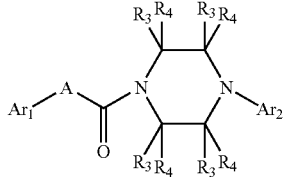

or a pharmaceutically acceptable salt thereof, wherein:

A is absent or is selected from the group consisting of O, S, NR$_A$, CR$_B$R$_B$', NR$_A$CR$_B$R$_B$', CR$_B$R$_B$'NR$_A$, —CR$_A$=CR$_B$—, and C$_3$H$_4$; where R$_A$, R$_B$, and R$_B$' are independently selected at each occurrence from hydrogen or alkyl;

each R$_3$ and R$_4$ is independently
(a) selected from the group consisting of hydrogen; halogen; hydroxy; amino; cyano; nitro; —COOH; —CHO, optionally substituted alkyl; optionally substituted alkenyl; optionally substituted alkynyl; optionally substituted alkoxy; optionally substituted mono or dialkylamino; optionally substituted alkylthio; optionally substituted alkyl ketone; optionally substituted alkylester; optionally substituted alkylsulfinyl; optionally substituted alkylsulfonyl; optionally substituted mono- or di-alkylcarboxamide; optionally substituted —S(O)$_n$NHalkyl; optionally substituted —S(O)$_n$N(alkyl)(alkyl); optionally substituted —NHC(=O)alkyl; optionally substituted —NC(=O)(alkyl)(alkyl); optionally substituted —NHS(O)$_n$alkyl; optionally substituted —NS(O)$_n$(alkyl)(alkyl); optionally substituted saturated heterocyclic ring or partially unsaturated heterocycle of from 5 to 8 atoms, which saturated heterocyclic ring or partially unsaturated heterocycle contains 1, 2, or 3 heteroatoms independently selected from N, O, and S; optionally substituted aryl having from 1 to 3 rings; and optionally substituted heteroaryl, said heteroaryl having from 1 to 3 rings, 5 to 8 ring members in each ring and, in at least one of said rings, from 1 to about 3 heteroatoms per ring independently selected from the group consisting of N, O, and S; or (b) joined to a R$_3$ or R$_4$ not attached to the same carbon to form an optionally substituted aryl ring; a saturated or partially unsaturated carbocyclic ring of from 5 to 8 members, which carbocyclic ring is optionally substituted; or a saturated, partially unsaturated, or aromatic heterocyclic ring of from 5 to 8 members, which heterocyclic ring is optionally substituted and contains 1, 2, or 3 heteroatoms independently selected from N, O, and S;

Ar$_1$ is selected from the group consisting of:
[(a)] cyclohexyl, cyclopentyl, piperidinyl, piperazinyl, pyrrolyl, furanyl, thienyl, pyrazolyl, imidazolyl, thiazolyl, isothiazolyl, oxazolyl, isoxazolyl, oxadiazolyl, triazolyl, tetrazolyl, [pyridyl,] pyrimidyl, pyrazinyl, benzimidazolyl, naphthyl, indolyl, isoindolyl, benzofuranyl, isobenzofuranyl, benzo[b]thiophenyl, benz[d]isoxazolyl, quinolinyl, isoquinolinyl, cinnolinyl, quinazolinyl, and quinoxalinyl, [wherein Ar$_1$ is optionally mono-, di-, or trisubstituted with R$_5$, and Ar$_2$ is optionally mono-, di-, or trisubstituted with R$_9$;]

[AR$_1$] Ar$_2$ is selected from the group consisting of: cyclohexyl, cyclopentyl, piperidinyl, piperazinyl, pyrrolyl, furanyl, thienyl, pyrazolyl, imidazolyl, thiazolyl, isothiazolyl, oxazolyl, isoxazolyl, oxadiazolyl, triazolyl, tetrazolyl, pyridyl, [pyrimidyl, benzimidazolyl, naphthyl, indolyl] pyrimidyl, isoindolyl, benzofuranyl, isobenzofuranyl, benzo[b]thiophenyl, benz[d]isoxazolyl, [quinolinyl, isoquinolinyl, cinnolinyl, quinazolinyl,] and quinoxalinyl; wherein Ar$_1$ is optionally mono-, di-, or trisubstituted with R$_5$, and Ar$_2$ is optionally mono-, di-, or trisubstituted with R$_9$; and

[(b)] groups of the formula:

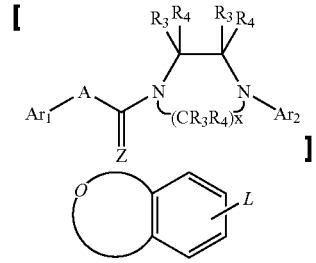

optionally mono-, di-, or trisubstituted with R$_5$, where L represents point of attachment and may be at any point on the benzene ring, and the oxygen-containing ring of the bicyclic oxygen-containing group consists of from 5 to 8 ring atoms, contains 1 to 2 oxygen atoms and remaining ring atoms are carbon;

R$_5$ is independently selected at each occurrence from the group consisting of cyano, nitro, haloalkyl, haloalkoxy, hydroxy, amino, alkyl substituted with 0–2 R$_6$, alkenyl substituted with 0–2 R$_6$, alkynyl substituted with 0–2 R$_6$, alkoxy and Y;

13

R$_9$ is independently selected at each occurrence from the group consisting of nitro, haloalkoxy, hydroxy, amino, alkyl substituted with 0–2 R$_6$, alkenyl substituted with 0–2 R$_6$, alkynyl substituted with 0–2 R$_6$, alkoxy substituted with 0–2 R$_6$, and Y;

R$_6$ is independently selected at each occurrence from the group consisting of halogen, hydroxy, cyano, alkyl, alkoxy, —S(O)$_n$(alkyl), haloalkyl, haloalkoxy, CO(alkyl), CONH(alkyl), CON(alkyl$_1$)(alkyl$_2$) where alkyl$_1$ and alkyl$_2$ may be joined to form a saturated heterocyclic ring of from 5 to 8 ring atoms and containing 1, 2, or 3 heteroatoms independently selected from N, O, and S, —XR$_7$, and Y;

X is independently selected at each occurrence from the group consisting of —CH$_2$—, —CHR$_B$—, —O—, —S(O)$_n$—, —NH—, —NR$_B$—, —C(=O)—, —C(=O)—, —C(=O)NH—, —C(=O)NR$_B$—, —S(O)$_n$NH—, —S(O)$_n$NR$_B$—, NHC(=O)—, —NR$_B$C(=O)—, —NHS(O)$_n$—, and —NR$_B$S(O)$_n$—;

R$_7$ and R$_8$ are independently selected at each occurrence from hydrogen, and straight, branched, and cyclic alkyl groups, and (cycloalkyl)alkyl groups, said straight, branched, and cyclic alkyl groups, and (cycloalkyl) alkyl groups consisting of 1 to 8 carbon atoms, and containing zero or one or more double or triple bonds, each of which 1 to 8 carbon atoms is unsubstituted or substituted with one or more substituent(s) independently selected from oxo, hydroxy, halogen, amino, cyano, nitro, haloalkyl, haloalkoxy, —O(alkyl), —NH (alkyl), —N(alkyl)(alkyl), —NHC(O)(alkyl), —N(alkyl)C(O)(alkyl), —NHS(O)$_n$(alkyl), —S(O)$_n$ (alkyl), —S(O)$_n$NH(alkyl), —S(O)$_n$N(alkyl$_3$)(alkyl$_4$) where alkyl$_3$ and alkyl$_4$ are optionally joined to form a saturated heterocyclic ring consisting of from 5 to 8 ring atoms and containing 1, 2, or 3 heteroatoms independently selected from N, O, and S, and Y';

Y and Y' are independently selected at each occurrence from 3- to 8-membered carbocyclic or heterocyclic groups which are saturated, unsaturated, or aromatic, which are unsubstituted or substituted with one or more substituents independently selected from halogen, oxo, hydroxy, amino, nitro, cyano, C$_{1-4}$alkyl, C$_{1-4}$alkoxy, halo(C$_{1-4}$)alkyl, halo (C$_{1-4}$)alkoxy, mono- or di(C$_{1-4}$) alkylamino, and C$_{1-4}$alkylthio;

wherein said 3- to 8-membered heterocyclic groups contain one or more heteroatom(s) independently selected from N, O, and S;

n is independently chosen at each occurrence from 0, 1, and 2.

5. A compound of the formula:

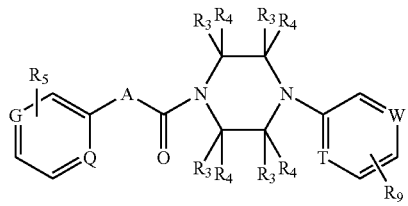

or a pharmaceutically acceptable salt thereof, wherein:

G, Q, T, and W are the same or different and are selected from the group consisting of N, CH, and CR$_5$, wherein T or W or both is N;

A is absent or is selected from the group consisting of O, S, NR$_A$, CR$_B$R$_B$', NR$_A$CR$_B$R$_B$', CR$_B$R$_B$'NR$_A$,

14

[—CR$_A$=CR$_B$—,] and C$_3$H$_4$; where R$_A$, R$_B$, and R$_B$' are independently selected at each occurrence from hydrogen and alkyl;

[Z is oxygen or sulfur;]

each R$_3$ and R$_4$ is independently
(a) selected from the group consisting of hydrogen; halogen; hydroxy; amino; cyano; nitro; —COOH; —CHO, optionally substituted C$_{1-6}$alkyl; optionally substituted C$_{2-6}$alkenyl; optionally substituted C$_{2-6}$ alkynyl; optionally substituted C$_{1-6}$alkoxy; optionally substituted mono or di(C$_{1-6}$)alkylamino; optionally substituted C$_{1-6}$alkylthio; optionally substituted C$_{1-6}$alkyl ketone; optionally substituted C$_{1-6}$ alkylester; optionally substituted C$_{1-6}$alkylsulfinyl; optionally substituted C$_{1-6}$alkylsufonyl; optionally substituted mono- or di(C$_{1-6}$)alkylcarboxamide; optionally substituted —S(O)$_n$NH C$_{1-6}$alkyl; optionally substituted —S(O)$_n$N(C$_{1-6}$alkyl)(C$_{1-6}$alkyl); optionally substituted —NHC(=O) C$_{1-6}$alkyl; optionally substituted NC(=O)(C$_{1-6}$alkyl)(C$_{1-6}$alkyl); optionally substituted —NHS(O)$_n$C$_{1-6}$alkyl; optionally substituted —NS (O)$_n$(C$_{1-6}$alkyl)(C$_{1-6}$alkyl); optionally substituted saturated heterocyclic ring or partially unsaturated heterocycle of from 5 to 8 atoms, which saturated heterocyclic ring or partially unsaturated heterocycle contains 1, 2, or 3 heteroatoms independently selected from N, O, and S; optionally substituted aryl having from 1 to 3 rings; and optionally substituted heteroaryl, said heteroaryl having from 1 to 3 rings, 5 to 8 ring members in each ring and, in at least one of said rings, from 1 to about 3 heteroatoms per ring independently selected from the group consisting of N, O, and S; or
(b) joined to a R$_3$ or R$_4$ not attached to the same carbon to form an optionally substituted aryl ring; a saturated or partially unsaturated carbocyclic ring of from 5 to 8 members, which carbocyclic ring is optionally substituted; or a saturated, partially unsaturated, or aromatic heterocyclic ring of from 5 to 8 members, which heterocyclic ring is optionally substituted and contains 1, 2, or 3 heteroatoms independently selected from N, O, and S;

R$_5$ represents 1 to 3 substituents independently selected at each occurrence from the group consisting of cyano, hydroxy, amino, C$_{3-6}$ alkyl substituted with 0–2 R$_6$, C$_{2-6}$ alkenyl substituted with 0–2 R$_6$, C$_{2-6}$ alkynl substituted with 0–2 R$_5$, C$_{3-6}$ alkoxy, —NH(C$_{1-6}$alkyl) substituted with 0–2 R$_6$, —N(C$_{1-6}$alkyl)(C$_{1-6}$alkyl) where each alkyl is independently substituted with 0–2 R$_6$, —XR$_7$, and Y;

R$_9$ represents [0] 1 to 3 substituents independently selected at each occurrence from the group consisting of halogen, nitro, halo(C$_{1-6}$)alkyl, halo(C$_{1-6}$) alkoxy, hydroxy, amino, C$_{1-6}$alkyl substituted with 0–2 R$_6$, C$_{2-6}$alkenyl substituted with 0–2 R$_6$, C$_{2-6}$alkynyl substituted with 0–2 R$_6$, [C$_{1-6}$alkoxy substituted with 0–2 R$_6$,] and Y;

R$_6$ is independently selected at each occurrence from the group consisting of halogen, hydroxy, cyano, C$_{1-4}$alkyl, C$_{1-4}$alkoxy, —S(O)$_n$(C$_{1-4}$alkyl), halo(C$_{1-4}$) alkyl, halo(C$_{1-4}$)alkoxy, CO(C$_{1-4}$alkyl), CONH (C$_{1-4}$alkyl), CON(C$_{1-4}$alkyl$_1$)(C$_{1-4}$alkyl$_2$) where alkyl$_1$ and alkyl$_2$ may be joined to form a saturated heterocyclic ring of from 5 to 8 ring atoms and containing 1, 2, or 3 heteroatoms independently selected from N, O, and S, —XR$_7$, and Y;

X is independently selected at each occurrence from the group consisting of —$CH_2$—, —$CHR_B$—, —O—, —$S(O)_n$—, —NH—, —$NR_B$—, —C(=O)—, —C(=O)O—, —(=O)NH—, —C(=O)$NR_B$—, —$S(O)_n$NH—, —$S(O)_nNR_B$—, NHC(=O)—, —$NR_B$C(=O)—, —NHS(O)$_n$—, and —$NR_BS(O)_n$—;

$R_7$ and $R_8$ are independently selected at each occurrence from hydrogen, and straight, branched, and cyclic alkyl groups, and (cycloalkyl)alkyl groups, said straight, branched, and cyclic alkyl groups, and (cycloalkyl) alkyl groups consisting of 1 to 8 carbon atoms, and containing zero or one or more double or triple bonds, each of which 1 to 8 carbon atoms is unsubstituted or substituted with one or more substituent(s) independently selected from oxo, hydroxy, halogen, amino, cyano, nitro, haloalkyl, haloalkoxy, —O($C_{1-4}$alkyl), —NH($C_{1-4}$alkyl), —N($C_{1-4}$alkyl)($C_{1-4}$alkyl), —NHC(O)($C_{1-4}$alkyl), —N($C_{1-4}$alkyl)C(O)($C_{1-4}$alkyl), —NHS(O)$_n$($C_{1-4}$alkyl), —S(O)$_n$($C_{1-4}$alkyl), —S(O)$_n$NH($C_{1-4}$alkyl), —S(O)$_n$N($C_{1-4}$alkyl$_3$)($C_{1-4}$alkyl$_4$) where $C_{1-4}$alkyl$_3$ and $C_{1-4}$alkyl$_4$ are optionally joined to form a saturated heterocyclic ring consisting of from 5 to 8 ring atoms and containing 1, 2, or 3 heteroatoms independently selected from N, O, and S, and Y';

Y and Y' are independently selected at each occurrence from 3- to 8-membered carbocyclic or heterocyclic groups which are saturated, unsaturated, or aromatic, which are unsubstituted or substituted with one or more substituents independently selected from halogen, oxo, hydroxy, amino, nitro, cyano, $C_{1-4}$alkyl, $C_{1-4}$alkoxy, halo($C_{1-4}$)alkyl, halo($C_{1-4}$)alkoxy, mono- or di($C_{1-4}$) alkylamino, and $C_{1-4}$alkylthio;

wherein said 3- to 8-membered heterocyclic groups contains one or more heteroatom(s) independently selected from N, O, and S; and n is independently chosen at each occurrence from 0, 1, and 2.

10. A compound according to claim 9 wherein $R_3$ and $R_4$ are hydrogen; and A is selected from the group consisting of NH, [—CH=CH—,] and —$CH_2$NH—.

26. A compound of the formula:

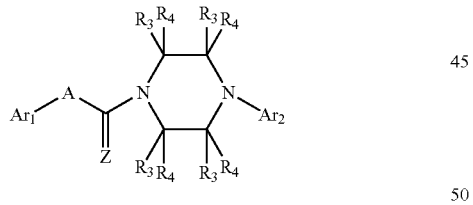

or a pharmaceutically acceptable salt thereof, wherein the compound or pharmaceutically acceptable salt thereof exhibits an EC50 or $K_i$ of 1 micromolar or less in a standard assay of capsaicin receptor mediated calcium mobilization; and wherein A is absent or is selected from the group consisting of O, S, $NR_A$, $NR_ACR_BR_B$', $CR_BR_B$'$NR_A$, [—$CR_A$=$CR_B$—,] and $C_3H_4$; where $R_A$, $R_B$, $R_B$' are independently selected at each occurrence from hydrogen and $C_{1-6}$ alkyl;

Z is oxygen or sulfur;

each $R_3$ and $R_4$ is independently (a) selected from the group consisting of hydrogen, halogen, cyano, nitro, halo($C_{1-6}$)alkyl, halo($C_{1-6}$) alkoxy, hydroxy, amino, $C_{1-6}$alkyl substituted with 0–2 $R_6$, $C_{2-6}$alkenyl substituted with 0–2 $R_6$; $C_{2-6}$alkynyl substituted with 0–2 $R_6$; $C_{1-6}$alkoxy substituted with 0–2 $R_6$, —NH($C_{1-6}$alkyl) substituted with 0–2 $R_6$; —N($C_{1-6}$alkyl)($C_{1-6}$alkyl) where each $C_{1-6}$alkyl is independently substituted with 0–2 $R_6$, —$XR_7$, and Y; or (b) joined to a $R_3$ or $R_4$ not attached to the same carbon to form an aryl ring substituted with 0–3 $R_6$, a saturated or partially unsaturated carbocyclic ring of from 5 to 8 members, which carbocyclic ring is substituted with 0–2 $R_6$, or a saturated, partially unsaturated, or aromatic heterocyclic ring of from 5 to 8 members, which heterocyclic ring is substituted with 0–2 $R_6$ and contains 1, 2, or 3 heteroatoms independently selected from N, O, and S;

$Ar_1$ is selected from the group consisting of:
(a) cyclohexyl, cyclopentyl, piperidinyl, piperazinyl, phenyl, pyrrolyl, furanyl, thienyl, pyrazolyl, imidazolyl, thiazolyl, isothiazolyl, oxazolyl, isoxazolyl, oxadiazolyl, triazolyl, tetrazolyl, [pyridyl,] pyrimidyl, pyrazinyl, benzimidazolyl, naphthyl, indolyl, isoindolyl, benzofuranyl, isobenzofuranyl, benzo[b]thiophenyl, benz[d] isoxazolyl, quinolinyl, isoquinolinyl, cinnolinyl, quinazolinyl, and quinoxalinyl, each of which is optionally mono-, [di-, or trisubstituted] *or disubstituted* with $R_5$; and
(b) bicyclic oxygen-containing groups of the formula:

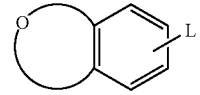

optionally mono-, di-, or trisubstituted with $R_5$, where L represents point of attachment and may be at any point on the benzene ring, and the oxygen-containing ring of the bicyclic oxygen-containing group consists of from 5 to 8 ring atoms, contains 1 to 2 oxygen atoms and remaining ring atoms are carbon;

$Ar_2$ is selected from the group consisting of:
(a) cyclohexyl, cyclopentyl, piperidinyl, piperazinyl, pyrrolyl, furanyl, thienyl, pyrazolyl, imidazolyl, [thiazolyl,] isothiazolyl, oxazolyl, isoxazolyl, oxadiazolyl, triazolyl, tetrazolyl, pyridyl, pyrimidyl, [benzimidazolyl, naphthyl, indolyl,] isoindolyl, benzofuranyl, isobenzofuranyl, benzo[b]thiophenyl, *and* benz[d]isoxazolyl, [quinolinyl, isoquinolinyl, cinnolinyl, quinazolinyl, and quinoxalinyl,] each of which is optionally mono-, di-, or trisubstituted with $R_5$; and
(b) bicyclic oxygen-containing groups of the formula:

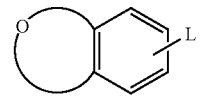

optionally mono-, di-, or trisubstituted with $R_5$, where L represents point of attachment and may be at any point on the benzene ring, and the oxygen-containing ring of the bicyclic oxygen-containing group consists of from 5 to 8 ring atoms, contains 1 to 2 oxygen atoms and remaining ring atoms are carbon;

$R_5$ is independently selected at each occurrence from the group consisting of halogen, nitro, halo($C_{1-6}$)alkyl, halo($C_{1-6}$)alkoxy, hydroxy, amino, $C_{1-6}$alkyl substituted with 0–2 $R_6$, $C_{2-6}$alkenyl substituted with 0–2 $R_6$, $C_{2-6}$alkynyl substituted with 0–2 $R_6$, $C_{1-6}$alkoxy and Y;

$R_6$ is independently selected at each occurrence from the group consisting of halogen, hydroxy, cyano, $C_{1-4}$alkyl, $C_{1-4}$alkoxy, —S(O)$_n$($C_{1-4}$alkyl), halo($C_{1-4}$)alkyl, halo($C_{1-4}$)alkoxy, CO($C_{1-4}$alkyl), CONH($C_{1-4}$alkyl), CON($C_{1-4}$alkyl$_1$)($C_{1-4}$alkyl$_2$) where alkyl$_1$ and alkyl$_2$ may be joined to form a saturated heterocyclic ring of from 5 to 8 ring atoms and containing 1, 2, or 3 heteroatoms independently selected from N, O, and S, —XR$_7$, and Y;

X is independently selected at each occurrence from the group consisting of —CH$_2$—, —CHR$_B$—, —O—, —S(O)$_n$—, —NH—, —NR$_B$—, —C(=O)—, —C(=O)O—, —C(=O)NH—, —C(=O)NR$_B$—, —S(O)$_n$NH—, —S(O)$_n$NR$_B$—, NHC(=O)—, —NR$_B$C(=O)—, —NHS(O)$_n$—, and —NR$_B$S(O)$_n$—;

$R_7$ and $R_8$ are independently selected at each occurrence from hydrogen, and straight, branched, and cyclic alkyl groups, and (cycloalkyl)alkyl groups, said straight, branched, and cyclic alkyl groups, and (cycloalkyl)alkyl groups consisting of 1 to 8 carbon atoms, and containing zero or one or more double or triple bonds, each of which 1 to 8 carbon atoms is unsubstituted or substituted with one or more substituent(s) independently selected from oxo, hydroxy, halogen, amino, cyano, nitro, haloalkyl, haloalkoxy, —O($C_{1-4}$alkyl), —NH($C_{1-4}$alkyl), —N($C_{1-4}$alkyl)($C_{1-4}$alkyl), —NHC(O)($C_{1-4}$alkyl), —N($C_{1-4}$alkyl)C(O)($C_{1-4}$alkyl), —NHS(O)$_n$($C_{1-4}$alkyl), —S(O)$_n$($C_{1-4}$alkyl), —S(O)$_n$NH($C_{1-4}$alkyl), —S(O)$_n$N($C_{1-4}$alkyl$_3$)($C_{1-4}$alkyl$_4$) where $C_{1-4}$alkyl$_3$ and $C_{1-4}$alkyl$_4$ are optionally joined to form a saturated heterocyclic ring consisting of from 5 to 8 ring atoms and containing 1, 2, or 3 heteroatoms independently selected from N, O, and S, and Y';

Y and Y' are independently selected at each occurrence from 3- to 8-membered carbocyclic or heterocyclic groups which are saturated, unsaturated, or aromatic, which may be further substituted with one or more substituents independently selected from halogen, oxo, hydroxy, amino, nitro, cyano, $C_{1-4}$alkyl, $C_{1-4}$alkoxy, halo($C_{1-4}$)alkyl, halo($C_{1-4}$)alkoxy, mono- or di($C_{1-4}$) alkylamino, and $C_{1-4}$alkylthio;

wherein said 3- to 8-membered heterocyclic groups contain one or more heteroatom(s) independently selected from N, O, and S; and n is independently chosen at each occurrence from 0, 1, and 2.

27. A compound of the Formula A, [Formula B,] Formula C, [Formula D, Formula E,] or Formula F:

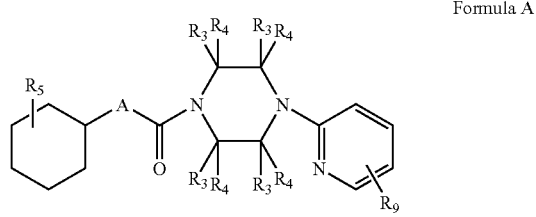
Formula A

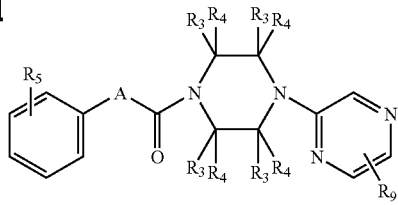
Formula B

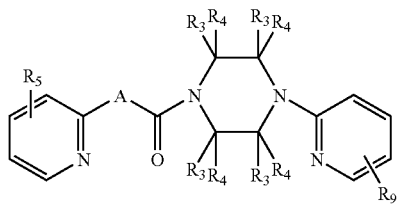
Formula C

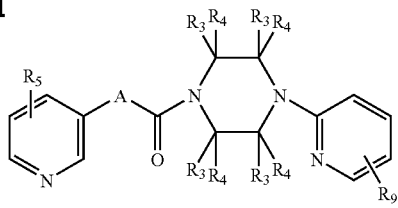
Formula D

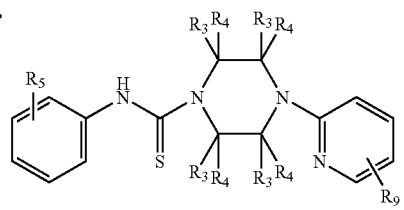
Formula E

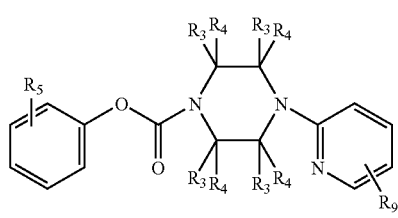
Formula F or a pharmaceutically acceptable salt of Formula A, [Formula B,] Formula C, [Formula D, Formula E,] or Formula F, wherein A represents NH or O;

each $R_3$ and $R_4$ is independently
(a) selected from the group consisting of hydrogen, halogen, cyano, nitro, halo($C_{1-6}$)alkyl, halo($C_{1-6}$)alkoxy, hydroxy, amino, $C_{1-6}$alkyl substituted with 0–2 $R_6$, $C_{2-6}$alkenyl substituted with 0–2 $R_6$; $C_{2-6}$alkynl substituted with 0–2 $R_6$; $C_{1-6}$alkoxy substituted with 0–2 $R_6$, —NH($C_{1-6}$alkyl) substituted with 0–2 $R_6$, —N($C_{1-6}$alkyl)($C_{1-6}$alkyl) where each $C_{1-6}$alkyl is independently substituted with 0–2 $R_6$, —XR$_7$, and Y; or
(b) joined to a $R_3$ or $R_4$ not attached to the same carbon to form an aryl ring substituted with 0–3 $R_6$, a saturated or partially unsaturated carbocyclic ring of from 5 to 8 members, which carbocyclic ring is substituted with 0–2 $R_6$, or a saturated, partially unsaturated, or aromatic heterocyclic ring of from 5 to 8 members, which heterocyclic ring is substituted with 0–2 $R_6$ and contains 1, 2, or 3 heteroatoms independently selected from N, O, and S;

$R_5$ represents from 1 to 3 substituents independently selected at each occurrence from the group consisting of halogen, cyano, nitro, halo(C$_{1-6}$)alkyl, halo(C$_{1-6}$) alkoxy, hydroxy, amino, C$_{1-6}$alkyl substituted with 0–2 R$_6$, C$_{2-6}$alkenyl substituted with 0–2 R$_6$, C$_{2-6}$alkynyl substituted with 0–2 R$_6$, C$_{1-6}$alkoxy, —NH(C$_{1-6}$alkyl) substituted with 0–2 R$_6$, —N(C$_{1-6}$alkyl)(C$_{1-6}$alkyl) where each C$_{1-6}$alkyl is independently substituted with 0–2 R$_6$, —XR$_7$, and Y;

R$_9$ represents from 1 to 3 substituents independently selected at each occurrence from the group consisting of halogen, cyano, nitro, halo(C$_{1-6}$)alkyl, halo(C$_{1-6}$) alkoxy, hydroxy, amino, C$_{1-6}$alkyl substituted with 0–2 R$_6$, C$_{2-6}$alkenyl substituted with 0–2 R$_6$, C$_{2-6}$alkynl substituted with 0–2 R$_6$, C$_{1-6}$alkoxy substituted with 0–2 R$_6$, and Y;

R$_6$ is independently selected at each occurrence from the group consisting of halogen, hydroxy, cyano, C$_{1-4}$alkyl, C$_{1-4}$alkoxy, —S(O)$_n$(C$_{1-4}$alkyl), halo(C$_{1-4}$) alkyl, halo(C$_{1-4}$)alkoxy, CO(C$_{1-4}$alkyl), CONH (C$_{1-4}$alkyl), CON(C$_{1-4}$alkyl$_1$)(C$_{1-4}$alkyl$_2$) where alkyl$_1$ and alkyl$_2$ may be joined to form a saturated heterocyclic ring of from 5 to 8 ring atoms and containing 1, 2, or 3 heteroatoms independently selected from N, O, and S, —XR$_7$, and Y;

X is independently selected at each occurrence from the group consisting of —CH$_2$—, —CHR$_8$—, —O—, —S(O)$_n$—, —NH—, —NR$_8$—, —C(=O)—, —C(=O)O—, —C(=O)NH—, —C(=O)NR$_B$—, —S(O)$_n$NH—, —S(O)$_n$NR$_B$—, NHC(=O)—, —NR$_B$C(=O)—, —NHS(O)$_n$—, and —NR$_B$S(O)$_n$—;

R$_7$ and R$_8$ are independently selected at each occurrence from hydrogen, and straight, branched, and cyclic alkyl groups, and (cycloalkyl)alkyl groups, said straight, branched, and cyclic alkyl groups, and (cycloalkyl) alkyl groups consisting of 1 to 8 carbon atoms, and containing zero or one or more double or triple bonds, each of which 1 to 8 carbon atoms is unsubstituted or substituted with one or more substituent(s) independently selected from oxo, hydroxy, halogen, amino, cyano, nitro, haloalkyl, haloalkoxy, —O(C$_{1-4}$alkyl), —NH(C$_{1-4}$alkyl), —N(C$_{1-4}$alkyl)(C$_{1-4}$alkyl), —NHC (O)(C$_{1-4}$alkyl), —N(C$_{1-4}$alkyl)C(O)(C$_{1-4}$alkyl), —NHS(O)$_n$(C$_{1-4}$alkyl), —S(O)$_n$(C$_{1-4}$alkyl), —S(O)$_n$NH(C$_{1-4}$alkyl), —S(O)$_n$N(C$_{1-4}$alkyl$_3$) (C$_{1-4}$alkyl$_4$) where C$_{1-4}$alkyl$_3$ and C$_{1-4}$alkyl$_4$ are optionally joined to form a saturated heterocyclic ring consisting of from 5 to 8 ring atoms and containing 1, 2, or 3 heteroatoms independently selected from N, O, and S, and Y';

Y and Y' are independently selected at each occurrence from 3- to 8-membered carbocyclic or heterocyclic groups which are saturated, unsaturated, or aromatic, which may be further substituted with one or more substituents independently selected from halogen, oxo, hydroxy, amino, nitro, cyano, C$_{1-4}$alkyl, C$_{1-4}$alkoxy, halo(C$_{1-4}$)alkyl, halo(C$_{1-4}$)alkoxy, mono- or di(C$_{1-4}$) alkylamino, and C$_{1-4}$alkylthio;

wherein said 3- to 8-membered heterocyclic groups contain one or more heteroatom(s) independently selected from N, O, and S; and n is independently chosen at each occurrence from 0, 1, and 2.

32. A compound or salt according to claim 27, wherein:
A represents NH;
R$_3$ represents hydrogen;
R$_4$ is independently chosen at each occurrence from hydrogen and methyl; and R$_5$ represents from 1 to 3 substituents independently selected at each occurrence from the group consisting of halogen, cyano, nitro, halo(C$_{1-6}$)alkyl, halo(C$_{1-6}$) alkoxy, hydroxy, amino, C$_{1-6}$alkyl, C$_{2-6}$alkenyl, C$_{2-6}$alkynyl, C$_{1-6}$alkoxy, —NH(C$_{1-6}$alkyl), —N(C$_{1-6}$alkyl)(C$_{1-6}$alkyl), and C$_{3-8}$ cycloalkyl; and R$_9$ represents from 1 to 3 substituents independently selected at each occurrence from the group consisting of halogen, nitro, halo(C$_{1-6}$)alkyl, halo(C$_{1-6}$)alkoxy, hydroxy, amino, C$_{1-6}$alkyl, C$_{2-6}$alkenyl, C$_{2-6}$alkynyl, C$_{1-6}$alkoxy, and C$_{3-8}$ cycloalkyl.

39. A compound [or salt according to claim 32] of Formula D-1

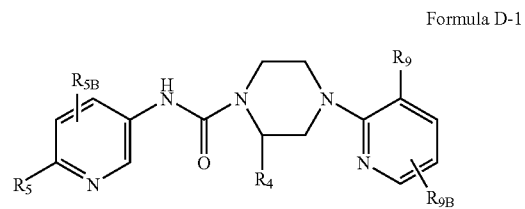

Formula D-1 or a pharmaceutically acceptable salt thereof, wherein:

R$_4$ is hydrogen or methyl;

R$_5$ is [selected from the group consisting of halogen, cyano, nitro, halo(C$_{1-6}$)alkyl, halo(C$_{1-6}$)alkoxy, hydroxy, amino, C$_{1-6}$alkyl, C$_{2-6}$alkenyl, C$_{2-6}$alkynyl, C$_{1-6}$alkoxy, —NH(C$_{1-6}$alkyl), —N(C$_{1-6}$alkyl) (C$_{1-6}$alkyl), and C$_{3-8}$ cycloalkyl] C$_{3-6}$ alkoxy; halo (C$_{1-3}$)alkyl, or halo(C$_{1-3}$)alkoxy;

R$_9$ is [selected from the group consisting of halogen, cyano, nitro, halo(C$_{1-6}$)alkyl, halo(C$_{1-6}$)alkoxy, hydroxy, amino, C$_{1-6}$alkyl, C$_{2-6}$alkenyl, C$_{2-6}$alkynyl, C$_{1-6}$alkoxy, and C$_{3-8}$ cycloalkyl] chloro or trifluoromethyl; and R$_{5B}$ and R$_{9B}$ [each represent from 0 to 2 substituents independently selected at each occurrence from hydrogen, halogen, cyano, nitro, halo(C$_{1-2}$)alkyl, halo (C$_{1-2}$)alkoxy, hydroxy, amino, C$_{1-3}$alkyl, C$_{1-3}$alkoxy, —NH(C$_{1-3}$alkyl), and —N(C$_{1-6}$alkyl)(C$_{1-5}$alkyl)] are hydrogen.

44. A compound or salt according to claim [42] 43, wherein:

R$_5$ is C$_{3-6}$ alkyl; C$_{3-6}$ alkoxy; halo(C$_{1-3}$)alkyl, halo(C$_{1-3}$) alkoxy, or C$_{3-8}$ cycloalkyl;

R$_9$ is chloro or trifluoromethyl; and

R$_{5B}$ and R$_{9B}$ are hydrogen.

157. A compound [according to claim 154,] which is (2R)-4-isoquinolin-1-yl-2-methyl-N-[4-(trifluoromethyl) phenyl]piperazine-1-carboxamide, or a pharmaceutically acceptable salt thereof.

158. A compound [according to claim 154,] which is (2R)-N-(4-tert-butylphenyl)-4-isoquinolin-1-yl-2-methylpiperazine-1-carboxamide, or a pharmaceutically acceptable salt thereof.

159. A compound [according to claim 154,] which is (2R)-N-(4-isopropylphenyl)-4-isoquinolin-1-yl-2-methylpiperazine-1-carboxamide, or a pharmaceutically acceptable salt thereof.

160. A compound [according to claim 154,] which is (2R)-N-(4-cyclopentylphenyl)-4-isoquinolin-1-yl-2-methylpiperazine-1-carboxamide, or a pharmaceutically acceptable salt thereof.

161. A compound [according to claim 154,] which is (2R)-N-(4-cyclohexylphenyl)-4-isoquinolin-1-yl-2- methylpiperazine-1-carboxamide, or a pharmaceutically acceptable salt thereof.

181. A pharmaceutical composition comprising a pharmaceutically acceptable carrier and a compound or salt according to claim [22] 25.

182. A compound or salt of claim [22] 25 wherein, in an in vitro assay of capsaicin receptor antagonism, the compound or salt exhibits capsaicin receptor antagonist activity, but in an in vitro assay of capsaicin receptor agonism the compound does not exhibit detectable agonist activity.

183. A compound or salt of claim [22] 25 wherein a dose of the compound of salt that is twice the minimum dose sufficient to provide analgesia in an animal model for determining pain relief does not produce sedation in an animal model assay of sedation.

*186. A compound which is 4-(3-Cyano-2-pyridinyl)-N-[4-(isopropyl)phenyl]-1-piperazinecarboxamide.*

\* \* \* \* \*